(12) United States Patent
Clark et al.

(10) Patent No.: US 12,234,216 B2
(45) Date of Patent: *Feb. 25, 2025

(54) ISOTOPOLOGUES SALTS, CRYSTALLINE FORMS, STEREOISOMERS, OF METHYLONE AND ETHYLONE AND METHODS OF USE THEREOF

(71) Applicant: Terran Biosciences Inc., Miami Beach, FL (US)

(72) Inventors: Samuel Clark, Miami Beach, FL (US); Matthew Duncton, Las Vegas, NV (US)

(73) Assignee: Terran Biosciences Inc., Miami Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/147,071

(22) Filed: Dec. 28, 2022

(65) Prior Publication Data

US 2023/0192642 A1 Jun. 22, 2023

Related U.S. Application Data

(63) Continuation of application No. PCT/US2022/049027, filed on Nov. 4, 2022.

(60) Provisional application No. 63/276,539, filed on Nov. 5, 2021, provisional application No. 63/280,071, filed on Nov. 16, 2021, provisional application No. 63/280,073, filed on Nov. 16, 2021, provisional application No. 63/280,075, filed on Nov. 16, 2021, provisional application No. 63/283,027, filed on Nov. 24, 2021, provisional application No. 63/311,874, filed on Feb. 18, 2022, provisional application No. 63/320,654, filed on Mar. 16, 2022, provisional application No. 63/326,774, filed on Apr. 1, 2022, provisional application No. 63/326,776, filed on Apr. 1, 2022, provisional application No. 63/326,782, filed on Apr. 1, 2022, provisional application No. 63/326,792, filed on Apr. 1, 2022, provisional application No. 63/367,445, filed on Jun. 30, 2022, provisional application No. 63/388,840, filed on Jul. 13, 2022, provisional application No. 63/377,328, filed on Sep. 27, 2022.

(51) Int. Cl.
| | | |
|---|---|---|
| *C07D 317/58* | (2006.01) | |
| *A61K 31/36* | (2006.01) | |
| *A61P 25/18* | (2006.01) | |
| *A61P 25/22* | (2006.01) | |

(52) U.S. Cl.
CPC ............ *C07D 317/58* (2013.01); *A61K 31/36* (2013.01); *A61P 25/18* (2018.01); *A61P 25/22* (2018.01); *C07B 2200/13* (2013.01)

(58) Field of Classification Search
CPC .................................................. C07D 317/58

USPC ........................................................ 514/466
See application file for complete search history.

(56) References Cited

U.S. PATENT DOCUMENTS

| | | |
|---|---|---|
| 5,323,907 A | 6/1994 | Kalvelage |
| 5,763,263 A | 6/1998 | Dehlinger |

FOREIGN PATENT DOCUMENTS

| | | |
|---|---|---|
| PL | 232830 B1 | 7/2019 |
| WO | WO-9639133 A1 | 12/1996 |
| WO | WO-2007069925 A2 | 6/2007 |
| WO | WO-2023081403 A1 | 5/2023 |
| WO | WO-2023137453 A1 | 7/2023 |

OTHER PUBLICATIONS

Al-Muhammed et al. In-vivo studies on dexamethasone sodium phosphate liposomes. J Microencapsul. 13(3):293-306 (1996).
Berge et al. Pharmaceutical Salts. Journal of Pharmaceutical Sciences 66(1): 1-19 (Jan. 1977).
Bernstein. Crystal Structure Prediction and Polymorphism. ACA Transactions 39:14-23 (2004).
Braga et al. Making crystals from crystals: a green route to crystal engineering and polymorphism. J. Royal Soc. Chem. Commun 29:3635-3645 (2005).
CAS: 1216808-12-6; Entry date: Apr. 5, 2010.
CAS: 1246820-21-2; Entry date: Oct. 22, 2010.
Chonn et al. Recent advances in liposomal drug-delivery systems. Curr Opin Biotechnol. 6(6):698-708 (1995).
Co-pending U.S. Appl. No. 18/162,591, inventors Duncton; Matthew et al., filed Jan. 31, 2023.
Eyles et al. Oral delivery and fate of poly(lactic acid) microsphere-encapsulated interferon in rats. J Pharm Pharmacol. 49(7):669-74 (1997).
Gao et al.: Controlled release of a contraceptive steroid from biodegradable and injectable gel formulations: in vitro evaluation. Pharm Res. 12(6):857-863 (1995).
Gatch et al. Locomotor stimulant and discriminative stimulus effects of 'bath salt' cathinones. Behav. Pharmacol., 24:437-447 (2013).
Glennon et al. Structure-Activity Relationships of Synthetic Cathinones. Curr Top Behav Neurosci 32:19-47 (2017).

(Continued)

*Primary Examiner* — Taofiq A Solola
(74) *Attorney, Agent, or Firm* — COOLEY LLP; Heidi A. Erlacher; Eric A. Owens

(57) ABSTRACT

Described herein are isotopically enriched analogs of methylone (e.g., deuterated analogs of methylone (e.g., (S)-methylone and (R)-methylone) with improved characteristics. Also described herein are salts (such as hydrochloride salt) and solid forms (e.g., crystalline forms) of methylone. Also described herein are stereoisomers (e.g., enantiomers) of methylone. The present disclosure also provides methods of making and methods of use of the methylone or methylone analogs and solid forms of 3,4-methylenedioxy-N-ethylcathinone hydrochloride described herein to treat brain and neurological disorders such as depression.

14 Claims, 69 Drawing Sheets

(56) References Cited

OTHER PUBLICATIONS

Gore et al. Synthetic cathinones and their phenethylamine analogues produce distinct psychomotor and reward behavior in crayfish. Behav. Brain Res., M79:112368 (2020).

Gould et al. Stress and hippocampal neurogenesis. Biol. Psychiatry 46:1472-1479 (1999).

Jones et al.: Pharmaceutical Cocrystals: An Emerging Approach to Physical Property Enhancement. MRS Bulletin 31:875-879 (2006).

Lopez-Arnau et al. Serotonergic impairment and memory deficits in adolescent rats after binge exposure of methylone. J. Psychopharmacol., 28:1053-1063 (2014).

Maheux et al. Identification of polymorphism in ethylone hydrochloride: synthesis and characterization. Drug Test Anal., 8:847-857 (2016).

Meyer et al. Beta-keto amphetamines: studies on the metabolism of the designer drug mephedrone and toxicological detection of mephedrone, butylone, and methylone in urine using gas chromatography-mass spectrometry. Anal Bioanal Chem 397:1225-1233 (2010).

Minto et al., Pharmacokinetics and pharmacodynamics of nandrolone esters in oil vehicle: effects of ester, injection site and injection vol. J. Pharmacol. Exp. Ther. 281:93-102 (1997).

Ostro et al. Use of Liposomes as Injectable-Drug Delivery Systems. Am J Hosp Pharm 46(8):1576-1587 (Aug. 1989).

PCT/US2022/049027 International Search Report and Written Opinion dated Feb. 13, 2023.

PCT/US2023/060669 International Search Report and Written Opinion dated Apr. 13, 2023.

Poyatos et al., A Comparison of Acute Pharmacological Effects of Methylone and MDMA Administration in Humans and Oral Fluid Concentrations as Biomarkers of Exposure. Biology (Basel) 10(8):788 (2021).

Price. The computational prediction of pharmaceutical crystal structures and polymorphism. Advanced Drug Delivery Reviews 56:301-319 (2004).

Prosser et al. The toxicology of bath salts: a review of synthetic cathinones. J Med Toxicol. 8(1):33-42 (2012).

Rao. Recent developments of collagen-based materials for medical applications and drug delivery systems. J Biomater Sci Polym Ed. 7(7):623-45 (1995).

Rohatagi et al. Pharmacokinetic and pharmacodynamic evaluation of triamcinolone acetonide after intravenous, oral, and inhaled administration. J. Clin. Pharmacol. 35:1187-1193 (1995).

Shepherd et al., Behavioural and pharmacological validation of the elevated "zero-maze" as an animal model of anxiety. Psychopharmacology (Berl) 116:56-64 (1994).

Tjwa. Budesonide inhaled via Turbuhaler: a more effective treatment for asthma than beclomethasone dipropionate via Rotahaler. Ann. Allergy Asthma Immunol. 75:107-111, 1995.

Westphal et al. Massenspektrometrische, infrarotspektroskopische and NMR-spektroskopische Daten von Mephedron, Butylon und Methylon sowie einigen ihrer Derivate (Mass spectrometric, infrared spectroscopic and NMR spectroscopic data of mephedrone, butylon and methylone and some of their derivatives). Toxichem Krimtech 77(2):95-116 (2010) (English Abstract) Available at https://www.academia.edu/download/41867677/Massenspektrometrische_infrarotspektrosk20160201-21753-hoh587.pdf.

Whalen, Richard William. Deuterium Isotope Studies On Selected Pesticides And Synergists. Fordham University. ProQuest Dissertations Publishing, 6613533. https://www.proguest.com/docview/302197417 (1966).

World Health Organization (WHO). Methylone (bk-MDMA). Critical Review Report; WHO: Geneva, Switzerland (2014).

Caplus Accession No. 2021:2317626, 1 page (2022).

CAS Reg No. 1137456-51-9, STN Entry Date: Apr. 21, 2009; 2-Piperazinone, 1-(1, 3-benzodioxol-5-yl)-3-methyl-, 1 page.

CAS Reg No. 1225535-82-9, STN Entry Date: May 28, 2010; 2-Oxazolidinone, 5-(1, 3-benzodioxol-5-yl)-3-methyl-, 1 page.

CAS Reg No. 861335-25-3, STN Entry Date: Aug. 23, 2005; 2-Oxazolidinone, 4-(1, 3-benzodioxol-5-yl)-5-methyl-, 1 page.

Chen, J-L., et al. Development of an analytical method to detect simultaneously 219 new psychoactive substances and 65 other substances in urine specimens using LC-QqQ MS/MS with CriticalPairFinder and TransitionFinder. Talanta; 238(Pt 1):122979, 9 pages (2022).

Co-pending U.S. Appl. No. 18/728,575, inventor Matthew Duncton; filed Jul. 12, 2024.

De Souza Junior, J.L., et al.: Seizures of Clandestinely Produced Tablets in Santa Catarina, Brazil: The Increase in NPS from 2011 to 2017. J Forensic Sci.; 65(3):906-912 (2020).

Haleblian, J., et al., "Pharmaceutical Applications of Polymorphism," J. Pharm. Sci., 1969, 58(8), 911-929.

International Conference on Harmonization of Technical Requirements for Registration of Pharmaceuticals for Human Use (ICH), "Impurities: Guidelines for Residual Solvents Q3C(R6)," (Oct. 2016), 38 pages.

Kamada et al., " Characterization and monitoring of pseudopolymorphs in manufacturing process by NIR," International Journal of Pharmaceutics (2009) 368, 103-108.

Karabas et al., "Analysis and stability of polymorphs in tablets: The case of Risperidone," Talanta (2007), 71(3), 1382-1386.

Mullard, A.; "Deuterated drugs draw heavier backing," Nat Rev Drug Discov. (2016); 15(4):219-221.

Newman et al.: Solid form changes during drug development: good, bad, and ugly case studies. (2016) AAPS Open 2(2), 11 pages.

Poyatos, L., et al.; "Pharmacological effects of methylone and MDMA in humans," Front Pharmacol.; 14:1122861, pp. 1-13 (2023).

Singhal, D., et al., "Drug Polymorphism and Dosage Form Design: A practical perspective," Advanced Drug Delivery Reviews (2004); 56: 335-347.

US 12,234,216 B2

ISOTOPOLOGUES SALTS, CRYSTALLINE FORMS, STEREOISOMERS, OF METHYLONE AND ETHYLONE AND METHODS OF USE THEREOF

CROSS-REFERENCE TO RELATED APPLICATIONS

This application is a Continuation of International Application No. PCT/US2022/049027 filed Nov. 4, 2022; which claims the benefit of U.S. Provisional Application No. 63/276,539, filed Nov. 5, 2021; U.S. Provisional Application No. 63/280,071, filed Nov. 16, 2021; U.S. Provisional Application No. 63/280,073, filed Nov. 16, 2021; U.S. Provisional Application No. 63/280,075, filed Nov. 16, 2021; U.S. Provisional Application No. 63/283,027, filed Nov. 24, 2021; U.S. Provisional Application No. 63/311,874, filed Feb. 18, 2022; U.S. Provisional Application No. 63/320,654, filed Mar. 16, 2022; U.S. Provisional Application No. 63/326,774, filed Apr. 1, 2022; U.S. Provisional Application No. 63/326,776, filed Apr. 1, 2022; U.S. Provisional Application No. 63/326,782, filed Apr. 1, 2022; U.S. Provisional Application No. 63/326,792, filed Apr. 1, 2022; U.S. Provisional Application No. 63/367,445, filed Jun. 30, 2022; U.S. Provisional Application No. 63/388,840, filed Jul. 13, 2022; U.S. Provisional Application No. 63/377,328, filed Sep. 27, 2022; each of which is incorporated herein by reference in its entirety.

FIELD

The present disclosure relates to isotopically enriched analogs of methylone (e.g., deuterated analogs of methylone (e.g., of (S)-methylone and (R)-methylone) with improved characteristics, salts (such as hydrochloride salt) and solid forms (e.g., crystalline forms), and stereoisomers (e.g., enantiomers) of methylone, methods of making, and their uses to treat brain and neurological disorders such as depression. The present disclosure also relates to solid forms of 3,4-methylenedioxy-N-ethylcathinone hydrochloride (ethylone HCl), methods of making, and their use to treat brain and neurological disorders

BACKGROUND

Major depressive disorder and related neuropsychiatric diseases are among the leading causes of disability worldwide. Despite recent advances, there remains a need for new therapeutics to support treatment of debilitating neuropsychiatric diseases.

Psychedelics have been shown to have therapeutic benefits. Recently, psychedelic compounds have received renewed interest for the treatment of depression and other disorders. For example, the Food and Drug Administration (FDA) recently approved the dissociative anesthetic ketamine for treatment-resistant depression, making it the first mechanistically distinct medicine to be introduced to psychiatry in nearly thirty years. Ketamine is a member of a class of compounds known as psychoplastogens. Psychoplastogens promote neuronal growth through a mechanism involving the activation of AMPA receptors, the tropomyosin receptor kinase B (TrkB), and the mammalian target of rapamycin (mTOR). As pyramidal neurons in the PFC exhibit top-down control over areas of the brain controlling motivation, fear, and reward, these effects support clinical development of psychoplastogenic compounds for their antidepressant, anxiolytic, and anti-addictive effects properties.

Methylone (3,4-methylenedioxy-N-methylcathinone) and ethylone (3,4-methylenedioxy-N-ethylcathinone) are synthetic analogs of the psychedelic phenethylamine class of compounds.

SUMMARY OF INVENTION

Described herein are cathinone compounds, such as (R)-methylone, (S)-methylone, (rac.)-methylone, or ethylone, deuterated analogues, pharmaceutically acceptable salts, cocrystals, solvates, hydrates, crystalline forms, and combinations thereof. The cathinone compounds are useful in the methods and uses described herein.

In one aspect, provided herein is a crystalline form of (R)-methylone hydrochloride, wherein the crystalline (R)-methylone hydrochloride is characterized as having at least one of the following properties:
  an X-ray powder diffraction (XRPD) pattern substantially the same as shown in FIG. 53;
  an XRPD pattern substantially the same as shown in FIG. 54;
  an XRPD pattern with peaks at $13.1°±0.2°$ 2-Theta, $17.9°±0.2°$ 2-Theta, and $19.0°±0.2°$ 2-Theta, and optionally with further peaks at $25.3°±0.2°$ 2-Theta and $26.3°±0.2°$ 2-Theta, as measured with Cu Kα radiation;
  an XRPD pattern with peaks at $7.1°±0.2°$ 2-Theta, $13.0°±0.2°$ 2-Theta, and $16.4°±0.2°$ 2-Theta, and optionally with further peaks at peaks at $17.9°±0.2°$ 2-Theta and $19.0°±0.2°$ 2-Theta, as measured with Cu Kα radiation;
  or combinations thereof.

In certain embodiments, the crystalline form is characterized as having an XRPD pattern substantially the same as shown in FIG. 53. In certain embodiments, the crystalline form is characterized as having an XRPD pattern with peaks at $13.1°±0.2°$ 2-Theta, $17.9°±0.2°$ 2-Theta, and $19.0°±0.2°$ 2-Theta, and optionally with further peaks at $25.3°±0.2°$ 2-Theta and $26.3°±0.2°$ 2-Theta, as measured with Cu Kα radiation In certain embodiments, the crystalline form is characterized as having an XRPD pattern substantially the same as shown in FIG. 54. In certain embodiments, the crystalline form is characterized as having an XRPD pattern with peaks at $7.1°±0.2°$ 2-Theta, $13.0°±0.2°$ 2-Theta, and $16.4°±0.2°$ 2-Theta, and optionally with further peaks at peaks at $17.9°±0.2°$ 2-Theta and $19.0°±0.2°$ 2-Theta, as measured with Cu Kα radiation.

In yet another aspect, provided herein is a crystalline form of (S)-methylone hydrochloride, wherein the crystalline (S)-methylone hydrochloride is crystalline Form A having at least one of the following properties:
  an X-ray powder diffraction (XRPD) pattern substantially the same as shown in FIG. 45;
  an XRPD pattern substantially the same as shown in FIG. 56;
  an XRPD pattern substantially the same as shown in FIG. 57;
  an XRPD pattern with characteristic peaks at $7.2°±0.2$ 2-Theta, $13.1°±0.2$ 2-Theta, and $18.0°±0.2$ 2-Theta, and optionally with further characteristic peaks at $14.5°±0.2$ 2-Theta and $25.3°±0.2$ 2-Theta, as measured with Cu Kα radiation;
  an XRPD pattern with characteristic peaks at $13.0°±0.2$ 2-Theta, $16.6°±0.2$ 2-Theta, and $17.9°±0.2$ 2-Theta, and optionally with further characteristic peaks at 19.0°±0.2 2-Theta and 22.7°±0.2 2-Theta, as measured with Cu Kα radiation;
an XRPD pattern with characteristic peaks at 7.1°±0.2 2-Theta, 13.0°±0.2 2-Theta, 16.5°±0.2 2-Theta, and optionally with further characteristic peaks at 17.9°±0.2 2-Theta and 19.0°±0.2 2-Theta, as measured with Cu Kα radiation;
or combinations thereof.

In certain embodiments, the crystalline form is characterized as having an XRPD pattern substantially the same as shown in FIG. 45. In certain embodiments, the crystalline form is characterized as having an XRPD pattern with characteristic peaks at 7.2°±0.2 2-Theta, 13.1°±0.2 2-Theta, and 18.0°±0.2 2-Theta, and optionally with further characteristic peaks at 14.5°±0.2 2-Theta and 25.3°±0.2 2-Theta, as measured with Cu Kα radiation. In certain embodiments, the XRPD pattern further comprises characteristic peaks at 16.6°±0.2 2-Theta, 19.0°±0.2 2-Theta, 25.6°±0.2 2-Theta, 26.4°±0.2 2-Theta, and 28.5°±0.2 2-Theta as measured with Cu Kα radiation.

In certain embodiments, the crystalline form is characterized as having an XRPD pattern substantially the same as shown in FIG. 56. In certain embodiments, the crystalline form is characterized as having an XRPD pattern with characteristic peaks at 13.0±0.2 2-Theta, 16.6°±0.2 2-Theta, and 17.9°±0.2 2-Theta, and optionally with further characteristic peaks at 19.0° 2-Theta and 22.7°±0.2 2-Theta, as measured with Cu Kα radiation.

In certain embodiments, the crystalline form is characterized as having an XRPD pattern substantially the same as shown in FIG. 57. In certain embodiments, the crystalline form is characterized as having an XRPD pattern with characteristic peaks at 7.1°±0.2 2-Theta, 13.0°±0.2 2-Theta, 16.5°±0.2 2-Theta, and optionally with further characteristic peaks at 17.9°±0.2 2-Theta and 19.0°±0.2 2-Theta, as measured with Cu Kα radiation.

In yet another aspect, provided herein is a crystalline form of (S)-methylone hydrochloride, wherein the crystalline(S)-methylone hydrochloride is crystalline Form B and is characterized as having at least one of the following properties: an X-ray powder diffraction (XRPD) pattern substantially the same as shown in FIG. 40; an X-ray powder diffraction (XRPD) pattern with characteristic peaks at 12.6°±0.2 2-Theta, 14.0°±0.2 2-Theta, and 16.1°±0.2 2-Theta, and optionally with further characteristic peaks at 15.8°±0.2 2-Theta and 22.2°±0.2 2-Theta, as measured with Cu Kα radiation; or combinations thereof. In certain embodiments, the crystalline form is characterized as having an XRPD pattern substantially the same as shown in FIG. 40. In certain embodiments, the crystalline form is characterized as having an X-ray powder diffraction (XRPD) pattern with characteristic peaks at 12.6°±0.2 2-Theta, 14.0°±0.2 2-Theta, and 16.1°±0.2 2-Theta, and optionally with further characteristic peaks at 15.8°±0.2 2-Theta and 22.2°±0.2 2-Theta, as measured with Cu Kα radiation. In certain embodiments, the XRPD pattern further comprises characteristic peaks at 21.5°±0.2 2-Theta, 24.2°±0.2 2-Theta, 27.5°±0.2 2-Theta, 28.2°±0.2 2-Theta, and 29.2°±0.2 2-Theta as measured with Cu Kα radiation.

In yet another aspect, provided herein is a crystalline form of (S)-methylone hydrochloride, wherein the crystalline(S)-methylone hydrochloride is crystalline Form C and is characterized as having an X-ray powder diffraction (XRPD) pattern with peaks at 6.2°±0.2 2-Theta, 14.4°±0.2 2-Theta, and 20.0°±0.2 2-Theta, and optionally with further peaks at 17.2°±0.2 2-Theta and 21.3°±0.2 2-Theta, as measured with Cu Kα radiation. In certain embodiments, the XRPD pattern further comprises one or more peaks at 19.2°±0.2 2-Theta, 24.7°±0.2 2-Theta, 24.9°±0.2 2-Theta, 28.7°±0.2 2-Theta, 29.0°±0.2 2-Theta, 29.4°±0.2 2-Theta, and 29.8°±0.2 2-Theta, as measured with Cu Kα radiation.

In one aspect, provided herein are compounds having a structure of Formula (II):

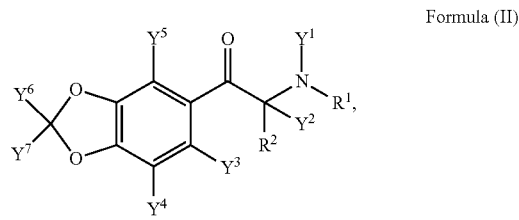

Formula (II)

wherein $R^1$ and $R^2$ are independently selected from $CD_3$, $CD_2H$, $CDH_2$, $CT_3$, $CT_2H$, $CTH_2$ and $CH_3$; and $Y^1$, $Y^2$, $Y^3$, $Y^4$, $Y^5$, $Y^6$ and $Y^7$ are independently selected from protium (H), deuterium (D) and tritium (T); and wherein at least one of $R^1$, $R^2$, $Y^1$, $Y^1$, $Y^2$, $Y^3$, $Y^4$, $Y^5$, $Y^6$ and $Y^7$ is enriched in at least one heavy isotope selected from D and T;

or an enantiomer, a mixture of enantiomers, a mixture of two or more diastereomers; or a pharmaceutically acceptable salt, solvate, or hydrate thereof.

In certain embodiments, at least one of $Y^1$, $Y^2$, $Y^3$, $Y^4$, $Y^5$, $Y^6$, and $Y^7$ is deuterium, or $R^1$ or $R^2$ comprises at least one deuterium.

In certain embodiments, at least one of $Y^1$, $Y^2$, $Y^3$, $Y^4$, $Y^5$, $Y^6$, and $Y^7$ is deuterium.

In certain embodiments, $R^1$ or $R^2$ comprises at least one deuterium.

In certain embodiments, the compound is selected from the group consisting of:

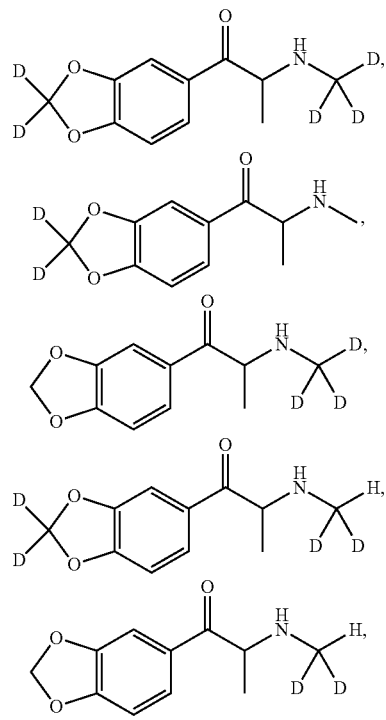

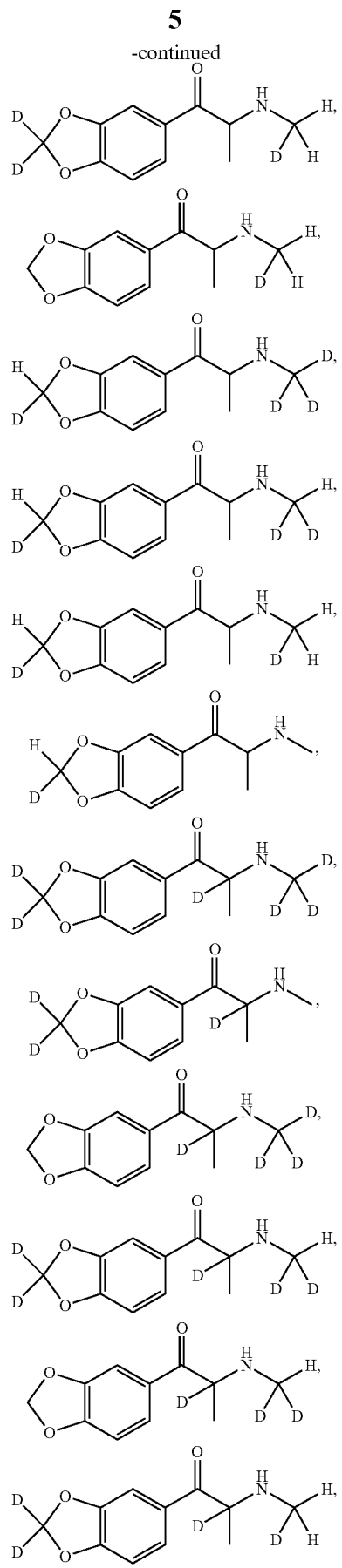
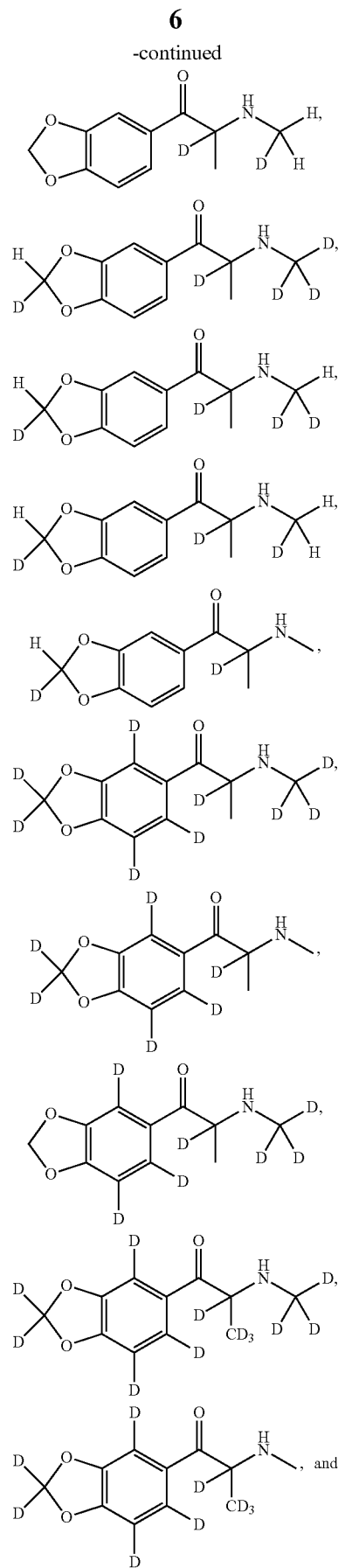

-continued

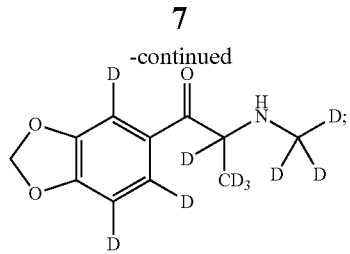

or an enantiomer, a mixture of enantiomers, a mixture of two or more diastereomers; or a pharmaceutically acceptable salt, solvate, or hydrate thereof.

In certain embodiments, the compound is optically active.

In certain embodiments, the compound is the (S) enantiomer.

In certain embodiments, the compound is the (R) enantiomer.

In certain embodiments, the compound has a structure of Formula (II-A):

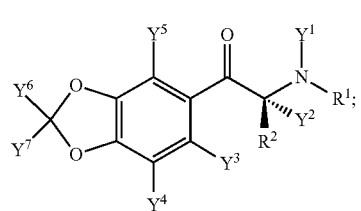

Formula (II-A)

or a pharmaceutically acceptable salt, solvate, or hydrate thereof.

In certain embodiments, the compound is selected from the group consisting of:

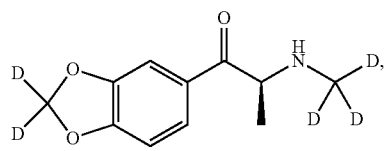

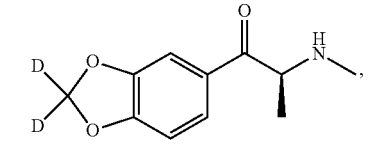

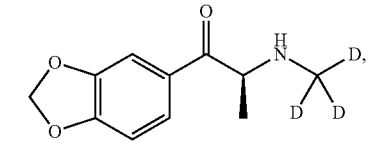

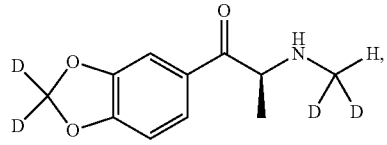

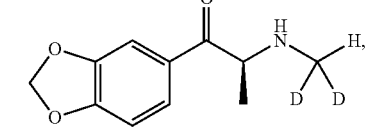

-continued

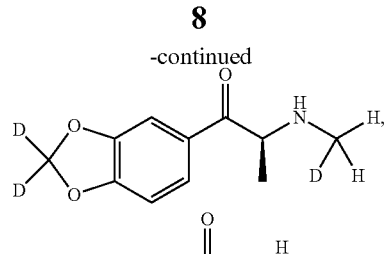

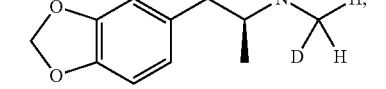

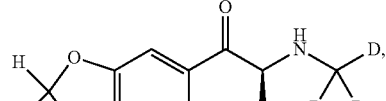

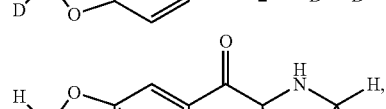

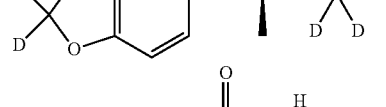

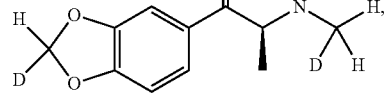

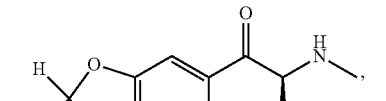

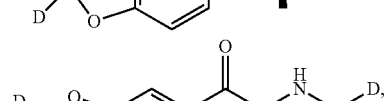

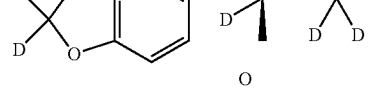

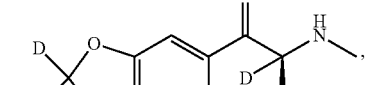

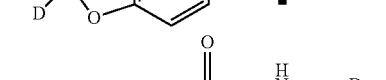

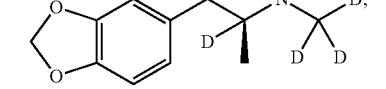

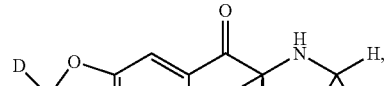

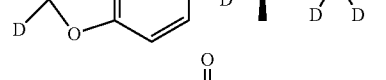

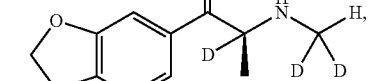

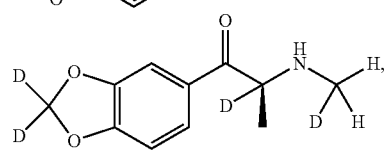

-continued
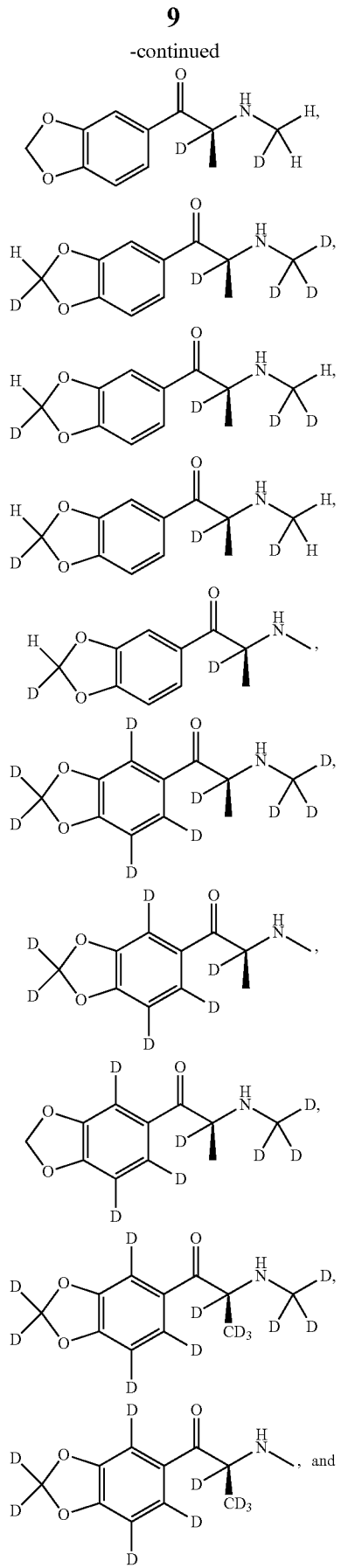
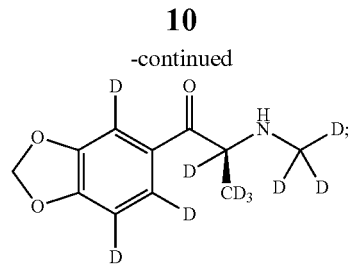
or a pharmaceutically acceptable salt, solvate, or hydrate thereof.
In certain embodiments, the compound has a structure of Formula (II-B):
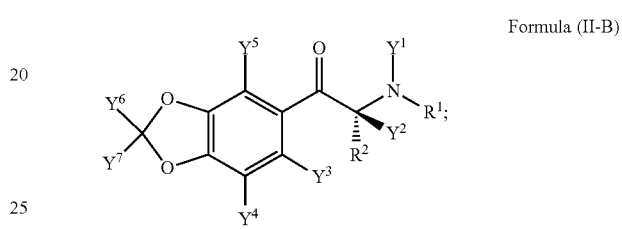
Formula (II-B)
or a pharmaceutically acceptable salt, solvate, or hydrate thereof.
In certain embodiments, the compound is selected from the group consisting of:
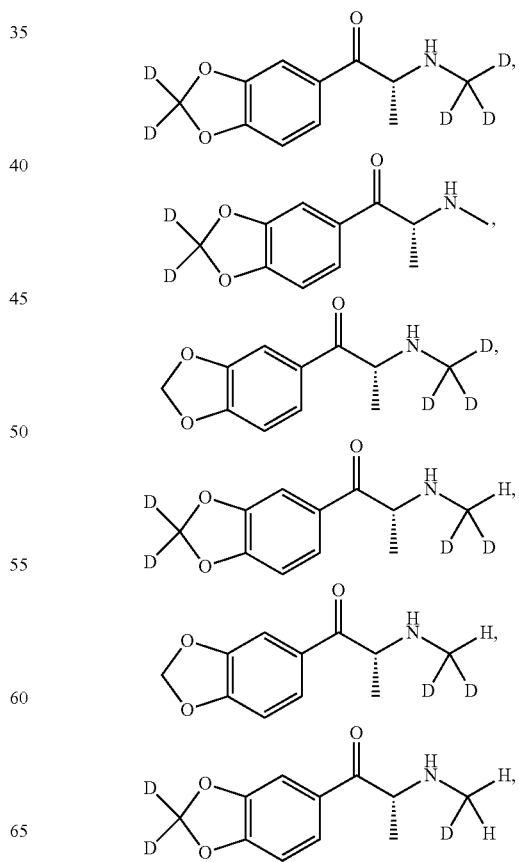

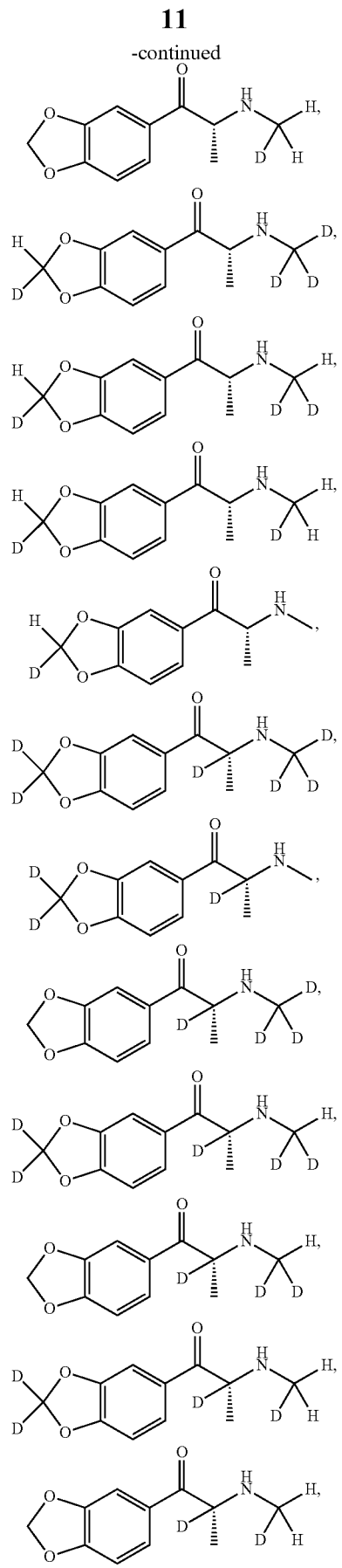
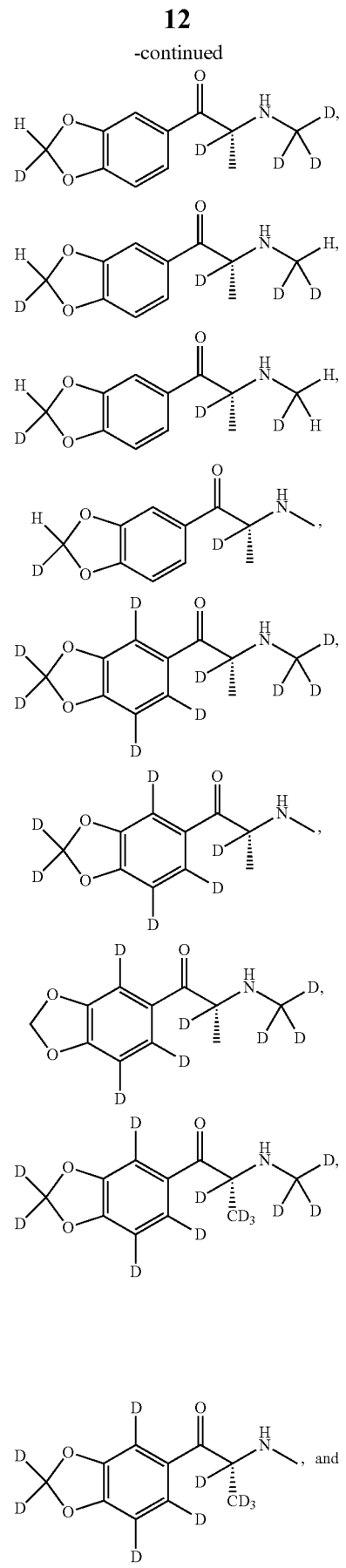

-continued

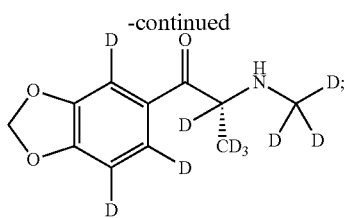

or pharmaceutically acceptable salt, hydrate, or solvate thereof.

In another aspect, provided herein are pharmaceutical compositions comprising a compound of compounds having a structure of Formula (II), or an enantiomer, a mixture of enantiomers, a mixture of two or more diastereomers; or a pharmaceutically acceptable salt, solvate, or hydrate thereof.

In another aspect, provided herein are methods for method for increasing neuronal plasticity in a subject in need thereof, comprising administering to the subject a therapeutically effective amount of a compounds having a structure of Formula (II), or an enantiomer, a mixture of enantiomers, a mixture of two or more diastereomers; or a pharmaceutically acceptable salt, solvate, or hydrate thereof.

In another aspect, provided herein are methods for treating a brain disease or disorder in a subject in need thereof, comprising administering to the subject a therapeutically effective amount of a compounds having a structure of Formula (II), or an enantiomer, a mixture of enantiomers, a mixture of two or more diastereomers; or a pharmaceutically acceptable salt, solvate, or hydrate thereof.

In certain embodiments, the brain disease or disorder is a neurological disease.

In certain embodiments, the brain disease or disorder is depression or related conditions.

In certain embodiments, the brain disease or disorder is psychological disorder, depression, addiction, anxiety, or a post-traumatic stress disorder.

In certain embodiments, the methods provided herein further comprise administering a serotonin receptor 2A antagonist to the subject.

In certain embodiments, the serotonin receptor 2A antagonist is selected from ketanserin, volinanserin (MDL-100907), eplivanserin (SR-46349), pimavanserin (ACP-103), glemanserin (MDL-11939), ritanserin, flibanserin, nelotanserin, blonanserin, mianserin, mirtazapine, roluperidone (CYR-101, MIN-101), quetiapine, olanzapine, altanserin, acepromazine, nefazodone, risperidone, pruvanserin, AC-90179, AC-279, adatanserin, fananserin, HY10275, benanserin, butanserin, manserin, iferanserin, lidanserin, pelanserin, seganserin, tropanserin, lorcaserin, ICI-169369, methiothepin, methysergide, trazodone, cinitapride, cyproheptadine, brexpiprazole, cariprazine, agomelatine, setoperone, 1-(1-Naphthyl) piperazine, LY-367265, pirenperone, metergoline, deramciclane, amperozide, cinanserin, LY-86057, GSK-215083, cyamemazine, mesulergine, BF-1, LY-215840, sergolexole, spiramide, LY-53857, amesergide, LY-108742, pipamperone, LY-314228, 5-I-R91150, 5-MeO-NBpBrT, 9-Aminomethyl-9,10-dihydroanthracene, niaprazine, SB-215505, SB-204741. SB-206553, SB-242084, LY-272015, SB-243213, SB-200646, RS-102221, zotepine, clozapine, chlorpromazine, sertindole, iloperidone, paliperidone, asenapine, amisulpride, aripiprazole, lurasidone, ziprasidone, lumateperone, perospirone, mosapramine, AMDA (9)-Aminomethyl-9,10-dihydroanthracene), methiothepin, an extended-release form of olanzapine (e.g., ZYPREXA RELPREVV), an extended-release form of quetiapine, an extended-release form of risperidone (e.g., Risperdal Consta), an extended-release form of paliperidone (e.g., Invega Sustenna and Invega Trinza), an extended-release form of fluphenazine decanoate including Prolixin Decanoate, an extended-release form of aripiprazole lauroxil including Aristada, and an extended-release form of aripiprazole including Abilify Maintena.

In another aspect, provided herein are methods for treating a brain disease or disorder in a subject in need thereof, comprising administering to the subject a therapeutically effective amount of (R)-methylone or a deuterated analogue, pharmaceutically acceptable salt, solvate, hydrate or a combination thereof, wherein the (R)-methylone or a deuterated analogue, pharmaceutically acceptable salt, solvate, or hydrate thereof has improved pharmacokinetic properties than the corresponding racemic counterpart.

In certain embodiments, the (R)-methylone or a deuterated analogue, pharmaceutically acceptable salt, solvate, or hydrate or a combination thereof has a longer Half-life (t1/2) and/or slower Intrinsic clearance (CLint) than the corresponding racemic counterpart.

In certain embodiments, the (R)-methylone or a deuterated analogue, pharmaceutically acceptable salt, solvate, or hydrate or a combination thereof has a longer Half-life (t1/2) than the corresponding racemic counterpart for at least 20 min, 30 min, 40 min, 50 min, or 1 hr.

In certain embodiments, the (R)-methylone or a deuterated analogue, pharmaceutically acceptable salt, solvate, or hydrate or a combination thereof has at least 10%, 20%, 30%, 40%, or 50% slower Intrinsic clearance (CLint) than the corresponding racemic counterpart.

In certain embodiments, (R)-methylone hydrochloride is administered.

In certain embodiments, a salt of a compound of Formula (II-B) is administered:

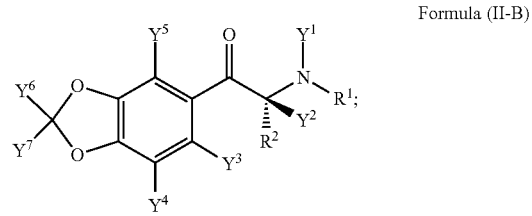

Formula (II-B)

wherein at least one of $Y^1$, $Y^2$, $Y^3$, $Y^4$, $Y^5$, $Y^6$, and $Y^7$ is deuterium, or $R^1$ or $R^2$ comprises at least one deuterium.

In certain embodiments, the salt is a hydrochloride salt.

In certain embodiments, the compound of Formula (II-B) is (R)-Methylone-d2 hydrochloride, (R)-Methylone-d3 hydrochloride, or (R)-Methylone-d5 hydrochloride.

In certain embodiments, the compound of Formula (II-B) is (R)-Methylone-d2 hydrochloride.

In certain embodiments, the compound of Formula (II-B) is (R)-Methylone-d3 hydrochloride.

In certain embodiments, the compound of Formula (II-B) is (R)-Methylone-d5 hydrochloride.

In yet another aspect, provided herein is a crystalline form of methylone hydrochloride, wherein the crystalline methylone hydrochloride is Form A having at least one of the following properties:
(a) an X-ray powder diffraction (XRPD) pattern substantially the same as shown in FIG. 21;

(b) an X-ray powder diffraction (XRPD) pattern with characteristic peaks at 7.6°±0.2 2-Theta, 10.5°±0.2 2-Theta, and 15.3°±0.2 2-Theta as measured with Cu Kα radiation;
(c) a DSC thermogram substantially similar to the one set forth in FIG. 22;
(d) a DSC thermogram with an endotherm at about 251° C.;
(e) a thermo-gravimetric analysis (TGA) substantially similar to the one set forth in FIG. 22; or
(f) combinations thereof.

In certain embodiments, the crystalline form has an X-ray powder diffraction (XRPD) pattern substantially the same as shown in FIG. 21. In certain embodiments, the crystalline form has an X-ray powder diffraction (XRPD) pattern comprising characteristic peaks at 7.6°±0.2 2-Theta, 10.5°±0.2 2-Theta, and 15.3°±0.2 2-Theta as measured with Cu Kα radiation.

In certain embodiments, the crystalline form has a DSC thermogram substantially similar to the one set forth in FIG. 22. In certain embodiments, the crystalline form has a DSC thermogram with an endotherm at about 251° C. In certain embodiments, the crystalline form has a thermogravimetric analysis (TGA) thermogram substantially similar to the one set forth in FIG. 22.

In certain embodiments, the crystalline form is characterized as having properties (a), (b), (c), (d), and (e).

In certain embodiments, the crystalline form is unsolvated. In certain embodiments, the crystalline form is anhydrous.

In yet another aspect, provided herein is a crystalline form of methylone hydrochloride, wherein the crystalline methylone hydrochloride is Form A having at least one of the following properties:
(a) an X-ray powder diffraction (XRPD) pattern substantially the same as shown in FIG. 14;
(b) an X-ray powder diffraction (XRPD) pattern with characteristic peaks at 7.7°±0.2 2-Theta, 10.5°±0.2 2-Theta, and 15.3°±0.2 2-Theta as measured with Cu Kα radiation;
(c) a DSC thermogram substantially similar to the one set forth in FIG. 22;
(d) a DSC thermogram with an endotherm at about 251° C.;
(e) a thermo-gravimetric analysis (TGA) substantially similar to the one set forth in FIG. 22; or
(f) combinations thereof.

In certain embodiments, the crystalline form has an X-ray powder diffraction (XRPD) pattern substantially the same as shown in FIG. 14. In certain embodiments, the crystalline form has an X-ray powder diffraction (XRPD) pattern comprising characteristic peaks at 7.7°±0.2 2-Theta, 10.5°±0.2 2-Theta, and 15.3°±0.2 2-Theta as measured with Cu Kα radiation.

In certain embodiments, the crystalline form has a DSC thermogram substantially similar to the one set forth in FIG. 22. In certain embodiments, the crystalline form has a DSC thermogram with an endotherm at about 251° C. In certain embodiments, the crystalline form has a thermogravimetric analysis (TGA) thermogram substantially similar to the one set forth in FIG. 22.

In certain embodiments, the crystalline form is characterized as having properties (a), (b), (c), (d), and (e).

In certain embodiments, the crystalline form is unsolvated. In certain embodiments, the crystalline form is anhydrous.

In yet another aspect, provided herein is a crystalline form of methylone hydrochloride, wherein the crystalline methylone hydrochloride is Form B having at least one of the following properties:
(a) an X-ray powder diffraction (XRPD) pattern substantially the same as shown in FIG. 17;
(b) an X-ray powder diffraction (XRPD) pattern with characteristic peaks at 7.5°±0.2 2-Theta, 9.5°±0.2 2-Theta, and 15.3°±0.2 2-Theta as measured with Cu Kα radiation;
(c) a DSC thermogram substantially similar to the one set forth in FIG. 23;
(d) a DSC thermogram with an endotherm at about 249° C.;
(e) a thermo-gravimetric analysis (TGA) substantially similar to the one set forth in FIG. 23; or
(f) combinations thereof.

In certain embodiments, the crystalline form has an X-ray powder diffraction (XRPD) pattern substantially the same as shown in FIG. 17. In certain embodiments, the crystalline form has an X-ray powder diffraction (XRPD) pattern comprising characteristic peaks at 7.5°±0.2 2-Theta, 9.5°±0.2 2-Theta, and 15.3°±0.2 2-Theta as measured with Cu Kα radiation.

In certain embodiments, the crystalline form has a thermogravimetric analysis (TGA) thermogram substantially similar to the one set forth in FIG. 23. In certain embodiments, the crystalline form has a DSC thermogram substantially similar to the one set forth in FIG. 23. In certain embodiments, the crystalline form has a DSC thermogram with a first endotherm at about 142° C. and a second endotherm at about 152° C.

In certain embodiments, the crystalline form is unsolvated. In certain embodiments, the crystalline form is anhydrous.

In certain embodiments, the crystalline form is characterized as having properties (a), (b), (c), (d), and (e).

In yet another aspect, provided herein is a crystalline form of methylone hydrochloride, wherein the crystalline methylone hydrochloride is Form C having at least one of the following properties:
(a) an X-ray powder diffraction (XRPD) pattern substantially the same as shown in FIG. 2;
(b) an X-ray powder diffraction (XRPD) pattern with characteristic peaks at 7.2°±0.2 2-Theta, 13.0°±0.2 2-Theta, and 14.4°±0.2 2-Theta as measured with Cu Kα radiation;
(c) a thermo-gravimetric analysis (TGA) substantially similar to the one set forth in FIG. 24;
(d) a DSC thermogram substantially similar to the one set forth in FIG. 24;
(e) a DSC thermogram with a first endotherm at about 53° C. and a second endotherm at about 241° C.; or
(f) combinations thereof.

In certain embodiments, the crystalline form has an X-ray powder diffraction (XRPD) pattern substantially the same as shown in FIG. 2. In certain embodiments, the crystalline form has an X-ray powder diffraction (XRPD) pattern comprising characteristic peaks at 7.2°±0.2 2-Theta, 13.0°±0.2 2-Theta, and 14.4°±0.2 2-Theta as measured with Cu Kα radiation.

In certain embodiments, the crystalline form has a DSC thermogram substantially similar to the one set forth in FIG. 24. In certain embodiments, in the crystalline form has a DSC thermogram with a first endotherm at about 53° C. and a second endotherm at about 241° C. In certain embodiments, the crystalline form has a thermogravimetric analysis (TGA) thermogram substantially similar to the one set forth in FIG. 24.

In certain embodiments, the crystalline form unsolvated. In certain embodiments, the crystalline form is anhydrous.

In certain embodiments, the crystalline form is characterized as having properties (a), (b), (c), (d), and (e).

In yet another aspect, provided herein is crystalline form of methylone hydrochloride, wherein the crystalline methylone hydrochloride is Form D having at least one of the following properties:
(a) an X-ray powder diffraction (XRPD) pattern substantially the same as shown in FIG. 13;
(b) an X-ray powder diffraction (XRPD) pattern with characteristic peaks at 12.5°±0.2 2-Theta, 14.0°±0.2 2-Theta, and 15.7°±0.2 2-Theta as measured with Cu Kα radiation;
(c) a DSC thermogram substantially similar to the one set forth in FIG. 25;
(d) a DSC thermogram with a first endotherm at about 238° C., a second endotherm at about 241° C.;
(e) a thermo-gravimetric analysis (TGA) substantially similar to the one set forth in FIG. 25; or
(f) combinations thereof.

In certain embodiments, the crystalline form has an X-ray powder diffraction (XRPD) pattern substantially the same as shown in FIG. 13. In certain embodiments, the crystalline form has an X-ray powder diffraction (XRPD) pattern comprising characteristic peaks at 12.5°±0.2 2-Theta, 14.0°±0.2 2-Theta, and 15.7°±0.2 2-Theta as measured with Cu Kα radiation.

In certain embodiments, the crystalline form has a DSC thermogram substantially similar to the one set forth in FIG. 25. In certain embodiments, the crystalline form has a DSC thermogram with a first endotherm at about 238° C., and a second endotherm at about 241° C. In certain embodiments, the crystalline form has a thermogravimetric analysis (TGA) thermogram substantially similar to the one set forth in FIG. 25.

In certain embodiments, the crystalline form is unsolvated. In certain embodiments, the crystalline form is anhydrous.

In certain embodiments, the crystalline form is characterized as having properties (a), (b), (c), (d), and (e).

In yet another aspect, provided herein are pharmaceutical compositions comprising a crystalline form described herein, and a pharmaceutically acceptable excipient.

In yet another aspect, provided herein are methods for treating a brain disease or disorder in a subject in need thereof, comprising administering to the subject a therapeutically effective amount of a crystalline form described herein.

In certain embodiments, the brain disease or disorder is a neurological disease.

In certain embodiments, the brain disease or disorder is depression or related conditions.

In certain embodiments, the brain disease or disorder is psychological disorder, depression, addiction, anxiety, or a post-traumatic stress disorder.

In certain embodiments, the methods provided herein further comprise administering a serotonin receptor 2A antagonist to the subject. In certain embodiments, the serotonin receptor 2A antagonist is selected from ketanserin, volinanserin (MDL-100907), eplivanserin (SR-46349), pimavanserin (ACP-103), glemanserin (MDL-11939), ritanserin, flibanserin, nelotanserin, blonanserin, mianserin, mirtazapine, roluperidone (CYR-101, MIN-101), quetiapine, olanzapine, altanserin, acepromazine, nefazodone, risperidone, pruvanserin, AC-90179, AC-279, adatanserin, fananserin, HY10275, benanserin, butanserin, manserin, iferanserin, lidanserin, pelanserin, seganserin, tropanserin, lorcaserin, ICI-169369, methiothepin, methysergide, trazodone, cinitapride, cyproheptadine, brexpiprazole, cariprazine, agomelatine, setoperone, 1-(1-Naphthyl) piperazine, LY-367265, pirenperone, metergoline, deramciclane, amperozide, cinanserin, LY-86057, GSK-215083, cyamemazine, mesulergine, BF-1, LY-215840, sergolexole, spiramide, LY-53857, amesergide, LY-108742, pipamperone, LY-314228, 5-I-R91150, 5-MeO-NBpBrT, 9-Aminomethyl-9,10-dihydroanthracene, niaprazine, SB-215505, SB-204741. SB-206553, SB-242084, LY-272015, SB-243213, SB-200646, RS-102221, zotepine, clozapine, chlorpromazine, sertindole, iloperidone, paliperidone, asenapine, amisulpride, aripiprazole, lurasidone, ziprasidone, lumateperone, perospirone, mosapramine, AMDA (9-Aminomethyl-9,10-dihydroanthracene), methiothepin, an extended-release form of olanzapine (e.g., ZYPREXA RELPREVV), an extended-release form of quetiapine, an extended-release form of risperidone (e.g., Risperdal Consta), an extended-release form of paliperidone (e.g., Invega Sustenna and Invega Trinza), an extended-release form of fluphenazine decanoate including Prolixin Decanoate, an extended-release form of aripiprazole lauroxil including Aristada, and an extended-release form of aripiprazole including Abilify Maintena.

In yet another aspect, provided herein is a solid form of a methylone salt wherein the solid form is racemic.

In yet another aspect, provided herein is a solid form of (S)-methylone.

In yet another aspect, provided herein is a solid form of (R)-methylone.

In certain embodiments, the methylone salt is formed from an acid selected from hydrochloric acid, galactaric (mucic) acid, naphthalene-1,5-disulfonic acid, citric acid, sulfuric acid, d-glucuronic acid, ethane-1,2-disulfonic acid, lactobionic acid, p-toluenesulfonic acid, D)-glucoheptonic acid, thiocyanic acid, (−)-L-pyroglutamic acid, methanesulfonic acid, L-malic acid, dodecylsulfuric acid, hippuric acid, naphthalene-2-sulfonic acid, D-gluconic acid, benzenesulfonic acid, D,L-lactic acid, oxalic acid, oleic acid, glycerophosphoric acid, succinic acid, ethanesulfonic acid 2-hydroxy, glutaric acid, L-aspartic acid, cinnamic acid, maleic acid, adipic acid, phosphoric acid, sebacic acid, ethanesulfonic acid, (+)-camphoric acid, glutamic acid, acetic acid, fumaric acid, xinafoic acid, or a combination thereof.

In certain embodiments, a stoichiometric ratio of acid to methylone is from about 0.4 molar equivalent to about 2.2 molar equivalents of the acid.

In certain embodiments, a stoichiometric ratio of acid to methylone is from about 0.5 molar equivalent to about 2 molar equivalents of the acid.

In certain embodiments, a stoichiometric ratio of acid to methylone is selected from about 0.5, 1, or 2 molar equivalents of the acid.

In certain embodiments, the solid form is a free base.

In certain embodiments, the solid form is a hydrate.

In certain embodiments, the solid form is a crystalline solid.

In certain embodiments, the crystalline solid is a substantially single polymorph.

In certain embodiments, the polymorph is selected to have one or more desired properties.

In certain embodiments, the one or more desired properties are selected from physical properties, chemical properties, pharmacokinetic properties, or a combination thereof.

In certain embodiments, the one or more desired properties comprise melting point, glass transition temperature, flowability, thermal stability, shelf life, stability against polymorphic transition, hygroscopic properties, solubility in water and/or organic solvents, reactivity, compatibility with excipients and/or delivery vehicles, bioavailability, absorption, distribution, metabolism, excretion, toxicity including cytotoxicity, dissolution rate, half-life, or a combination thereof.

In another aspect, described herein is a cocrystal of methylone and a coformer.

In certain embodiments, the coformer is an organic acid.

In certain embodiments, the coformer is an organic acid selected from the group consisting of mucic acid, naphthalene-1,5-disulfonic acid, citric acid, d-glucuronic acid, lactobionic acid, p-toluenesulfonic acid, D-glucoheptonic acid, (−)-L-pyroglutamic acid, D,L-malic acid, hippuric acid, naphthalene-2-sulfonic acid, D-gluconic acid, benzenesulfonic acid, D,L-lactic acid, oxalic acid, oleic acid, L-aspartic acid, D-gluconic acid, D,L-lactic acid, oxalic acid, oleic acid, glycerophosphoric acid, succinic acid, glutaric acid, L-aspartic acid, cinnamic acid, maleic acid, adipic acid, sebacic acid, camphoric acid, glutamic acid, fumaric acid, gentisic acid, tartaric acid, dibenzoyl-tartaric acid, malonic acid, picolinic acid, nicotinic acid, hippuric acid, salicylic acid, cinnamic acid, mandelic acid, ascorbic acid, ferulic acid, 1-hydroxy-2-naphthoic acid, 6-hydroxy-2-naphthoic acid, benzoic acid, 4-hydroxy benzoic acid, 3,4-dihydroxy benzoic acid, trimesic acid, syringic acid, and phenylalanine, oxalic acid, malonic acid, succinic acid, glutaric acid, adipic acid, pimelic acid, suberic acid, azelaic acid, sebacic acid, brassylic acid, thapsic acid, maleic acid, fumaric acid, glutaconic acid, traumatic acid, muconic acid, glutinic acid, citraconic acid, mesaconic acid, itaconic acid, tartronic acid, mesoxalic acid, malic acid, tartaric acid, oxaloacetic acid, aspartic acid, dioxosuccinic acid, α-hydroxyglutaric acid, arabinaric acid, α-ketoglutaric acid, glutamic acid, diaminopimelic acid, and saccharic acid.

In certain embodiments, the coformer is an organic acid selected from the group consisting of maleic acid, camphoric acid, glutamic acid, fumaric acid, gentisic acid, tartaric acid, dibenzoyl-tartaric acid, and mandelic acid.

In certain embodiments, the coformer is an organic acid selected from the group consisting of L-malic acid, D-malic acid, (+)-dibenzoyl-D-tartaric acid, (−)-dibenzoyl-L-tartaric acid, (R)-(−)-mandelic acid, (S)-(+)-mandelic acid, L-(+)-tartaric acid, D-(−)-tartaric acid, R-(−)-camphor-10-sulfonic acid, and S-(+)-camphor-10-sulfonic acid.

In certain embodiments, the coformer is fumaric acid and the cocrystal is characterized as having: an X-ray powder diffraction (XRPD) pattern substantially the same as shown in FIG. 28; an X-ray powder diffraction (XRPD) pattern substantially the same as shown in FIG. 31; or an X-ray powder diffraction (XRPD) pattern substantially the same as shown in, FIG. 32.

In certain embodiments, the coformer is gentisic acid and the cocrystal is characterized as having: an X-ray powder diffraction (XRPD) pattern substantially the same as shown in FIG. 29; or an X-ray powder diffraction (XRPD) pattern substantially the same as shown in, FIG. 34.

In certain embodiments, the coformer is maleic acid and the cocrystal is characterized as having: an X-ray powder diffraction (XRPD) pattern substantially the same as shown in FIG. 30; or an X-ray powder diffraction (XRPD) pattern with characteristic peaks at 15.4°±0.2 2-Theta, 17.0°±0.2 2-Theta, and 19.7°±0.2 2-Theta, and optionally with further characteristic peaks at 12.0°±0.2 2-Theta and 24.1°±0.2 2-Theta, as measured with Cu Kα radiation.

In certain embodiments, the coformer is citric acid and the cocrystal is characterized as having an X-ray powder diffraction (XRPD) pattern substantially the same as shown in FIG. 33.

In certain embodiments, the coformer is citric acid and the cocrystal is characterized as having an X-ray powder diffraction (XRPD) pattern substantially the same as shown in FIG. 35.

In another aspect, described herein is a cocrystal of (R)-methylone and a coformer. In certain embodiments, the coformer is an organic acid selected from the group consisting of gentisic acid, (S)-(+)-mandelic acid, (S)-(+)-mandelic acid, and S-(+)-camphor-10-sulfonic acid.

In another aspect, described herein is a cocrystal of (S)-methylone and a coformer. In certain embodiments, the coformer is an organic acid selected from the group consisting of maleic acid, gentisic acid, (R)-(−)-mandelic acid, and R-(−)-camphor-10-sulfonic acid. In certain embodiments, the coformer is gentisic acid and the cocrystal is characterized as having: an X-ray powder diffraction (XRPD) pattern substantially the same as shown in FIG. 43; an X-ray powder diffraction (XRPD) pattern substantially the same as shown in FIG. 44; an X-ray powder diffraction (XRPD) pattern with characteristic peaks at 7.5°±0.2 2-Theta, 8.7°±0.2 2-Theta, and 10.8°±0.2 2-Theta, and optionally with further characteristic peaks at 14.7°±0.2 2-Theta and 16.1°±0.2 2-Theta, as measured with Cu Kα radiation; or an X-ray powder diffraction (XRPD) pattern with characteristic peaks at 7.5°±0.2 2-Theta, 8.6°±0.2 2-Theta, and 10.8°±0.2 2-Theta, and optionally with further characteristic peaks at 14.7°±0.2 2-Theta and 16.0°±0.2 2-Theta, as measured with Cu Kα radiation.

Also disclosed herein is a solid form of 3,4-methylenedioxy-N-ethylcathinone hydrochloride that is made by the method described in Example 3-25. The solid form of 3,4-methylenedioxy-N-ethylcathinone hydrochloride made by the disclosed method may have at least one improved property compared to a known form of 3,4-methylenedioxy-N-ethylcathinone. In one embodiment, the 3,4-methylenedioxy-N-ethylcathinone chloride solid form disclosed herein is a crystalline form that has an improved property relative to amorphous 3,4-methylenedioxy-N-ethylcathinone hydrochloride. In one embodiment a crystalline form disclosed herein is a polymorph of 3,4-methylenedioxy-N-ethylcathinone hydrochloride. In certain embodiments, a disclosed polymorph of 3,4-methylenedioxy-N-ethylcathinone hydrochloride has an improved property over one or more other solid forms of 3,4-methylenedioxy-N-ethylcathinone.

In any embodiments, the at least one improved property of the solid form of 3,4-methylenedioxy-N-ethylcathinone hydrochloride disclosed herein may comprise a physical property, chemical property, pharmacokinetic property, or a combination thereof. In some embodiments, the at least one improved property comprises a melting point, glass transition temperature, flowability, thermal stability, shelf life, stability against polymorphic transition, hygroscopic properties, solubility in water and/or organic solvents, reactivity, compatibility with excipients and/or delivery vehicles, bioavailability, absorption, distribution, metabolism, excretion, toxicity including cytotoxicity, dissolution rate, half-life, or a combination thereof, that is improved compared to an amorphous sample of 3,4-methylenedioxy-N-ethylcathinone.

In any embodiments, the solid form of 3,4-methylenedioxy-N-ethylcathinone may be a solvate, such as a hydrate.

In some embodiments, the crystalline form of ethylone hydrochloride is characterized as having: an X-ray powder diffraction (XRPD) pattern substantially the same as shown in FIG. 58; an X-ray powder diffraction (XRPD) pattern substantially the same as shown in FIG. 59; or an X-ray powder diffraction (XRPD) pattern substantially the same as shown in FIG. 60. In some embodiments, the crystalline form of ethylone hydrochloride is characterized as having an X-ray powder diffraction (XRPD) pattern substantially the same as shown in FIG. 58. In some embodiments, the crystalline form of ethylone hydrochloride is characterized as having an X-ray powder diffraction (XRPD) pattern substantially the same as shown in FIG. 59. In some embodiments, the crystalline form of ethylone hydrochloride is characterized as having an X-ray powder diffraction (XRPD) pattern substantially the same as shown in FIG. 60. In some embodiments, the crystalline form of ethylone hydrochloride is characterized as having an X-ray powder diffraction (XRPD) pattern with representative peaks at $13.0°±0.2$ 2-Theta, $17.9°±0.2$ 2-Theta, and $25.3°±0.2$ 2-Theta as measured with Cu Kα radiation. In some embodiments, the crystalline form of ethylone hydrochloride is characterized as having an X-ray powder diffraction (XRPD) pattern with representative peaks at $13.0°±0.2$ 2-Theta, $17.9°±0.2$ 2-Theta, and $25.3°±0.2$ 2-Theta, and optionally with further representative peaks at $18.9°±0.2$ 2-Theta and $28.4°±0.2$ 2-Theta, as measured with Cu Kα radiation. In some embodiments, the crystalline form of ethylone hydrochloride is characterized as having an X-ray powder diffraction (XRPD) pattern with representative peaks at $13.0°±0.2$ 2-Theta, $17.9°±0.2$ 2-Theta, and $25.3°±0.2$ 2-Theta, and optionally with further representative peaks at $18.9°±0.2$ 2-Theta and $28.4°±0.2$ 2-Theta, and optionally with further one or more peaks at $16.2°±0.2$ 2-Theta, $22.5°±0.2$ 2-Theta, or $27.5°±0.2$ 2-Theta, as measured with Cu Kα radiation.

Also disclosed herein are embodiments, of a pharmaceutical composition, comprising a solid form of and/or a previously known crystalline form of 3,4-methylenedioxy-N-ethylcathinone hydrochloride, and a pharmaceutically acceptable excipient.

In yet another aspect, provided herein pharmaceutical compositions, comprising a solid form described herein, and a pharmaceutically acceptable excipient.

In yet another aspect, provided herein are methods for increasing neuronal plasticity or for treating a brain disease or disorder in a human subject, comprising administering to the human subject in need thereof a therapeutically effective amount of (R)-methylone, (S)-methylone, (rac.)-methylone, or ethylone, or a deuterated analogue, pharmaceutically acceptable salt, cocrystal, solvate, hydrate, crystalline form, or a combination thereof.

In yet another aspect, provided herein are methods of treating a brain disease or disorder in a subject in need thereof, comprising administering to the subject a therapeutically effective amount of a solid form described herein.

In certain embodiments, the method comprises administering to the human subject in need thereof a therapeutically effective amount of (R)-methylone, or a deuterated analogue, pharmaceutically acceptable salt, cocrystal, solvate, hydrate, crystalline form, or a combination thereof. In certain embodiments, the deuterated analogue of (R)-methylone, or a pharmaceutically acceptable salt, cocrystal, solvate, hydrate, crystalline form, or a combination thereof, is a compound of Formula (II-B) as described herein. In certain embodiments, the deuterated analogue of (R)-methylone is (R)-methylone-d2, (R)-methylone-d3, or (R)-methylone-d5, or a pharmaceutically acceptable salt, cocrystal, solvate, hydrate, crystalline form, or a combination thereof.

In certain embodiments, the method comprises administering to the human subject in need thereof a therapeutically effective amount of crystalline (R)-methylone hydrochloride, or solvate, or hydrate thereof. In certain embodiments, the crystalline (R)-methylone hydrochloride, or solvate, or hydrate thereof, is as described herein. In certain embodiments, the method comprises administering to the human subject in need thereof a therapeutically effective amount of a cocrystal of (R)-methylone, wherein the cocrystal of (R)-methylone is as described herein.

In certain embodiments, the method comprises administering to the human subject in need thereof a therapeutically effective amount of (S)-methylone, or a deuterated analogue, pharmaceutically acceptable salt, cocrystal, solvate, hydrate, crystalline form, or a combination thereof. In certain embodiments, the deuterated analogue of (S)-methylone, or a pharmaceutically acceptable salt, cocrystal, solvate, hydrate, crystalline form, or a combination thereof, is a compound of Formula (II-A) as described herein. In certain embodiments, the deuterated analogue of (S)-methylone is (S)-methylone-d2, (S)-methylone-d3, or (S)-methylone-d5, or a pharmaceutically acceptable salt, cocrystal, solvate, hydrate, crystalline form, or a combination thereof.

In certain embodiments, the method comprises administering to the human subject in need thereof a therapeutically effective amount of crystalline (S)-methylone hydrochloride, or solvate, or hydrate thereof. In certain embodiments, the crystalline (S)-methylone hydrochloride, or solvate, or hydrate thereof, is as described herein. In certain embodiments, the method comprises administering to the human subject in need thereof a therapeutically effective amount of a cocrystal of (S)-methylone, wherein the cocrystal of (S)-methylone is as described herein.

In certain embodiments, the method comprises administering to the human subject in need thereof a therapeutically effective amount of (rac.)-methylone, or a deuterated analogue, pharmaceutically acceptable salt, cocrystal, solvate, hydrate, crystalline form, or a combination thereof. In certain embodiments, the deuterated analogue of (rac.)-methylone, or a pharmaceutically acceptable salt, cocrystal, solvate, hydrate, crystalline form, or a combination thereof, is a compound of Formula (II) as described herein. In certain embodiments, the deuterated analogue of (rac.)-methylone is (rac.)-methylone-d2, (rac.)-methylone-d3, or (rac.)-methylone-d5, or a pharmaceutically acceptable salt, cocrystal, solvate, hydrate, crystalline form, or a combination thereof.

In certain embodiments, the method comprises administering to the human subject in need thereof a therapeutically effective amount of crystalline (rac.)-methylone hydrochloride, or solvate, or hydrate thereof. In certain embodiments, the crystalline (rac.)-methylone hydrochloride, or solvate, or hydrate thereof, is as described herein. In certain embodiments, the method comprises administering to the human subject in need thereof a therapeutically effective amount of a cocrystal of (rac.)-methylone, wherein the cocrystal of (rac.)-methylone is as described herein.

In certain embodiments, the method comprises administering to the human subject in need thereof a therapeutically effective amount of crystalline ethylone, or a deuterated analogue, pharmaceutically acceptable salt, cocrystal, solvate, hydrate, form, or a combination thereof. In certain embodiments, the method comprises administering to the human subject in need thereof a therapeutically effective amount of crystalline ethylone hydrochloride as described herein.

In certain embodiments, the brain disease or disorder is a neurological disease.

In certain embodiments, the brain disease or disorder is depression or related conditions.

In certain embodiments, the brain disease or disorder is psychological disorder, depression, addiction, anxiety, or a post-traumatic stress disorder.

In certain embodiments, the methods provided herein further comprise administering a serotonin receptor 2A antagonist to the subject.

In certain embodiments, the serotonin receptor 2A antagonist is selected from ketanserin, volinanserin (MDL-100907), eplivanserin (SR-46349), pimavanserin (ACP-103), glemanserin (MDL-11939), ritanserin, flibanserin, nelotanserin, blonanserin, mianserin, mirtazapine, roluperidone (CYR-101, MIN-101), quetiapine, olanzapine, altanserin, acepromazine, nefazodone, risperidone, pruvanserin, AC-90179, AC-279, adatanserin, fananserin, HY10275, benanserin, butanserin, manserin, iferanserin, lidanserin, pelanserin, seganserin, tropanserin, lorcaserin, ICI-169369, methiothepin, methysergide, trazodone, cinitapride, cyproheptadine, brexpiprazole, cariprazine, agomelatine, setoperone, 1-(1-Naphthyl)piperazine, LY-367265, pirenperone, metergoline, deramciclane, amperozide, cinanserin, LY-86057, GSK-215083, cyamemazine, mesulergine, BF-1, LY-215840, sergolexole, spiramide, LY-53857, amesergide, LY-108742, pipamperone, LY-314228, 5-I-R91150, 5-MeO-NBpBrT, 9-Aminomethyl-9,10-dihydroanthracene, niaprazine, SB-215505, SB-204741, SB-206553, SB-242084, LY-272015, SB-243213, SB-200646, RS-102221, zotepine, clozapine, chlorpromazine, sertindole, iloperidone, paliperidone, asenapine, amisulpride, aripiprazole, lurasidone, ziprasidone, lumateperone, perospirone, mosapramine, AMDA (9-Aminomethyl-9,10-dihydroanthracene), methiothepin, an extended-release form of olanzapine (e.g., ZYPREXA RELPREVV), an extended-release form of quetiapine, an extended-release form of risperidone (e.g., Risperdal Consta), an extended-release form of paliperidone (e.g., Invega Sustenna and Invega Trinza), an extended-release form of fluphenazine decanoate including Prolixin Decanoate, an extended-release form of aripiprazole lauroxil including Aristada, and an extended-release form of aripiprazole including Abilify Maintena.

DETAILED DESCRIPTION

1. Definitions

Figure 1:
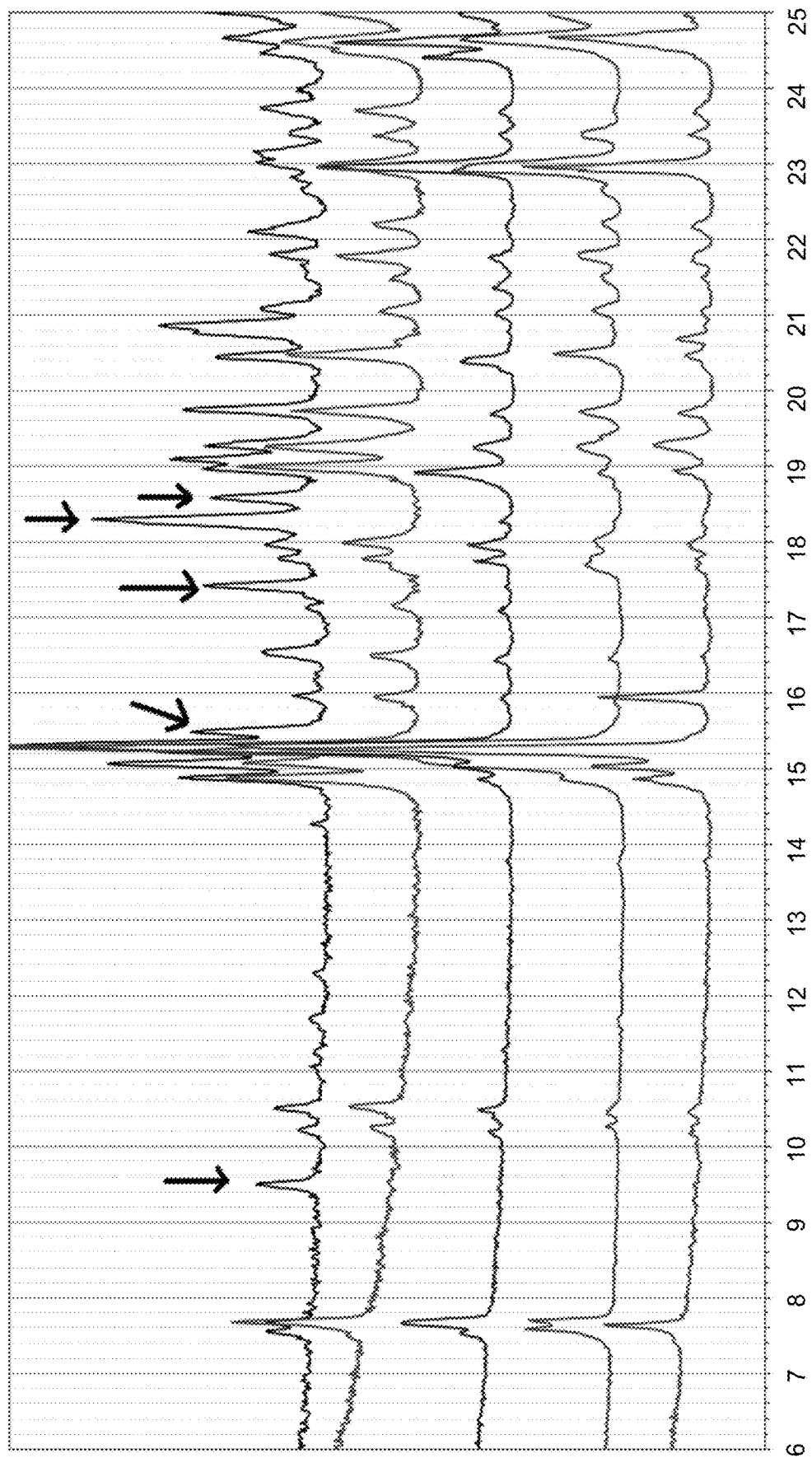
FIG. 1 is an overlay of X-ray powder diffraction (XRPD) diffractograms with arrows highlighting the peaks attributable to methylone hydrochloride Form B. The XRPD diffractograms are (from top to bottom): mixture of methylone hydrochloride Forms A+B (XRPD at the top); Form A; Form A; Form A (XRPD at the bottom). The XRPD of the mixture of Forms A+B was obtained from a sample of (rac.)-Methylone HCl salt purchased from Cayman Chemical Group, Item No. 10986, sample prepared February 2018.

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. The term "about" when referring to a number or a numerical range means that the number or numerical range referred to is an approximation within experimental variability (or within statistical experimental error), and thus the number or numerical range may vary between 1% and 15% of the stated number or numerical range.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety.

"Bioavailability" refers to the percentage of a compound described herein dosed that is delivered into the general circulation of the animal or human being studied. The total exposure (AUC(0-∞)) of a drug when administered intravenously is usually defined as 100% bioavailable (F %). "Oral bioavailability" refers to the extent to which compound described herein is absorbed into the general circulation when the pharmaceutical composition is taken orally as compared to intravenous injection.

"Blood plasma concentration" refers to the concentration of a compound described herein in the plasma component of blood of a subject. It is understood that the plasma concentration of a compound described herein may vary significantly between subjects, due to variability with respect to metabolism and/or possible interactions with other therapeutic agents. In accordance with one embodiment disclosed herein, the blood plasma concentration of a compound described herein may vary from subject to subject. Likewise, values such as maximum plasma concentration (Cmax) or time to reach maximum plasma concentration (Tmax), or total area under the plasma concentration time curve (AUC (0-∞)) may vary from subject to subject. Due to this variability, the amount necessary to constitute "a therapeutically effective amount" of a compound described herein may vary from subject to subject.

The term "isotopic enrichment factor" as used herein means the ratio between the isotopic abundance and the natural abundance of a specified isotope. It will be recognized that some variations of natural isotopic abundance occurs in a synthesized compound depending upon the origin of chemical materials used in the synthesis. Thus, a preparation of any compound will inherently contain small amounts of isotopologues, including deuterated analogs. The concentration of naturally abundant stable hydrogen isotopes, notwithstanding this variation, is small and immaterial as compared to the degree of stable isotopic substitution of compounds of this disclosure. In compounds described herein, when a particular position is designated as having a particular isotope, such as deuterium, it is understood that the abundance of deuterium at that position is substantially greater than the natural abundance of deuterium, which is about 0.015% (on a mol/mol basis). A position designated as a particular isotope will have a minimum isotopic enrichment factor of at least 3000 (45% incorporation of the indicated isotope). Thus, isotopically enriched compounds disclosed herein having deuterium will have a minimum isotopic enrichment factor of at least 3000 (45% deuterium incorporation) at each atom designated as deuterium in the compound. Such compounds may be referred to herein as "deuterated" compounds.

In other embodiments, disclosed compounds have an isotopic enrichment factor for each designated atom of at least 3500 (52.5%). For example, for such disclosed compounds that are deuterium isotopologues, the compounds have an isotopic enrichment factor for each designated hydrogen atom of at least 3500 (52.5% deuterium incorporation at each designated atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the compounds of this disclosure any atom not specifically designated as a particular isotope is meant to represent any stable isotope of that atom. Unless otherwise stated, when a position is designated specifically as "H", the position is understood to have hydrogen at about its natural abundance isotopic composition.

The term "isotope analog" or "isotopologue" refers to a species that has the same chemical structure and formula as another compound, with the exception of the isotopic composition at one or more positions, e.g., H vs. D. Thus, isotopologues differ in their isotopic composition.

"Salt" refers to acid or base salts of the compounds used in the methods of the present disclosure, in particular pharmaceutically acceptable salts. Illustrative examples of pharmaceutically acceptable salts are mineral acid (hydrochloric acid, hydrobromic acid, phosphoric acid, and the like) salts, organic acid (fumaric acid, acetic acid, propionic acid, glutamic acid, citric acid, tartaric acid and the like) salts, quaternary ammonium (methyl iodide, ethyl iodide, and the like) salts. It is understood that the pharmaceutically acceptable salts are non-toxic. Additional suitable pharmaceutically acceptable salts are known to those of skill in the art. See, e.g., *Remington: The Science and Practice of Pharmacy, volume I and volume II*. (22$^{nd}$ Ed., University of the Sciences, Philadelphia), which is incorporated herein by reference.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

"Pharmaceutically acceptable salt" refers to a compound in salt form, wherein the salt form is suitable for administration to a subject. Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

"Pharmaceutically acceptable excipient" refers to a substance that aids the administration of an active agent to and absorption by a subject. Pharmaceutical excipients useful in the present disclosure include, but are not limited to, binders, fillers, disintegrants, lubricants, coatings, sweeteners, flavors and colors. One of skill in the art will recognize that other pharmaceutical excipients are useful in the present disclosure.

"Racemic" or "racemic mixture" refers to a compound which comprises equal proportions of the dextrorotatory and levorotatory forms of a compound or salt thereof, such that the racemic compound is not optically active.

"Composition" refers to a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation.

"Isomers" refers to compounds with same chemical formula but different connectivity between the atoms in the molecule, leading to distinct chemical structures. Isomers include structural isomers and stereoisomers. Examples of structural isomers include, but are not limited to tautomers and regioisomers. Examples of stereoisomers include but are not limited to diastereomers and enantiomers.

"Administering" refers to any suitable mode of administration, including, oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject. In certain embodiments, administering refers to oral administration.

"Methylone" or "3,4-methylenedioxy-N-methylcathinone" refers to the compound having the following structure:

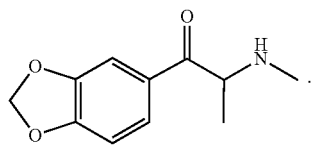

Methylone is a synthetic analog of the psychedelic phenethylamine class of compounds.

"(R)-Methylone" or "(R)-3,4-methylenedioxy-N-methylcathinone" refers to the compound having the following structure:

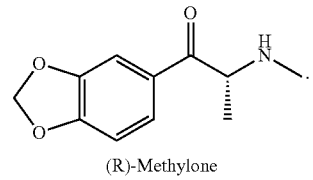
(R)-Methylone

"(S)-Methylone" or "(S)-3,4-methylenedioxy-N-methylcathinone" refers to the compound having the following structure:

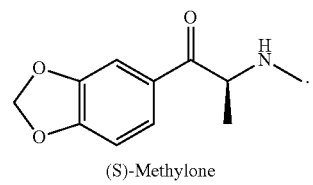
(S)-Methylone

"Ethylone" or "3,4-methylenedioxy-N-ethylcathinone" refers to the compound having the following structure:

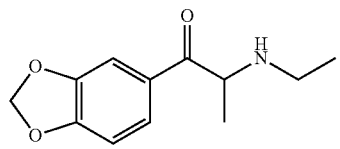 [SMILES: CCNC(C)C(=O)c1ccc2c(c1)OCO2]

Ethylone is a synthetic analog of the psychedelic phenethylamine class of compounds.

"(R)-Ethylone" or "(R)-3,4-methylenedioxy-N-ethylcathinone" refers to the compound having the following structure:

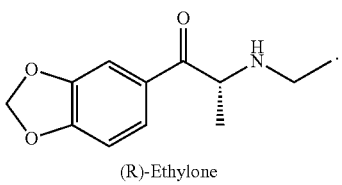 [SMILES: CCN[C@H](C)C(=O)c1ccc2c(c1)OCO2]
(R)-Ethylone

"(S)-Ethylone" or "(R)-3,4-methylenedioxy-N-methylcathinone" refers to the compound having the following structure:

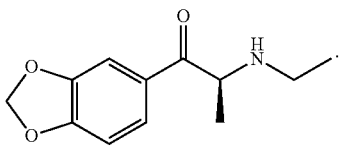
(S)-Methylone

"Subject" refers to an animal, such as a mammal, including, but not limited to, primates (e.g., humans), cows, sheep, goats, horses, dogs, cats, rabbits, rats, mice and the like. In certain embodiments, the subject is a human subject.

"Therapeutically effective amount" or "therapeutically sufficient amount" or "effective amount or sufficient amount" refers to a dose amount that produces therapeutic effects for which it is administered. In some embodiments, an effective amount relieves to some extent one or more of the symptoms of the disease or disorder being treated. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins). An appropriate effective amount in any individual case is optionally determined using techniques, such as a dose escalation study.

The terms "treat," "treating" or "treatment," as used herein, include alleviating, abating or ameliorating at least one symptom of a disease or disorder, preventing additional symptoms, inhibiting the disease or disorder, e.g., arresting the development of the disease or disorder, relieving the disease or disorder, causing regression of the disease or disorder, relieving a condition caused by the disease or disorder, or stopping the symptoms of the disease or disorder either prophylactically and/or therapeutically.

"Neuronal plasticity" refers to the ability of the brain to change its structure and/or function continuously throughout a subject's life. Examples of the changes to the brain include, but are not limited to, the ability to adapt or respond to internal and/or external stimuli, such as due to an injury, and the ability to produce new neurites, dendritic spines, and synapses.

"Brain disorder" refers to a neurological disorder which affects the brain's structure and function. Brain disorders can include, but are not limited to, Alzheimer's, Parkinson's disease, psychological disorder, depression, treatment resistant depression, addiction, anxiety, post-traumatic stress disorder, suicidal ideation, major depressive disorder, bipolar disorder, schizophrenia, stroke, traumatic brain injury, and substance use disorder.

"Combination therapy" refers to a method of treating a disease or disorder, wherein two or more different pharmaceutical agents are administered in overlapping regimens so that the subject is simultaneously exposed to both agents. For example, the compounds of the invention can be used in combination with other pharmaceutically active compounds. The compounds of the invention can be administered simultaneously (as a single preparation or separate preparation) or sequentially to the other drug therapy. In general, a combination therapy envisions administration of two or more drugs during a single cycle or course of therapy.

"Neurotrophic factors" refers to a family of soluble peptides or proteins which support the survival, growth, and differentiation of developing and mature neurons.

"Modulate" or "modulating" or "modulation" refers to an increase or decrease in the amount, quality, or effect of a particular activity, function or molecule. By way of illustration and not limitation, agonists, partial agonists, antagonists, and allosteric modulators (e.g., a positive allosteric modulator) of a G protein-coupled receptor (e.g., $5HT_{2A}$) are modulators of the receptor.

"Agonism" refers to the activation of a receptor or enzyme by a modulator, or agonist, to produce a biological response.

"Agonist" refers to a modulator that binds to a receptor or enzyme and activates the receptor to produce a biological response. By way of example only, "$5HT_{2A}$ agonist" can be used to refer to a compound that exhibits an $EC_{50}$ with respect to $5HT_{2A}$ activity of no more than about 100 mM. In some embodiments, the term "agonist" includes full agonists or partial agonists. "Full agonist" refers to a modulator that binds to and activates a receptor with the maximum response that an agonist can elicit at the receptor. "Partial agonist" refers to a modulator that binds to and activates a given receptor, but has partial efficacy, that is, less than the maximal response, at the receptor relative to a full agonist.

"Positive allosteric modulator" refers to a modulator that binds to a site distinct from the orthosteric binding site and enhances or amplifies the effect of an agonist.

"Antagonism" refers to the inactivation of a receptor or enzyme by a modulator, or antagonist. Antagonism of a receptor, for example, is when a molecule binds to the receptor and does not allow activity to occur.

"Antagonist" or "neutral antagonist" refers to a modulator that binds to a receptor or enzyme and blocks a biological response. An antagonist has no activity in the absence of an agonist or inverse agonist but can block the activity of either, causing no change in the biological response.

2. Isotopologues of Methylone

Methylone has intriguing biological activity, however, compounds such as methylone do not have the drug-like pharmacokinetic and pharmacodynamic properties to support their wider use in the clinical treatment of brain disorders.

In the present disclosure, it is found that the metabolic properties of the methylone could be improved by isotopic enrichment, in particular, deuterium or tritium enrichment. In this approach, one attempts to slow the CYP-mediated metabolism of a drug or to reduce the formation of undesirable metabolites by replacing one or more protium ($^1H$) atoms with deuterium atoms. Deuterium is a safe, stable, non-radioactive isotope of hydrogen. Compared to protium, deuterium forms stronger bonds with carbon. In select cases, the increased bond strength imparted by deuterium can positively affect the pharmacokinetic properties of a drug, creating the potential for improved drug efficacy, safety, and/or tolerability. At the same time, because the size and shape of deuterium are essentially identical to those of protium, replacement of protium by deuterium would not be expected to affect the biochemical potency and selectivity of the drug as compared to the original chemical entity that contains only hydrogen. Tritium, $^3H$, forms still stronger bonds with carbon than deuterium. Thus, replacement of protium with tritium also can affect the pharmacokinetic properties of a molecule. Moreover, tritium is a beta emitter, meaning that enriching a molecule with tritium allows determination of pharmacokinetic and pharmacodynamic properties of the molecule to better understand its activity and ADME properties.

In one aspect, disclosed herein are methylone analogs, in particular, isotopically labeled methylone analogs, or isotopologues. The presently disclosed isotopologues are useful for the treatment of a variety of brain disorders and other conditions. Without limitation to any particular theory, the isotopologues of methylone provided herein increase neuronal plasticity, and increase at least one of translation, transcription, or secretion of neurotrophic factors. Moreover, by virtue of their isotopic enrichment, in some embodiments, the isotopologues of methylone provided herein have improved pharmacokinetic and pharmacodynamic properties as compared to methylone. In some embodiments, the isotopic labels of the isotopologues of methylone provided herein allow monitoring of its pharmacodynamic and ADME behavior following in vivo administration. In some embodiments, the isotopically enriched compounds described herein provide better therapeutic potential for neurological diseases than known compounds (e.g., (non-deuterated) methylone).

In certain embodiments, provided herein are isotopically enriched compounds of methylone, which has a structure of Formula I:

Formula I

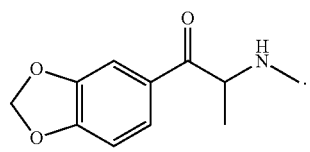

In certain embodiments, for example, compounds of Formula I may be enriched in one or more of deuterium, tritium and 4C.

In some embodiments, isotopically enriched compounds of Formula I disclosed herein have Formula (II):

Formula (II)

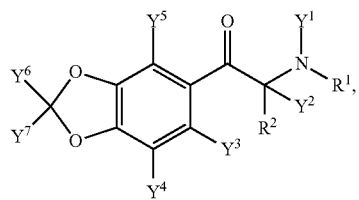

wherein at least one of $R^1$, $R^2$, $Y^1$, $Y^2$, $Y^3$, $Y^4$, $Y^5$, $Y^6$, $Y^7$ is enriched in at least one heavy isotope; or pharmaceutically acceptable salt, hydrate, or solvate thereof.

In some embodiments, $R^1$ and $R^2$ are independently selected from —$CD_3$, —$CD_2H$, —$CDH_2$, —$CT_3$, —$CT_2H$, —$CTH_2$ and —$CH_3$; and $Y^1$, $Y^2$, $Y^3$, $Y^4$, $Y^5$, $Y^6$ and $Y^7$ are independently selected from protium (hydrogen), deuterium and tritium.

In some embodiments, at least one of $Y^1$, $Y^2$, $Y^3$, $Y^4$, $Y^5$, $Y^6$, and $Y^7$ is deuterium, or $R^1$ or $R^2$ comprises at least one deuterium or tritium. In some embodiments, $R^1$ or $R^2$ comprises at least one deuterium.

In some embodiments, at least one of $Y^1$, $Y^2$, $Y^3$, $Y^4$, $Y^5$, $Y^6$, and $Y^7$ is deuterium, and $R^1$ and $R^2$ are both —$CH_3$.

In some embodiments, each of $Y^1$, $Y^2$, $Y^3$, $Y^4$, $Y^5$, $Y^6$, and $Y^7$ is protium (hydrogen), and $R^1$ or $R^2$ comprises at least one deuterium or tritium. In some embodiments, $R^1$ or $R^2$ comprises at least one deuterium.

In some embodiments, compounds of Formula (II) are selected from the group consisting of

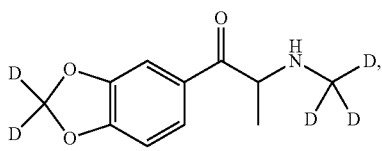

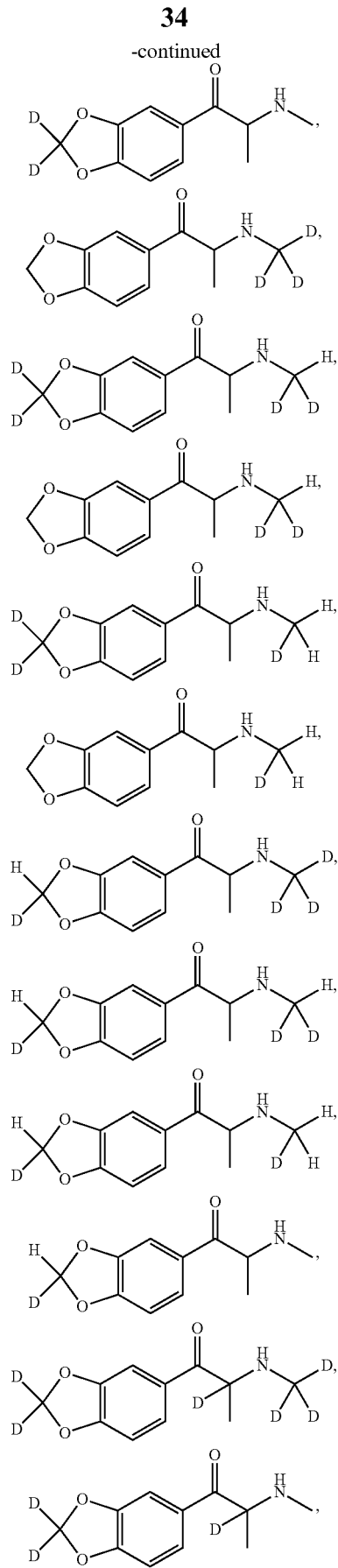

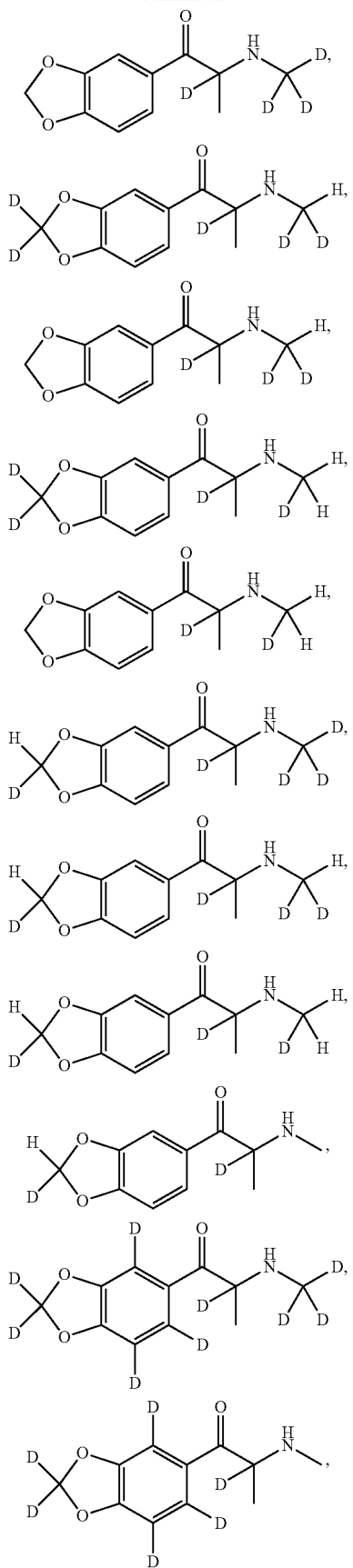

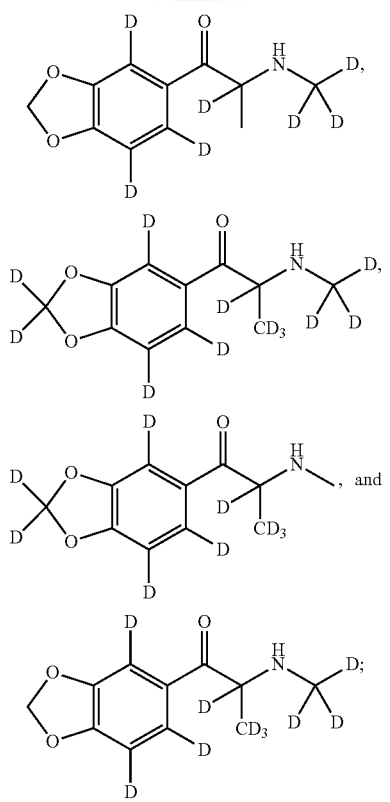

or an enantiomer, a mixture of enantiomers, a mixture of two or more diastereomers; or a pharmaceutically acceptable salt, solvate, or hydrate thereof.

As is understood by those of skill in the art, examples illustrated above have one or more chiral centers. Accordingly, in one embodiment, the compound is optically active. In another embodiment, the compound is an enantiomer ((R)- or (S)-enantiomer) or a racemic mixture of two enantiomers. For example, examples of disclosed compounds have one or more chiral centers, with each chiral center being in the (S) configuration or the (R) configuration. In embodiments with a single chiral center, the compound is the (S) enantiomer or the (R) enantiomer. When a mixture of a compound comprises of an equal mixture of two enantiomers, it is referred to as a racemic mixture.

In one embodiment, the compounds of Formula (II) are (S)-enantiomers having a structure of Formula (II-A):

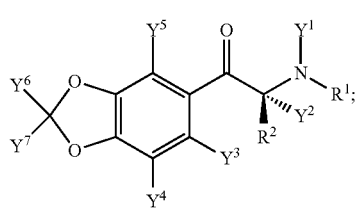

Formula (II-A)

or a pharmaceutically acceptable salt, solvate, or hydrate thereof.

In another embodiment, the compounds of Formula (II) are (R)-enantiomers having a structure of Formula (II-B):
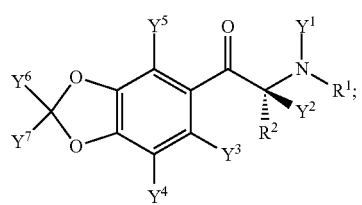
Formula (II-B)
or a pharmaceutically acceptable salt, solvate, or hydrate thereof.
In more particular embodiments, the compounds of Formula (II-A) are selected from the group consisting of
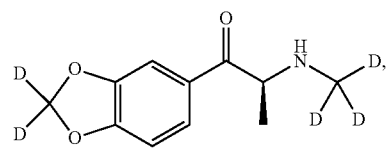
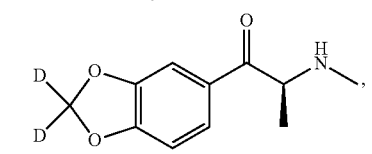
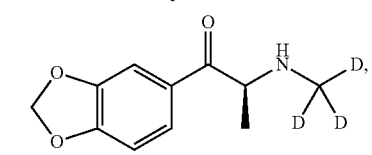
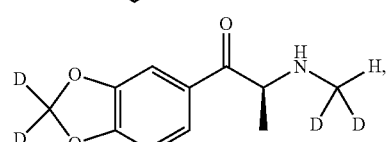
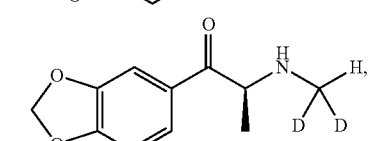
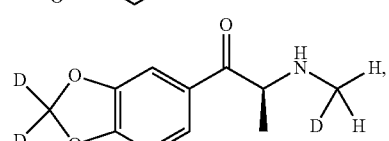
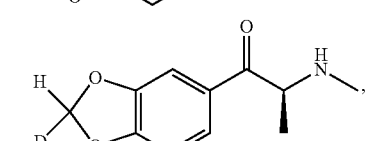
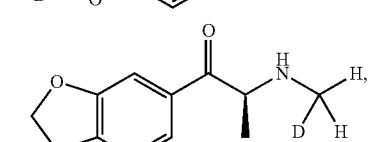
-continued
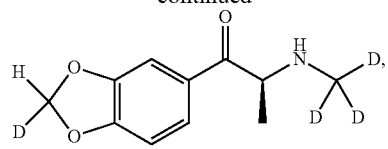
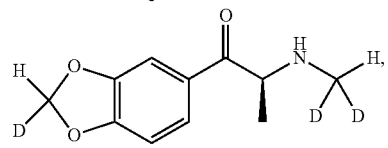
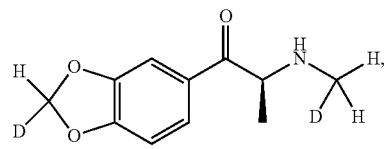
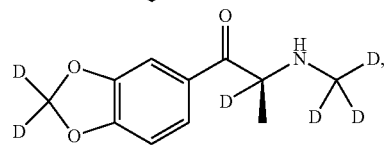
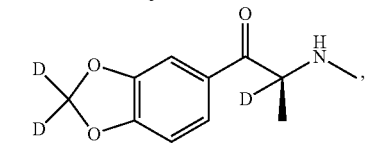
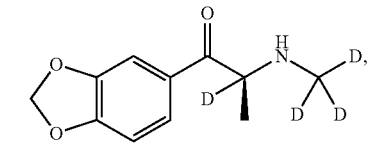
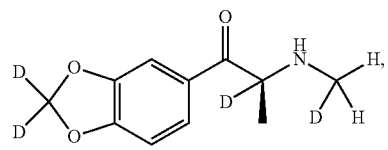
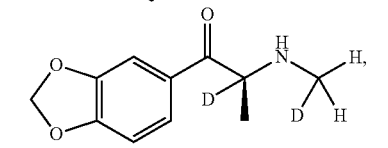
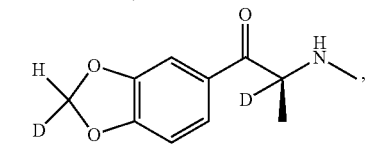
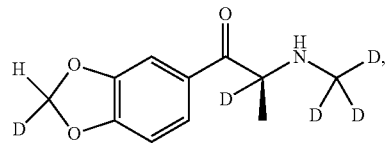
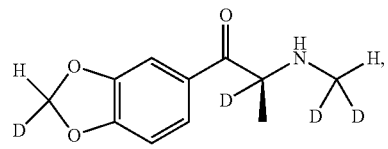
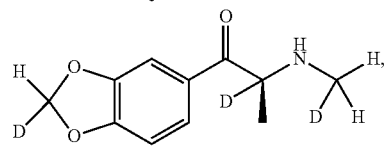

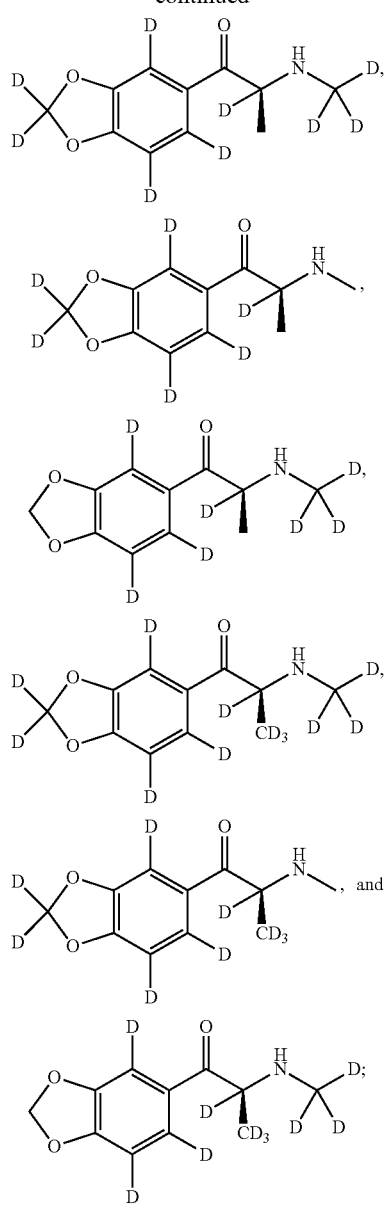
pharmaceutically acceptable salt, hydrate, or solvate thereof.
In more particular embodiments, the compounds of Formula (II-B) are selected from the group consisting of:
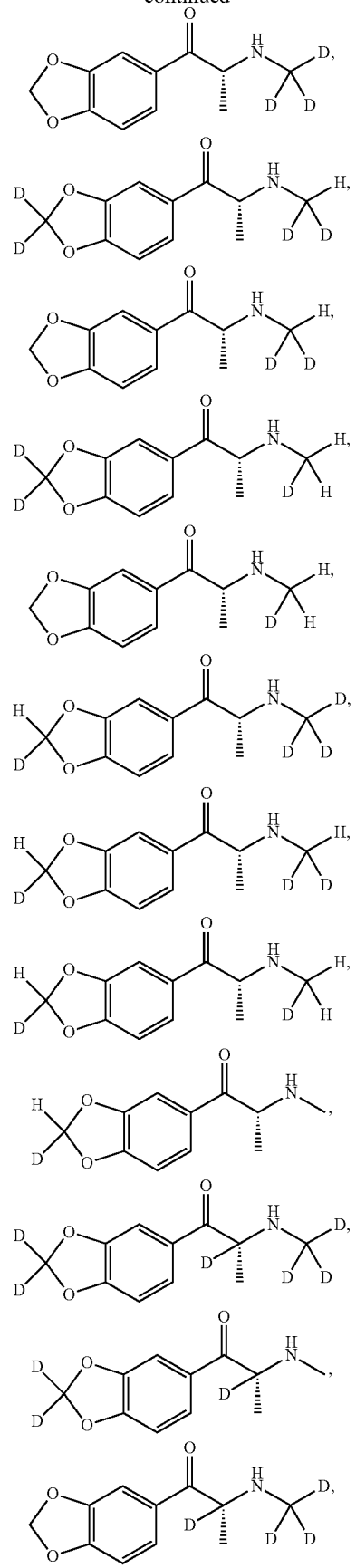

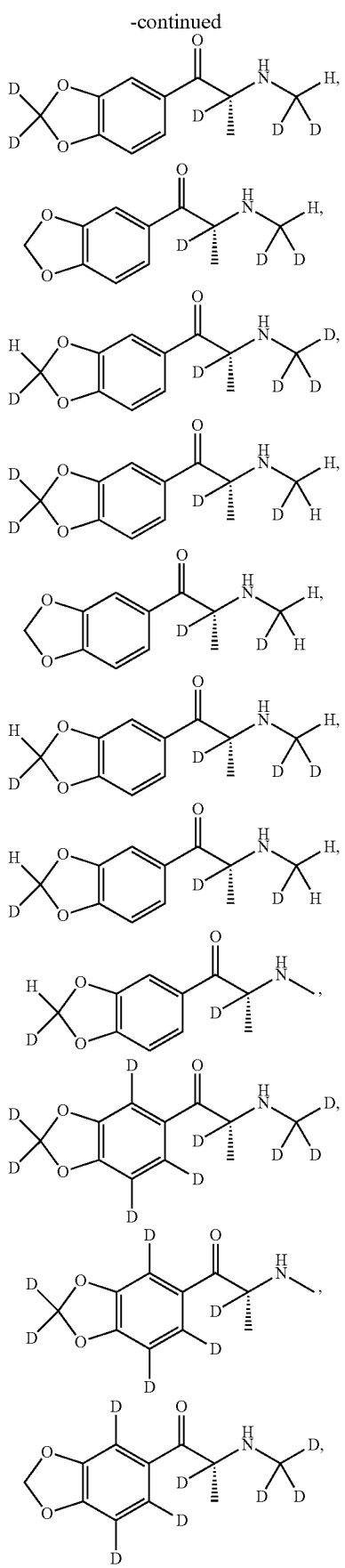

or pharmaceutically acceptable salt, hydrate, or solvate thereof.

The compounds of the present disclosure can also be in salt forms, such as acid or base salts of the compounds of the present disclosure. Illustrative examples of pharmaceutically acceptable acid salts are mineral acid (hydrochloric acid, hydrobromic acid, phosphoric acid, and the like) salts, organic acid (fumaric acid, acetic acid, propionic acid, glutamic acid, citric acid, tartaric acid and the like) salts. In some embodiments, the compounds of the present disclosure can be in any salt forms disclosed herein.

In some embodiments, a salt of the compound of Formula (II) is a hydrochloride salt of Formula (II):

In particular embodiments, the salt of the compound is an HCl salt having a structure such as those illustrated below:

It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

The present disclosure includes all tautomers and stereoisomers of compounds of Formula (II), either in admixture or in pure or substantially pure form. The compounds of the present disclosure can have asymmetric centers at the carbon atoms, and therefore the compounds of the present disclosure can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers.

In addition, all physical forms of the compounds of Formula I are intended herein, including the compounds of Formula I, in the form of solvates, such as hydrates. Moreover, non-crystalline and crystalline forms of the compounds of Formula I, including amorphous forms, isomorphs and polymorphs are within the scope of the present disclosure.

Exemplary compounds according to the present disclosure are chiral. Such compounds can be prepared as is known to those of skill in the art can be prepared as single enantiomers, or enantiomerically enriched mixtures, or racemic mixtures as contemplated herein; such compounds having more than one stereocenter can also be prepared as diastereomeric, enantiomeric or racemic mixtures as contemplated herein. Furthermore, diastereomer and enantiomer products can be separated by chromatography, fractional crystallization or other methods known to those of skill in the art.

General Method of Making Isotopologues of Methylone

The isotopologues (e.g., deuterated analogs) disclosed herein may be made by any method known to a person of ordinary skill in the art. In some embodiments, the compound is made using a known synthetic method for making the analogous non-deuterated compound, but with one or more deuterated starting materials, and/or reactants used in the synthesis. Methods for making non-deuterium enriched methylone are known in the art and a person of ordinary skill in the art understands which deuterated reactants and reagents are available and may be used in the synthesis of the disclosed compounds. Additional information concerning synthetic methods to make non-deuterated analogs of the disclosed compounds is available in the art.

An exemplary method for making deuterated compounds of the present disclosure is provided by Scheme 1.

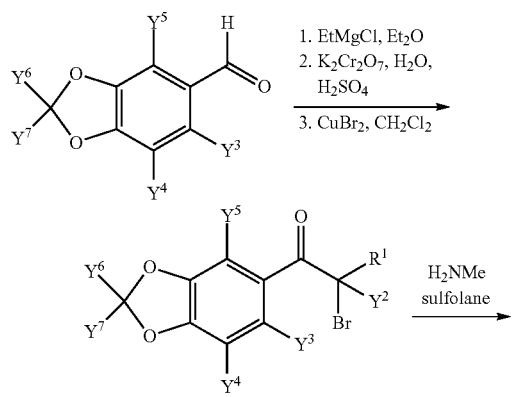

Scheme 1

As illustrated above, the cited methods for non-isotopically enriched molecules are adapted to the presently disclosed compounds as is known to those of skill in the art by substituting appropriate isotopically enriched building blocks for those disclosed by Whalen and Shulgin et al., including in WO 96/39133, some of which are illustrated below and are readily/commercially available.

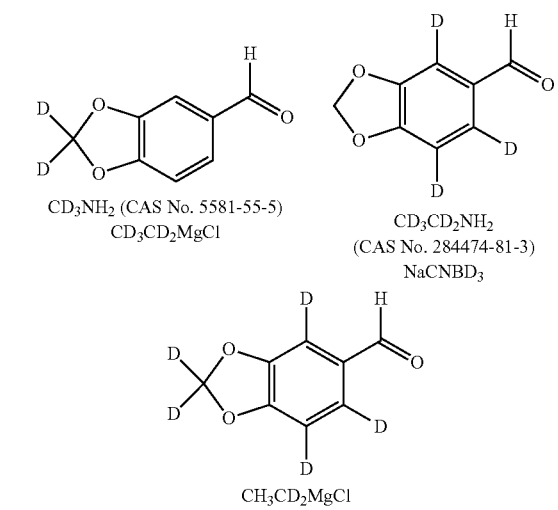

CD$_3$NH$_2$ (CAS No. 5581-55-5)
CD$_3$CD$_2$MgCl

CD$_3$CD$_2$NH$_2$
(CAS No. 284474-81-3)
NaCNBD$_3$

CH$_3$CD$_2$MgCl

3. Solid Forms of Methylone Hydrochloride

In another aspect, also provided herein are solid forms of methylone hydrochloride that are useful to treat various disorders, such as brain disorders. Also disclosed are methods for making the solid forms of the compounds and method of administering the solid forms of the compounds.

Methylone hydrochloride has the structure below, and may be also referred to herein as 3,4-methylenedioxy-N-methylcathinone hydrochloride or 3,4-methylenedioxy-N-methylcathinone·HCl, the middle dot, "·", represents that the compound is the acid addition salt of methylone.

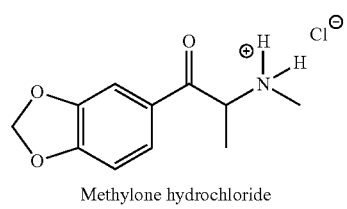

Methylone hydrochloride

Crystalline Forms

The identification and selection of a solid form of a pharmaceutical compound are complex, given that a change in solid form may affect a variety of physical and chemical properties, which may provide benefits or drawbacks in processing, formulation, stability, bioavailability, storage, and handling (e.g., shipping), among other important pharmaceutical characteristics. Useful pharmaceutical solids include crystalline solids and amorphous solids, depending on the product and its mode of administration. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability.

Whether crystalline or amorphous, solid forms of a pharmaceutical compound include single-component and multiple-component solids. Single-component solids consist essentially of the pharmaceutical compound or active ingredient in the absence of other compounds. Variety among single-component crystalline materials may potentially arise from the phenomenon of polymorphism, wherein multiple three-dimensional arrangements exist for a particular pharmaceutical compound.

Notably, it is not possible to predict a priori if crystalline forms of a compound even exist, let alone how to successfully prepare them (see, e.g., Braga and Grepioni, 2005, "Making crystals from crystals: a green route to crystal engineering and polymorphism," Chem. Commun.:3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," MRS Bulletin 31:875-879 (At present it is not generally possible to computationally predict the number of observable polymorphs of even the simplest molecules); Price, 2004, "The computational prediction of pharmaceutical crystal structures and polymorphism," Advanced Drug Delivery Reviews 56:301-319 ("Price"); and Bernstein, 2004, "Crystal Structure Prediction and Polymorphism," ACA Transactions 39:14-23 (a great deal still needs to be learned and done before one can state with any degree of confidence the ability to predict a crystal structure, much less polymorphic forms)).

The variety of possible solid forms creates potential diversity in physical and chemical properties for a given pharmaceutical compound. The discovery and selection of solid forms are of great importance in the development of an effective, stable, and marketable pharmaceutical product.

In some embodiments, the solid form of the compound is a crystalline form of the compound. In some embodiments, the solid form of the compound is a polymorph of the compound, such as a novel polymorph that is not previously known in the art.

A solid form of a salt may be a crystalline form or an amorphous form. A person of ordinary skill in the art understands that solid forms of compounds, such as crystalline forms of methylone hydrochloride, may exist in more than one crystal form. Such different forms are referred to as polymorphs. In some embodiments, the disclosed compound is a novel polymorph of methylone hydrochloride.

Crystalline Methylone Hydrochloride

In some embodiments, the solid form of methylone hydrochloride disclosed herein is a crystalline form, such as a particular polymorph of a crystalline form of methylone hydrochloride, that provides one or more desired properties. In one embodiment, the crystalline form offers advantages over the amorphous form of methylone. In another embodiment, the disclosed polymorph offers improved properties as compared to another polymorph of methylone. The one or more desired properties may include, but are not limited to, physical properties, including but not limited to, melting point, glass transition temperature, flowability, and/or stability, such as thermal stability, mechanical stability, shelf life, stability against polymorphic transition, etc.; chemical properties, such as, but not limited to, hygroscopic properties, solubility in water and/or organic solvents, reactivity, compatibility with excipients and/or delivery vehicles; and/or pharmacokinetic properties, such as, but not limited to, bioavailability, absorption, distribution, metabolism, excretion, toxicity including cytotoxicity, dissolution rate, and/or half-life.

The desired polymorph of methylone hydrochloride may be produced by techniques as described herein and also are known to persons of ordinary skill in the art. Such techniques include, but are not limited to, crystallization in particular solvents and/or at particular temperatures, supersaturation, using a precipitation agent, such as a salt, glycol, alcohol, etc., co-crystallization, lyophilization, spray drying, freeze drying, and/or complexing with an inert agent.

In some embodiments, crystallinity of a solid form is determined by X-Ray Powder Diffraction (XRPD), solid state NMR, Fourier Transform IR Spectroscopy (FTIR), and Fourier Transform Raman Spectroscopy.

Techniques to identify a particular solid form of methylone hydrochloride and also are known to persons of ordinary skill in the art, and include, but are not limited to, X-ray crystallography, X-ray diffraction, electron crystallography, powder diffraction, including X-ray, neutron, or electron diffraction, X-ray fiber diffraction, small-angle X-ray scattering, and/or melting point.

In some embodiments provided herein, the crystalline form of methylone hydrochloride is a single crystalline form. In some embodiments provided herein, the crystalline form of methylone hydrochloride is a single crystalline form that is substantially free of any other crystalline form. In some embodiments, the crystalline solid form is a single solid state form, e.g. crystalline Form A, crystalline Form B. crystalline Form C. or crystalline Form D. In some embodiments, "substantially free" means less than about 10% w/w, less than about 9% w/w, less than about 8% w/w, less than about 7% w/w, less than about 6% w/w, less than about 5% w/w, less than about 4% w/w, less than about 3% w/w, less than about 2.5% w/w, less than about 2% w/w, less than about 1.5% w/w, less than about 1% w/w, less than about 0.75% w/w, less than about 0.50% w/w, less than about 0.25% w/w, less than about 0.10% w/w, or less than about 0.05% w/w of any other crystalline form (e.g., crystalline Form B, Form C, and/or Form D) in a sample of crystalline Form A. In some embodiments, "substantially free" means an undetectable amount.

In some embodiments, "consists essentially of" when used in reference to a particular enantiomer means less than about 10%, less than about 9%, less than about 8%, less than about 7%, less than about 6%, less than about 5%, less than about 4%, less than about 3%, less than about 2.5%, less than about 2%, less than about 1.5%, less than about 1% less than about 0.75%, less than about 0.50%, less than about 0.25%, less than about 0.10% or less than about 0.05% of the other enantiomer. In some embodiments, "consists essentially of" when used in reference to a particular enantiomer means that the chiral purity (% enantiomeric excess; % e.e.) is greater than 95%, greater than 96%, greater than 97%, greater than 98%, greater than 99%. In some embodiments, "consists essentially of" means an undetectable amount of the opposite enantiomer.

In some embodiments, in any of the uses, methods, formulations described herein comprise racemic methylone hydrochloride. In some embodiments, in any of the uses, methods, formulations described herein comprise (S)-methylone hydrochloride. In some embodiments, in any of the uses, methods, formulations described herein comprise (R)-methylone hydrochloride.

(R)-Methylone hydrochloride has the following structure:

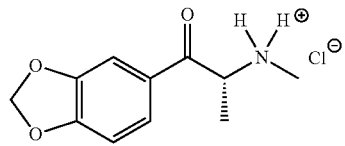

(S)-Methylone hydrochloride has the following structure:

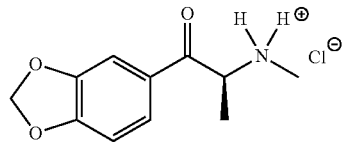

3.1 Crystalline Methylone Hydrochloride, Form A

Figure 21:
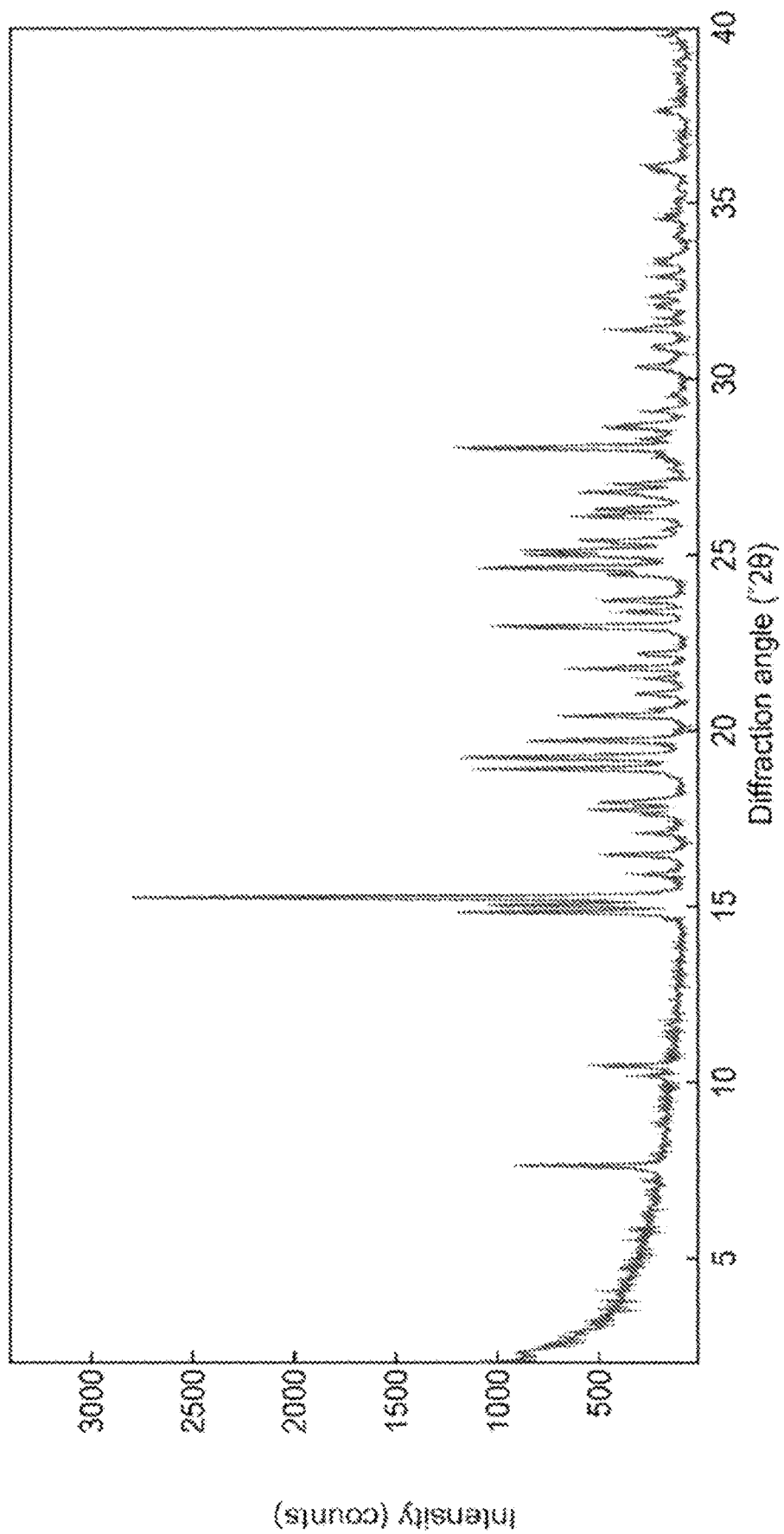
FIG. 21 illustrates an XRPD) diffractogram of crystalline methylone hydrochloride (racemate), Form A.

In some embodiments, the crystalline form of methylone hydrochloride is Form A. In some embodiments, crystalline methylone hydrochloride Form A is characterized as having at least one of the following properties:
(a) an X-ray powder diffraction (XRPD) pattern substantially the same as shown in FIG. 21;
(b) an X-ray powder diffraction (XRPD) pattern with characteristic peaks at 7.6°±0.2 2-Theta, 10.5°±0.2 2-Theta, and 15.3°±0.2 2-Theta, and optionally with further characteristic peaks at 14.8°±0.2 2-Theta and 15.0°±0.2 2-Theta, and optionally with further one or more peaks at 18.9°±0.2 2-Theta, 19.2°±0.2 2-Theta, 19.7°±0.2 2-Theta, 20.4°±0.2 2-Theta, 23.0° ±0.2 2-Theta, 24.6°±0.2 2-Theta, 25.1°±0.2 2-Theta, or 28.0°±0.2 2-Theta as measured with Cu Kα radiation;
(c) a DSC thermogram substantially similar to the one set forth in FIG. 22;
(d) a DSC thermogram with an endotherm at about 251° C.;
(e) a thermo-gravimetric analysis (TGA) substantially similar to the one set forth in FIG. 22; or
(f) combinations thereof.

In some embodiments, crystalline methylone hydrochloride Form A, is characterized as having at least two of the properties selected from (a) to (e). In some embodiments, crystalline methylone hydrochloride Form A, is characterized as having at least three of the properties selected from (a) to (e). In some embodiments, crystalline methylone hydrochloride Form A, is characterized as having at least four of the properties selected from (a) to (e). In some embodiments, crystalline methylone hydrochloride Form A, is characterized as having properties (a) to (e).

In some embodiments, crystalline methylone hydrochloride Form A, has an X-ray powder diffraction (XRPD) pattern substantially the same as shown in FIG. 21. In some embodiments, crystalline methylone hydrochloride Form A, has an X-ray powder diffraction (XRPD) pattern comprising characteristic peaks at 7.6°±0.2 2-Theta, 10.5°±0.2 2-Theta, and 15.3°±0.2 2-Theta as measured with Cu Kα radiation. In some embodiments, crystalline methylone hydrochloride Form A, has an X-ray powder diffraction (XRPD) pattern further comprising characteristic peaks at 14.8°±0.2 2-Theta and 15.0°±0.2 2-Theta as measured with Cu Kα radiation. In some embodiments, crystalline methylone hydrochloride Form A, has an X-ray powder diffraction (XRPD) pattern further comprising one or more peaks at 18.9°±0.2 2-Theta, 19.2°±0.2 2-Theta, 19.7°±0.2 2-Theta, 20.4°±0.2 2-Theta, 23.0°±0.2 2-Theta, 24.6°±0.2 2-Theta, 25.1°±0.2 2-Theta, or 28.0°±0.2 2-Theta as measured with Cu Kα radiation. In some embodiments, crystalline methylone hydrochloride Form A, has a DSC thermogram substantially similar to the one set forth in FIG. 22. In some embodiments, crystalline methylone hydrochloride Form A, has a DSC thermogram with an endotherm at about 251° C. In some embodiments, crystalline methylone hydrochloride Form A, has a thermo-gravimetric analysis (TGA) thermogram substantially similar to the one set forth in FIG. 22. In some embodiments, crystalline methylone hydrochloride Form A, has an XRPD pattern substantially the same as shown in FIG. 21; a DSC thermogram substantially similar to the one set forth in FIG. 22; and optionally a TGA thermogram substantially similar to the one set forth in FIG. 22. In some embodiments, crystalline methylone hydrochloride Form A, has an XRPD pattern comprising characteristic peaks at 7.6°±0.2 2-Theta, 10.5°±0.2 2-Theta, and 15.3°±0.2 2-Theta as measured with Cu Kα radiation; and a DSC thermogram with an endotherm at about 251° C. In some embodiments, crystalline methylone hydrochloride Form A, is non-hygroscopic. In some embodiments, crystalline methylone hydrochloride Form A is solvated. In some embodiments, crystalline methylone hydrochloride Form A is unsolvated. In some embodiments, crystalline methylone hydrochloride Form A is anhydrous.

Figure 14:
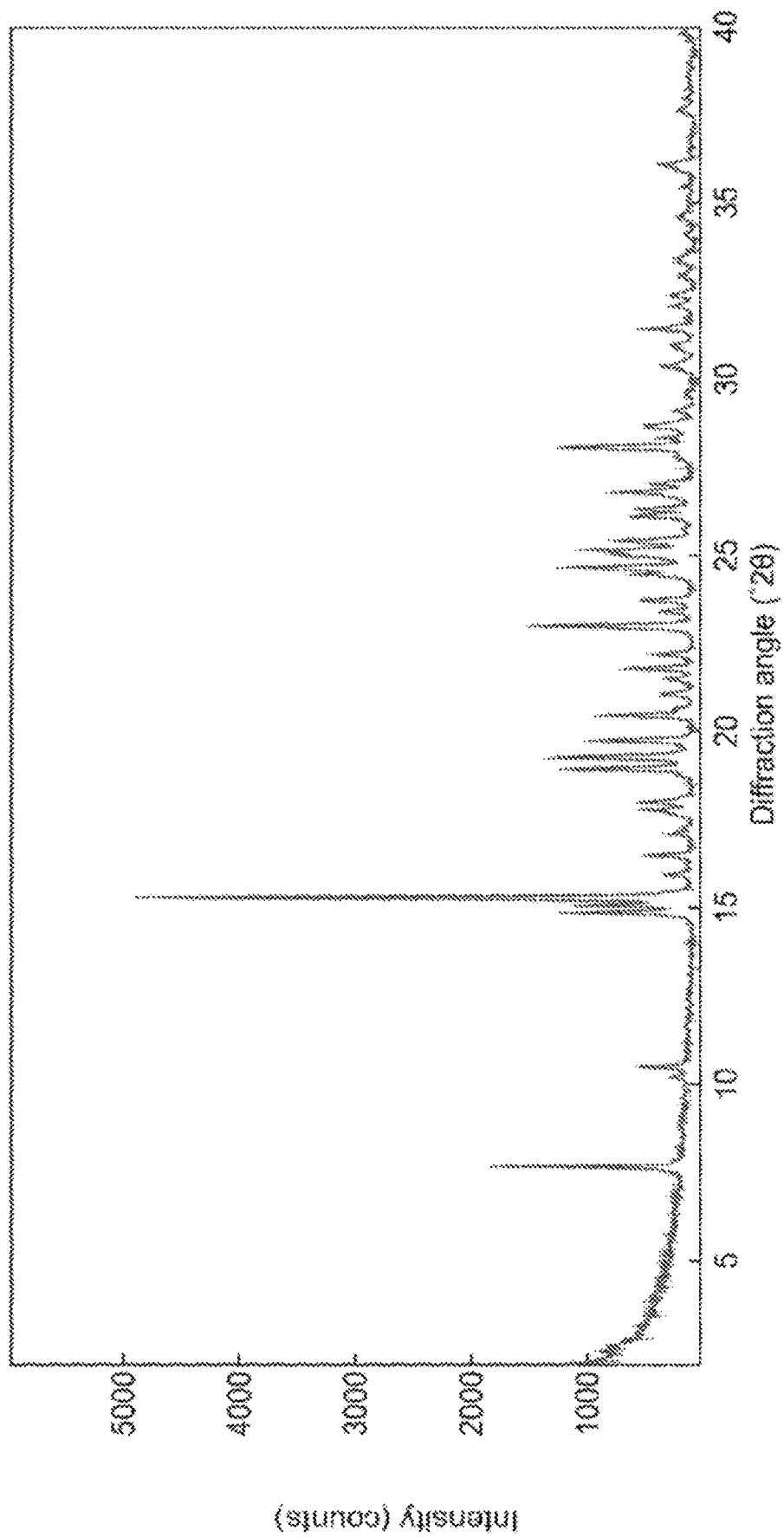
FIG. 14 illustrates an XRPD diffractogram of crystalline methylone hydrochloride (racemate), Form A.

In some embodiments, crystalline methylone hydrochloride Form A is characterized as having at least one of the following properties:
(a) an X-ray powder diffraction (XRPD) pattern substantially the same as shown in FIG. 14;
(b) an X-ray powder diffraction (XRPD) pattern with characteristic peaks at 7.7°±0.2 2-Theta, 10.5°±0.2 2-Theta, and 15.3°±0.2 2-Theta, and optionally with further characteristic peaks at 14.9°±0.2 2-Theta, and 15.1°±0.2 2-Theta, and optionally with further one or more peaks at 18.9°±0.2 2-Theta, 19.3°±0.2 2-Theta, 19.7°±0.2 2-Theta, 20.4°±0.2 2-Theta, 23.0°±0.2 2-Theta, 24.6°±0.2 2-Theta, 25.1°±0.2 2-Theta, or 28.0°±0.2 2-Theta as measured with Cu Kα radiation;
(c) a DSC thermogram substantially similar to the one set forth in FIG. 22;
(d) a DSC thermogram with an endotherm at about 251° C.;
(e) a thermo-gravimetric analysis (TGA) substantially similar to the one set forth in FIG. 22; or
(f) combinations thereof.

In some embodiments, crystalline methylone hydrochloride Form A, is characterized as having at least two of the properties selected from (a) to (e). In some embodiments, crystalline methylone hydrochloride Form A, is characterized as having at least three of the properties selected from (a) to (e). In some embodiments, crystalline methylone hydrochloride Form A, is characterized as having at least four of the properties selected from (a) to (e). In some embodiments, crystalline methylone hydrochloride Form A, is characterized as having properties (a) to (e).

In some embodiments, crystalline methylone hydrochloride Form A, has an X-ray powder diffraction (XRPD) pattern substantially the same as shown in FIG. 14. In some embodiments, crystalline methylone hydrochloride Form A, has an X-ray powder diffraction (XRPD) pattern comprising characteristic peaks at 7.7°±0.2 2-Theta, 10.5°±0.2 2-Theta, and 15.3°±0.2 2-Theta as measured with Cu Kα radiation. In some embodiments, crystalline methylone hydrochloride Form A, has an X-ray powder diffraction (XRPD) pattern further comprising characteristic peaks at 14.9°±0.2 2-Theta and 15.1°±0.2 2-Theta as measured with Cu Kα radiation. In some embodiments, crystalline methylone hydrochloride Form A, has an X-ray powder diffraction (XRPD) pattern further comprising one or more peaks at 18.9°±0.2 2-Theta, 19.3°±0.2 2-Theta, 19.7°±0.2 2-Theta, 20.4°±0.2 2-Theta, 23.0°±0.2 2-Theta, 24.6°±0.2 2-Theta, 25.1°±0.2 2-Theta, or 28.0°±0.2 2-Theta as measured with Cu Kα radiation. In some embodiments, crystalline methylone hydrochloride Form A, has a DSC thermogram substantially similar to the one set forth in FIG. 22. In some embodiments, crystalline methylone hydrochloride Form A, has a DSC thermogram with an endotherm at about 251° C. In some embodiments, crystalline methylone hydrochloride Form A, has a thermo-gravimetric analysis (TGA) thermogram substantially similar to the one set forth in FIG. 22. In some embodiments, crystalline methylone hydrochloride Form A, has an XRPD pattern substantially the same as shown in FIG. 14; a DSC thermogram substantially similar to the one set forth in FIG. 22; and optionally a TGA thermogram substantially similar to the one set forth in FIG. 22. In some embodiments, crystalline methylone hydrochloride Form A, has an XRPD pattern comprising characteristic peaks at 7.7°±0.2 2-Theta, 10.5°±0.2 2-Theta, and 15.3°±0.2 2-Theta as measured with Cu Kα radiation; and a DSC thermogram with an endotherm at about 251° C. In some embodiments, crystalline methylone hydrochloride Form A, is non-hygroscopic. In some embodiments, crystalline methylone hydrochloride Form A is solvated. In some embodiments, crystalline methylone hydrochloride Form A is unsolvated. In some embodiments, crystalline methylone hydrochloride Form A is anhydrous.

In some embodiments, crystalline methylone hydrochloride Form A comprises hydrochloride salts of racemic methylone. In some embodiments, crystalline methylone hydrochloride Form A comprises (S)-methylone hydrochloride and (R)-methylone hydrochloride.

3.2 Crystalline Methylone Hydrochloride, Form B

Figure 17:
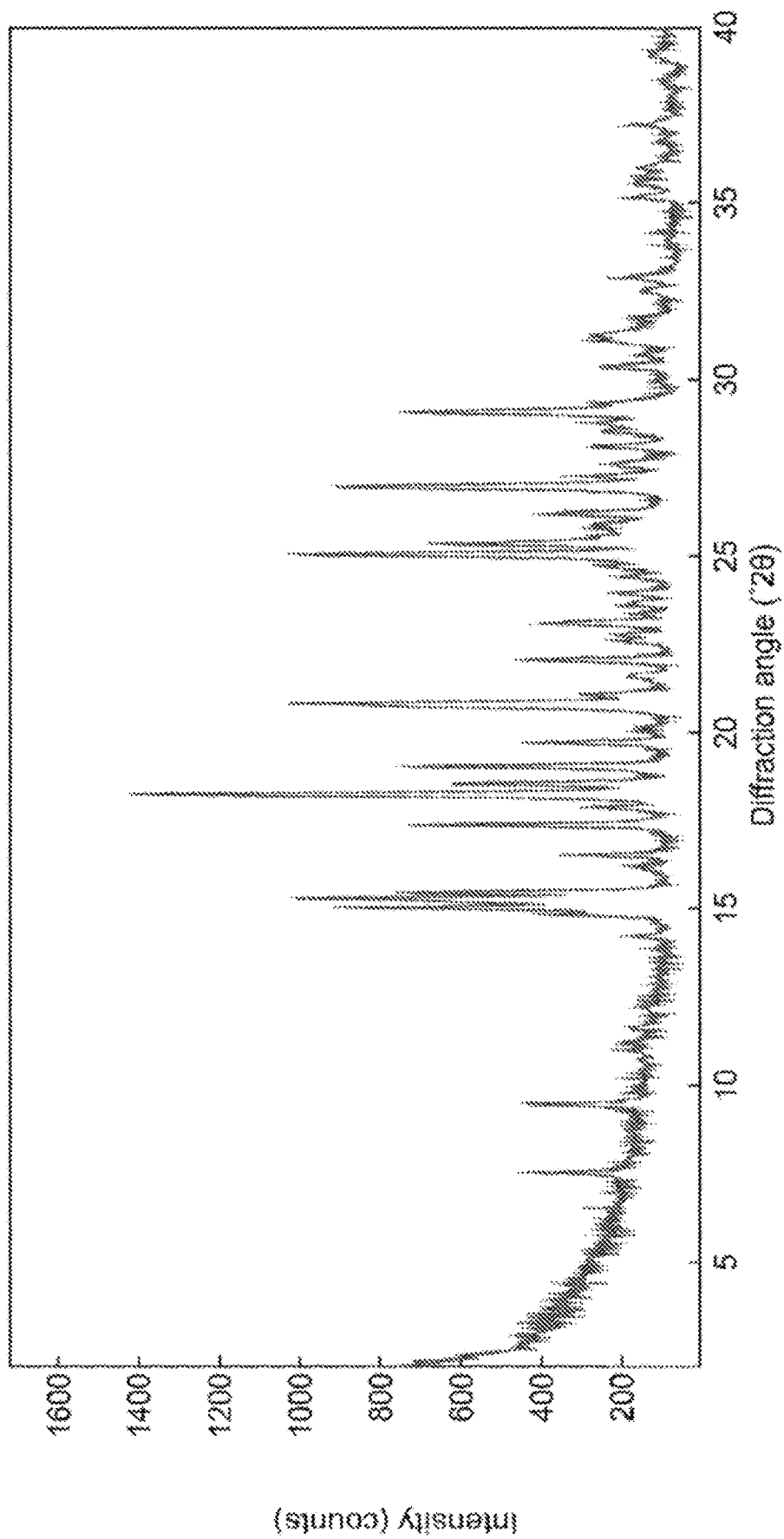
FIG. 17 illustrates an XRPD diffractogram of crystalline methylone hydrochloride (racemate), Form B.

In some embodiments, the crystalline form of methylone hydrochloride is Form B. In some embodiments, crystalline methylone hydrochloride Form B is characterized as having at least one of the following properties:

(a) an X-ray powder diffraction (XRPD) pattern substantially the same as shown in FIG. 17;
(b) an X-ray powder diffraction (XRPD) pattern with characteristic peaks at 7.5°±0.2 2-Theta, 9.5°±0.2 2-Theta, and 15.3°±0.2 2-Theta, and optionally with further characteristic peaks at 15.0°±0.2 2-Theta and 15.5°±0.2 2-Theta, and optionally with further one or more peaks at 14.8°±0.2 2-Theta, 17.4°±0.2 2-Theta, 18.3°±0.2 2-Theta, 18.5°±0.2 2-Theta, 19.0°±0.2 2-Theta, 19.7°±0.2 2-Theta, 20.8°±0.2 2-Theta, 22.1°±0.2 2-Theta, 23.1°±0.2 2-Theta, 25.1°±0.2 2-Theta, 25.4°±0.2 2-Theta, 26.2°±0.2 2-Theta, 27.0°±0.2 2-Theta, or 29.1°±0.2 2-Theta as measured with Cu Kα radiation;
(c) a DSC thermogram substantially similar to the one set forth in FIG. 23;
(d) a DSC thermogram with an endotherm at about 249° C.;
(e) a thermo-gravimetric analysis (TGA) substantially similar to the one set forth in FIG. 23; or
(f) combinations thereof.

In some embodiments, crystalline methylone hydrochloride Form B, is characterized as having at least two of the properties selected from (a) to (e). In some embodiments, crystalline methylone hydrochloride Form B, is characterized as having at least three of the properties selected from (a) to (e). In some embodiments, crystalline methylone hydrochloride Form B, is characterized as having at least four of the properties selected from (a) to (e). In some embodiments, crystalline methylone hydrochloride Form B, is characterized as having properties (a) to (e).

In some embodiments, crystalline methylone hydrochloride Form B, has an X-ray powder diffraction (XRPD) pattern substantially the same as shown in FIG. 17. In some embodiments, crystalline methylone hydrochloride Form B, has an X-ray powder diffraction (XRPD) pattern comprising characteristic peaks at 7.5°±0.2 2-Theta, 9.5°±0.2 2-Theta, and 15.3°±0.2 2-Theta as measured with Cu Kα radiation. In some embodiments, crystalline methylone hydrochloride Form B, has an X-ray powder diffraction (XRPD) pattern further comprising characteristic peaks at 15.0°±0.2 2-Theta and 15.5°±0.2 2-Theta as measured with Cu Kα radiation. In some embodiments, crystalline methylone hydrochloride Form B, has an X-ray powder diffraction (XRPD) pattern further comprising one or more peaks selected from 14.8°±0.2 2-Theta, 17.4°±0.2 2-Theta, 18.3°±0.2 2-Theta, 18.5°±0.2 2-Theta, 19.0°±0.2 2-Theta, 19.7°±0.2 2-Theta, 20.8°±0.2 2-Theta, 22.1°±0.2 2-Theta, 23.1°±0.2 2-Theta, 25.1°±0.2 2-Theta, 25.4°±0.2 2-Theta, 26.2°±0.2 2-Theta, 27.0°±0.2 2-Theta, or 29.1°±0.2 2-Theta as measured with Cu Kα radiation. In some embodiments, crystalline methylone hydrochloride Form B, has a thermogravimetric analysis (TGA) thermogram substantially similar to the one set forth in FIG. 23. In some embodiments, crystalline methylone hydrochloride Form B, has a DSC thermogram substantially similar to the one set forth in FIG. 23. In some embodiments, crystalline methylone hydrochloride Form B, has a DSC thermogram with a first endotherm at about 142° C. and a second endotherm at about 152° C. In some embodiments, crystalline methylone hydrochloride Form B, has an XRPD pattern substantially the same as shown in FIG. 17; a DSC thermogram substantially similar to the one set forth in FIG. 23; and optionally a TGA thermogram substantially similar to the one set forth in FIG. 23. In some embodiments, crystalline methylone hydrochloride Form B, has an XRPD pattern comprising characteristic peaks at 7.5°±0.2 2-Theta, 9.5°±0.2 2-Theta, and 15.3°±0.2 2-Theta as measured with Cu Kα radiation; and a DSC thermogram with a first endotherm at about 142° C. and a second endotherm at about 152° C. In some embodiments, crystalline methylone hydrochloride Form B, is non-hygroscopic. In some embodiments, crystalline methylone hydrochloride Form B is unsolvated. In some embodiments, crystalline methylone hydrochloride Form B is solvated. In some embodiments, crystalline methylone hydrochloride Form B is anhydrous.

In some embodiments, crystalline methylone hydrochloride Form B comprises hydrochloride salts of racemic methylone. In some embodiments, crystalline methylone hydrochloride Form B comprises (S)-methylone hydrochloride and (R)-methylone hydrochloride.

3.3 Crystalline Methylone Hydrochloride, Form C

Figure 2:
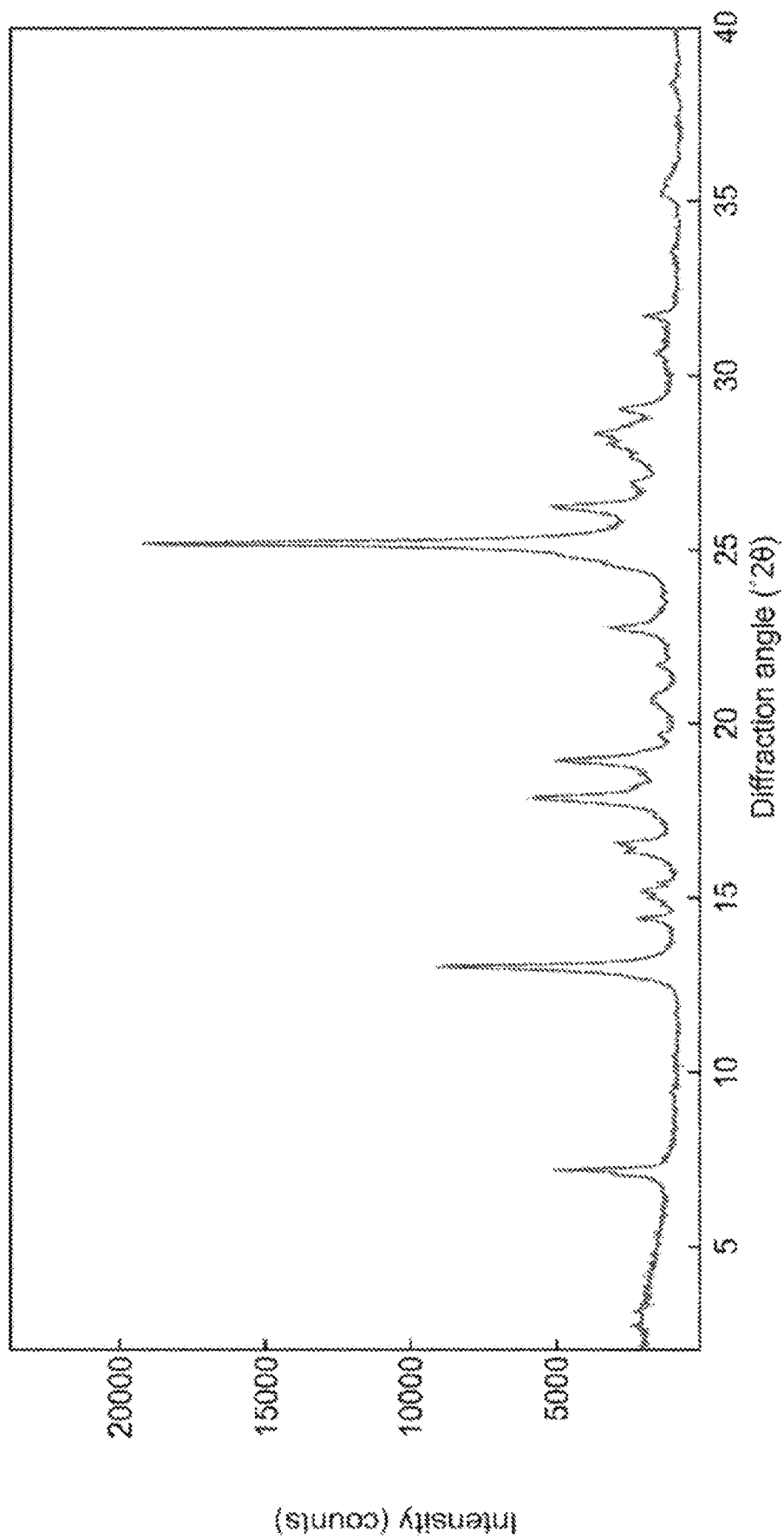
FIG. 2 illustrates an XRPD diffractogram of crystalline methylone hydrochloride (racemate), Form C, prepared by evaporation from wet ethyl acetate.

In some embodiments, the crystalline form of methylone hydrochloride is Form C. In some embodiments, crystalline methylone hydrochloride Form C is characterized as having at least one of the following properties:
(a) an X-ray powder diffraction (XRPD) pattern substantially the same as shown in FIG. 2;
(b) an X-ray powder diffraction (XRPD) pattern with characteristic peaks at 7.2°±0.2 2-Theta, 13.0°±0.2 2-Theta, and 14.4°±0.2 2-Theta, and optionally with further characteristic peaks at 17.9°±0.2 2-Theta and 19.0°±0.2 2-Theta, and optionally with further one or more peaks at 25.2°±0.2 2-Theta and 26.2°±0.2 2-Theta as measured with Cu Kα radiation;
(c) a thermo-gravimetric analysis (TGA) substantially similar to the one set forth in FIG. 24;
(d) a DSC thermogram substantially similar to the one set forth in FIG. 24;
(e) a DSC thermogram with a first endotherm at about 53° C. and a second endotherm at about 241° C.; or
(f) combinations thereof.

In some embodiments, crystalline methylone hydrochloride Form C is characterized as having at least two of the properties selected from (a) to (e). In some embodiments, crystalline methylone hydrochloride Form C is characterized as having at least three of the properties selected from (a) to (e). In some embodiments, crystalline methylone hydrochloride Form C is characterized as having at least four of the properties selected from (a) to (e). In some embodiments, crystalline methylone hydrochloride Form C is characterized as having properties (a) to (e).

In some embodiments, crystalline methylone hydrochloride Form C has an X-ray powder diffraction (XRPD) pattern substantially the same as shown in FIG. 2. In some embodiments, crystalline methylone hydrochloride Form C has an X-ray powder diffraction (XRPD) pattern comprising characteristic peaks at 7.2°±0.2 2-Theta, 13.0°±0.2 2-Theta, and 14.4°±0.2 2-Theta as measured with Cu Kα radiation. In some embodiments, crystalline methylone hydrochloride Form C has an X-ray powder diffraction (XRPD) pattern further comprising characteristic peaks at 17.9°±0.2 2-Theta and 19.0°±0.2 2-Theta as measured with Cu Kα radiation. In some embodiments, crystalline methylone hydrochloride Form C has an X-ray powder diffraction (XRPD) pattern further comprising one or more peaks at 25.2°±0.2 2-Theta and 26.2°±0.2 2-Theta as measured with Cu Kα radiation. In some embodiments, crystalline methylone hydrochloride Form C has a DSC thermogram substantially similar to the one set forth in FIG. 24. In some embodiments, crystalline methylone hydrochloride Form C has a DSC thermogram with a first endotherm at about 53° C. and a second endotherm at about 241° C. In some embodiments, crystalline methylone hydrochloride Form C has a thermogravimetric analysis (TGA) thermogram substantially similar to the one set forth in FIG. 24. In some embodiments, crystalline methylone hydrochloride Form C has an XRPD pattern substantially the same as shown in FIG. 2; a DSC thermogram substantially similar to the one set forth in FIG. 24; and optionally a TGA thermogram substantially similar to the one set forth in FIG. 24. In some embodiments, crystalline methylone hydrochloride Form C has an XRPD pattern comprising characteristic peaks at 7.2°±0.2 2-Theta, 13.0°±0.2 2-Theta, and 14.4°±0.2 2-Theta as measured with Cu Kα radiation; and a DSC thermogram with a first endotherm at about 53° C. and a second endotherm at about 241° C. In some embodiments, crystalline methylone hydrochloride Form C is non-hygroscopic. In some embodiments, crystalline methylone hydrochloride Form C is unsolvated. In some embodiments, crystalline methylone hydrochloride Form C is solvated. In some embodiments, crystalline methylone hydrochloride Form C is anhydrous.

In some embodiments, crystalline methylone hydrochloride Form C comprises hydrochloride salts of racemic methylone. In some embodiments, crystalline methylone hydrochloride Form C comprises (S)-methylone hydrochloride and (R)-methylone hydrochloride.

3.4 Crystalline Methylone Hydrochloride, Form D

Figure 13:
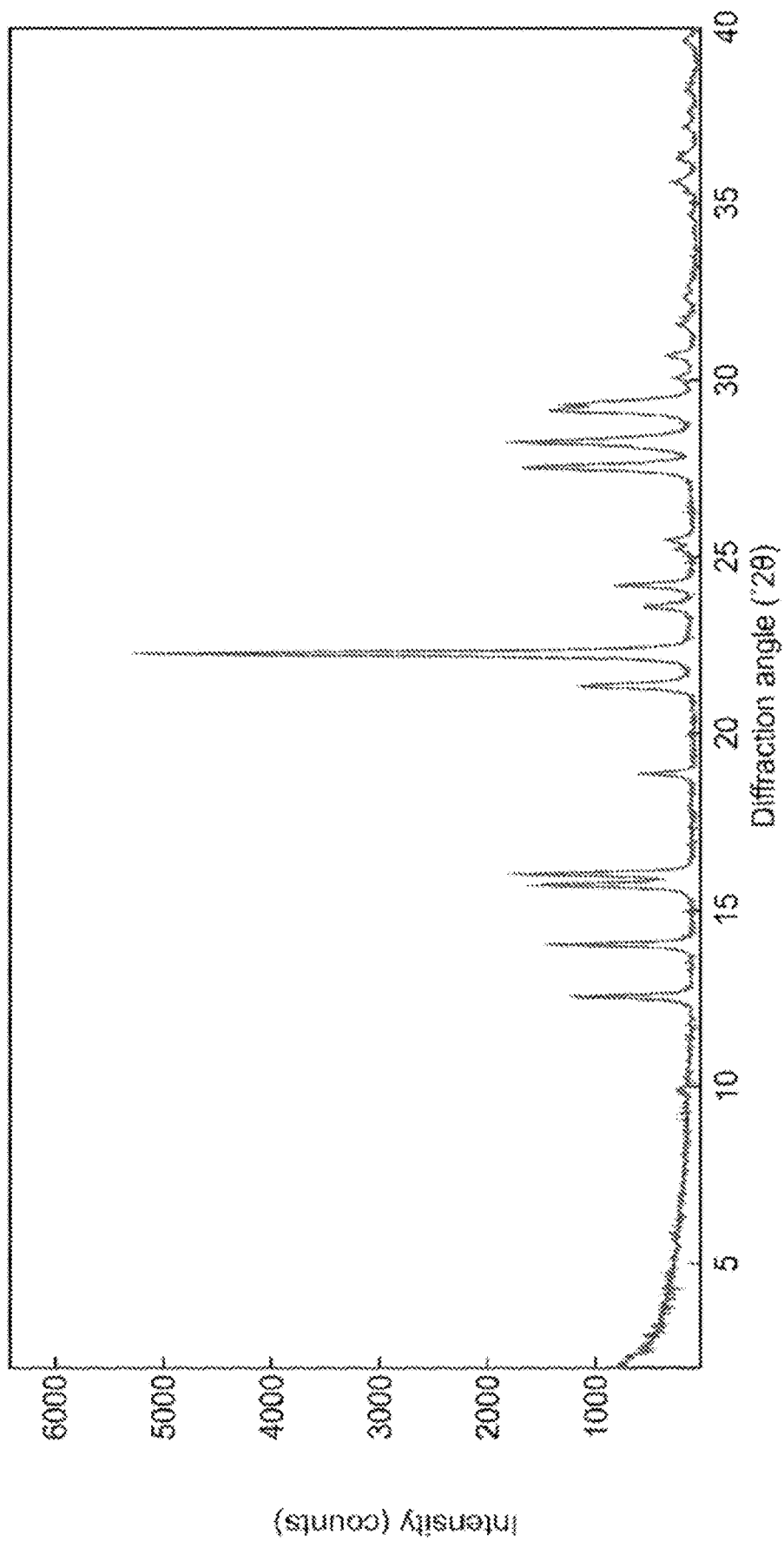
FIG. 13 illustrates an XRPD pattern of crystalline methylone hydrochloride (racemate), Form D.

In some embodiments, the crystalline form of methylone hydrochloride is Form D. In some embodiments, crystalline methylone hydrochloride Form D is characterized as having at least one of the following properties:
(a) an X-ray powder diffraction (XRPD) pattern substantially the same as shown in FIG. 13;
(b) an X-ray powder diffraction (XRPD) pattern with characteristic peaks at 12.5°±0.2 2-Theta, 14.0°±0.2 2-Theta, and 15.7°±0.2 2-Theta, and optionally with further characteristic peaks at 16.0°±0.2 2-Theta and 22.3°±0.2 2-Theta, and optionally with further one or more peaks at 27.5°±0.2 2-Theta, 28.2°±0.2 2-Theta, 29.1°±0.2 2-Theta, and 29.3°±0.2 2-Theta as measured with Cu Kα radiation;
(c) a DSC thermogram substantially similar to the one set forth in FIG. 25;
(d) a DSC thermogram with a first endotherm at about 238° C., a second endotherm at about 241° C.;
(e) a thermo-gravimetric analysis (TGA) substantially similar to the one set forth in FIG. 25; or
(f) combinations thereof.

In some embodiments, crystalline methylone hydrochloride Form D is characterized as having at least two of the properties selected from (a) to (e). In some embodiments, crystalline methylone hydrochloride Form D is characterized as having at least three of the properties selected from (a) to (e). In some embodiments, crystalline methylone hydrochloride Form D is characterized as having at least four of the properties selected from (a) to (e). In some embodiments, crystalline methylone hydrochloride Form D is characterized as having properties (a) to (e).

In some embodiments, crystalline methylone hydrochloride Form D has an X-ray powder diffraction (XRPD) pattern substantially the same as shown in FIG. 13. In some embodiments, crystalline methylone hydrochloride Form D has an X-ray powder diffraction (XRPD) pattern comprising characteristic peaks at 12.5°±0.2 2-Theta, 14.0°±0.2 2-Theta, and 15.7°±0.2 2-Theta as measured with Cu Kα radiation. In some embodiments, crystalline methylone hydrochloride Form D has an X-ray powder diffraction (XRPD) pattern further comprising characteristic peaks at 16.0°±0.2 2-Theta and 22.3°±0.2 2-Theta as measured with Cu Kα radiation. In some embodiments, crystalline methylone hydrochloride Form D has an X-ray powder diffraction (XRPD) pattern further comprising one or more peaks at 27.5°±0.2 2-Theta, 28.2°±0.2 2-Theta, 29.1°±0.2 2-Theta, and 29.3°±0.2 2-Theta as measured with Cu Kα radiation. In some embodiments, crystalline methylone hydrochloride Form D has a DSC thermogram substantially similar to the one set forth in FIG. 25. In some embodiments, crystalline methylone hydrochloride Form D has a DSC thermogram with a first endotherm at about 238° C., and a second endotherm at about 241° C. In some embodiments, crystalline methylone hydrochloride Form D has a thermogravimetric analysis (TGA) thermogram substantially similar to the one set forth in FIG. 25. In some embodiments, crystalline methylone hydrochloride Form D has an XRPD pattern substantially the same as shown in FIG. 13; a DSC thermogram substantially similar to the one set forth in FIG. 25; and optionally a TGA thermogram substantially similar to the one set forth in FIG. 25. In some embodiments, crystalline methylone hydrochloride Form D has an XRPD pattern comprising characteristic peaks at 12.5°±0.2 2-Theta, 14.0°±0.2 2-Theta, and 15.7°±0.2 2-Theta as measured with Cu Kα radiation; and a DSC thermogram with a first endotherm at about 238° C., and a second endotherm at about 241° C. In some embodiments, crystalline methylone hydrochloride Form D is non-hygroscopic. In some embodiments, crystalline methylone hydrochloride Form D is solvated. In some embodiments, crystalline methylone hydrochloride Form D is unsolvated. In some embodiments, crystalline methylone hydrochloride Form D is anhydrous.

In some embodiments, crystalline methylone hydrochloride Form D comprises hydrochloride salts of racemic methylone. In some embodiments, crystalline methylone hydrochloride Form D comprises (S)-methylone hydrochloride and (R)-methylone hydrochloride.

3.5 Crystalline (S)-Methylone Hydrochloride, Form A

Figure 45:
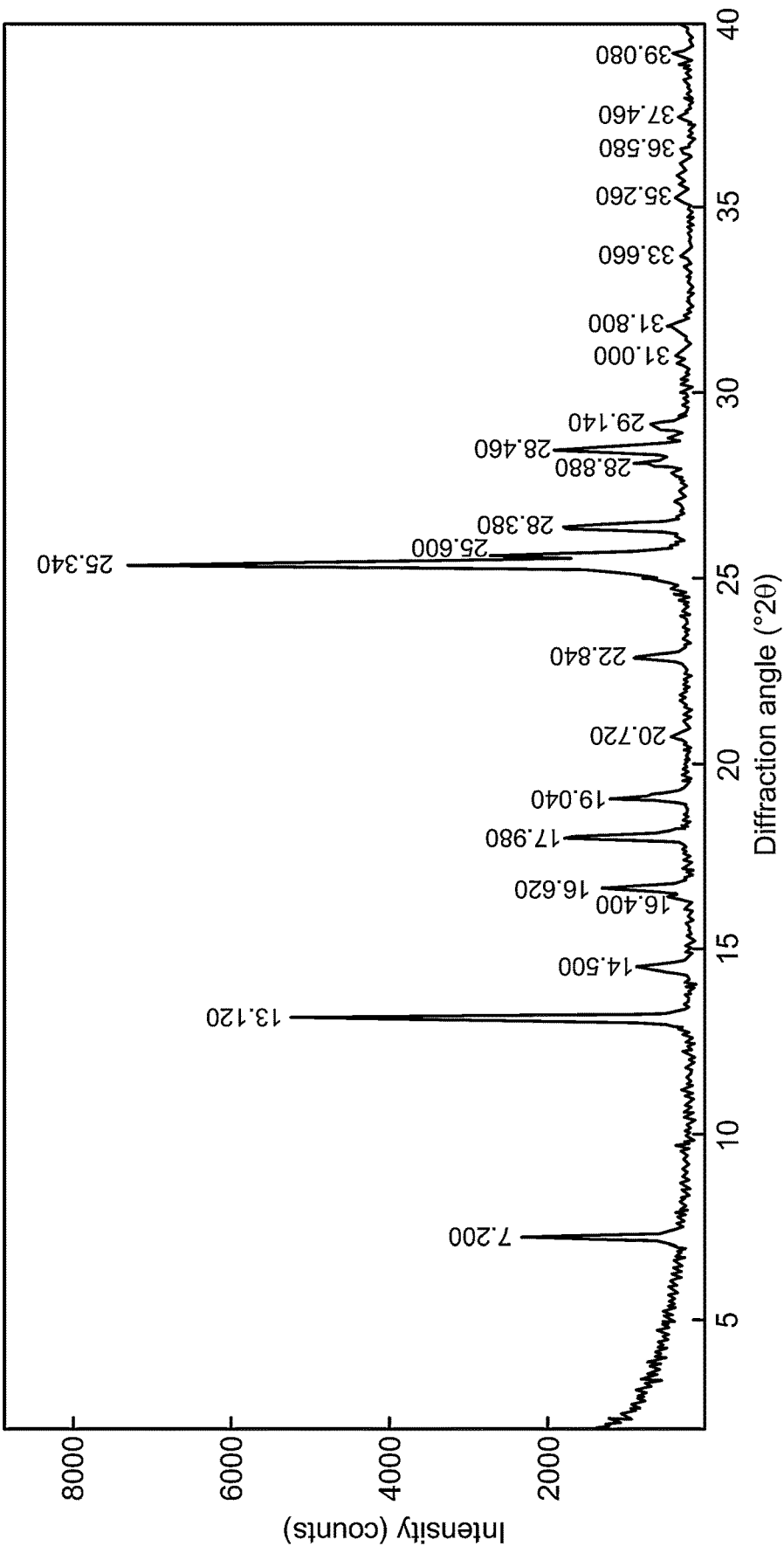
FIG. 45 provides an XRPD diffractogram of a crystalline (S)-methylone·hydrochloride, Form A.

In some embodiments, the crystalline form of (S)-methylone hydrochloride is Form A. In some embodiments, (S)-methylone hydrochloride Form A is characterized as having at least one of the following properties:
  (a) an X-ray powder diffraction (XRPD) pattern substantially the same as shown in FIG. 45;
  (b) an X-ray powder diffraction (XRPD) pattern with characteristic peaks at 7.2°±0.2 2-Theta, 13.1°±0.2 2-Theta, and 18.0°±0.2 2-Theta, and optionally with further characteristic peaks at 14.5°±0.2 2-Theta and 25.3°±0.2 2-Theta, and optionally with further one or more peaks at 16.6°±0.2 2-Theta, 19.0°±0.2 2-Theta, 25.6°±0.2 2-Theta, 26.4°±0.2 2-Theta, and 28.5°±0.2 2-Theta as measured with Cu Kα radiation; or
  (c) combinations thereof.

In some embodiments, crystalline (S)-methylone hydrochloride Form A has an X-ray powder diffraction (XRPD) pattern substantially the same as shown in FIG. 45. In some embodiments, crystalline (S)-methylone hydrochloride Form A has an X-ray powder diffraction (XRPD) pattern comprising characteristic peaks at 7.2°±0.2 2-Theta, 13.1°±0.2 2-Theta, and 18.0°±0.2 2-Theta as measured with Cu Kα radiation. In some embodiments, crystalline (S)-methylone hydrochloride Form A has an X-ray powder diffraction (XRPD) pattern further comprising characteristic peaks at 14.5°±0.2 2-Theta and 25.3°±0.2 2-Theta as measured with Cu Kα radiation. In some embodiments, crystalline (S)-methylone hydrochloride Form A has an X-ray powder diffraction (XRPD) pattern further comprising one or more peaks at 16.6°±0.2 2-Theta, 19.0°±0.2 2-Theta, 25.6°±0.2 2-Theta, 26.4°±0.2 2-Theta, and 28.5°±0.2 2-Theta as measured with Cu Kα radiation. In some embodiments, crystalline (S)-methylone hydrochloride Form A is non-hygroscopic. In some embodiments, crystalline (S)-methylone hydrochloride Form A is solvated. In some embodiments, crystalline (S)-methylone hydrochloride Form A is unsolvated. In some embodiments, crystalline (S)-methylone hydrochloride Form A is anhydrous.

In some embodiments, crystalline (S)-methylone hydrochloride Form A consists essentially of (S)-methylone hydrochloride.

3.6 Crystalline (S)-Methylone Hydrochloride, Form 2 (Form B)

Figure 40:
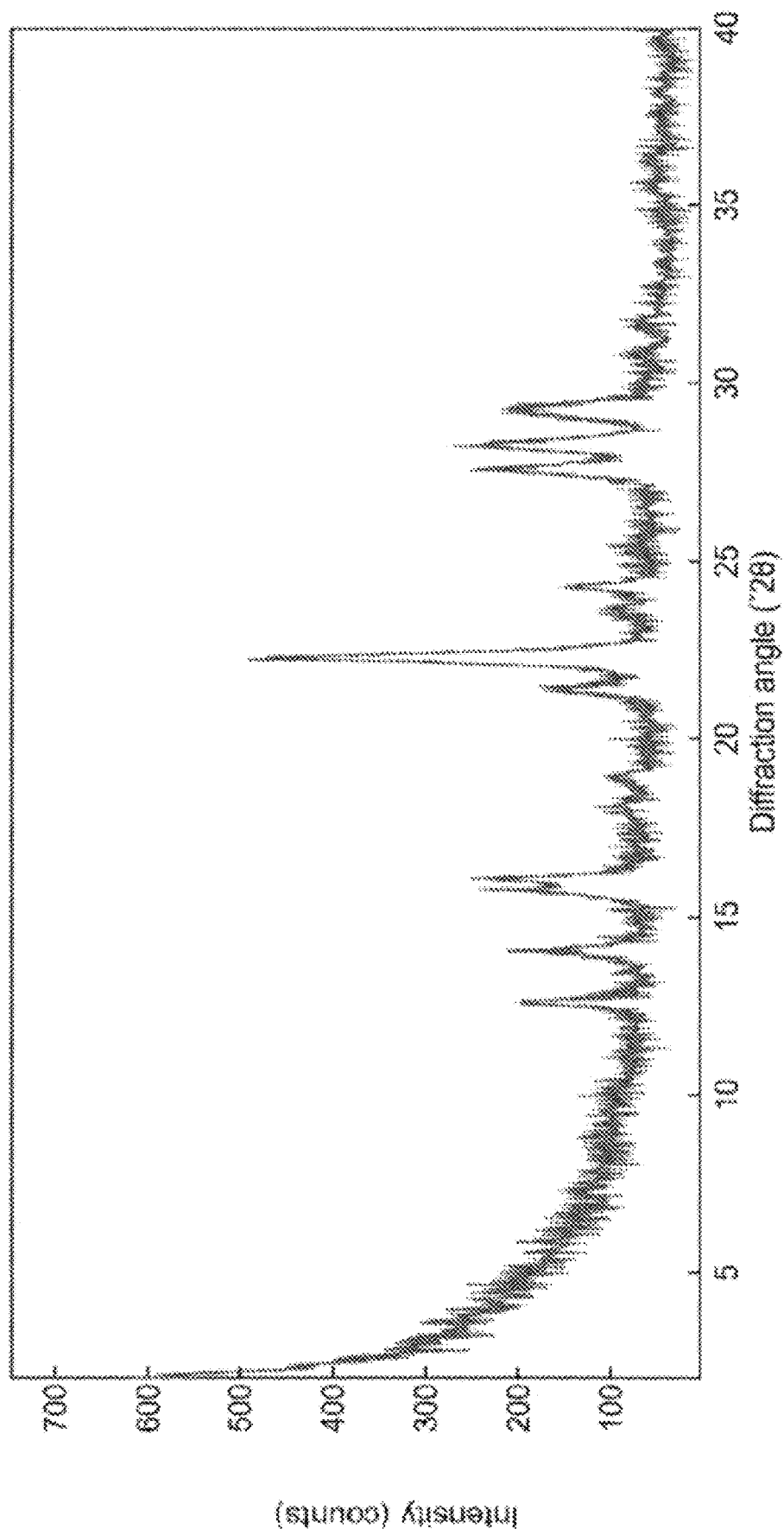
FIG. 40 provides an XRPD diffractogram of a crystalline (S)-methylone·hydrochloride Form 2 (Form B).

In some embodiments, the crystalline form of (S)-methylone hydrochloride is Form 2 (Form B). In some embodiments, (S)-methylone hydrochloride Form 2 (Form B) is characterized as having at least one of the following properties:
  (a) an X-ray powder diffraction (XRPD) pattern substantially the same as shown in FIG. 40;
  (b) an X-ray powder diffraction (XRPD) pattern with characteristic peaks at 12.6°±0.2 2-Theta, 14.0°±0.2 2-Theta, and 16.1°±0.2 2-Theta, and optionally with further characteristic peaks at 15.8°±0.2 2-Theta and 22.2°±0.2 2-Theta, and optionally with further one or more peaks at 21.5°±0.2 2-Theta, 24.2°±0.2 2-Theta, 27.5°±0.2 2-Theta, 28.2°±0.2 2-Theta, and 29.2°±0.2 2-Theta as measured with Cu Kα radiation; or
  (c) combinations thereof.

In some embodiments, crystalline (S)-methylone hydrochloride Form B has an X-ray powder diffraction (XRPD) pattern substantially the same as shown in FIG. 40. In some embodiments, crystalline (S)-methylone hydrochloride Form B has an X-ray powder diffraction (XRPD) pattern comprising characteristic peaks at 12.6°±0.2 2-Theta, 14.0°±0.2 2-Theta, and 16.1°±0.2 2-Theta as measured with Cu Kα radiation. In some embodiments, crystalline (S)-methylone hydrochloride Form B has an X-ray powder diffraction (XRPD) pattern further comprising characteristic peaks at 15.8°±0.2 2-Theta and 22.2°±0.2 2-Theta as measured with Cu Kα radiation. In some embodiments, crystalline (S)-methylone hydrochloride Form B has an X-ray powder diffraction (XRPD) pattern further comprising one or more peaks at 21.5°±0.2 2-Theta, 24.2°±0.2 2-Theta, 27.5°±0.2 2-Theta, 28.2°±0.2 2-Theta, and 29.2°±0.2 2-Theta as measured with Cu Kα radiation. In some embodiments, crystalline (S)-methylone hydrochloride Form B is non-hygroscopic. In some embodiments, crystalline (S)-methylone hydrochloride Form B is solvated. In some embodiments, crystalline (S)-methylone hydrochloride Form B is unsolvated. In some embodiments, crystalline (S)-methylone hydrochloride Form B is anhydrous.

In some embodiments, crystalline (S)-methylone hydrochloride Form B consists essentially of (S)-methylone hydrochloride.

3.7 Crystalline (S)-Methylone Hydrochloride, Form C

In some embodiments, the crystalline form of (S)-methylone hydrochloride is Form C. In some embodiments, crystalline (S)-methylone hydrochloride Form C is characterized as having an X-ray powder diffraction (XRPD) pattern with characteristic peaks at 6.2°±0.2 2-Theta, 14.4°±0.2 2-Theta, and 20.0°±0.2 2-Theta, and optionally with further characteristic peaks at 17.2°±0.2 2-Theta and 21.3°±0.2 2-Theta, and optionally with further one or more peaks at 19.2°±0.2 2-Theta, 24.7°±0.2 2-Theta, 24.9°±0.2 2-Theta, 28.7°±0.2 2-Theta, 29.0°±0.2 2-Theta, 29.4°±0.2 2-Theta, and 29.8°±0.2 2-Theta as measured with Cu Kα radiation.

In some embodiments, crystalline (S)-methylone hydrochloride Form C has an X-ray powder diffraction (XRPD) pattern comprising characteristic peaks at 6.2°±0.2 2-Theta, 14.4°±0.2 2-Theta, and 20.0°±0.2 2-Theta as measured with Cu Kα radiation. In some embodiments, crystalline (S)-methylone hydrochloride Form C has an X-ray powder diffraction (XRPD) pattern further comprising characteristic peaks at 17.2°±0.2 2-Theta and 21.3°±0.2 2-Theta as measured with Cu Kα radiation. In some embodiments, crystalline (S)-methylone hydrochloride Form C has an X-ray powder diffraction (XRPD) pattern further comprising one or more peaks at 19.2°±0.2 2-Theta, 24.7°±0.2 2-Theta, 24.9°±0.2 2-Theta, 28.7°±0.2 2-Theta, 29.0°±0.2 2-Theta, 29.4°±0.2 2-Theta, and 29.8°±0.2 2-Theta as measured with Cu Kα radiation. In some embodiments, crystalline (S)-methylone hydrochloride Form C is non-hygroscopic. In some embodiments, crystalline (S)-methylone hydrochloride Form C is solvated. In some embodiments, crystalline (S)-methylone hydrochloride Form C is unsolvated. In some embodiments, crystalline (S)-methylone hydrochloride Form C is anhydrous.

In some embodiments, crystalline (S)-methylone hydrochloride Form C consists essentially of (S)-methylone hydrochloride.

Preparation of Crystalline Methylone Hydrochloride Salts

In some embodiments, crystalline forms of methylone hydrochloride are prepared as outlined in the Examples. It is noted that solvents, temperatures and other reaction conditions presented herein may vary.

In certain embodiments, provided herein are methods for making a solid form of a methylone hydrochloride, comprising 1) obtaining a saturated solution of a methylone hydrochloride in a solvent at a first temperature (e.g., about 50° C.); 2) adding an anti-solvent into the saturated solution at the first temperature; 3) cooling down to a second temperature (e.g., about −5° C. to room temperature); 4) collecting a solid if there is precipitation, and evaporating the solvent to collect a solid if there is no precipitation; and 5) optionally drying. In certain embodiments, the ratio by volume of solvent and anti-solvent is about 1:9. In certain embodiments, the ratio by volume of solvent and anti-solvent is about 1:4. In certain embodiments, the ratio by volume of solvent and anti-solvent is about 1:2. In certain embodiments, the ratio by volume of solvent and anti-solvent is about 1:1.

In certain embodiments, provided herein are methods for making a solid form of a methylone hydrochloride, comprising 1) obtaining a slurry of a methylone hydrochloride in a solvent, or mixtures of solvents, at a first temperature (e.g., about room temperature to 50° C.); 2) stirring the slurry for 12 to 48 hours; 3) collecting the solid by filtration; and 4) optionally drying.

In another embodiment, crystalline methylone hydrochloride Form A, is substantially pure. In certain embodiments, the substantially pure crystalline methylone hydrochloride Form A, is substantially free of other solid forms, e.g., amorphous solid. In certain embodiments, the purity of the substantially pure crystalline methylone hydrochloride Form A, is no less than about 95%, no less than about 96%, no less than about 97%, no less than about 98%, no less than about 98.5%, no less than about 99%, no less than about 99.5%, or no less than about 99.8%.

In another embodiment, crystalline methylone hydrochloride Form B, is substantially pure. In certain embodiments, the substantially pure crystalline methylone hydrochloride Form B, is substantially free of other solid forms, e.g., amorphous solid. In certain embodiments, the purity of the substantially pure crystalline methylone hydrochloride Form B, is no less than about 95%, no less than about 96%, no less than about 97%, no less than about 98%, no less than about 98.5%, no less than about 99%, no less than about 99.5%, or no less than about 99.8%.

In another embodiment, crystalline methylone hydrochloride Form C, is substantially pure. In certain embodiments, the substantially pure crystalline methylone hydrochloride Form C, is substantially free of other solid forms, e.g., amorphous solid. In certain embodiments, the purity of the substantially pure crystalline methylone hydrochloride Form C, is no less than about 95%, no less than about 96%, no less than about 97%, no less than about 98%, no less than about 98.5%, no less than about 99%, no less than about 99.5%, or no less than about 99.8%.

In another embodiment, crystalline methylone hydrochloride Form D, is substantially pure. In certain embodiments, the substantially pure crystalline methylone hydrochloride Form D, is substantially free of other solid forms, e.g., amorphous solid. In certain embodiments, the purity of the substantially pure crystalline methylone hydrochloride Form D, is no less than about 95%, no less than about 96%, no less than about 97%, no less than about 98%, no less than about 98.5%, no less than about 99%, no less than about 99.5%, or no less than about 99.8%.

Suitable Solvents

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. In some embodiments, solvents disclosed herein are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents Q3C(R6)," (October 2016).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cumene, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethylene glycol, formamide, hexane, methanol, 2-methoxyethanol, methylbutyl ketone, methylcyclohexane, methylisobutylketone, N-methylpyrrolidone, nitromethane, pyridine, sulfolane, tetrahydrofuran, tetralin, toluene, 1,1,2-trichloroethene and xylene.

Class 3 solvents, which possess low toxicity, include: acetic acid, acetone, anisole, 1-butanol, 2-butanol, butyl acetate, tert-butyl methyl ether (MTBE), dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, 2-methyl-1-propanol, pentane, 1-pentanol, 1-propanol, 2-propanol, propyl acetate, and triethylamine.

Residual solvents in active pharmaceutical ingredients (APIs) originate from the manufacture of APIs. In some cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process.

In some embodiments, crystalline forms of methylone hydrochloride described herein comprise an organic solvent(s). In some embodiments, crystalline forms of methylone hydrochloride described herein comprise a residual amount of an organic solvent(s). In some embodiments, crystalline forms of methylone hydrochloride described herein comprise a residual amount of a Class 3 solvent. In some embodiments, the organic solvent is a Class 3 solvent. In some embodiments, the Class 3 solvent is selected from the group consisting of acetic acid, acetone, anisole, 1-butanol, 2-butanol, butyl acetate, tert-butyl methyl ether (MTBE), dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, 2-methyl-1-propanol, pentane, 1-pentanol, 1-propanol, 2-propanol, propyl acetate, and triethylamine. In some embodiments, the Class 3 solvent is selected from the group consisting of acetone, ethyl acetate, isopropyl acetate, tert-butyl methyl ether, heptane, isopropanol, and ethanol.

In some embodiments, crystalline forms of methylone hydrochloride described herein comprise a residual amount of a Class 2 solvent. In some embodiments, the organic solvent is a Class 2 solvent. In some embodiments, the Class 2 solvent is selected from the group consisting of acetonitrile, chlorobenzene, chloroform, cumene, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethylene glycol, formamide, hexane, methanol, 2-methoxyethanol, methylbutyl ketone, methylcyclohexane, methylisobutylketone, N-methylpyrrolidone, nitromethane, pyridine, sulfolane, tetrahydrofuran, tetralin, toluene, 1,1,2-trichloroethene and xylene. In some embodiments, the Class 2 solvent is selected from the group consisting of acetonitrile, tetrahydrofuran, and toluene. In some embodiments, the Class 2 solvent is acetonitrile.

In some embodiments, crystalline forms of methylone hydrochloride described herein comprise a residual amount of a solvent for which no adequate toxicological data were found. In some embodiments, the organic solvent is a solvent for which no adequate toxicological data were found. In some embodiments, the solvent is selected from the group consisting of 2-butanone and 2-methyltetrahydrofuran.

4. Solid Forms of Additional Methylone Salts

In another aspect, also provided herein are solid forms of methylone salts in addition to hydrochlorides. Also disclosed are methods for making the solid forms of the methylone salts solid forms and method of administering these the methylone salts solid forms.

In some embodiments, the salt form of methylone may be formed from a suitable pharmaceutically acceptable acid, including, without limitation, inorganic acids such as hydrobromic acid, sulfuric acid, nitric acid, phosphoric acid, and the like, as well as organic acids such as formic acid, acetic acid, trifluoroacetic acid, propionic acid, glycolic acid, pyruvic acid, oxalic acid, maleic acid, malonic acid, succinic acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid and the like.

In other embodiments, the methylone salt may be formed from a suitable pharmaceutically acceptable base, including, without limitation, inorganic bases such as sodium, potassium, lithium, ammonium, calcium, magnesium, iron, zinc, copper, manganese, aluminum salts and the like. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, tris(hydroxymethyl)aminomethane (Tris), ethanolamine, 2-dimethylaminoethanol, 2-diethylaminoethanol, dicyclohexylamine, lysine, arginine, histidine, caffeine, procane, hydrabamine, choline, betaine, ethylenediamine, glucosamine, methylgucamine, theobromine, puines, piperazine, piperidine, N-ethylpiperidine, polyamie resins, and the like. Additional information concerning pharmaceutically acceptable salts can be found in, for example, S. M. Berge, et al., "Pharmaceutical Salts," J. Pharm. Sci., 1977; 66:1-19 which is incorporated herein by reference.

In some embodiments, the disclosed methylone salt may be formed using an acid from Table 1.

TABLE 1

| | |
|---|---|
| naphthalene-1,5-disulfonic acid | citric acid |
| sulfuric acid | d-glucuronic acid |
| ethane-1,2-disulfonic acid | lactobionic acid |
| p-toluenesulfonic acid | D-glucoheptonic acid |
| thiocyanic acid | (-)-L-pyroglutamic acid |
| methanesulfonic acid | L-malic acid |
| dodecylsulfuric acid | hippuric acid |
| naphthalene-2-sulfonic acid | D-gluconic acid |
| benzenesulfonic acid | D,L-lactic acid |
| oxalic acid | oleic acid |
| glycerophosphoric acid | succinic acid |
| ethanesulfonic acid, 2-hydroxy | glutaric acid |
| L-aspartic acid | cinnamic acid |
| maleic acid | adipic acid |
| phosphoric acid | sebacic acid |
| ethanesulfonic acid | (+)-camphoric acid |
| glutamic acid | acetic acid |
| pamoic (embonic) acid | nicotinic acid |
| glutaric acid, 2-oxo- | isobutyric acid |
| 2-naphthoic acid, 1-hydroxy | propionic acid |
| malonic acid | lauric acid |
| gentisic acid | stearic acid |
| L-tartaric acid | orotic acid |
| Fumaric acid | carbonic acid |
| galactaric (mucic) acid | xinafoic acid |

The acid salts of methylone disclosed herein can have any suitable stoichiometric ratio of acid to methylone. In one embodiment, the molar ratio of acid to methylone is from about 0.4 to about 2.2, such as forms wherein the salt has a stoichiometric ratio of acid to methylone of from about 0.5 to about 2, such as about 0.5, about 1 or about 2.

Solid Forms

Embodiments of the salt form of methylone of the present disclosure are in a solid form. The salt form may be a crystalline form or an amorphous form. In some embodiments, the salt form is a crystalline form, and may be a polymorph of the crystalline salt form. A person of ordinary skill in the art understands that salt forms of methylone may exist in more than one crystal form. Such different forms are referred to as polymorphs. In some embodiments, the disclosed compounds are particular polymorphs of the disclosed methylone salts.

In some embodiments, the salt form of methylone disclosed herein is selected to be a crystalline form, such as a particular polymorph of a crystalline form of methylone salt that provides one or more desired properties. In one embodiment, the crystalline form offers advantages over the amorphous form of the molecule. In another embodiment, the disclosed polymorph offers improved properties as compared to another polymorph of methylone. The one or more desired properties may include, but are not limited to, physical properties, including but not limited to, melting point, glass transition temperature, flowability, and/or stability, such as thermal stability, mechanical stability, shelf life, stability against polymorphic transition, etc.; chemical properties, such as, but not limited to, hygroscopic properties, solubility in water and/or organic solvents, reactivity, compatibility with excipients and/or delivery vehicles; and/or pharmacokinetic properties, such as, but not limited to, bioavailability, absorption, distribution, metabolism, excretion, toxicity including cytotoxicity, dissolution rate, and/or half-life.

The desired polymorph may be produced by techniques known to persons of ordinary skill in the art. Such techniques include, but are not limited to, crystallization in particular solvents and/or at particular temperatures, supersaturation, using a precipitation agent, such as a salt, glycol, alcohol, etc., co-crystallization, lyophilization, spray drying, freeze drying, and/or complexing with an inert agent.

Techniques to identify a particular solid form of methylone are known to persons of ordinary skill in the art, and include, but are not limited to, X-ray crystallography, X-ray diffraction, electron crystallography, powder diffraction, including X-ray, neutron, or electron diffraction, X-ray fiber diffraction, small-angle X-ray scattering, and/or melting point.

Crystalline Methylone Maleate

Figure 30:
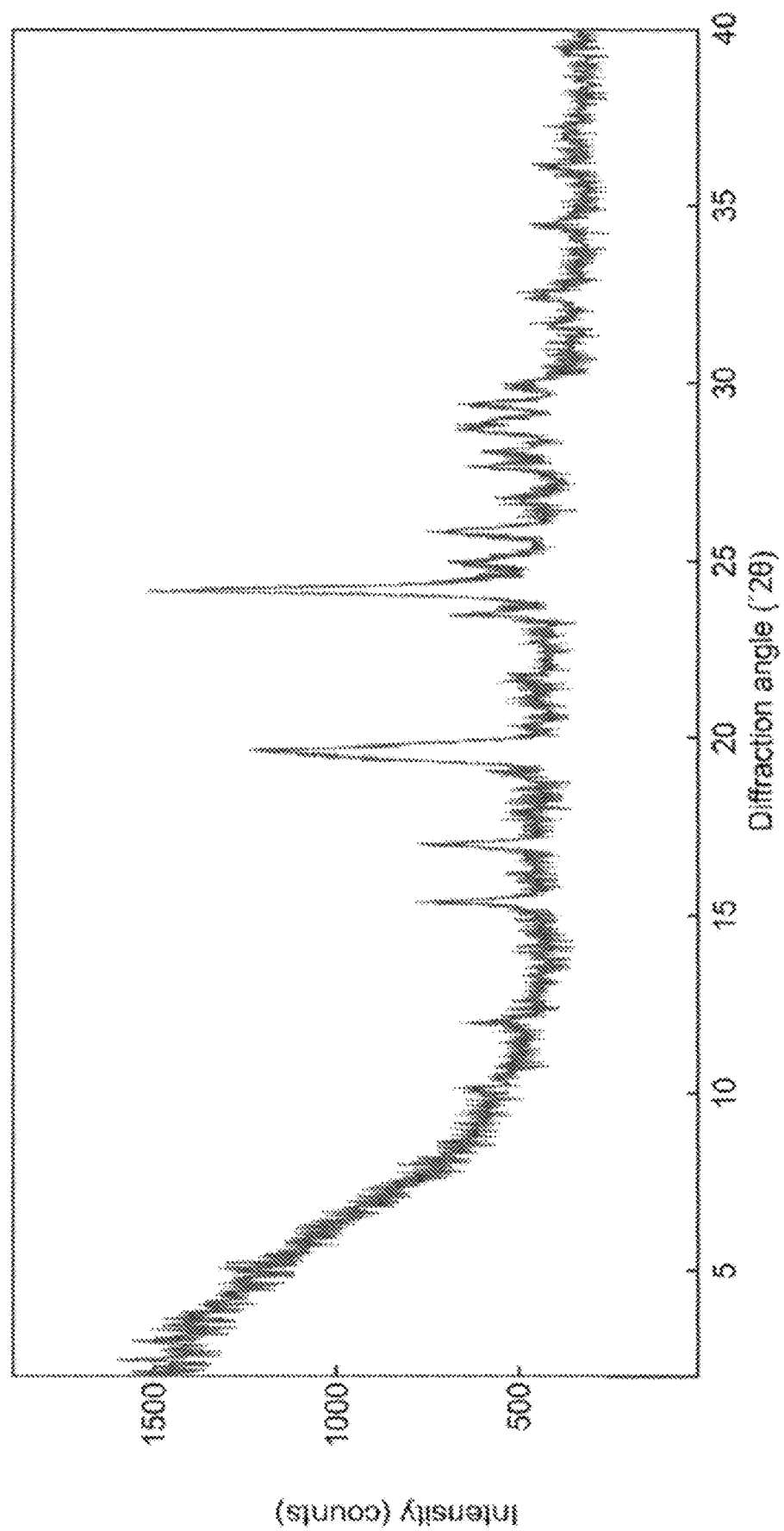
FIG. 30 provides an XRPD diffractogram of a crystalline methylone·maleate (racemate).

In some embodiments, crystalline methylone maleate is characterized as having at least one of the following properties:
(a) an X-ray powder diffraction (XRPD) pattern substantially the same as shown in FIG. 30;
(b) an X-ray powder diffraction (XRPD) pattern with characteristic peaks at 15.4°±0.2 2-Theta, 17.0°±0.2 2-Theta, and 19.7°±0.2 2-Theta, and optionally with further characteristic peaks at 12.0°±0.2 2-Theta and 24.1°±0.2 2-Theta, and optionally with further one or more peaks at 10.1°±0.2 2-Theta, 23.5°±0.2 2-Theta, 24.9°±0.2 2-Theta, 25.8°±0.2 2-Theta, 28.7°±0.2 2-Theta, or 29.4°±0.2 2-Theta as measured with Cu Kα radiation; or
(c) combinations thereof.

In some embodiments, crystalline methylone·maleate has an X-ray powder diffraction (XRPD) pattern substantially the same as shown in FIG. 30. In some embodiments, crystalline methylone·maleate has an X-ray powder diffraction (XRPD) pattern comprising characteristic peaks at 15.4°±0.2 2-Theta, 17.0°±0.2 2-Theta, and 19.7°±0.2 2-Theta as measured with Cu Kα radiation. In some embodiments, crystalline methylone·maleate has an X-ray powder diffraction (XRPD) pattern further comprising characteristic peaks at 12.0°±0.2 2-Theta and 24.1°±0.2 2-Theta as measured with Cu Kα radiation. In some embodiments, crystalline methylone·maleate has an X-ray powder diffraction (XRPD) pattern further comprising one or more peaks at 10.1°±0.2 2-Theta, 23.5°±0.2 2-Theta, 24.9°±0.2 2-Theta, 25.8°±0.2 2-Theta, 28.7°±0.2 2-Theta, or 29.4°±0.2 2-Theta as measured with Cu Kα radiation. In some embodiments, crystalline methylone·maleate is non-hygroscopic. In some embodiments, crystalline methylone·maleate is solvated. In some embodiments, crystalline methylone·maleate is unsolvated. In some embodiments, crystalline methylone·maleate is anhydrous.

In some embodiments, crystalline methylone·maleate comprises maleate salts of racemic methylone. In some embodiments, crystalline methylone·maleate comprises (S)-methylone maleate and (R)-methylone maleate. In some embodiments, crystalline methylone·maleate consists essentially of (S)-methylone maleate. In some embodiments, crystalline methylone·maleate consists essentially of (R)-methylone maleate.

Co-Crystal of (S)-Methylone and Gentisic Acid (1:1 Stoichiometry)

Figure 43:
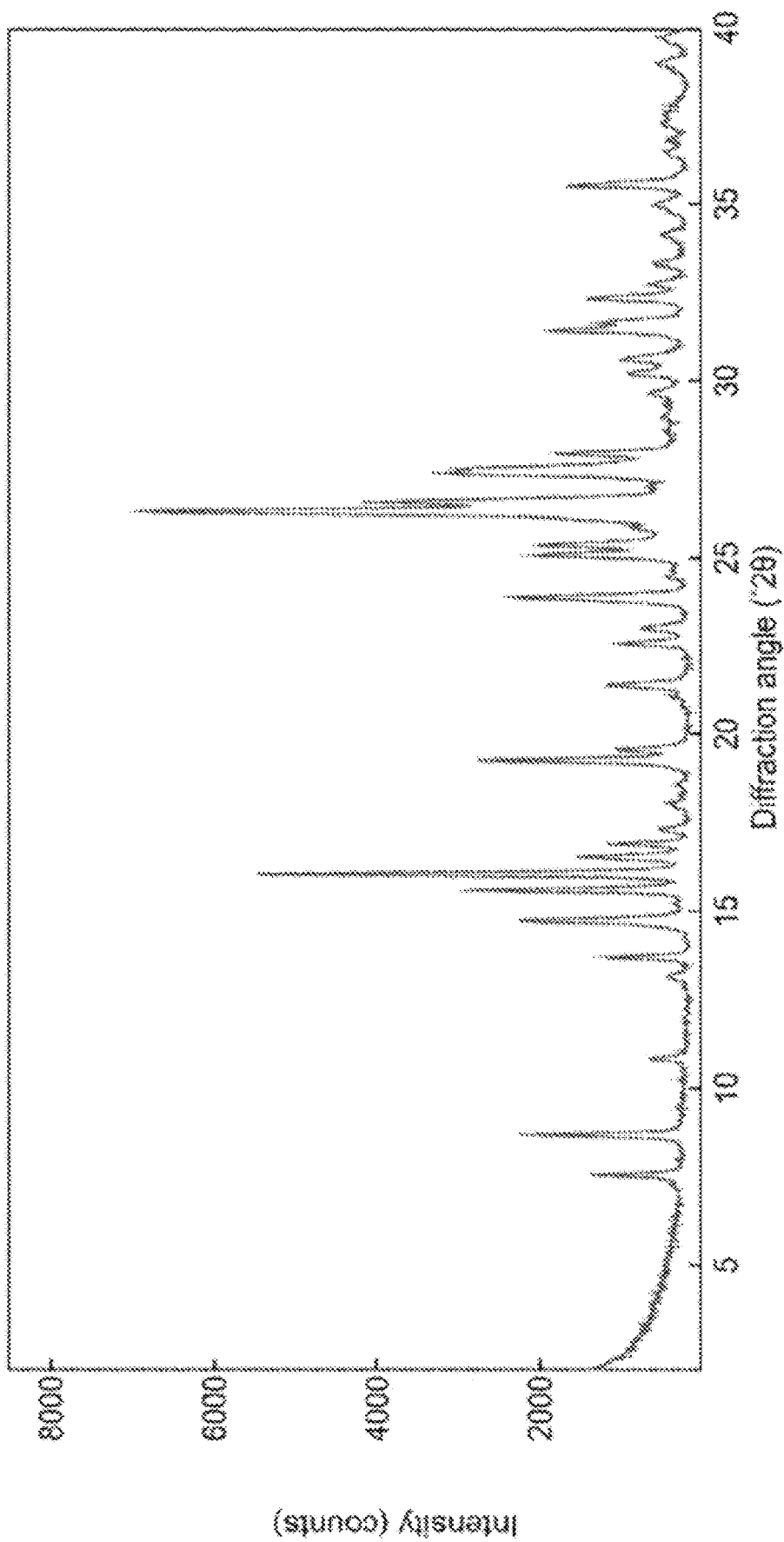
FIG. 43 illustrates an XRPD diffractogram of a crystalline (S)-methylone:gentisic acid (1:1 stoichiometry) produced from co-crystal screen experiments.

In some embodiments, co-crystalline of (S)-methylone and gentisic acid (1:1 stoichiometry) is characterized as having at least one of the following properties:
(a) an X-ray powder diffraction (XRPD) pattern substantially the same as shown in FIG. 43;
(b) an X-ray powder diffraction (XRPD) pattern with characteristic peaks at 7.5°±0.2 2-Theta, 8.7°±0.2 2-Theta, and 10.8°±0.2 2-Theta, and optionally with further characteristic peaks at 14.7°±0.2 2-Theta and 16.1°±0.2 2-Theta, and optionally with further one or more peaks at 15.6°±0.2 2-Theta, 19.3°±0.2 2-Theta, 23.9°±0.2 2-Theta, 26.3°±0.2 2-Theta, 26.6°±0.2 2-Theta, and 27.4°±0.2 2-Theta as measured with Cu Kα radiation; or
(c) combinations thereof.

In some embodiments, co-crystalline of (S)-methylone and gentisic acid (1:1 stoichiometry) has an X-ray powder diffraction (XRPD) pattern substantially the same as shown in FIG. 43. In some embodiments, co-crystalline of (S)-methylone and gentisic acid (1:1 stoichiometry) has an X-ray powder diffraction (XRPD) pattern comprising characteristic peaks at 7.5°±0.2 2-Theta, 8.7°±0.2 2-Theta, and 10.8°±0.2 2-Theta as measured with Cu Kα radiation. In some embodiments, co-crystalline of (S)-methylone and gentisic acid (1:1 stoichiometry) has an X-ray powder diffraction (XRPD) pattern further comprising characteristic peaks at 14.7°±0.2 2-Theta and 16.1°±0.2 2-Theta as measured with Cu Kα radiation. In some embodiments, co-crystalline of (S)-methylone and gentisic acid (1:1 stoichiometry) has an X-ray powder diffraction (XRPD) pattern further comprising one or more peaks at 15.6°±0.2 2-Theta, 19.3°±0.2 2-Theta, 23.9°±0.2 2-Theta, 26.3°±0.2 2-Theta, 26.6°±0.2 2-Theta, and 27.4°±0.2 2-Theta as measured with Cu Kα radiation. In some embodiments, co-crystalline of (S)-methylone and gentisic acid (1:1 stoichiometry) is non-hygroscopic. In some embodiments, co-crystalline of (S)-methylone and gentisic acid (1:1 stoichiometry) is solvated. In some embodiments, co-crystalline of (S)-methylone and gentisic acid (1:1 stoichiometry) is unsolvated. In some embodiments, co-crystalline of (S)-methylone and gentisic acid (1:1 stoichiometry) is anhydrous.

Figure 44:
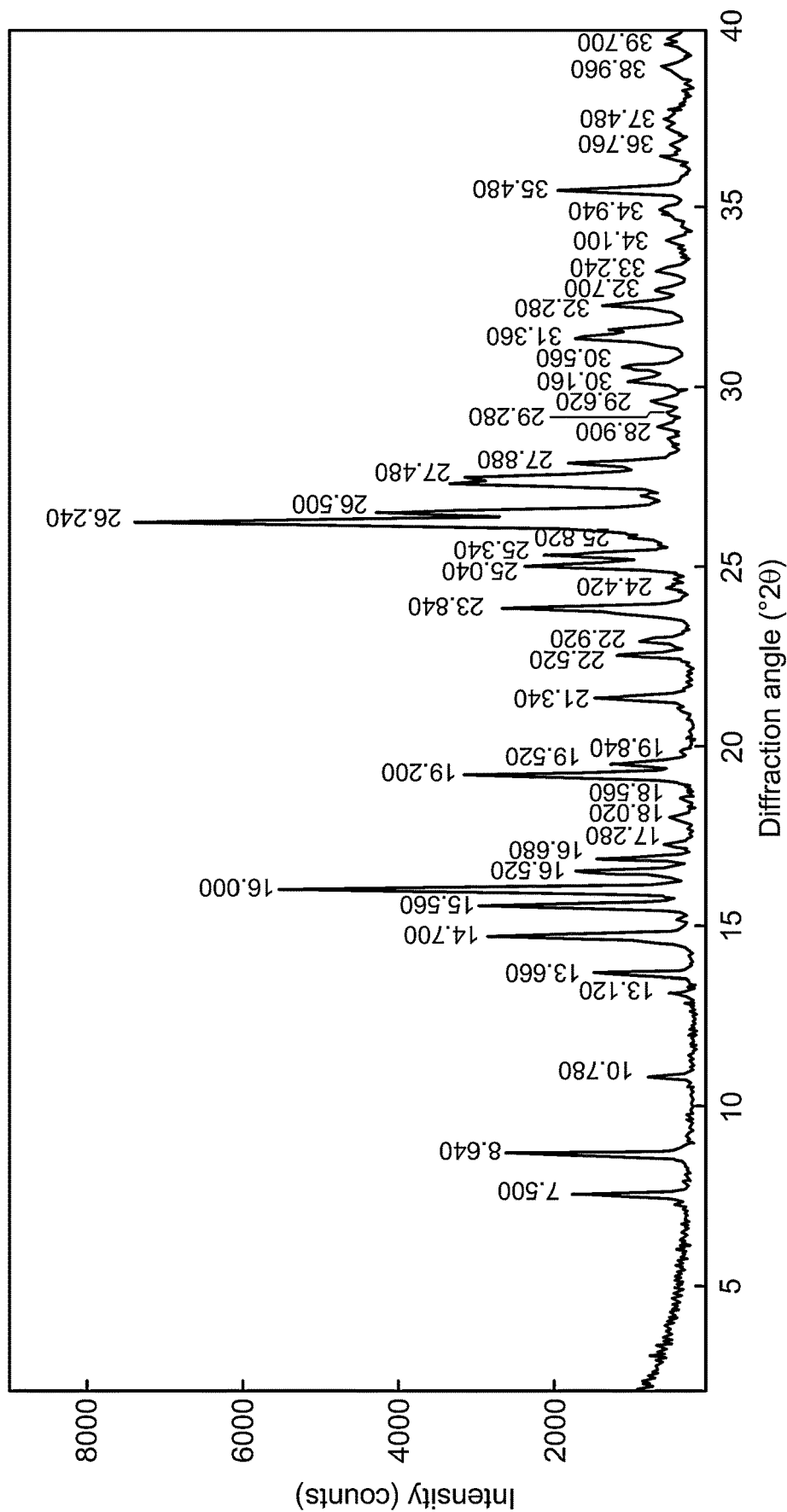
FIG. 44 illustrates an XRPD diffractogram of a crystalline (S)-methylone:gentisic acid (1:1 stoichiometry) produced from co-crystal screen experiments.

In some embodiments, co-crystalline of (S)-methylone and gentisic acid (1:1 stoichiometry) is characterized as having at least one of the following properties:
(a) an X-ray powder diffraction (XRPD) pattern substantially the same as shown in FIG. 44;
(b) an X-ray powder diffraction (XRPD) pattern with characteristic peaks at 7.5°±0.2 2-Theta, 8.6°±0.2 2-Theta, and 10.8°±0.2 2-Theta, and optionally with further characteristic peaks at 14.7°±0.2 2-Theta and 16.0°±0.2 2-Theta, and optionally with further one or more peaks at 15.6°±0.2 2-Theta, 19.2°±0.2 2-Theta, 23.8°±0.2 2-Theta, 26.2°±0.2 2-Theta, 26.5°±0.2 2-Theta, 27.3°±0.2 2-Theta and 27.5°±0.2 2-Theta as measured with Cu Kα radiation; or
(c) combinations thereof.

In some embodiments, co-crystalline of (S)-methylone and gentisic acid (1:1 stoichiometry) has an X-ray powder diffraction (XRPD) pattern substantially the same as shown in FIG. 44. In some embodiments, co-crystalline of (S)-methylone and gentisic acid (1:1 stoichiometry) has an X-ray powder diffraction (XRPD) pattern comprising characteristic peaks at 7.5°±0.2 2-Theta, 8.6°±0.2 2-Theta, and 10.8°±0.2 2-Theta as measured with Cu Kα radiation. In some embodiments, co-crystalline of (S)-methylone and gentisic acid (1:1 stoichiometry) has an X-ray powder diffraction (XRPD) pattern further comprising characteristic peaks at 14.7°±0.2 2-Theta and 16.0°±0.2 2-Theta as measured with Cu Kα radiation. In some embodiments, co-crystalline of (S)-methylone and gentisic acid (1:1 stoichiometry) has an X-ray powder diffraction (XRPD) pattern further comprising one or more peaks at 15.6°±0.2 2-Theta, 19.2°±0.2 2-Theta, 23.8°±0.2 2-Theta, 26.2°±0.2 2-Theta, 26.5°±0.2 2-Theta, 27.3°±0.2 2-Theta and 27.5°±0.2 2-Theta as measured with Cu Kα radiation. In some embodiments, co-crystalline of (S)-methylone and gentisic acid (1:1 stoichiometry) is non-hygroscopic. In some embodiments, co-crystalline of (S)-methylone and gentisic acid (1:1 stoichiometry) is solvated. In some embodiments, co-crystalline of (S)-methylone and gentisic acid (1:1 stoichiometry) is unsolvated. In some embodiments, co-crystalline of (S)-methylone and gentisic acid (1:1 stoichiometry) is anhydrous.

Figure 47:
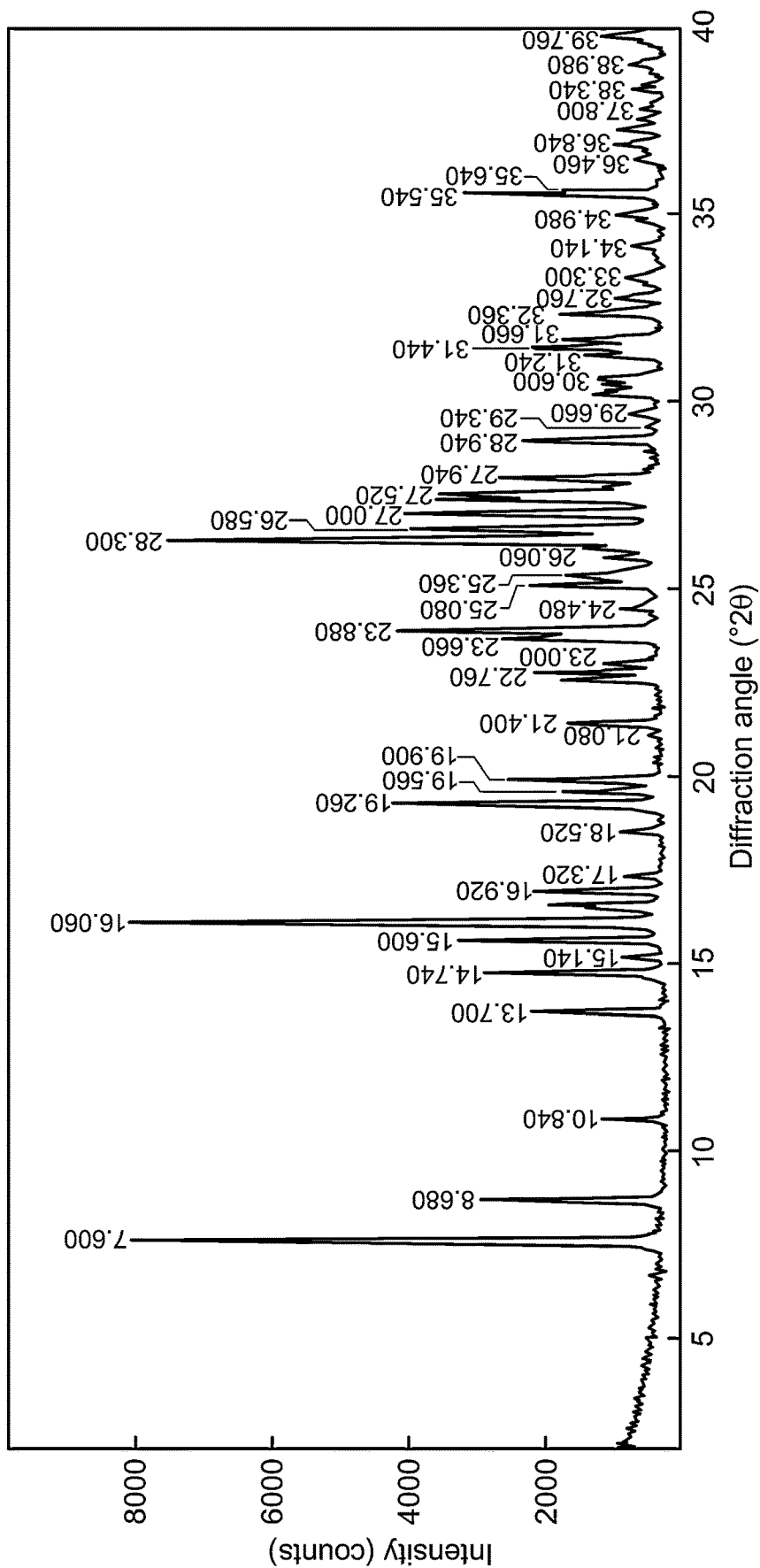
FIG. 47 illustrates an XRPD diffractogram of a crystalline (S)-methylone:gentisic acid (1:1 stoichiometry) produced from a solution-based preparation method.

In some embodiments, co-crystalline of (S)-methylone and gentisic acid (1:1 stoichiometry) has an X-ray powder diffraction (XRPD) pattern substantially the same as shown in FIG. 47. In some embodiments, co-crystalline of (S)-methylone and gentisic acid (1:1 stoichiometry) has an X-ray powder diffraction (XRPD) pattern comprising characteristic peaks at 7.6°±0.2 2-Theta, 8.7°±0.2 2-Theta, and 10.8°±0.2 2-Theta as measured with Cu Kα radiation. In some embodiments, co-crystalline of (S)-methylone and gentisic acid (1:1 stoichiometry) has an X-ray powder diffraction (XRPD) pattern further comprising characteristic peaks at 14.7°±0.2 2-Theta and 16.1°±0.2 2-Theta as measured with Cu Kα radiation. In some embodiments, co-crystalline of (S)-methylone and gentisic acid (1:1 stoichiometry) has an X-ray powder diffraction (XRPD) pattern further comprising one or more peaks at 15.6°±0.2 2-Theta, 19.3°±0.2 2-Theta, 23.9°±0.2 2-Theta, 26.3°±0.2 2-Theta, 26.6°±0.2 2-Theta, 27.0°±0.2 2-Theta and 27.5°±0.2 2-Theta as measured with Cu Kα radiation. In some embodiments, co-crystalline of (S)-methylone and gentisic acid (1:1 stoichiometry) is non-hygroscopic. In some embodiments, co-crystalline of (S)-methylone and gentisic acid (1:1 stoichiometry) is solvated. In some embodiments, co-crystalline of (S)-methylone and gentisic acid (1:1 stoichiometry) is unsolvated. In some embodiments, co-crystalline of (S)-methylone and gentisic acid (1:1 stoichiometry) is anhydrous.

In some embodiments, co-crystalline of (S)-methylone and gentisic acid (1:1 stoichiometry) consists essentially of (S)-methylone.

5. Solid Forms of Ethylone Hydrochloride

"3,4-methylenedioxy-N-ethylcathinone hydrochloride" or "ethylone HCl" refers to the hydrochloric acid salt of 3,4-methylenedioxy-N-ethylcathinone:

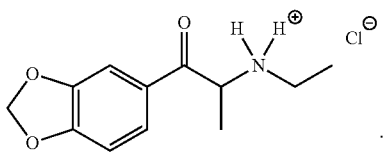

The present inventors observed that the properties of 3,4-methylenedioxy-N-ethylcathinone hydrochloride could be improved upon to support its use in the clinical treatment of brain disorders. Accordingly, disclosed herein are solid forms of 3,4-methylenedioxy-N-ethylcathinone hydrochloride with improved properties. The disclosed forms are useful to treat various disorders, such as brain disorders. Also disclosed are methods for making the solid forms of the compounds and method of administering the solid forms of the compounds.

In some embodiments, the solid form of the compound is a crystalline form of the compound. In some embodiments, the solid form of the compound is a polymorph of the compound, such as a novel polymorph that is not previously known in the art.

A solid form of a salt may be a crystalline form or an amorphous form. A person of ordinary skill in the art understands that solid forms of compounds, such as crystalline forms of 3,4-methylenedioxy-N-ethylcathinone hydrochloride, may exist in more than one crystal form. Such different forms are referred to as polymorphs. In some embodiments, the disclosed compound is a novel polymorph of 3,4-methylenedioxy-N-ethylcathinone hydrochloride.

In some embodiments, the solid form of 3,4-methylenedioxy-N-ethylcathinone hydrochloride disclosed herein is selected to be a crystalline form, such as a particular polymorph of a crystalline form of 3,4-methylenedioxy-N-ethylcathinone hydrochloride, that provides one or more desired properties. In one embodiment, the crystalline form offers advantages over the amorphous form of the molecule. In another embodiment, the disclosed polymorph offers improved properties as compared to another polymorph of the molecule. The one or more desired properties may include, but are not limited to, physical properties, including but not limited to, melting point, glass transition temperature, flowability, and/or stability, such as thermal stability, mechanical stability, shelf life, stability against polymorphic transition, etc.; chemical properties, such as, but not limited to, hygroscopic properties, solubility in water and/or organic solvents, reactivity, compatibility with excipients and/or delivery vehicles; and/or pharmacokinetic properties, such as, but not limited to, bioavailability, absorption, distribution, metabolism, excretion, toxicity including cytotoxicity, dissolution rate, and/or half-life.

The desired polymorph may be produced by techniques as described herein and also are known to persons of ordinary skill in the art. Such techniques include, but are not limited to, crystallization in particular solvents and/or at particular temperatures, supersaturation, using a precipitation agent, such as a salt, glycol, alcohol, etc., co-crystallization, lyophilization, spray drying, freeze drying, and/or complexing with an inert agent.

Techniques to identify a particular solid form of a compound are described herein and also are known to persons of ordinary skill in the art, and include, but are not limited to, X-ray crystallography, X-ray diffraction, electron crystallography, powder diffraction, including X-ray, neutron, or electron diffraction, X-ray fiber diffraction, small-angle X-ray scattering, and/or melting point.

5.1 Crystalline Ethylone Hydrochloride

Figure 58:
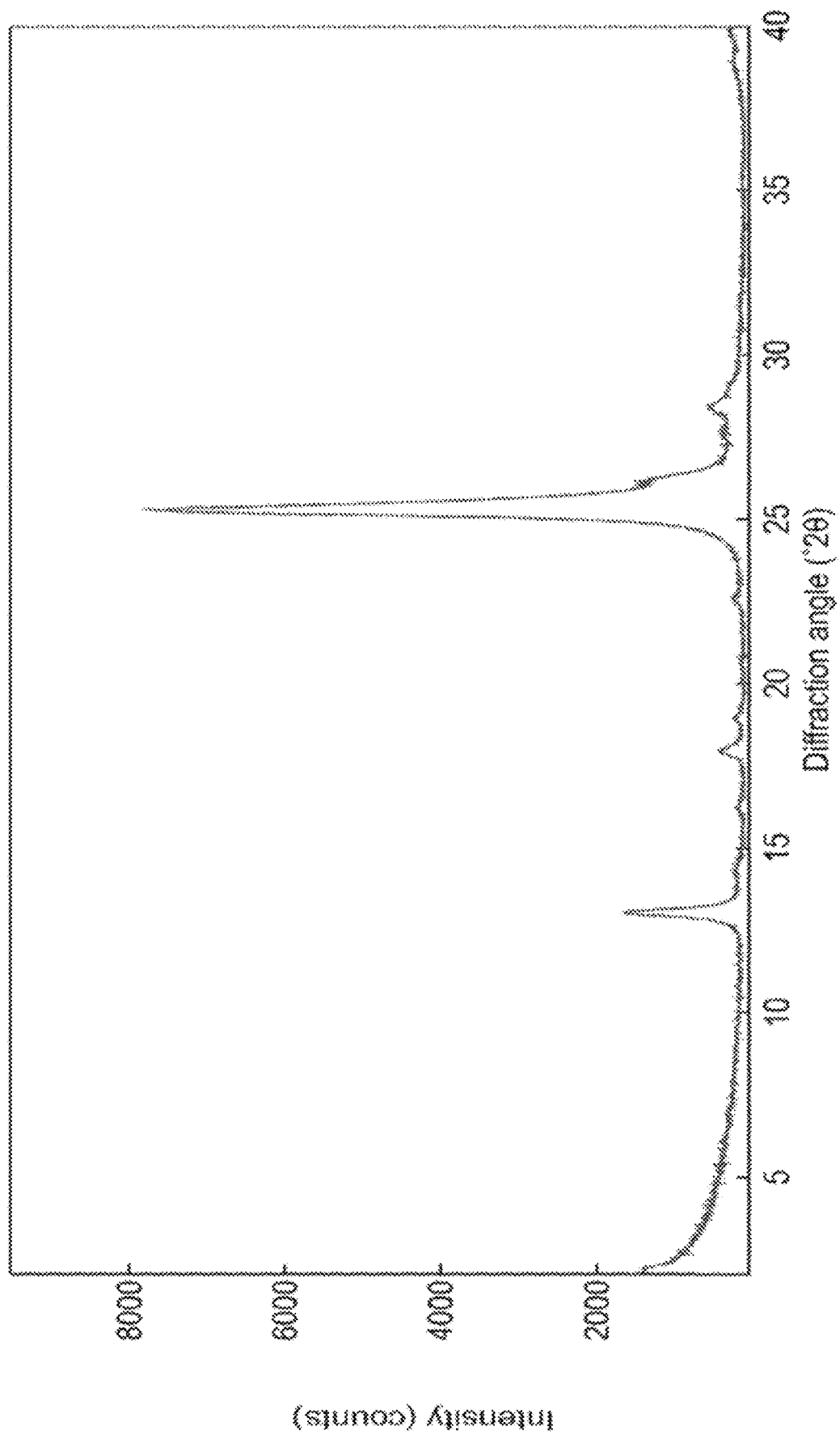
FIG. 58 illustrates an XRPD diffractogram of crystalline Ethylone HCl isolated from DMF at low temperature.
Figure 59:
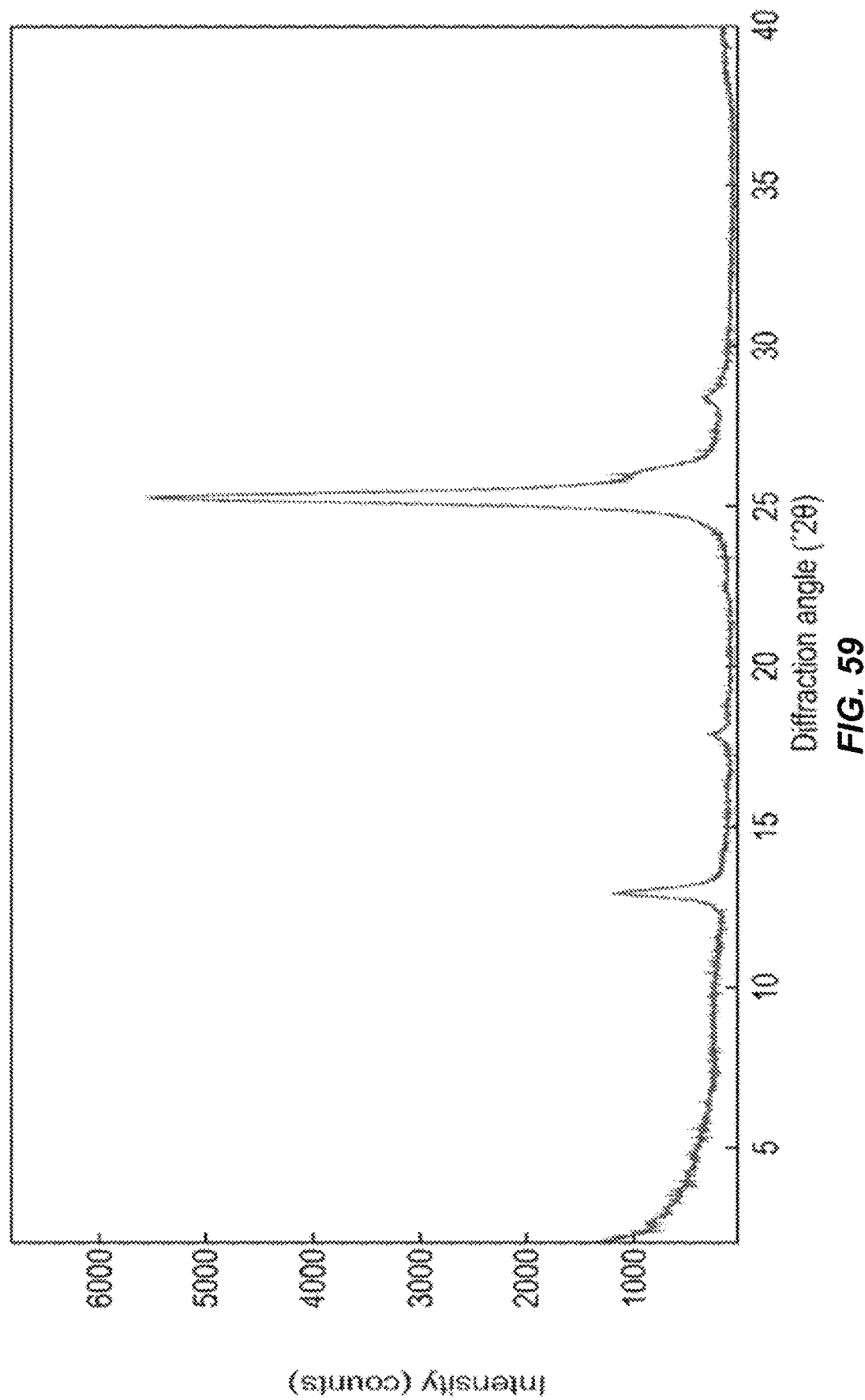
FIG. 59 illustrates an XRPD diffractogram of crystalline Ethylone HCl isolated from 2-propanol.
Figure 60:
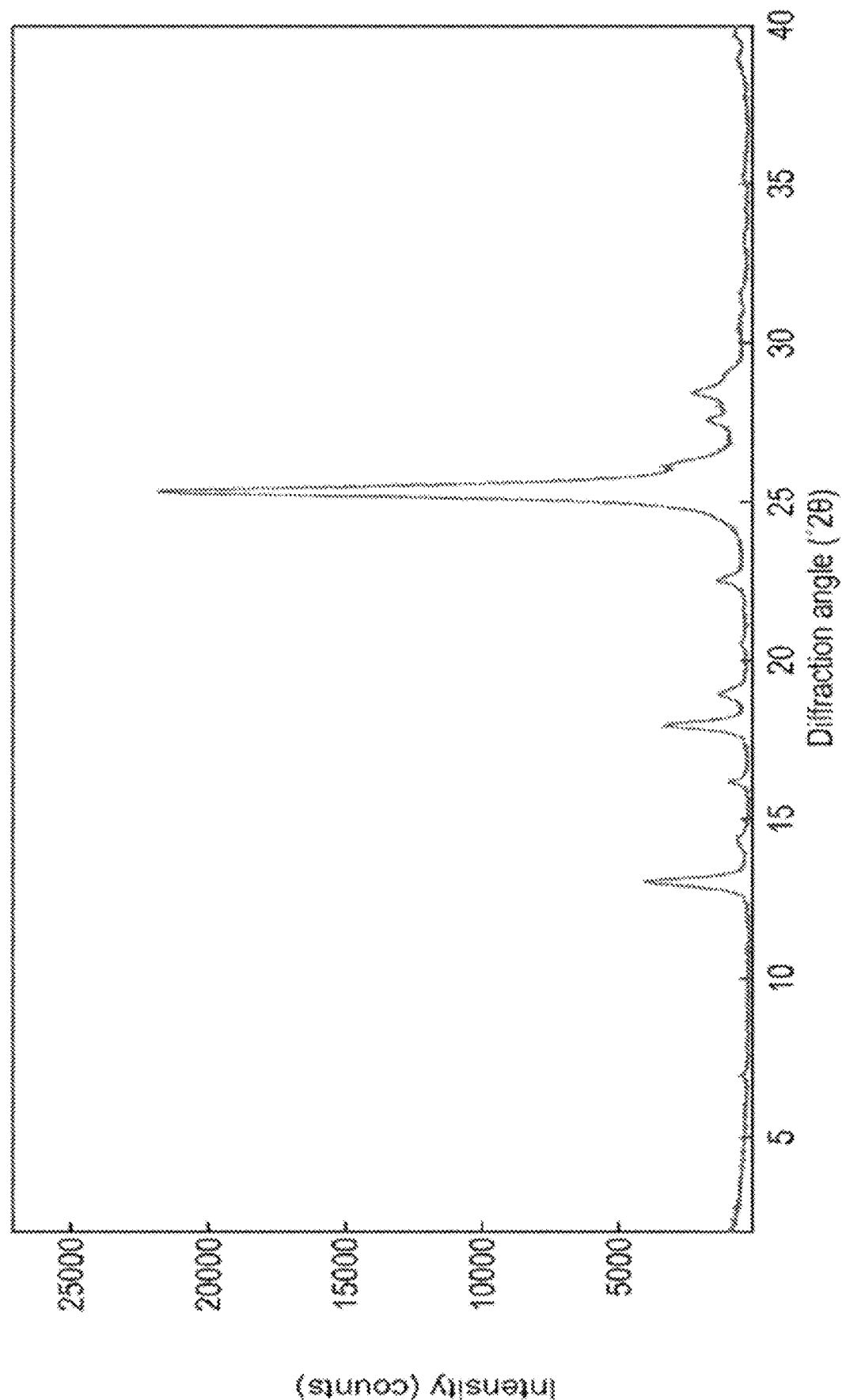
FIG. 60 illustrates an XRPD diffractogram of crystalline Ethylone HCl isolated from DMF at room temperature.

In some embodiments, the crystalline form of ethylone hydrochloride is characterized as having: an X-ray powder diffraction (XRPD) pattern substantially the same as shown in FIG. 58; an X-ray powder diffraction (XRPD) pattern substantially the same as shown in FIG. 59; or an X-ray powder diffraction (XRPD) pattern substantially the same as shown in FIG. 60.

In some embodiments, the crystalline form of ethylone hydrochloride is characterized as having an X-ray powder diffraction (XRPD) pattern substantially the same as shown in FIG. 58.

In some embodiments, the crystalline form of ethylone hydrochloride is characterized as having an X-ray powder diffraction (XRPD) pattern substantially the same as shown in FIG. 59.

In some embodiments, the crystalline form of ethylone hydrochloride is characterized as having an X-ray powder diffraction (XRPD) pattern substantially the same as shown in FIG. 60.

In some embodiments, the crystalline form of ethylone hydrochloride is characterized as having an X-ray powder diffraction (XRPD) pattern with representative peaks at 13.0°±0.2 2-Theta, 17.9°±0.2 2-Theta, 25.3°±0.2 2-Theta, and 26.1°±0.2 2-Theta, as measured with Cu Kα radiation.

In some embodiments, the crystalline form of ethylone hydrochloride is characterized as having an X-ray powder diffraction (XRPD) pattern with representative peaks at 13.0°±0.2 2-Theta, 17.9°±0.2 2-Theta, 25.3°±0.2 2-Theta, and 26.1°±0.2 2-Theta, with at least one additional peak at 16.2°±0.2 2-Theta, 18.9°±0.2 2-Theta, 22.5°±0.2 2-Theta, 27.5°±0.2 2-Theta, or 28.4°±0.2 2-Theta, as measured with Cu Kα radiation.

In some embodiments, the crystalline form of ethylone hydrochloride is characterized as having an X-ray powder diffraction (XRPD) pattern with representative peaks at 13.0°±0.2 2-Theta, 17.9°±0.2 2-Theta, 25.3°±0.2 2-Theta, and 26.1°±0.2 2-Theta, and optionally with further representative peaks at 16.2°±0.2 2-Theta, 18.9° 2-Theta, 22.5°±0.2 2-Theta, 27.5°±0.2 2-Theta, and 28.4°±0.2 2-Theta, as measured with Cu Kα radiation.

In some embodiments, crystalline ethylone hydrochloride is precipitated from DMF. In some embodiments, crystalline ethylone hydrochloride is precipitated from DMF at room temperature. In some embodiments, crystalline ethylone hydrochloride is precipitated from DMF at low temperature (e.g., −15° C.). In some embodiments, crystalline ethylone hydrochloride is precipitated from 2-propanol.

In some embodiments, crystalline ethylone hydrochloride comprises hydrochloride salts of racemic ethylone. In some embodiments, crystalline ethylone hydrochloride comprises (S)-ethylone hydrochloride and (R)-ethylone hydrochloride.

(R)-Ethylone hydrochloride has the following structure:

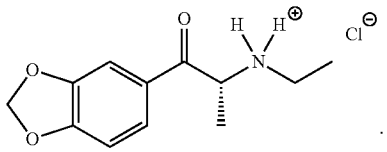

(S)-Ethylone hydrochloride has the following structure:

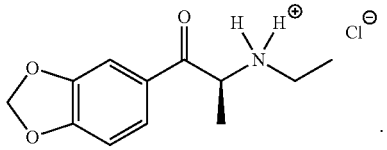

6. Pharmaceutical Compositions and Formulations

In some embodiments, the present disclosure provides a pharmaceutical composition comprising a pharmaceutically acceptable excipient and a compound of the present disclosure, such as a composition comprising a compound described herein (e.g., a compound of Formula (II) or an enantiomer, a mixture of enantiomers, a mixture of two or more diastereomers thereof; or pharmaceutically acceptable salt, hydrate, or solvate thereof; and one or more of the disclosed solid forms (e.g., crystalline forms of methylone or an enantiomer or a mixture of enantiomers thereof (such as rac-methylone hydrochloride))). In some embodiments, the present disclosure provides a pharmaceutical composition comprising one or more of the disclosed solid forms 3,4-methylenedioxy-N-ethylcathinone hydrochloride, and a pharmaceutically acceptable excipient. Such compositions are suitable for administration to a subject. In some embodiment, the subject is a human.

The presently disclosed pharmaceutical compositions can be prepared in a wide variety of oral, parenteral and topical dosage forms. Oral preparations include tablets, pills, powder, capsules, liquids, lozenges, cachets, gels, syrups, slurries, suspensions, etc., suitable for ingestion by the patient. The compositions of the present disclosure can also be administered by injection, that is, intravenously, intramuscularly, intracutaneously, subcutaneously, intraduodenally, or intraperitoneally. Also, the compositions described herein can be administered by inhalation, for example, intranasally. Additionally, the compositions of the present disclosure can be administered transdermally. The compositions of this invention can also be administered by intraocular, intravaginal, and intrarectal routes including suppositories, insufflation, powders and aerosol formulations (for examples of steroid inhalants, see Rohatagi, *J Clin. Pharmacol.* 35:1187-1193, 1995; Tjwa, *Ann. Allergy Asthma Immunol.* 75:107-111, 1995). Accordingly, the present disclosure also provides pharmaceutical compositions including a pharmaceutically acceptable carrier or excipient and the compounds of the present disclosure.

For preparing pharmaceutical compositions from the compounds disclosed herein, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Mack Publishing Co, Easton PA ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% to 70% or 10% to 70% of the compounds of the present disclosure.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; as well as proteins including, but not limited to, gelatin and collagen.

If desired, disintegrating or solubilizing agents may be added, such as the cross-linked polyvinyl pyrrolidone, agar, alginic acid, or a salt thereof, such as sodium alginate.

For preparing suppositories, a low melting wax, such as a mixture of fatty acid glycerides or cocoa butter, is first melted and the compounds of the present disclosure are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the compounds of the present disclosure in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compound of the present disclosure in a vegetable oil, such as *arachis* oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present disclosure can also be delivered as microspheres for slow release in the body. For example, microspheres can be formulated for administration via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

In some embodiments, the pharmaceutical compositions of the present disclosure can be formulated for parenteral administration, such as intravenous (IV) administration or administration into a body cavity or lumen of an organ. The formulations for administration will commonly comprise a solution of the compositions of the present disclosure dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose, any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present disclosure in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In some embodiments, the formulations of the compositions of the present disclosure can be delivered by the use of liposomes which fuse with the cellular membrane or are endocytosed, for example, by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present disclosure into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

Dosage Forms

The pharmaceutical compositions described herein can be formulated for administration to a mammal via any conventional means including, but not limited to, oral, parenteral (e.g., intravenous, subcutaneous, or intramuscular), buccal, intranasal, rectal, or transdermal administration routes.

Moreover, the pharmaceutical compositions described herein can be formulated into any suitable dosage form, including but not limited to, solid oral dosage forms, controlled release formulations, fast melt formulations, effervescent formulations, tablets, powders, pills, capsules, delayed release formulations, extended release formulations, pulsatile release formulations, multiparticulate formulations, and mixed immediate release and controlled release formulations.

In some embodiments, the pharmaceutical solid dosage forms described herein include a compound described herein, and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington's Pharmaceutical Sciences, 20th Edition (2000), a film coating is provided around the formulation of a compound described herein.

7. Administration

The compositions of the present disclosure can be administered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of the compounds of the present disclosure. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compound of the present disclosure can be present in any suitable amount, and can depend on various factors including, but not limited to, weight and age of the subject, state of the disease, and the like as is known to those of ordinary skill in the art. Suitable dosage ranges for the compounds disclosed herein include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the compound of the present disclosure include about 1 mg, 5, 10, 20, 30, 40, 50, 60, 70, 80, 90, 100, 200, 300, 400, 500, 600, 700, 800, 900 or 1000 mg.

The daily dosages appropriate for the compounds described herein are from about 0.01 mg/kg to about 20 mg/kg. In one embodiment, the daily dosages are from about 0.1 mg/kg to about 10 mg/kg. An indicated daily dosage in the larger mammal, including, but not limited to, humans, is in the range from about 0.5 mg to about 1000 mg, conveniently administered in a single dose or in divided doses, including, but not limited to, up to four times a day or in extended release form. Suitable unit dosage forms for oral administration include from about 1 to about 500 mg active ingredient. In one embodiment, the unit dosage is about 1 mg, about 5 mg, about, 10 mg, about 20 mg, about 50 mg, about 100 mg, about 200 mg, about 250 mg, about 400 mg, or about 500 mg. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

The compounds disclosed herein can be administered at any suitable frequency, interval and duration. For example, the compounds can be administered once an hour, or two, three or more times an hour, once a day, or two, three, or more times per day, or once every 2, 3, 4, 5, 6, or 7 days, so as to provide the preferred dosage level. When the compound of the present disclosure is administered more than once a day, representative intervals include 5, 10, 15, 20, 30, 45 and 60 minutes, as well as 1, 2, 4, 6, 8, 10, 12, 16, 20, and 24 hours. The compound of the present disclosure can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

Toxicity and therapeutic efficacy of such therapeutic regimens can be determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it can be expressed as the ratio between LD50 and ED50. The data obtained from cell culture assays and animal studies can be used in formulating a range of dosage for use in human. The dosage of such compounds lies preferably within a range of circulating concentrations that include the ED50 with minimal toxicity. The dosage may vary within this range depending upon the dosage form employed and the route of administration utilized.

The composition can also contain other compatible therapeutic agents. The compounds described herein can be used in combination with one another, with other active agents known to be useful in modulating a glucocorticoid receptor, or with adjunctive agents that may not be effective alone, but may contribute to the efficacy of the active agent.

The compounds of the present disclosure can be co-administered with a second active agent. Co-administration includes administering the compound of the present disclosure and active agent within 0.5, 1, 2, 4, 6, 8, 10, 12, 16, 20, or 24 hours of each other. Co-administration also includes administering the compound of the present disclosure and active agent simultaneously, approximately simultaneously (e.g., within about 1, 5, 10, 15, 20, or 30 minutes of each other), or sequentially in any order. Moreover, the compound of the present disclosure and the active agent can each be administered once a day, or two, three, or more times per day so as to provide the preferred dosage level per day.

The compounds of the present disclosure can be co-administered with a second active agent. In some embodiments, co-administration can be accomplished by co-formulation, such as by preparing a single pharmaceutical composition including both the compound of the present disclosure and a second active agent. In other embodiments, the compound of the present disclosure and the second active agent can be formulated separately.

The disclosed compounds and the second active agent can be present in the compositions of the present disclosure in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). The compound of the present disclosure and the second active agent can be present in any suitable weight ratio, such as about 1:100 (w/w), 1:50, 1:25, 1:10, 1:5, 1:4, 1:3, 1:2, 1:1, 2:1, 3:1, 4:1, 5:1, 10:1, 25:1, 50:1 or 100:1 (w/w). Other dosages and dosage ratios of the compound of the present disclosure and the active agent are suitable in the compositions and methods disclosed herein.

Kits/Articles of Manufacture

For use in the therapeutic methods of use described herein, kits and articles of manufacture are also described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Packaging materials for use in packaging pharmaceutical products include, e.g., U.S. Pat. No. 5,323,907. Examples of pharmaceutical packaging materials include, but are not limited to, blister packs, bottles, tubes, bags, containers, bottles, and any packaging material suitable for a selected formulation and intended mode of administration and treatment.

In some embodiments, the compounds or compositions described herein, are presented in a package or dispenser device which may contain one or more unit dosage forms containing the active ingredient. The compound or composition described herein is packaged alone, or packaged with another compound or another ingredient or additive. In some embodiments, the package contains one or more containers filled with one or more of the ingredients of the pharmaceutical compositions. In some embodiments, the package comprises metal or plastic foil, such as a blister pack. In some embodiments, the package or dispenser device is accompanied by instructions for administration, such as instructions for administering the compounds or compositions for treating a neoplastic disease. In some embodiments, the package or dispenser is accompanied with a notice associated with the container in form prescribed by a governmental agency regulating the manufacture, use, or sale of pharmaceuticals, which notice is reflective of approval by the agency of the form of the drug for human or veterinary administration. In some embodiments, such notice, for example, is the labeling approved by the U.S. Food and Drug Administration for prescription drugs, or the approved product insert. In some embodiments, compositions include a compound described herein formulated in a compatible pharmaceutical carrier are prepared, placed in an appropriate container, and labeled for treatment of an indicated condition.

For example, the container(s) include a compound described herein, optionally in a composition or in combination with another agent as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself, a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

8. Methods of Treatment

The cathinone compounds of the present disclosure can be used for increasing neuronal plasticity. The compounds of the present disclosure can also be used to treat any brain disease. The compounds of the present disclosure can also be used for increasing at least one of translation, transcription or secretion of neurotrophic factors.

In some embodiments, a cathinone compound of the present disclosure is used to treat neurological diseases. In some embodiments, the cathinone compounds provided herein have, for example, anti-addictive properties, antidepressant properties, anxiolytic properties, or a combination thereof.

As used herein, "cathinone compound" refers to methylone or ethylone, or a deuterated analogue, pharmaceutically acceptable salt, cocrystal, solvate, hydrate, crystalline form, or a combination thereof. In some embodiments, "cathinone compound" refers to (R)-methylone, (S)-methylone, (rac.)-methylone, or ethylone, or a deuterated analogue, pharmaceutically acceptable salt, cocrystal, solvate, hydrate, crystalline form, or a combination thereof. In some embodiments, "cathinone compound" refers to a compound of Formula (II) or an enantiomer, a mixture of enantiomers, a mixture of two or more diastereomers thereof; or pharmaceutically acceptable salt, hydrate, or solvate thereof. In some embodiments, "cathinone compound" refers to deuterated (rac.)-methylone, or a pharmaceutically acceptable salt, cocrystal, solvate, hydrate, crystalline form, or a combination thereof. In some embodiments, "cathinone compound" refers to deuterated (rac.)-methylone hydrochloride. In some embodiments, "cathinone compound" refers to deuterated (rac.)-methylone, or a pharmaceutically acceptable salt, cocrystal, solvate, hydrate, crystalline form, or a combination thereof, wherein (rac.)-methylone is (rac.)-methylone-d2, (rac.)-methylone-d3, or (rac.)-methylone-d5. In some embodiments, "cathinone compound" refers to (rac.)-methylone-d2 hydrochloride, (rac.)-methylone-d3 hydrochloride, or (rac.)-methylone-d5 hydrochloride. In some embodiments, "cathinone compound" refers to a compound of Formula (II-A) or an enantiomer, a mixture of enantiomers, a mixture of two or more diastereomers thereof, or pharmaceutically acceptable salt, hydrate, or solvate thereof. In some embodiments, "cathinone compound" refers to deuterated (R)-methylone, or a pharmaceutically acceptable salt, cocrystal, solvate, hydrate, crystalline form, or a combination thereof. In some embodiments, "cathinone compound" refers to deuterated (R)-methylone, or a pharmaceutically acceptable salt, cocrystal, solvate, hydrate, crystalline form, or a combination thereof, wherein (R)-methylone is (R)-methylone-d2, (R)-methylone-d3, or (R)-methylone-d5. In some embodiments, "cathinone compound" refers to deuterated (R)-methylone hydrochloride. In some embodiments, "cathinone compound" refers to (R)-methylone-d2 hydrochloride, (R)-methylone-d3 hydrochloride, or (R)-methylone-d5 hydrochloride. In some embodiments, "cathinone compound" refers to a compound of Formula (II-B) or an enantiomer, a mixture of enantiomers, a mixture of two or more diastereomers thereof, or pharmaceutically acceptable salt, hydrate, or solvate thereof. In some embodiments, "cathinone compound" refers to deuterated (S)-methylone, or a pharmaceutically acceptable salt, cocrystal, solvate, hydrate, crystalline form, or a combination thereof. In some embodiments, "cathinone compound" refers to deuterated (S)-methylone hydrochloride. In some embodiments, "cathinone compound" refers to deuterated (S)-methylone, or a pharmaceutically acceptable salt, cocrystal, solvate, hydrate, crystalline form, or a combination thereof, wherein (S)-methylone is (S)-methylone-d2, (S)-methylone-d3, or (S)-methylone-d5. In some embodiments, "cathinone compound" refers to (S)-methylone-d2 hydrochloride, (S)-methylone-d3 hydrochloride, or (S)-methylone-d5 hydrochloride. In some embodiments, "cathinone compound" refers to (R)-methylone hydrochloride. In some embodiments, "cathinone compound" refers to crystalline (R)-methylone hydrochloride as described in Examples 3-19, 3-20 or -3-21. In some embodiments, "cathinone compound" refers to a cocrystal of (R)-methylone. In some embodiments, "cathinone compound" refers to (S)-methylone hydrochloride. In some embodiments, "cathinone compound" refers to crystalline (S)-methylone hydrochloride as described in Examples 3-22, 3-23, or 3-24. In some embodiments, "cathinone compound" refers to crystalline (S)-methylone hydrochloride, Form A, Form B, or Form C. In some embodiments, "cathinone compound" refers to crystalline (S)-methylone hydrochloride, Form A. In some embodiments, "cathinone compound" refers to crystalline (S)-methylone hydrochloride, Form B. In some embodiments, "cathinone compound" refers to crystalline (S)-methylone hydrochloride, Form C. In some embodiments, "cathinone compound" refers to a cocrystal of (S)-methylone. In some embodiments, "cathinone compound" refers to a cocrystal of (S)-methylone as described in Examples 3-6, 3-7 or 3-10. In some embodiments, "cathinone compound" refers to crystalline (rac.)-methylone hydrochloride, Form A, Form B, Form C, or Form D as described in Examples 2-1, 3-15, 3-16, or 3-17. In some embodiments, "cathinone compound" refers to crystalline (rac.)-methylone hydrochloride, Form A. In some embodiments, "cathinone compound" refers to crystalline (rac.)-methylone hydrochloride, Form B. In some embodiments, "cathinone compound" refers to crystalline (rac.)-methylone hydrochloride, Form C. In some embodiments, "cathinone compound" refers to crystalline (rac.)-methylone hydrochloride, Form D. In some embodiments, "cathinone compound" refers to a cocrystal of (rac.)-methylone. In some embodiments, "cathinone compound" refers to a cocrystal of (rac.)-methylone as described in Example 3-6, 3-7 or 3-10. In some embodiments, "cathinone compound" refers to crystalline ethylone hydrochloride as described in Example 3-25. In some embodiments, "cathinone compound" refers to a salt form of methylone as described in Example 3-1. In some embodiments, "cathinone compound" refers to a salt form of methylone as described in Table 9. In some embodiments, "cathinone compound" refers to a fumaric acid salt form of methylone as described in Table 9. In some embodiments, "cathinone compound" refers to a gentisic acid salt form of methylone as described in Table 9. In some embodiments, "cathinone compound" refers to a maleic acid salt form of methylone as described in Table 9. In some embodiments, "cathinone compound" refers to a citric acid salt form of methylone as described in Table 9. In some embodiments, "cathinone compound" refers to a tartaric acid salt form of methylone as described in Table 9. In some embodiments, "cathinone compound" refers to a salt form of methylone as described in Table 10. In some embodiments, "cathinone compound" refers to a fumaric acid salt form of methylone as described in Table 10. In some embodiments, "cathinone compound" refers to a fumaric acid salt form of methylone as described in Table 10. In some embodiments, "cathinone compound" refers to a gentisic acid salt form of methylone as described in Table 10. In some embodiments, "cathinone compound" refers to a hydrochloric acid salt form of methylone as described in Table 10. In some embodiments, "cathinone compound" refers to a L-tartaric salt form of methylone as described in Table 10. In some embodiments, "cathinone compound" refers to a sulfuric acid salt form of methylone as described in Table 10.

In some embodiments, the methods described herein are for treating a disease or disorder that is a brain disease or disorder. In some embodiments, the methods described herein are for increasing at least one of translation, transcription or secretion of neurotrophic factors.

In some embodiments, the brain disease or disorder is a neurological disease. In some embodiments, the neurological disease is selected from a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, hypoxic brain injury, chronic traumatic encephalopathy (CTE), traumatic brain injury, dementia, and addiction (e.g., substance use disorder). In some embodiments, the neurological disease is a migraine or cluster headache. In some embodiments, the neurological disease is a neurodegenerative disorder, dementia, Alzheimer's disease, or Parkinson's disease. In some embodiments, the neurological disease is dementia. In some embodiments, the neurological disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety.

In some embodiments, the brain disease or disorder is depression or related conditions. Accordingly, in some embodiments, the disease or disorder treated herein is depression or a disease or disorder related to depression. In some embodiments, the depression is major depressive disorder, persistent depressive disorder, bipolar disorder, treatment resistant depression (TRD), postpartum depression, premenstrual dysphoric disorder, or seasonal affective disorder. In some embodiments, the disease or disorder related to depression is anxiety. In some embodiments, methods of treating depression or a disease or disorder related to depression comprise treating the symptoms associated with the depression or the disease or disorder related to depression.

In some embodiments, the brain disease or disorder is psychological disorder, depression, addiction, anxiety, or a post-traumatic stress disorder. In some embodiments, the brain disorder is depression. In some embodiments, the brain disorder is addiction. In some embodiments, the brain disorder is treatment resistant depression, suicidal ideation, major depressive disorder, bipolar disorder, schizophrenia, stroke, traumatic brain injury or substance use disorder. In some embodiments, the brain disorder is treatment resistant depression, suicidal ideation, major depressive disorder, bipolar disorder, schizophrenia, or substance use disorder. In some embodiments, the brain disorder is stroke or traumatic brain injury. In some embodiments, the brain disorder is treatment resistant depression, suicidal ideation, major depressive disorder, bipolar disorder, or substance use disorder. In some embodiments, the brain disorder is schizophrenia. In some embodiments, the brain disorder is alcohol use disorder.

In some embodiments, the neuropsychiatric disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease or neurological disease is post-traumatic stress disorder (PTSD), addiction (e.g., substance use disorder), schizophrenia, depression, or anxiety. In some embodiments, the neuropsychiatric disease or neurological disease is addiction (e.g., substance use disorder). In some embodiments, the neuropsychiatric disease or neurological disease is depression. In some embodiments, the neuropsychiatric disease or neurological disease is anxiety. In some embodiments, the neuropsychiatric disease or neurological disease is post-traumatic stress disorder (PTSD). In some embodiments, the neurological disease is stroke or traumatic brain injury. In some embodiments, the neuropsychiatric disease or neurological disease is schizophrenia.

In some embodiments, the cathinone compounds described herein are used for increasing neuronal plasticity. In some embodiments, decreased neuronal plasticity is associated with a neuropsychiatric disease. In some embodiments, the cathinone compounds described herein are used for increasing at least one of translation, transcription, or secretion of neurotrophic factors.

In some embodiments, the present disclosure provides a method of treating a disease, including administering to a subject in need thereof, a therapeutically effective amount of a cathinone compound of the present disclosure. In some embodiments, the disease is a musculoskeletal pain disorder including fibromyalgia, muscle pain, joint stiffness, osteoarthritis, rheumatoid arthritis, and muscle cramps. In some embodiments, the present disclosure provides a method of treating a disease of women's reproductive health including premenstrual dysphoric disorder (PMDD), premenstrual syndrome (PMS), post-partum depression, and menopause.

In yet another aspect, also provided herein are methods of treating fibromyalgia or a disease or disorder related to chronic widespread pain, fatigue or hypersensitivity, wherein the methods comprise administering to the subject a therapeutically effective amount of a cathinone compound described herein.

In some embodiments, the cathinone compounds of the present disclosure have activity as $5\text{-HT}_{2A}$ modulators. In some embodiments, the cathinone compounds of the present disclosure elicit a biological response by activating the $5\text{-HT}_{2A}$ receptor (e.g., allosteric modulation or modulation of a biological target that activates the $5\text{-HT}_{2A}$ receptor). $5\text{-HT}_{2A}$ agonism has been correlated with the promotion of neural plasticity (Ly et al., 2018). $5\text{-HT}_{2A}$ antagonists abrogate the neuritogenesis and spinogenesis effects of hallucinogenic compounds with $5\text{-HT}_{2A}$ agonist activity, for example, DMT, LSD, and DOI. In some embodiments, the cathinone compounds of the present disclosure are $5\text{-HT}_{2A}$ modulators and promote neural plasticity (e.g., cortical structural plasticity). In some embodiments, the cathinone compounds of the present disclosure are selective $5\text{-HT}_{2A}$ modulators and promote neural plasticity (e.g., cortical structural plasticity). In some embodiments, promotion of neural plasticity includes, for example, increased dendritic spine growth, increased synthesis of synaptic proteins, strengthened synaptic responses, increased dendritic arbor complexity, increased dendritic branch content, increased spinogenesis, increased neuritogenesis, or any combination thereof. In some embodiments, increased neural plasticity includes, for example, increased cortical structural plasticity in the anterior parts of the brain.

In some embodiments, the $5\text{-HT}_{2A}$ modulators (e.g., $5\text{-HT}_{2A}$ agonists) are non-hallucinogenic. In some embodiments, non-hallucinogenic $5\text{-HT}_{2A}$ modulators (e.g., $5\text{-HT}_{2A}$ agonists) are used to treat neurological diseases, which modulators do not elicit dissociative side-effects. In some embodiments, the hallucinogenic potential of the cathinone compounds described herein is assessed in vitro. In some embodiments, the hallucinogenic potential assessed in vitro of the cathinone compounds described herein is compared to the hallucinogenic potential assessed in vitro of hallucinogenic homologs. In some embodiments, the cathinone compounds described herein elicit less hallucinogenic potential in vitro than the hallucinogenic homologs. In some embodiments, serotonin receptor modulators, such as modulators of serotonin receptor 2A ($5\text{-HT}_{2A}$ modulators, e.g., $5\text{-HT}_{2A}$ agonists), are used to treat a brain disorder. The presently disclosed compounds can function as $5\text{-HT}_{2A}$ agonists alone, or in combination with a second therapeutic agent that also is a $5\text{-HT}_{2A}$ modulator. In such cases the second therapeutic agent can be an agonist or an antagonist. In some instances, it may be helpful administer a $5\text{-HT}_{2A}$ antagonist in combination with a compound of the present disclosure to mitigate undesirable effects of $5\text{-HT}_{2A}$ agonism, such as potential hallucinogenic effects. Serotonin receptor modulators useful as second therapeutic agents for combination therapy as described herein are known to those of skill in the art and include, without limitation, ketanserin, volinanserin (MDL-100907), eplivanserin (SR-46349), pimavanserin (ACP-103), glemanserin (MDL-11939), ritanserin, flibanserin, nelotanserin, blonanserin, mianserin, mirtazapine, roluperiodone (CYR-101, MIN-101), quetiapine, olanzapine, altanserin, acepromazine, nefazodone, risperidone, pruvanserin, AC-90179, AC-279, adatanserin, fananserin, HY10275, benanserin, butanserin, manserin, iferanserin, lidanserin, pelanserin, seganserin, tropanserin, lorcaserin, ICI-169369, methiothepin, methysergide, trazodone, cinitapride, cyproheptadine, brexpiprazole, cariprazine, agomelatine, setoperone, 1-(1-Naphthyl)piperazine, LY-367265, pirenperone, metergoline, deramciclane, amperozide, cinanserin, LY-86057, GSK-215083, cyamemazine, mesulergine, BF-1, LY-215840, sergolexole, spiramide, LY-53857, amesergide, LY-108742, pipamperone, LY-314228, 5-I-R91150, 5-MeO-NBpBrT, 9-Aminomethyl-9,10-dihydroanthracene, niaprazine, SB-215505, SB-204741, SB-206553, SB-242084, LY-272015, SB-243213, SB-200646, RS-102221, zotepine, clozapine, chlorpromazine, sertindole, iloperidone, paliperidone, asenapine, amisulpride, aripiprazole, lurasidone, ziprasidone, lumateperone, perospirone, mosapramine, AMDA (9-Aminomethyl-9,10-dihydroanthracene), methiothepin, an extended-release form of olanzapine (e.g., ZYPREXA RELPREVV), an extended-release form of quetiapine, an extended-release form of risperidone (e.g., Risperdal Consta), an extended-release form of paliperidone (e.g., Invega Sustenna and Invega Trinza), an extended-release form of fluphenazine decanoate including Prolixin Decanoate, an extended-release form of aripiprazole lauroxil including Aristada, and an extended-release form of aripiprazole including Abilify Maintena, or a pharmaceutically acceptable salt, solvate, metabolite, deuterated analog, derivative, prodrug, or combinations thereof.

In some embodiments, the serotonin receptor modulator described herein comprises kMDL-11,939, eplivanserin (SR-46,349), ketanserin, ritanserin, altanserin, acepromazine, mianserin, mirtazapine, quetiapine, SB204741, SB206553, SB242084, LY272015, SB243213, Blonanserin, SB200646, RS102221, nefazodone, MDL-100,907, pimavanserin, nelotanserin, lorcaserin, flibanserin, and roluperiodone. In some embodiments, the serotonin receptor modulator is ketanserin. In some embodiments, the serotonin receptor modulator is pimavanserin.

In some embodiments, the serotonin receptor modulator for combination with the presently disclosed compounds is selected from MDL-11,939, eplivanserin (SR-46,349), ketanserin, ritanserin, altanserin, acepromazine, mianserin, mirtazapine, quetiapine, SB204741, SB206553, SB242084, LY272015, SB243213, blonanserin, SB200646, RS102221, nefazodone, MDL-100,907, pimavanserin, nelotanserin and lorcaserin.

In certain embodiments the serotonin receptor modulator is selected from the group consisting of altanserin, blonanserin, eplivanserin, glemanserin, volinanserin, ketanserin, ritanserin, pimavanserin, nelotanserin, pruvanserin, and flibanserin. In one embodiment, the serotonin receptor modulator is selected from the group consisting of eplivanserin, volinanserin, ketanserin, ritanserin, pimavanserin, nelotanserin, pruvanserin, flibanserin, olanzapine, quetiapine, and risperidone.

In some embodiments, the serotonin receptor modulator is ketanserin or a pharmaceutically acceptable salt, solvate, metabolite, deuterated analog, derivative, or prodrug thereof. In some embodiments, the serotonin receptor modulator is pimavanserin or a pharmaceutically acceptable salt, solvate, metabolite, deuterated analog, derivative, or prodrug thereof. In some embodiments, the serotonin receptor modulator is eplivanserin or a pharmaceutically acceptable salt, solvate, metabolite, deuterated analog, derivative, or prodrug thereof. In some embodiments, the serotonin receptor modulator is flibanserin or a pharmaceutically acceptable salt, solvate, metabolite, deuterated analog, derivative, or prodrug thereof. In some embodiments, the serotonin receptor modulator is roluperiodone or a pharmaceutically acceptable salt, solvate, metabolite, deuterated analog, derivative, or prodrug thereof. In some embodiments, the serotonin receptor modulator is administered prior to a cathinone compound disclosed herein, such as about from about one to about three or about hours prior administration of a cathinone compound described herein. In some embodiments, the serotonin receptor modulator is administered at most about one hour prior to the presently disclosed compound. Thus, in some embodiments of combination therapy with the presently disclosed compounds, the second therapeutic agent is a serotonin receptor modulator. In some embodiments the second therapeutic agent serotonin receptor modulator is provided at a dose of from about 10 mg to about 350 mg. In some embodiments, the serotonin receptor modulator is provided at a dose of from about 20 mg to about 200 mg. In some embodiments, the serotonin receptor modulator is provided at a dose of from about 10 mg to about 100 mg. In certain such embodiments, the compound of the present disclosure is provided at a dose of from about 10 mg to about 100 mg, or from about 20 to about 200 mg, or from about 15 to about 300 mg, and the serotonin receptor modulator is provided at a dose of from about 10 mg to about 100 mg. In certain other embodiments, the compound of the present disclosure is provided at a dose from about 10 mg to about 500 mg, or from about 100 mg to about 250 mg, or about 120 mg, or about 150 mg, or about 180 mg, or about 250 mg.

In some embodiments, the serotonin receptor modulator for use with the cathinone compounds disclosed herein is eplivanserin, wherein the eplivanserin is administered in from about 1 mg to about 40 mg, such as from about 5 mg to about 10 mg, and the cathinone compounds disclosed herein are administered in about 10 mg to about 500 mg or about 100 mg to about 250 mg or about 120 mg or about 150 mg or about 180 mg or about 250 mg.

In some embodiments, the serotonin receptor modulator for use with the cathinone compounds disclosed herein is volinanserin, wherein the volinanserin is administered in from about 1 mg to about 60 mg, or about 5 mg to about 20 mg, and the cathinone compounds disclosed herein are administered in about 10 mg to about 500 mg or about 100 mg to about 250 mg or about 120 mg or about 150 mg or about 180 mg or about 250 mg.

In some embodiments, the serotonin receptor modulator for use with the cathinone compounds disclosed herein is ketanserin, wherein the ketanserin is administered in from about 10 mg to about 80 mg, such as from about 30 mg to about 50 mg, such as about 40 mg, and the cathinone compounds disclosed herein are administered in about 10 mg to about 500 mg or about 100 mg to about 250 mg or about 120 mg or about 150 mg or about 180 mg or about 250 mg.

In some embodiments, the serotonin receptor modulator for use with the cathinone compounds disclosed herein is ritanserin, wherein the ritanserin is administered in from about 1 mg to about 40 mg, such as from about 2.5 mg to about 10 mg, and the cathinone compounds disclosed herein are administered in about 10 mg to about 500 mg or about 100 mg to about 250 mg or about 120 mg or about 150 mg or about 180 mg or about 250 mg.

In some embodiments, the serotonin receptor modulator for use with the cathinone compounds disclosed herein is pimavanserin, wherein the pimavanserin is administered in from about 1 mg to about 60 mg, such as from about 17 mg to about 34 mg, and the cathinone compounds disclosed herein are administered in about 10 mg to about 500 mg or about 100 mg to about 250 mg or about 120 mg or about 150 mg or about 180 mg or about 250 mg.

In some embodiments, the serotonin receptor modulator for use with the cathinone compounds disclosed herein is nelotanserin, wherein the nelotanserin is administered in from about 1 mg to about 80 mg, such as from about 40 mg to about 80 mg, and the cathinone compounds disclosed herein are administered in about 10 mg to about 500 mg or about 100 mg to about 250 mg or about 120 mg or about 150 mg or about 180 mg or about 250 mg.

In some embodiments, the serotonin receptor modulator for use with the cathinone compounds disclosed herein is pruvanserin, wherein the pruvanserin is administered in from about 1 mg to about 40 mg, such as from about 3 mg to about 10 mg, and the cathinone compounds disclosed herein are administered in about 10 mg to about 500 mg or about 100 mg to about 250 mg or about 120 mg or about 150 mg or about 180 mg or about 250 mg.

In some embodiments, the serotonin receptor modulator for use with the cathinone compounds disclosed herein is flibanserin, wherein the flibanserin is administered in from about 10 mg to about 200 mg, such as from about 80 mg to about 120 mg, or about 100 mg, and the cathinone compounds disclosed herein are administered in about 10 mg to about 500 mg or about 100 mg to about 250 mg or about 120 mg or about 150 mg or about 180 mg or about 250 mg.

In some embodiments, the serotonin receptor modulator for use with the cathinone compounds disclosed herein is olanzapine, wherein the olanzapine is administered in from about 2.5 mg to about 30 mg, such as about 5 mg or about 10 mg, or about 20 mg or about 25 mg, and the cathinone compounds disclosed herein are administered in about 10 mg to about 500 mg or about 100 mg to about 250 mg or about 120 mg or about 150 mg or about 180 mg or about 250 mg.

In some embodiments, the serotonin receptor modulator for use with the cathinone compounds disclosed herein is an extended-release of olanzapine such as ZYPREXA REL-PREVV, wherein the extended release olanzapine is administered in from about 50 mg to about 450 mg, such as about 150 mg or about 210 mg, or about 300 mg or about 405 mg or about 450 mg, and the cathinone compounds disclosed herein are administered in about 10 mg to about 500 mg or about 100 mg to about 250 mg or about 120 mg or about 150 mg or about 180 mg or about 250 mg.

In some embodiments, the serotonin receptor modulator for use with the cathinone compounds disclosed herein is quetiapine, wherein the quetiapine is administered in from about 25 mg to about 800 mg, or from about 50 mg to about 100 mg, or about 150 mg or about 200 mg or about 250 mg or about 300 mg, and the cathinone compounds disclosed herein are administered in about 10 mg to about 500 mg or about 100 mg to about 250 mg or about 120 mg or about 150 mg or about 180 mg or about 250 mg.

In some embodiments, the serotonin receptor modulator for use with the cathinone compounds disclosed herein is an extended-release of quetiapine, wherein the extended-release of quetiapine is administered in from about 50 mg to about 300 mg, such as about 50 mg or about 100 mg or about 200 mg, or about 300 mg, and the cathinone compounds disclosed herein are administered in about 10 mg to about 500 mg or about 100 mg to about 250 mg or about 120 mg or about 150 mg or about 180 mg or about 250 mg.

In some embodiments, the serotonin receptor modulator for use with the cathinone compounds disclosed herein is risperidone, wherein the risperidone is administered in from about 0.5 mg to about 20 mg or about 0.5 mg, or about 1 mg, or about 2 mg, or about 3 mg or about 4 mg or about 5 mg or about 7.5 mg or about 10 mg or about 16 mg, and the cathinone compounds disclosed herein are administered in about 10 mg to about 500 mg or about 100 mg to about 250 mg or about 120 mg or about 150 mg or about 180 mg or about 250 mg.

In certain embodiments, such as those described above a disclosed cathinone compound is co-administered with a serotonin receptor modulator in the same or in separate compositions. In one embodiment, the cathinone compound is administered in a modified release formulation such that the subject is effectively pretreated with serotonin receptor modulator prior to release of an effective amount of the methylone.

In some embodiments the serotonin receptor modulator is part of a single fixed dose formulation that releases serotonin receptor modulator first followed by the cathinone compound on two different release profiles. In another embodiment the serotonin receptor modulator is administered first as a single dosage and after a length of time, the cathinone compound is administered as a second dosage separate from the first dosage.

Thus, in some embodiments, the serotonin receptor modulator is administered or released from a composition provided herein prior to the administration and/or release of the cathinone compound. This allows pretreatment to attenuate activation of the serotonin receptor by the methylone.

In some embodiments, the serotonin receptor modulator is administered or released from the composition provided herein to pretreat a subject by at least about 5 minutes, 10 minutes, 20 minutes, 30 minutes, 40 minutes, 50 minutes, 1 hour, 1.25 hours, 1.5 hours, 2 hours, or 3 hours prior to the release of the cathinone compound. In some embodiments, the serotonin receptor modulator attenuates the activation of the serotonin receptor when the serotonin receptor modulator is used to pretreat at most about 3 hours, 4 hours, 5 hours, 6 hours, 7 hours, 8 hours, 9 hours, or more than 9 hours prior to the release of cathinone compound. In some embodiments, the serotonin receptor modulator attenuates the activation of the serotonin receptor when the serotonin receptor modulator is used to pretreat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour prior to the release of the cathinone compound.

In a preferred embodiment, the serotonin receptor modulator is administered at about 1 hour to about 3 hours prior to the administration of the cathinone compound.

In some embodiments, the serotonin receptor modulator is eplivanserin, wherein the eplivanserin is administered to pretreat at least 15 minutes prior to the administration of the cathinone compound. In some embodiments, the serotonin receptor modulator is eplivanserin, wherein the eplivanserin is administered to pretreat between at least 30 minutes prior and 360 minutes prior to the release or administration of the cathinone compound. In some embodiments, the serotonin receptor modulator is eplivanserin, wherein the eplivanserin is administered to pretreat between at least 60 minutes prior and 360 minutes prior to the release or administration the cathinone compound. In some embodiments, the serotonin receptor modulator is eplivanserin, wherein the eplivanserin is administered to pretreat between at least 90 minutes and 240 minutes prior to the cathinone compound. In some embodiments, the serotonin receptor modulator is eplivanserin, wherein the eplivanserin is administered to pretreat at least 120 minutes prior to the cathinone compound.

In some embodiments, the serotonin receptor modulator is eplivanserin, wherein the eplivanserin is administered to pretreat at least 150 minutes prior to the cathinone compound. In some embodiments, the serotonin receptor modulator is eplivanserin, wherein the eplivanserin is administered to pretreat between about 15 minutes and about 150 minutes prior to the cathinone compound. In some embodiments, the serotonin receptor modulator is eplivanserin, wherein the eplivanserin is administered to pretreat at least 180 minutes prior to the cathinone compound. In some embodiments, the serotonin receptor modulator is eplivanserin, wherein the eplivanserin is administered to pretreat at least 210 minutes prior to the cathinone compound. In some embodiments, the serotonin receptor modulator is eplivanserin, wherein the eplivanserin is administered to pretreat at least 240 minutes prior to the cathinone compound.

In some embodiments, the serotonin receptor modulator is eplivanserin, wherein the eplivanserin is administered to pretreat at least 270 minutes prior to the cathinone compound. In some embodiments, the serotonin receptor modulator is eplivanserin, wherein the eplivanserin is administered to pretreat at least 300 minutes prior to the cathinone compound. In some embodiments, the serotonin receptor modulator is eplivanserin, wherein the eplivanserin is administered to pretreat at least 330 minutes prior to the cathinone compound. In some embodiments, the serotonin receptor modulator is eplivanserin, wherein the eplivanserin is administered to pretreat at least 360 minutes prior to administration or release of the cathinone compound.

In some preferred embodiments, the serotonin receptor modulator is eplivanserin, wherein eplivanserin is administered to pretreat between about 60 minutes and about 180 minutes prior to the administration or release of the cathinone compound.

In some embodiments, the serotonin receptor modulator is volinanserin, wherein the volinanserin is administered to pretreat a subject between at least 15 minutes and 360 minutes prior to the administration or release of the cathinone compound. In some embodiments, the serotonin receptor modulator is volinanserin, wherein the volinanserin is administered to pretreat between at least 30 minutes and 360 minutes prior to the administration or release of the cathinone compound. In some embodiments, the serotonin receptor modulator is volinanserin, wherein the volinanserin is administered to pretreat between at least 60 minutes and 240 minutes prior to the administration or release of the cathinone compound. In some embodiments, the serotonin receptor modulator is volinanserin, wherein the volinanserin is administered to pretreat at least 90 minutes prior to cathinone compound. In some embodiments, the serotonin receptor modulator is volinanserin, wherein the volinanserin is administered to pretreat at least 120 minutes prior to the cathinone compound.

In some embodiments, the serotonin receptor modulator is volinanserin, wherein the volinanserin is administered to pretreat at least 150 minutes prior to the cathinone compound. In some embodiments, the serotonin receptor modulator is volinanserin, wherein the volinanserin is administered to pretreat between about 15 minutes and about 150 minutes prior to the cathinone compound. In some embodiments, the serotonin receptor modulator is volinanserin, wherein the volinanserin is administered to pretreat at least 180 minutes prior to the cathinone compound. In some embodiments, the serotonin receptor modulator is volinanserin, wherein the volinanserin is administered to pretreat at least 210 minutes prior to the cathinone compound. In some embodiments, the serotonin receptor modulator is volinanserin, wherein the volinanserin is administered to pretreat at least 240 minutes prior to the cathinone compound. In some embodiments, the serotonin receptor modulator is volinanserin, wherein the volinanserin is administered to pretreat at least 270 minutes prior to the cathinone compound. In some embodiments, the serotonin receptor modulator is volinanserin, wherein the volinanserin is administered to pretreat at least 300 minutes prior to the cathinone compound. In some embodiments, the serotonin receptor modulator is volinanserin, wherein the volinanserin is administered to pretreat at least 330 minutes prior to cathinone compound. In some embodiments, the serotonin receptor modulator is volinanserin, wherein the volinanserin is administered to pretreat at least 360 minutes prior to the cathinone compound. In some preferred embodiments, the serotonin receptor modulator is volinanserin, wherein volinanserin is administered to pretreat between about 60 minutes and about 180 minutes prior to the administration of the cathinone compound.

In some embodiments, the serotonin receptor modulator is ketanserin, wherein the ketanserin is administered to pretreat at least 15 minutes prior to the administration of the cathinone compound. In some embodiments, the serotonin receptor modulator is ketanserin, wherein the ketanserin is administered to pretreat between at least 30 minutes and 360 minutes prior to the administration or release of the cathinone compound. In some embodiments, the serotonin receptor modulator is ketanserin, wherein the ketanserin is administered to pretreat between at least 60 minutes and 240 minutes prior to the administration or release of the cathinone compound. In some embodiments, the serotonin receptor modulator is ketanserin, wherein the ketanserin is administered to pretreat at least 90 minutes prior to the cathinone compound. In some embodiments, the serotonin receptor modulator is ketanserin, wherein the ketanserin is administered to pretreat at least 120 minutes prior to the cathinone compound. In some embodiments, the serotonin receptor modulator is ketanserin, wherein the ketanserin is administered to pretreat at least 150 minutes prior to the methylone analog. In some embodiments, the serotonin receptor modulator is ketanserin, wherein the ketanserin is administered to pretreat between about 15 minutes and about 150 minutes prior to the cathinone compound. In some embodiments, the serotonin receptor modulator is ketanserin, wherein the ketanserin is administered to pretreat at least 180 minutes prior to the cathinone compound. In some embodiments, the serotonin receptor modulator is ketanserin, wherein the ketanserin is administered to pretreat at least 210 minutes prior to the cathinone compound. In some embodiments, the serotonin receptor modulator is ketanserin, wherein the ketanserin is administered to pretreat at least 240 minutes prior to the cathinone compound. In some embodiments, the serotonin receptor modulator is ketanserin, wherein the ketanserin is administered to pretreat at least 270 minutes prior to the cathinone compound. In some embodiments, the serotonin receptor modulator is ketanserin, wherein the ketanserin is administered to pretreat at least 300 minutes prior to the cathinone compound. In some embodiments, the serotonin receptor modulator is ketanserin, wherein the ketanserin is administered to pretreat at least 330 minutes prior to the cathinone compound. In some embodiments, the serotonin receptor modulator is ketanserin, wherein the ketanserin is administered to pretreat at least 360 minutes prior to the cathinone compound. In some preferred embodiments, the serotonin receptor modulator is ketanserin, wherein ketanserin is administered to pretreat between about 60 minutes and about 180 minutes prior to the administration of the cathinone compound.

In some embodiments, the serotonin receptor modulator is ritanserin, wherein the ritanserin is administered to pretreat at least 15 minutes prior to the administration of the cathinone compound. In some embodiments, the serotonin receptor modulator is ritanserin, wherein the ritanserin is administered to pretreat at least 30 minutes prior to the cathinone compound. In some embodiments, the serotonin receptor modulator is ritanserin wherein the ritanserin is administered to pretreat between at least 60 minutes and 240 minutes prior to the administration or release of the cathinone compound. In some embodiments, the serotonin receptor modulator is ritanserin, wherein the ritanserin is administered to pretreat at least 90 minutes prior to the cathinone compound. In some embodiments, the serotonin receptor modulator is ritanserin, wherein the ritanserin is administered to pretreat at least 120 minutes prior to the cathinone compound. In some embodiments, the serotonin receptor modulator is ritanserin, wherein the ritanserin is administered to pretreat at least 150 minutes prior to the cathinone compound. In some embodiments, the serotonin receptor modulator is ritanserin, wherein the ritanserin is administered to pretreat between about 15 minutes and about 150 minutes prior to the cathinone compound. In some embodiments, the serotonin receptor modulator is ritanserin, wherein the ritanserin is administered to pretreat at least 180 minutes prior to the cathinone compound. In some embodiments, the serotonin receptor modulator is ritanserin, wherein the ritanserin is administered to pretreat at least 210 minutes prior to the cathinone compound. In some embodiments, the serotonin receptor modulator is ritanserin, wherein the ritanserin is administered to pretreat at least 240 minutes prior to the cathinone compound. In some embodiments, the serotonin receptor modulator is ritanserin, wherein the ritanserin is administered to pretreat at least 270 minutes prior to the cathinone compound. In some embodiments, the serotonin receptor modulator is ritanserin, wherein the ritanserin is administered to pretreat at least 300 minutes prior to the cathinone compound. In some embodiments, the serotonin receptor modulator is ritanserin, wherein the ritanserin is administered to pretreat at least 330 minutes prior to the cathinone compound. In some embodiments, the serotonin receptor modulator is ritanserin, wherein the ritanserin is administered to pretreat at least 360 minutes prior to the cathinone compound. In some preferred embodiments, the serotonin receptor modulator is ritanserin, wherein ritanserin is administered to pretreat between about 60 minutes and about 180 minutes prior to the administration of the cathinone compound.

In some embodiments, the serotonin receptor modulator is pimavanserin, wherein the pimavanserin is administered to pretreat at least 15 minutes prior to the administration of the cathinone compound. In some embodiments, the serotonin receptor modulator is pimavanserin, wherein the pimavanserin is administered to pretreat at least 30 minutes prior to the cathinone compound. In some embodiments, the serotonin receptor modulator is pimavanserin, wherein the pimavanserin is administered to pretreat between at least 60 minutes and 240 minutes prior to the administration or release of the cathinone compound. In some embodiments, the serotonin receptor modulator is pimavanserin, wherein the pimavanserin is administered to pretreat at least 90 minutes prior to the cathinone compound. In some embodiments, the serotonin receptor modulator is pimavanserin, wherein the pimavanserin is administered to pretreat at least 120 minutes prior to the cathinone compound. In some embodiments, the serotonin receptor modulator is pimavanserin, wherein the pimavanserin is administered to pretreat at least 150 minutes prior to the cathinone compound. In some embodiments, the serotonin receptor modulator is pimavanserin, wherein the pimavanserin is administered to pretreat between about 15 minutes and about 150 minutes prior to the cathinone compound. In some embodiments, the serotonin receptor modulator is pimavanserin, wherein the pimavanserin is administered to pretreat at least 180 minutes prior to the cathinone compound. In some embodiments, the serotonin receptor modulator is pimavanserin, wherein the pimavanserin is administered to pretreat at least 210 minutes prior to the cathinone compound. In some embodiments, the serotonin receptor modulator is pimavanserin, wherein the pimavanserin is administered to pretreat at least 240 minutes prior to the cathinone compound. In some embodiments, the serotonin receptor modulator is pimavanserin, wherein the pimavanserin is administered to pretreat at least 270 minutes prior to the cathinone compound. In some embodiments, the serotonin receptor modulator is pimavanserin, wherein the pimavanserin is administered to pretreat at least 300 minutes prior to the cathinone compound. In some embodiments, the serotonin receptor modulator is pimavanserin, wherein the pimavanserin is administered to pretreat at least 330 minutes prior to the cathinone compound. In some embodiments, the serotonin receptor modulator is pimavanserin, wherein the pimavanserin is administered to pretreat at least 360 minutes prior to the cathinone compound. In some preferred embodiments, the serotonin receptor modulator is pimavanserin, wherein pimavanserin is administered to pretreat between about 60 minutes and about 180 minutes prior to the administration of the cathinone compound.

In some embodiments, the serotonin receptor modulator is nelotanserin, wherein the nelotanserin is administered to pretreat at least 15 minutes prior to the administration of the cathinone compound. In some embodiments, the serotonin receptor modulator is nelotanserin, wherein the nelotanserin is administered to pretreat at least 30 minutes prior to the cathinone compound. In some embodiments, the serotonin receptor modulator is nelotanserin, wherein the nelotanserin is administered to pretreat between at least 60 minutes and 240 minutes prior to the administration or release of the cathinone compound. In some embodiments, the serotonin receptor modulator is nelotanserin, wherein the nelotanserin is administered to pretreat at least 90 minutes prior to the cathinone compound. In some embodiments, the serotonin receptor modulator is nelotanserin, wherein the nelotanserin is administered to pretreat at least 120 minutes prior to the cathinone compound.

In some embodiments, the serotonin receptor modulator is nelotanserin, wherein the nelotanserin is administered to pretreat at least 150 minutes prior to the cathinone compound. In some embodiments, the serotonin receptor modulator is nelotanserin, wherein the nelotanserin is administered to pretreat between about 15 minutes and about 150 minutes prior to the cathinone compound. In some embodiments, the serotonin receptor modulator is nelotanserin, wherein the nelotanserin is administered to pretreat at least 180 minutes prior to the cathinone compound. In some embodiments, the serotonin receptor modulator is nelotanserin, wherein the nelotanserin is administered to pretreat at least 210 minutes prior to the cathinone compound. In some embodiments, the serotonin receptor modulator is nelotanserin, wherein the nelotanserin is administered to pretreat at least 240 minutes prior to the cathinone compound. In some embodiments, the serotonin receptor modulator is nelotanserin, wherein the nelotanserin is administered to pretreat at least 270 minutes prior to the cathinone compound.

In some embodiments, the serotonin receptor modulator is nelotanserin, wherein the nelotanserin is administered to pretreat at least 300 minutes prior to the cathinone compound. In some embodiments, the serotonin receptor modulator is nelotanserin, wherein the nelotanserin is administered to pretreat at least 330 minutes prior to the cathinone compound. In some embodiments, the serotonin receptor modulator is nelotanserin, wherein the nelotanserin is administered to pretreat at least 360 minutes prior to the cathinone compound. In some preferred embodiments, the serotonin receptor modulator is nelotanserin, wherein nelotanserin is administered to pretreat between about 60 minutes and about 180 minutes prior to the administration of the cathinone compound.

In some embodiments, the serotonin receptor modulator is pruvanserin, wherein the pruvanserin is administered to pretreat at least 15 minutes prior to the administration of the cathinone compound. In some embodiments, the serotonin receptor modulator is pruvanserin, wherein the pruvanserin is administered to pretreat at least 30 minutes prior to the methylone analog. In some embodiments, the serotonin receptor modulator is pruvanserin, wherein the pruvanserin is administered to pretreat between at least 60 minutes and 240 minutes prior to the administration or release of the cathinone compound. In some embodiments, the serotonin receptor modulator is pruvanserin, wherein the pruvanserin is administered to pretreat at least 90 minutes prior to the cathinone compound. In some embodiments, the serotonin receptor modulator is pruvanserin, wherein the pruvanserin is administered to pretreat at least 120 minutes prior to the cathinone compound. In some embodiments, the serotonin receptor modulator is pruvanserin, wherein the pruvanserin is administered to pretreat at least 150 minutes prior to the cathinone compound. In some embodiments, the serotonin receptor modulator is pruvanserin, wherein the pruvanserin is administered to pretreat between about 15 minutes and about 150 minutes prior to the cathinone compound. In some embodiments, the serotonin receptor modulator is pruvanserin, wherein the pruvanserin is administered to pretreat at least 180 minutes prior to the cathinone compound. In some embodiments, the serotonin receptor modulator is pruvanserin, wherein the pruvanserin is administered to pretreat at least 210 minutes prior to the cathinone compound.

In some embodiments, the serotonin receptor modulator is pruvanserin, wherein the pruvanserin is administered to pretreat at least 240 minutes prior to the cathinone compound. In some embodiments, the serotonin receptor modulator is pruvanserin, wherein the pruvanserin is administered to pretreat at least 270 minutes prior to the cathinone compound. In some embodiments, the serotonin receptor modulator is pruvanserin, wherein the pruvanserin is administered to pretreat at least 300 minutes prior to the cathinone compound. In some embodiments, the serotonin receptor modulator is pruvanserin, wherein the pruvanserin is administered to pretreat at least 330 minutes prior to the cathinone compound. In some embodiments, the serotonin receptor modulator is pruvanserin, wherein the pruvanserin is administered to pretreat at least 360 minutes prior to the cathinone compound. In some preferred embodiments, the serotonin receptor modulator is pruvanserin, wherein pruvanserin is administered to pretreat between about 60 minutes and about 180 minutes prior to the administration of the cathinone compound.

In some embodiments, the serotonin receptor modulator is flibanserin, wherein the flibanserin is administered to pretreat at least 15 minutes prior to the administration of the cathinone compound. In some embodiments, the serotonin receptor modulator is flibanserin, wherein the flibanserin is administered to pretreat at least 30 minutes prior to the methylone analog. In some embodiments, the serotonin receptor modulator is flibanserin, wherein the flibanserin is administered to pretreat between at least 60 minutes and 240 minutes prior to the administration or release of the cathinone compound. In some embodiments, the serotonin receptor modulator is flibanserin, wherein the flibanserin is administered to pretreat at least 90 minutes prior to the cathinone compound. In some embodiments, the serotonin receptor modulator is flibanserin, wherein the flibanserin is administered to pretreat at least 120 minutes prior to the cathinone compound. In some embodiments, the serotonin receptor modulator is flibanserin, wherein the flibanserin is administered to pretreat at least 150 minutes prior to the cathinone compound. In some embodiments, the serotonin receptor modulator is flibanserin, wherein the flibanserin is administered to pretreat between about 15 minutes and about 150 minutes prior to the cathinone compound. In some embodiments, the serotonin receptor modulator is flibanserin, wherein the flibanserin is administered to pretreat at least 180 minutes prior to the cathinone compound. In some embodiments, the serotonin receptor modulator is flibanserin, wherein the flibanserin is administered to pretreat at least 210 minutes prior to the cathinone compound.

In some embodiments, the serotonin receptor modulator is flibanserin, wherein the flibanserin is administered to pretreat at least 240 minutes prior to the cathinone compound. In some embodiments, the serotonin receptor modulator is flibanserin, wherein the flibanserin is administered to pretreat at least 270 minutes prior to the cathinone compound. In some embodiments, the serotonin receptor modulator is flibanserin, wherein the flibanserin is administered to pretreat at least 300 minutes prior to the cathinone compound. In some embodiments, the serotonin receptor modulator is flibanserin, wherein the flibanserin is administered to pretreat at least 330 minutes prior to the cathinone compound. In some embodiments, the serotonin receptor modulator is flibanserin, wherein the flibanserin is administered to pretreat at least 360 minutes prior to the cathinone compound. In some preferred embodiments, the serotonin receptor modulator is flibanserin, wherein flibanserin is administered to pretreat between about 60 minutes and about 180 minutes prior to the administration of the cathinone compound.

In some embodiments, the serotonin receptor modulator is olanzapine, wherein the olanzapine is administered to pretreat at least 15 minutes prior to the administration of the cathinone compound. In some embodiments, the serotonin receptor modulator is olanzapine, wherein the olanzapine is administered to pretreat at least 30 minutes prior to the methylone analog. In some embodiments, the serotonin receptor modulator is olanzapine, wherein the olanzapine is administered to pretreat between at least 60 minutes and 240 minutes prior to the administration or release of the cathinone compound. In some embodiments, the serotonin receptor modulator is olanzapine, wherein the olanzapine is administered to pretreat at least 90 minutes prior to the cathinone compound. In some embodiments, the serotonin receptor modulator is olanzapine, wherein the olanzapine is administered to pretreat at least 120 minutes prior to the cathinone compound. In some embodiments, the serotonin receptor modulator is olanzapine, wherein the olanzapine is administered to pretreat at least 150 minutes prior to the cathinone compound. In some embodiments, the serotonin receptor modulator is olanzapine, wherein the olanzapine is administered to pretreat between about 15 minutes and about 150 minutes prior to the cathinone compound. In some embodiments, the serotonin receptor modulator is olanzapine, wherein the olanzapine is administered to pretreat at least 180 minutes prior to the cathinone compound. In some embodiments, the serotonin receptor modulator is olanzapine, wherein the olanzapine is administered to pretreat at least 210 minutes prior to the cathinone compound.

In some embodiments, the serotonin receptor modulator is olanzapine, wherein the olanzapine is administered to pretreat at least 240 minutes prior to the cathinone compound. In some embodiments, the serotonin receptor modulator is olanzapine, wherein the olanzapine is administered to pretreat at least 270 minutes prior to the cathinone compound. In some embodiments, the serotonin receptor modulator is olanzapine, wherein the olanzapine is administered to pretreat at least 300 minutes prior to the cathinone compound. In some embodiments, the serotonin receptor modulator is olanzapine, wherein the olanzapine is administered to pretreat at least 330 minutes prior to the cathinone compound. In some embodiments, the serotonin receptor modulator is olanzapine, wherein the olanzapine is administered to pretreat at least 360 minutes prior to the cathinone compound. In some preferred embodiments, the serotonin receptor modulator is olanzapine, wherein olanzapine is administered to pretreat between about 60 minutes and about 180 minutes prior to the administration of the cathinone compound.

In some embodiments, the serotonin receptor modulator is quetiapine, wherein the quetiapine is administered to pretreat at least 15 minutes prior to the administration of the cathinone compound. In some embodiments, the serotonin receptor modulator is quetiapine, wherein the quetiapine is administered to pretreat at least 30 minutes prior to the methylone analog. In some embodiments, the serotonin receptor modulator is quetiapine, wherein the quetiapine is administered to pretreat between at least 60 minutes and 240 minutes prior to the administration or release of the cathinone compound. In some embodiments, the serotonin receptor modulator is quetiapine, wherein the quetiapine is administered to pretreat at least 90 minutes prior to the cathinone compound. In some embodiments, the serotonin receptor modulator is quetiapine, wherein the quetiapine is administered to pretreat at least 120 minutes prior to the cathinone compound. In some embodiments, the serotonin receptor modulator is quetiapine, wherein the quetiapine is administered to pretreat at least 150 minutes prior to the cathinone compound. In some embodiments, the serotonin receptor modulator is quetiapine, wherein the quetiapine is administered to pretreat between about 15 minutes and about 150 minutes prior to the cathinone compound. In some embodiments, the serotonin receptor modulator is quetiapine, wherein the quetiapine is administered to pretreat at least 180 minutes prior to the cathinone compound. In some embodiments, the serotonin receptor modulator is quetiapine, wherein the quetiapine is administered to pretreat at least 210 minutes prior to the cathinone compound.

In some embodiments, the serotonin receptor modulator is quetiapine, wherein the quetiapine is administered to pretreat at least 240 minutes prior to the cathinone compound. In some embodiments, the serotonin receptor modulator is quetiapine, wherein the quetiapine is administered to pretreat at least 270 minutes prior to the cathinone compound. In some embodiments, the serotonin receptor modulator is quetiapine, wherein the quetiapine is administered to pretreat at least 300 minutes prior to the cathinone compound. In some embodiments, the serotonin receptor modulator is quetiapine, wherein the quetiapine is administered to pretreat at least 330 minutes prior to the cathinone compound. In some embodiments, the serotonin receptor modulator is quetiapine, wherein the quetiapine is administered to pretreat at least 360 minutes prior to the cathinone compound. In some preferred embodiments, the serotonin receptor modulator is quetiapine, wherein quetiapine is administered to pretreat between about 60 minutes and about 180 minutes prior to the administration of the cathinone compound.

In some embodiments, the serotonin receptor modulator is risperidone, wherein the risperidone is administered to pretreat at least 15 minutes prior to the administration of the cathinone compound. In some embodiments, the serotonin receptor modulator is risperidone, wherein the risperidone is administered to pretreat at least 30 minutes prior to the methylone analog. In some embodiments, the serotonin receptor modulator is risperidone, wherein the risperidone is administered to pretreat between at least 60 minutes and 240 minutes prior to the administration or release of the cathinone compound. In some embodiments, the serotonin receptor modulator is risperidone, wherein the risperidone is administered to pretreat at least 90 minutes prior to the cathinone compound. In some embodiments, the serotonin receptor modulator is risperidone, wherein the risperidone is administered to pretreat at least 120 minutes prior to the cathinone compound. In some embodiments, the serotonin receptor modulator is risperidone, wherein the risperidone is administered to pretreat at least 150 minutes prior to the cathinone compound. In some embodiments, the serotonin receptor modulator is risperidone, wherein the risperidone is administered to pretreat between about 15 minutes and about 150 minutes prior to the cathinone compound. In some embodiments, the serotonin receptor modulator is risperidone, wherein the risperidone is administered to pretreat at least 180 minutes prior to the cathinone compound. In some embodiments, the serotonin receptor modulator is risperidone, wherein the risperidone is administered to pretreat at least 210 minutes prior to the cathinone compound.

In some embodiments, the serotonin receptor modulator is risperidone, wherein the risperidone is administered to pretreat at least 240 minutes prior to the cathinone compound. In some embodiments, the serotonin receptor modulator is risperidone, wherein the risperidone is administered to pretreat at least 270 minutes prior to the cathinone compound. In some embodiments, the serotonin receptor modulator is risperidone, wherein the risperidone is administered to pretreat at least 300 minutes prior to the cathinone compound. In some embodiments, the serotonin receptor modulator is risperidone, wherein the risperidone is administered to pretreat at least 330 minutes prior to the cathinone compound. In some embodiments, the serotonin receptor modulator is risperidone, wherein the risperidone is administered to pretreat at least 360 minutes prior to the cathinone compound. In some preferred embodiments, the serotonin receptor modulator is risperidone, wherein risperidone is administered to pretreat between about 60 minutes and about 180 minutes prior to the administration of the cathinone compound.

In some embodiments, the serotonin receptor modulator is administered after a compound disclosed herein, such as from about one to about three hours post to administration of a compound disclosed herein. In some embodiments, the serotonin receptor modulator is administered at most about one hour post to the presently disclosed compound.

In certain embodiments, such as those described above a disclosed cathinone compound is co-administered with a serotonin receptor modulator in the same or in separate compositions. In one embodiment, the cathinone compound is administered in a modified release formulation such that the subject is effectively post-treated with serotonin receptor modulator post to release of an effective amount of the methylone. In some embodiments, the serotonin receptor modulator is part of a single fixed dose formulation that releases the methylone first followed by serotonin receptor modulator on two different release profiles. In another embodiment, the cathinone compound is administered first as a single dosage and, after a length of time, serotonin receptor modulator is administered as a second dosage separate from the first dosage. Thus, in some embodiments, the serotonin receptor modulator is administered or released from a composition provided herein post to the administration and/or release of the cathinone compound. This allows post-treatment to attenuate activation of the serotonin receptor by the cathinone compound.

In some embodiments, the serotonin receptor modulator is administered or released from the composition provided herein to post-treat a subject by at least about 5 minutes, 10 minutes, 20 minutes, 30 minutes, 40 minutes, 50 minutes, 1 hour, 1.25 hours, 1.5 hours, 2 hours, or 3 hours post to the release of the cathinone compound. In some embodiments, the serotonin receptor modulator attenuates the activation of the serotonin receptor when the serotonin receptor modulator is used to post-treat at most about 3 hours, 4 hours, 5 hours, 6 hours, 7 hours, 8 hours, 9 hours, or more than 9 hours post to the release of cathinone compound. In some embodiments, the serotonin receptor modulator attenuates the activation of the serotonin receptor when the serotonin receptor modulator is used to post-treat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour post to the release of the cathinone compound.

In a preferred embodiment, the serotonin receptor modulator is administered at about 1 hour to about 3 hours post to the administration of the cathinone compound.

In some embodiments, the serotonin receptor modulator is eplivanserin, wherein the eplivanserin is administered to post-treat at least 15 minutes post to the administration of the cathinone compound. In some embodiments, the serotonin receptor modulator is eplivanserin, wherein the eplivanserin is administered to post-treat between at least 30 minutes post and 360 minutes post to the release or administration of the cathinone compound. In some embodiments, the serotonin receptor modulator is eplivanserin, wherein the eplivanserin is administered to post-treat between at least 60 minutes post and 360 minutes post to the release or administration the cathinone compound. In some embodiments, the serotonin receptor modulator is eplivanserin, wherein the eplivanserin is administered to post-treat between at least 90 minutes and 240 minutes post to the cathinone compound. In some embodiments, the serotonin receptor modulator is eplivanserin, wherein the eplivanserin is administered to post-treat at least 120 minutes post to the cathinone compound.

In some embodiments, the serotonin receptor modulator is eplivanserin, wherein the eplivanserin is administered to post-treat at least 150 minutes post to the cathinone compound. In some embodiments, the serotonin receptor modulator is eplivanserin, wherein the eplivanserin is administered to post-treat between about 15 minutes and about 150 minutes post to the cathinone compound. In some embodiments, the serotonin receptor modulator is eplivanserin, wherein the eplivanserin is administered to post-treat at least 180 minutes post to the cathinone compound. In some embodiments, the serotonin receptor modulator is eplivanserin, wherein the eplivanserin is administered to post-treat at least 210 minutes post to the cathinone compound. In some embodiments, the serotonin receptor modulator is eplivanserin, wherein the eplivanserin is administered to post-treat at least 240 minutes post to the cathinone compound.

In some embodiments, the serotonin receptor modulator is eplivanserin, wherein the eplivanserin is administered to post-treat at least 270 minutes post to the cathinone compound. In some embodiments, the serotonin receptor modulator is eplivanserin, wherein the eplivanserin is administered to post-treat at least 300 minutes post to the cathinone compound. In some embodiments, the serotonin receptor modulator is eplivanserin, wherein the eplivanserin is administered to post-treat at least 330 minutes post to the cathinone compound. In some embodiments, the serotonin receptor modulator is eplivanserin, wherein the eplivanserin is administered to post-treat at least 360 minutes post to administration or release of the cathinone compound.

In some preferred embodiments, the serotonin receptor modulator is eplivanserin, wherein eplivanserin is administered to post-treat between about 60 minutes and about 180 minutes post to the administration or release of the cathinone compound.

In some embodiments, the serotonin receptor modulator is volinanserin, wherein the volinanserin is administered to post-treat a subject between at least 15 minutes and 360 minutes post to the administration or release of the cathinone compound. In some embodiments, the serotonin receptor modulator is volinanserin, wherein the volinanserin is administered to post-treat between at least 30 minutes and 360 minutes post to the administration or release of the cathinone compound. In some embodiments, the serotonin receptor modulator is volinanserin, wherein the volinanserin is administered to post-treat between at least 60 minutes and 240 minutes post to the administration or release of the cathinone compound. In some embodiments, the serotonin receptor modulator is volinanserin, wherein the volinanserin is administered to post-treat at least 90 minutes post to cathinone compound. In some embodiments, the serotonin receptor modulator is volinanserin, wherein the volinanserin is administered to post-treat at least 120 minutes post to the cathinone compound.

In some embodiments, the serotonin receptor modulator is volinanserin, wherein the volinanserin is administered to post-treat at least 150 minutes post to the cathinone compound. In some embodiments, the serotonin receptor modulator is volinanserin, wherein the volinanserin is administered to post-treat between about 15 minutes and about 150 minutes post to the cathinone compound. In some embodiments, the serotonin receptor modulator is volinanserin, wherein the volinanserin is administered to post-treat at least 180 minutes post to the cathinone compound. In some embodiments, the serotonin receptor modulator is volinanserin, wherein the volinanserin is administered to post-treat at least 210 minutes post to the cathinone compound. In some embodiments, the serotonin receptor modulator is volinanserin, wherein the volinanserin is administered to post-treat at least 240 minutes post to the cathinone compound. In some embodiments, the serotonin receptor modulator is volinanserin, wherein the volinanserin is administered to post-treat at least 270 minutes post to the cathinone compound. In some embodiments, the serotonin receptor modulator is volinanserin, wherein the volinanserin is administered to post-treat at least 300 minutes post to the cathinone compound. In some embodiments, the serotonin receptor modulator is volinanserin, wherein the volinanserin is administered to post-treat at least 330 minutes post to cathinone compound. In some embodiments, the serotonin receptor modulator is volinanserin, wherein the volinanserin is administered to post-treat at least 360 minutes post to the cathinone compound. In some preferred embodiments, the serotonin receptor modulator is volinanserin, wherein volinanserin is administered to post-treat between about 60 minutes and about 180 minutes post to the administration of the cathinone compound.

In some embodiments, the serotonin receptor modulator is ketanserin, wherein the ketanserin is administered to post-treat at least 15 minutes post to the administration of the cathinone compound. In some embodiments, the serotonin receptor modulator is ketanserin, wherein the ketanserin is administered to post-treat between at least 30 minutes and 360 minutes post to the administration or release of the cathinone compound. In some embodiments, the serotonin receptor modulator is ketanserin, wherein the ketanserin is administered to post-treat between at least 60 minutes and 240 minutes post to the administration or release of the cathinone compound. In some embodiments, the serotonin receptor modulator is ketanserin, wherein the ketanserin is administered to post-treat at least 90 minutes post to the cathinone compound. In some embodiments, the serotonin receptor modulator is ketanserin, wherein the ketanserin is administered to post-treat at least 120 minutes post to the cathinone compound. In some embodiments, the serotonin receptor modulator is ketanserin, wherein the ketanserin is administered to post-treat at least 150 minutes post to the cathinone compound. In some embodiments, the serotonin receptor modulator is ketanserin, wherein the ketanserin is administered to post-treat between about 15 minutes and about 150 minutes post to the cathinone compound. In some embodiments, the serotonin receptor modulator is ketanserin, wherein the ketanserin is administered to post-treat at least 180 minutes post to the cathinone compound. In some embodiments, the serotonin receptor modulator is ketanserin, wherein the ketanserin is administered to post-treat at least 210 minutes post to the cathinone compound. In some embodiments, the serotonin receptor modulator is ketanserin, wherein the ketanserin is administered to post-treat at least 240 minutes post to the cathinone compound. In some embodiments, the serotonin receptor modulator is ketanserin, wherein the ketanserin is administered to post-treat at least 270 minutes post to the cathinone compound. In some embodiments, the serotonin receptor modulator is ketanserin, wherein the ketanserin is administered to post-treat at least 300 minutes post to the cathinone compound. In some embodiments, the serotonin receptor modulator is ketanserin, wherein the ketanserin is administered to post-treat at least 330 minutes post to the cathinone compound. In some embodiments, the serotonin receptor modulator is ketanserin, wherein the ketanserin is administered to post-treat at least 360 minutes post to the cathinone compound. In some preferred embodiments, the serotonin receptor modulator is ketanserin, wherein ketanserin is administered to post-treat between about 60 minutes and about 180 minutes post to the administration of the cathinone compound.

In some embodiments, the serotonin receptor modulator is ritanserin, wherein the ritanserin is administered to post-treat at least 15 minutes post to the administration of the cathinone compound. In some embodiments, the serotonin receptor modulator is ritanserin, wherein the ritanserin is administered to post-treat at least 30 minutes post to the cathinone compound. In some embodiments, the serotonin receptor modulator is ritanserin wherein the ritanserin is administered to post-treat between at least 60 minutes and 240 minutes post to the administration or release of the cathinone compound. In some embodiments, the serotonin receptor modulator is ritanserin, wherein the ritanserin is administered to post-treat at least 90 minutes post to the cathinone compound. In some embodiments, the serotonin receptor modulator is ritanserin, wherein the ritanserin is administered to post-treat at least 120 minutes post to the cathinone compound. In some embodiments, the serotonin receptor modulator is ritanserin, wherein the ritanserin is administered to post-treat at least 150 minutes post to the cathinone compound. In some embodiments, the serotonin receptor modulator is ritanserin, wherein the ritanserin is administered to post-treat between about 15 minutes and about 150 minutes post to the cathinone compound. In some embodiments, the serotonin receptor modulator is ritanserin, wherein the ritanserin is administered to post-treat at least 180 minutes post to the cathinone compound. In some embodiments, the serotonin receptor modulator is ritanserin, wherein the ritanserin is administered to post-treat at least 210 minutes post to the cathinone compound. In some embodiments, the serotonin receptor modulator is ritanserin, wherein the ritanserin is administered to post-treat at least 240 minutes post to the cathinone compound. In some embodiments, the serotonin receptor modulator is ritanserin, wherein the ritanserin is administered to post-treat at least 270 minutes post to the cathinone compound. In some embodiments, the serotonin receptor modulator is ritanserin, wherein the ritanserin is administered to post-treat at least 300 minutes post to the cathinone compound. In some embodiments, the serotonin receptor modulator is ritanserin, wherein the ritanserin is administered to post-treat at least 330 minutes post to the cathinone compound. In some embodiments, the serotonin receptor modulator is ritanserin, wherein the ritanserin is administered to post-treat at least 360 minutes post to the cathinone compound. In some preferred embodiments, the serotonin receptor modulator is ritanserin, wherein ritanserin is administered to post-treat between about 60 minutes and about 180 minutes post to the administration of the cathinone compound.

In some embodiments, the serotonin receptor modulator is pimavanserin, wherein the pimavanserin is administered to post-treat at least 15 minutes post to the administration of the cathinone compound. In some embodiments, the serotonin receptor modulator is pimavanserin, wherein the pimavanserin is administered to post-treat at least 30 minutes post to the cathinone compound. In some embodiments, the serotonin receptor modulator is pimavanserin, wherein the pimavanserin is administered to post-treat between at least 60 minutes and 240 minutes post to the administration or release of the cathinone compound. In some embodiments, the serotonin receptor modulator is pimavanserin, wherein the pimavanserin is administered to post-treat at least 90 minutes post to the cathinone compound. In some embodiments, the serotonin receptor modulator is pimavanserin, wherein the pimavanserin is administered to post-treat at least 120 minutes post to the cathinone compound. In some embodiments, the serotonin receptor modulator is pimavanserin, wherein the pimavanserin is administered to post-treat at least 150 minutes post to the cathinone compound. In some embodiments, the serotonin receptor modulator is pimavanserin, wherein the pimavanserin is administered to post-treat between about 15 minutes and about 150 minutes post to the cathinone compound. In some embodiments, the serotonin receptor modulator is pimavanserin, wherein the pimavanserin is administered to post-treat at least 180 minutes post to the cathinone compound. In some embodiments, the serotonin receptor modulator is pimavanserin, wherein the pimavanserin is administered to post-treat at least 210 minutes post to the cathinone compound. In some embodiments, the serotonin receptor modulator is pimavanserin, wherein the pimavanserin is administered to post-treat at least 240 minutes post to the cathinone compound. In some embodiments, the serotonin receptor modulator is pimavanserin, wherein the pimavanserin is administered to post-treat at least 270 minutes post to the cathinone compound. In some embodiments, the serotonin receptor modulator is pimavanserin, wherein the pimavanserin is administered to post-treat at least 300 minutes post to the cathinone compound. In some embodiments, the serotonin receptor modulator is pimavanserin, wherein the pimavanserin is administered to post-treat at least 330 minutes post to the cathinone compound. In some embodiments, the serotonin receptor modulator is pimavanserin, wherein the pimavanserin is administered to post-treat at least 360 minutes post to the cathinone compound. In some preferred embodiments, the serotonin receptor modulator is pimavanserin, wherein pimavanserin is administered to post-treat between about 60 minutes and about 180 minutes post to the administration of the cathinone compound.

In some embodiments, the serotonin receptor modulator is nelotanserin, wherein the nelotanserin is administered to post-treat at least 15 minutes post to the administration of the cathinone compound. In some embodiments, the serotonin receptor modulator is nelotanserin, wherein the nelotanserin is administered to post-treat at least 30 minutes post to the cathinone compound. In some embodiments, the serotonin receptor modulator is nelotanserin, wherein the nelotanserin is administered to post-treat between at least 60 minutes and 240 minutes post to the administration or release of the cathinone compound. In some embodiments, the serotonin receptor modulator is nelotanserin, wherein the nelotanserin is administered to post-treat at least 90 minutes post to the cathinone compound. In some embodiments, the serotonin receptor modulator is nelotanserin, wherein the nelotanserin is administered to post-treat at least 120 minutes post to the cathinone compound.

In some embodiments, the serotonin receptor modulator is nelotanserin, wherein the nelotanserin is administered to post-treat at least 150 minutes post to the cathinone compound. In some embodiments, the serotonin receptor modulator is nelotanserin, wherein the nelotanserin is administered to post-treat between about 15 minutes and about 150 minutes post to the cathinone compound. In some embodiments, the serotonin receptor modulator is nelotanserin, wherein the nelotanserin is administered to post-treat at least 180 minutes post to the cathinone compound. In some embodiments, the serotonin receptor modulator is nelotanserin, wherein the nelotanserin is administered to post-treat at least 210 minutes post to the cathinone compound. In some embodiments, the serotonin receptor modulator is nelotanserin, wherein the nelotanserin is administered to post-treat at least 240 minutes post to the cathinone compound. In some embodiments, the serotonin receptor modulator is nelotanserin, wherein the nelotanserin is administered to post-treat at least 270 minutes post to the cathinone compound.

In some embodiments, the serotonin receptor modulator is nelotanserin, wherein the nelotanserin is administered to post-treat at least 300 minutes post to the cathinone compound. In some embodiments, the serotonin receptor modulator is nelotanserin, wherein the nelotanserin is administered to post-treat at least 330 minutes post to the cathinone compound. In some embodiments, the serotonin receptor modulator is nelotanserin, wherein the nelotanserin is administered to post-treat at least 360 minutes post to the cathinone compound. In some preferred embodiments, the serotonin receptor modulator is nelotanserin, wherein nelotanserin is administered to post-treat between about 60 minutes and about 180 minutes post to the administration of the cathinone compound.

In some embodiments, the serotonin receptor modulator is pruvanserin, wherein the pruvanserin is administered to post-treat at least 15 minutes post to the administration of the cathinone compound. In some embodiments, the serotonin receptor modulator is pruvanserin, wherein the pruvanserin is administered to post-treat at least 30 minutes post to the cathinone compound. In some embodiments, the serotonin receptor modulator is pruvanserin, wherein the pruvanserin is administered to post-treat between at least 60 minutes and 240 minutes post to the administration or release of the cathinone compound. In some embodiments, the serotonin receptor modulator is pruvanserin, wherein the pruvanserin is administered to post-treat at least 90 minutes post to the cathinone compound. In some embodiments, the serotonin receptor modulator is pruvanserin, wherein the pruvanserin is administered to post-treat at least 120 minutes post to the cathinone compound. In some embodiments, the serotonin receptor modulator is pruvanserin, wherein the pruvanserin is administered to post-treat at least 150 minutes post to the cathinone compound. In some embodiments, the serotonin receptor modulator is pruvanserin, wherein the pruvanserin is administered to post-treat between about 15 minutes and about 150 minutes post to the cathinone compound. In some embodiments, the serotonin receptor modulator is pruvanserin, wherein the pruvanserin is administered to post-treat at least 180 minutes post to the cathinone compound. In some embodiments, the serotonin receptor modulator is pruvanserin, wherein the pruvanserin is administered to post-treat at least 210 minutes post to the cathinone compound.

In some embodiments, the serotonin receptor modulator is pruvanserin, wherein the pruvanserin is administered to post-treat at least 240 minutes post to the cathinone compound. In some embodiments, the serotonin receptor modulator is pruvanserin, wherein the pruvanserin is administered to post-treat at least 270 minutes post to the cathinone compound. In some embodiments, the serotonin receptor modulator is pruvanserin, wherein the pruvanserin is administered to post-treat at least 300 minutes post to the cathinone compound. In some embodiments, the serotonin receptor modulator is pruvanserin, wherein the pruvanserin is administered to post-treat at least 330 minutes post to the cathinone compound. In some embodiments, the serotonin receptor modulator is pruvanserin, wherein the pruvanserin is administered to post-treat at least 360 minutes post to the cathinone compound. In some preferred embodiments, the serotonin receptor modulator is pruvanserin, wherein pruvanserin is administered to post-treat between about 60 minutes and about 180 minutes post to the administration of the cathinone compound.

In some embodiments, the serotonin receptor modulator is flibanserin, wherein the flibanserin is administered to post-treat at least 15 minutes post to the administration of the cathinone compound. In some embodiments, the serotonin receptor modulator is flibanserin, wherein the flibanserin is administered to post-treat at least 30 minutes post to the cathinone compound. In some embodiments, the serotonin receptor modulator is flibanserin, wherein the flibanserin is administered to post-treat between at least 60 minutes and 240 minutes post to the administration or release of the cathinone compound. In some embodiments, the serotonin receptor modulator is flibanserin, wherein the flibanserin is administered to post-treat at least 90 minutes post to the cathinone compound. In some embodiments, the serotonin receptor modulator is flibanserin, wherein the flibanserin is administered to post-treat at least 120 minutes post to the cathinone compound. In some embodiments, the serotonin receptor modulator is flibanserin, wherein the flibanserin is administered to post-treat at least 150 minutes post to the cathinone compound. In some embodiments, the serotonin receptor modulator is flibanserin, wherein the flibanserin is administered to post-treat between about 15 minutes and about 150 minutes post to the cathinone compound. In some embodiments, the serotonin receptor modulator is flibanserin, wherein the flibanserin is administered to post-treat at least 180 minutes post to the cathinone compound. In some embodiments, the serotonin receptor modulator is flibanserin, wherein the flibanserin is administered to post-treat at least 210 minutes post to the cathinone compound.

In some embodiments, the serotonin receptor modulator is flibanserin, wherein the flibanserin is administered to post-treat at least 240 minutes post to the cathinone compound. In some embodiments, the serotonin receptor modulator is flibanserin, wherein the flibanserin is administered to post-treat at least 270 minutes post to the cathinone compound. In some embodiments, the serotonin receptor modulator is flibanserin, wherein the flibanserin is administered to post-treat at least 300 minutes post to the cathinone compound. In some embodiments, the serotonin receptor modulator is flibanserin, wherein the flibanserin is administered to post-treat at least 330 minutes post to the cathinone compound. In some embodiments, the serotonin receptor modulator is flibanserin, wherein the flibanserin is administered to post-treat at least 360 minutes post to the cathinone compound. In some preferred embodiments, the serotonin receptor modulator is flibanserin, wherein flibanserin is administered to post-treat between about 60 minutes and about 180 minutes post to the administration of the cathinone compound.

In some embodiments, the serotonin receptor modulator is olanzapine, wherein the olanzapine is administered to post-treat at least 15 minutes post to the administration of the cathinone compound. In some embodiments, the serotonin receptor modulator is olanzapine, wherein the olanzapine is administered to post-treat at least 30 minutes post to the cathinone compound. In some embodiments, the serotonin receptor modulator is olanzapine, wherein the olanzapine is administered to post-treat between at least 60 minutes and 240 minutes post to the administration or release of the cathinone compound. In some embodiments, the serotonin receptor modulator is olanzapine, wherein the olanzapine is administered to post-treat at least 90 minutes post to the cathinone compound. In some embodiments, the serotonin receptor modulator is olanzapine, wherein the olanzapine is administered to post-treat at least 120 minutes post to the cathinone compound. In some embodiments, the serotonin receptor modulator is olanzapine, wherein the olanzapine is administered to post-treat at least 150 minutes post to the cathinone compound. In some embodiments, the serotonin receptor modulator is olanzapine, wherein the olanzapine is administered to post-treat between about 15 minutes and about 150 minutes post to the cathinone compound. In some embodiments, the serotonin receptor modulator is olanzapine, wherein the olanzapine is administered to post-treat at least 180 minutes post to the cathinone compound. In some embodiments, the serotonin receptor modulator is olanzapine, wherein the olanzapine is administered to post-treat at least 210 minutes post to the cathinone compound.

In some embodiments, the serotonin receptor modulator is olanzapine, wherein the olanzapine is administered to post-treat at least 240 minutes post to the cathinone compound. In some embodiments, the serotonin receptor modulator is olanzapine, wherein the olanzapine is administered to post-treat at least 270 minutes post to the cathinone compound. In some embodiments, the serotonin receptor modulator is olanzapine, wherein the olanzapine is administered to post-treat at least 300 minutes post to the cathinone compound. In some embodiments, the serotonin receptor modulator is olanzapine, wherein the olanzapine is administered to post-treat at least 330 minutes post to the cathinone compound. In some embodiments, the serotonin receptor modulator is olanzapine, wherein the olanzapine is administered to post-treat at least 360 minutes post to the cathinone compound. In some preferred embodiments, the serotonin receptor modulator is olanzapine, wherein olanzapine is administered to post-treat between about 60 minutes and about 180 minutes post to the administration of the cathinone compound.

In some embodiments, the serotonin receptor modulator is quetiapine, wherein the quetiapine is administered to post-treat at least 15 minutes post to the administration of the cathinone compound. In some embodiments, the serotonin receptor modulator is quetiapine, wherein the quetiapine is administered to post-treat at least 30 minutes post to the cathinone compound. In some embodiments, the serotonin receptor modulator is quetiapine, wherein the quetiapine is administered to post-treat between at least 60 minutes and 240 minutes post to the administration or release of the cathinone compound. In some embodiments, the serotonin receptor modulator is quetiapine, wherein the quetiapine is administered to post-treat at least 90 minutes post to the cathinone compound. In some embodiments, the serotonin receptor modulator is quetiapine, wherein the quetiapine is administered to post-treat at least 120 minutes post to the cathinone compound. In some embodiments, the serotonin receptor modulator is quetiapine, wherein the quetiapine is administered to post-treat at least 150 minutes post to the cathinone compound. In some embodiments, the serotonin receptor modulator is quetiapine, wherein the quetiapine is administered to post-treat between about 15 minutes and about 150 minutes post to the cathinone compound. In some embodiments, the serotonin receptor modulator is quetiapine, wherein the quetiapine is administered to post-treat at least 180 minutes post to the cathinone compound. In some embodiments, the serotonin receptor modulator is quetiapine, wherein the quetiapine is administered to post-treat at least 210 minutes post to the cathinone compound.

In some embodiments, the serotonin receptor modulator is quetiapine, wherein the quetiapine is administered to post-treat at least 240 minutes post to the cathinone compound. In some embodiments, the serotonin receptor modulator is quetiapine, wherein the quetiapine is administered to post-treat at least 270 minutes post to the cathinone compound. In some embodiments, the serotonin receptor modulator is quetiapine, wherein the quetiapine is administered to post-treat at least 300 minutes post to the cathinone compound. In some embodiments, the serotonin receptor modulator is quetiapine, wherein the quetiapine is administered to post-treat at least 330 minutes post to the cathinone compound. In some embodiments, the serotonin receptor modulator is quetiapine, wherein the quetiapine is administered to post-treat at least 360 minutes post to the cathinone compound. In some preferred embodiments, the serotonin receptor modulator is quetiapine, wherein quetiapine is administered to post-treat between about 60 minutes and about 180 minutes post to the administration of the cathinone compound.

In some embodiments, the serotonin receptor modulator is risperidone, wherein the risperidone is administered to post-treat at least 15 minutes post to the administration of the cathinone compound. In some embodiments, the serotonin receptor modulator is risperidone, wherein the risperidone is administered to post-treat at least 30 minutes post to the cathinone compound. In some embodiments, the serotonin receptor modulator is risperidone, wherein the risperidone is administered to post-treat between at least 60 minutes and 240 minutes post to the administration or release of the cathinone compound. In some embodiments, the serotonin receptor modulator is risperidone, wherein the risperidone is administered to post-treat at least 90 minutes post to the cathinone compound. In some embodiments, the serotonin receptor modulator is risperidone, wherein the risperidone is administered to post-treat at least 120 minutes post to the cathinone compound. In some embodiments, the serotonin receptor modulator is risperidone, wherein the risperidone is administered to post-treat at least 150 minutes post to the cathinone compound. In some embodiments, the serotonin receptor modulator is risperidone, wherein the risperidone is administered to post-treat between about 15 minutes and about 150 minutes post to the cathinone compound. In some embodiments, the serotonin receptor modulator is risperidone, wherein the risperidone is administered to post-treat at least 180 minutes post to the cathinone compound. In some embodiments, the serotonin receptor modulator is risperidone, wherein the risperidone is administered to post-treat at least 210 minutes post to the cathinone compound.

In some embodiments, the serotonin receptor modulator is risperidone, wherein the risperidone is administered to post-treat at least 240 minutes post to the cathinone compound. In some embodiments, the serotonin receptor modulator is risperidone, wherein the risperidone is administered to post-treat at least 270 minutes post to the cathinone compound. In some embodiments, the serotonin receptor modulator is risperidone, wherein the risperidone is administered to post-treat at least 300 minutes post to the cathinone compound. In some embodiments, the serotonin receptor modulator is risperidone, wherein the risperidone is administered to post-treat at least 330 minutes post to the cathinone compound. In some embodiments, the serotonin receptor modulator is risperidone, wherein the risperidone is administered to post-treat at least 360 minutes post to the cathinone compound. In some preferred embodiments, the serotonin receptor modulator is risperidone, wherein risperidone is administered to post-treat between about 60 minutes and about 180 minutes post to the administration of the cathinone compound.

In some embodiments, non-hallucinogenic 5-HT2A modulators (e.g., 5-HT2A agonists) are used to treat neurological diseases. In some embodiments, the neurological diseases comprise decreased neural plasticity, decreased cortical structural plasticity, decreased 5-HT2A receptor content, decreased dendritic arbor complexity, loss of dendritic spines, decreased dendritic branch content, decreased spinogenesis, decreased neuritogenesis, retraction of neurites, or any combination thereof.

In some embodiments, non-hallucinogenic 5-HT2A modulators (e.g., 5-HT2A agonists) are used for increasing neuronal plasticity. In some embodiments, non-hallucinogenic 5-HT2A modulators (e.g., 5-HT2A agonists) are used for treating a brain disorder. In some embodiments, non-hallucinogenic 5-HT2A modulators (e.g., 5-HT2A agonists) are used for increasing at least one of translation, transcription, or secretion of neurotrophic factors.

In some embodiments the presently disclosed compounds are given to patients in a low dose that is lower than would produce noticeable psychedelic effects but high enough to provide a therapeutic benefit. This dose range is predicted to be between 200 μg (micrograms) and 2 mg.

Methods for Increasing Neuronal Plasticity

Neuronal plasticity refers to the ability of the brain to change structure and/or function throughout a subject's life. New neurons can be produced and integrated into the central nervous system throughout the subject's life. Increasing neuronal plasticity includes, but is not limited to, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing neuronal plasticity comprises promoting neuronal growth, promoting neuritogenesis, promoting synaptogenesis, promoting dendritogenesis, increasing dendritic arbor complexity, and increasing dendritic spine density.

In some embodiments, increasing neuronal plasticity by treating a subject with a compound provided herein can treat neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In some embodiments, the present disclosure provides methods for increasing neuronal plasticity, comprising contacting a neuronal cell with a cathinone compound disclosed herein. In some embodiments, increasing neuronal plasticity improves a brain disorder described herein.

In some embodiments, a compound of the present disclosure is used to increase neuronal plasticity. In some embodiments, the compounds used to increase neuronal plasticity have, for example, anti-addictive properties, antidepressant properties, anxiolytic properties, or a combination thereof. In some embodiments, decreased neuronal plasticity is associated with a neuropsychiatric disease. In some embodiments, the neuropsychiatric disease is a mood or anxiety disorder. In some embodiments, the neuropsychiatric disease includes, for example, migraine, cluster headache, post-traumatic stress disorder (PTSD), schizophrenia, anxiety, depression, and addiction (e.g., substance abuse disorder). In some embodiments, brain disorders include, for example, migraines, addiction (e.g., substance use disorder), depression, and anxiety.

In some embodiments, the experiment or assay to determine increased neuronal plasticity of any compound of the present disclosure is a phenotypic assay, a dendritogenesis assay, a spinogenesis assay, a synaptogenesis assay, a Sholl analysis, a concentration-response experiment, a 5-HT2A agonist assay, a 5-HT2A antagonist assay, a 5-HT2A binding assay, or a 5-HT2A blocking experiment (e.g., ketanserin blocking experiments). In some embodiments, the experiment or assay to determine the hallucinogenic potential of any compound of the present disclosure is a mouse head-twitch response (HTR) assay.

In some embodiments, the present disclosure provides a method for increasing neuronal plasticity, comprising contacting a neuronal cell with a cathinone compound disclosed herein.

Methods of Treating a Brain Disorder

In some embodiments, the present disclosure provides a method of treating a disease, including administering to a subject in need thereof, a therapeutically effective amount of a cathinone compound disclosed herein. In some embodiments, the disease is a musculoskeletal pain disorder including fibromyalgia, muscle pain, joint stiffness, osteoarthritis, rheumatoid arthritis, muscle cramps. In some embodiments, the present disclosure provides a method of treating a disease of women's reproductive health including premenstrual dysphoric disorder (PMDD), premenstrual syndrome (PMS), post-partum depression, and menopause. In some embodiments, the present disclosure provides a method of treating a brain disorder, including administering to a subject in need thereof, a therapeutically effective amount of a cathinone compound disclosed herein. In some embodiments, the present disclosure provides a method of treating a brain disorder with combination therapy, including administering to a subject in need thereof, a therapeutically effective amount of a cathinone compound disclosed herein and at least one additional therapeutic agent.

In some embodiments, 5-HT2A modulators (e.g., 5-HT2A agonists) are used to treat a brain disorder. In some embodiments, the brain disorders comprise decreased neural plasticity, decreased cortical structural plasticity, decreased 5-HT2A receptor content, decreased dendritic arbor complexity, loss of dendritic spines, decreased dendritic branch content, decreased spinogenesis, decreased neuritogenesis, retraction of neurites, or any combination thereof.

In some embodiments, a cathinone compound disclosed herein is used to treat brain disorders. In some embodiments, the cathinone compounds have, for example, anti-addictive properties, antidepressant properties, anxiolytic properties, or a combination thereof. In some embodiments, the brain disorder is a neuropsychiatric disease. In some embodiments, the neuropsychiatric disease is a mood or anxiety disorder. In some embodiments, brain disorders include, for example, migraine, cluster headache, post-traumatic stress disorder (PTSD), anxiety, depression, panic disorder, suicidality, schizophrenia, and addiction (e.g., substance abuse disorder). In some embodiments, brain disorders include, for example, migraines, addiction (e.g., substance use disorder), depression, and anxiety.

In some embodiments, the present disclosure provides a method of treating a brain disorder, comprising administering to a subject in need thereof a therapeutically effective amount of a cathinone compound disclosed herein.

In some embodiments, the brain disorder is a neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In some embodiments, the brain disorder is a neurodegenerative disorder, Alzheimer's, or Parkinson's disease. In some embodiments, the brain disorder is a psychological disorder, depression, addiction, anxiety, or a post-traumatic stress disorder. In some embodiments, the brain disorder is depression. In some embodiments, the brain disorder is addiction. In some embodiments, the brain disorder is treatment resistant depression, suicidal ideation, major depressive disorder, bipolar disorder, schizophrenia, stroke, traumatic brain injury or substance use disorder. In some embodiments, the brain disorder is treatment resistant depression, suicidal ideation, major depressive disorder, bipolar disorder, schizophrenia, or substance use disorder. In some embodiments, the brain disorder is stroke or traumatic brain injury. In some embodiments, the brain disorder is treatment resistant depression, suicidal ideation, major depressive disorder, bipolar disorder, or substance use disorder. In some embodiments, the brain disorder is schizophrenia. In some embodiments, the brain disorder is alcohol use disorder.

In some embodiments, the method further comprises administering one or more additional therapeutic agent that is lithium, olanzapine (Zyprexa), quetiapine (Seroquel), risperidone (Risperdal), ariprazole (Abilify), ziprasidone (Geodon), clozapine (Clozaril), divalproex sodium (Depakote), lamotrigine (Lamictal), valproic acid (Depakene), carbamazepine (Equetro), topiramate (Topamax), levomilnacipran (Fetzima), duloxetine (Cymbalta, Yentreve), venlafaxine (Effexor), citalopram (Celexa), fluvoxamine (Luvox), escitalopram (Lexapro), fluoxetine (Prozac), paroxetine (Paxil), sertraline (Zoloft), clomipramine (Anafranil), amitriptyline (Elavil), desipramine (Norpramin), imipramine (Tofranil), nortriptyline (Pamelor), phenelzine (Nardil), tranylcypromine (Pamate), diazepam (Valium), alprazolam (Xanax), or clonazepam (Klonopin).

In certain embodiments of the method for treating a brain disorder disclosed herein with a cathinone compound disclosed herein, a second therapeutic agent that is an empathogenic agent is administered. Examples of suitable empathogenic agents for use in combination with a cathinone compound disclosed herein are selected from the phenethylamines, such as 3,4-methylenedioxymethamphetamine (MDMA) and analogs thereof. Other suitable empathogenic agents for use in combination with the presently disclosed compounds include, without limitation, N-Allyl-3,4-methylenedioxy-amphetamine (MDAL); N-Butyl-3,4-methylenedioxyamphetamine (MDBU); N-Benzyl-3,4-methylenedioxyamphetamine (MDBZ); N-Cyclopropylmethyl-3,4-methylenedioxy amphetamine (MDCPM); N,N-Dimethyl-3,4-methylenedioxyamphetamine (MDDM); N-Ethyl-3,4-methylenedioxyamphetamine (MDE; MDEA); N-(2-Hydroxyethyl)-3,4-methylenedioxy amphetamine (MDHOET); N-Isopropyl-3,4-methylenedioxyamphetamine (MDIP); N-Methyl-3,4-ethylenedioxyamphetamine (MDMC); N-Methoxy-3,4-methylenedioxyamphetamine (MDMEO); N-(2-Methoxyethyl)-3,4-methylenedioxyamphetamine (MDMEOET); alpha,alpha,N-Trimethyl-3,4-methylenedioxyphenethylamine (MDMP; 3,4-Methylenedioxy-N-methylphentermine); N-Hydroxy-3,4-methylenedioxyamphetamine (MDOH); 3,4-Methylenedioxyphenethylamine (MDPEA); alpha,alpha-Dimethyl-3,4-methylenedioxyphenethylamine (MDPH; 3,4-methylenedioxyphentermine); N-Propargyl-3,4-methylenedioxyamphetamine (MDPL); Methylenedioxy-2-aminoindane (MDAI); 1,3-Benzodioxolyl-N-methylbutanamine (MBDB); 3,4-methylenedioxy-N-methyl-α-ethylphenylethylamine; 3,4-Methylenedioxyamphetamine (MDA); Ethylone, also known as 3,4-methylenedioxy-N-ethylcathinone;

GHB or Gamma Hydroxybutyrate or sodium oxybate; N-Propyl-3,4-methylenedioxyamphetamine (MDPR), and the like.

In some embodiments, the cathinone compounds disclosed herein are used in combination with the standard of care therapy for a neurological disease described herein. Non-limiting examples of the standard of care therapies, may include, for example, lithium, olanzapine, quetiapine, risperidone, ariprazole, ziprasidone, clozapine, divalproex sodium, lamotrigine, valproic acid, carbamazepine, topiramate, levomilnacipran, duloxetine, venlafaxine, citalopram, fluvoxamine, escitalopram, fluoxetine, paroxetine, sertraline, clomipramine, amitriptyline, desipramine, imipramine, nortriptyline, phenelzine, tranylcypromine, diazepam, alprazolam, clonazepam, or any combination thereof. Nonlimiting examples of standard of care therapy for depression are sertraline, fluoxetine, escitalopram, venlafaxine, or aripiprazole. Non-limiting examples of standard of care therapy for depression are citralopram, escitalopram, fluoxetine, paroxetine, diazepam, or sertraline. Additional examples of standard of care therapeutics are known to those of ordinary skill in the art.

Methods of Increasing at Least One of Translation, Transcription, or Secretion of Neurotrophic Factors Neurotrophic factors refers to a family of soluble peptides or proteins which support the survival, growth, and differentiation of developing and mature neurons. Increasing at least one of translation, transcription, or secretion of neurotrophic factors can be useful for, but not limited to, increasing neuronal plasticity, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing at least one of translation, transcription, or secretion of neurotrophic factors can increasing neuronal plasticity. In some embodiments, increasing at least one of translation, transcription, or secretion of neurotrophic factors can promoting neuronal growth, promoting neuritogenesis, promoting synaptogenesis, promoting dendritogenesis, increasing dendritic arbor complexity, and/or increasing dendritic spine density.

In some embodiments, 5-$HT_{2A}$ modulators (e.g., 5-$HT_{2A}$ agonists) are used to increase at least one of translation, transcription, or secretion of neurotrophic factors. In some embodiments, a cathinone compound disclosed herein is used to increase at least one of translation, transcription, or secretion of neurotrophic factors. In some embodiments, increasing at least one of translation, transcription or secretion of neurotrophic factors treats a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, traumatic brain injury, and addiction (e.g., substance use disorder).

In some embodiments, the experiment or assay used to determine increase translation of neurotrophic factors includes ELISA, western blot, immunofluorescence assays, proteomic experiments, and mass spectrometry. In some embodiments, the experiment or assay used to determine increase transcription of neurotrophic factors includes gene expression assays, PCR, and microarrays. In some embodiments, the experiment or assay used to determine increase secretion of neurotrophic factors includes ELISA, western blot, immunofluorescence assays, proteomic experiments, and mass spectrometry.

In some embodiments, the present disclosure provides a method for increasing at least one of translation, transcription or secretion of neurotrophic factors, comprising contacting a neuronal cell with a cathinone compound disclosed herein.

EXAMPLES

List of Abbreviations

As used throughout the description of the invention, the following abbreviations, unless otherwise indicated, shall be understood to have the following meanings:

ACN or MeCN acetonitrile
Bn benzyl
BOC or Boc tert-butyl carbamate
t-Bu tert-butyl
Cy cyclohexyl
DCE dichloroethane ($ClCH_2CH_2Cl$)
DCM dichloromethane ($CH_2Cl_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
eq or equiv equivalent(s)
Et ethyl
$Et_2O$ diethyl ether
EtOH ethanol
EtOAc ethyl acetate
HPLC high performance liquid chromatography
IPA isopropanol
Me methyl
MeOH methanol
MS mass spectroscopy
GC gas chromatography
h hour(s)
KF Karl Fischer
min minutes
MsOH methanesulfonic acid
NMP N-methylpyrrolidine
NMR nuclear magnetic resonance
RP-HPLC reverse phase-high performance liquid chromatography
rt room temperature
TFA trifluoroacetic acid
THF tetrahydrofuran
TLC thin layer chromatography
V volumes Materials and Methods Chemicals were purchased primarily from Sigma-Aldrich (Merck Life Science U.K. Ltd, The Old Brickyard, New Rd, Gillingham, Dorset SP8 4XT, U.K.); Alfa Aesar, Heysham, Morecambe, Lancashire LA3 2XY and were used without further purification. Solvents were purchased as anhydrous. Petrol (pet ether) was the alkane fraction boiling between 40-60° C.

TLC was carried out using aluminum plates pre-coated with silica gel (Kieselgel 60 F254, 0.2 mm, Merck, Darmstadt, Germany). Visualization was by UV light.

$^1$H NMR spectra were recorded on a Bruker Avance BVT3200 spectrometer using the residual proton(s) in the deuterated solvents as internal standards.

HPLC analyses were performed with a Shimadzu Prominence instrument (Shimadzu UK Ltd., Unit 1A Mill Court, Featherstone Road, Milton Keynes MK12 5RD, U.K.) with diode array detection and a Kinetex EVO C18, 5 μm, 250 mm×4.6 mm column. Chiral HPLC analysis were performed using a Phenomenex Lux Cellulose 2, 250 mm×4.6 mm column.

LC-MS analyses were performed on a Shimadzu 2020 instrument operating in positive or negative ESI mode with UV detection at 254 nm.

Automated chromatography was performed on a Biotage Selekt purification system (Biotage GB Limited, Distribution Way, Dyffryn Business Park, Ystrad Mynach, Hengoed, Mid Glamorgan CF82 7TS, Wales).

Example 1-1: Synthesis of tert-butyl (S)-(1-(methoxy(methyl)amino)-1-oxopropan-2-yl)(methyl-d₃)carbamate

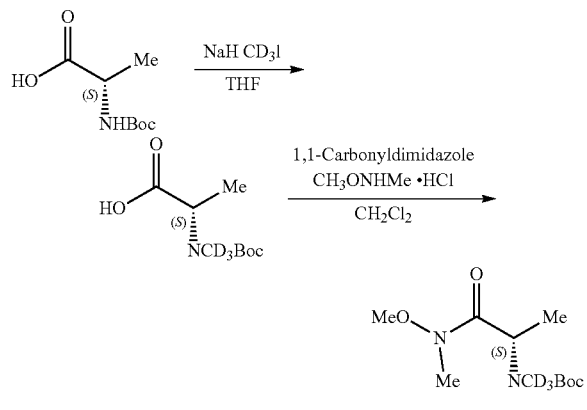

Step 1: Preparation of N-Boc-(N-methyl-d₃)-L-alanine

To an ice-cold mixture of N-Boc-L-alanine (500 mg, 2.65 mmol) and iodomethane-d₃ (3.83 g, 1.65 mL, 26.5 mmol) in anhydrous THF (15 mL) was added sodium hydride, 60% dispersion in oil (1.06 g, 26.5 mmol) portion-wise. The mixture was stirred at rt overnight (a suspension forms), then diluted with Et₂O (10 mL) and carefully quenched with H₂O (15 mL). The layers were separated and the aqueous layer was washed with Et₂O (20 mL). The aqueous layer was acidified to pH ~ 3 with 10% citric acid and extracted with EtOAc (3×20 mL). The combined organic layers were washed with saturated brine (50 mL), dried (MgSO₄) and concentrated to give N-Boc-(N-methyl-d₃)-L-alanine (0.57 g) as a solid that was used without further purification. $^1$H NMR (300 MHz, CDCl₃) δ 4.79 (m, 0.59H, α-CH), 4.47 (m, 0.41H, α-CH), 2.85 (br. s, 3H, NMe amide), 1.45 (s, 12H, t-Bu and Me).

Step 2: Preparation of tert-butyl (S)-(1-(methoxy(methyl)amino)-1-oxopropan-2-yl)(methyl-d₃)carbamate To a mixture of N-Boc-(N-methyl-d₃)-L-alanine (0.57 g, 2.77 mmol) in DCM (14 mL) under an atmosphere of N₂ was added 1,1-carbonyldiimidazole (494 mg, 3.04 mmol). The mixture was stirred at rt for 40 min, then N,O-dimethylhydroxylamine HCl (297 mg, 3.04 mmol) was added in one portion and the mixture was stirred at rt overnight. The reaction was quenched by the addition of 1M HCl (15 mL) and the layers were separated. The aqueous layer was extracted with DCM (2×10 mL) and the combined organic layers were washed with H₂O (15 mL), saturated sodium bicarbonate (15 mL), saturated brine (15 mL), dried (MgSO₄) and concentrated to give a crude oil. This material was purified by column chromatography on silica gel (EtOAc/PE, 0:1 to 1:0) to give tert-butyl (S)-(1-(methoxy(methyl)amino)-1-oxopropan-2-yl)(methyl-d₃)carbamate (495 mg, 75% over 2 steps) as an oil. TLC: $R_f$=0.49 (EtOAc/PE, 3:7 v/v); $^1$H NMR (300 MHz, CDCl₃) δ 5.16 (m, 0.60H, α-CH), 4.88 (m, 0.40H, α-CH), 3.68 (m, 3H, OMe), 3.14 (s, 3H, NMe amide), 1.42 (s, 9H, t-Bu), 1.26 (d, J=7.1 Hz, 3H, Me); $^{13}$C NMR (75.5 MHz, CDCl₃) δ 173.3, 155.8, 80.0, 79.7, 61.5, 61.3, 51.6, 49.9, 32.3, 28.5, 14.7.

Synthesis of Catechol-d₂

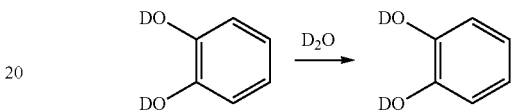

A mixture of catechol (5.0 g, 45.4 mmol) in D₂O (25 mL) was stirred for 4 h and the mixture was freeze-dried overnight to give a pale-brown solid (one exchange). This process was repeated a further two times.

Example 1-2: Synthesis of (S)-methylone-d₂ from the Weinreb amide of Boc N-methyl-L-alanine

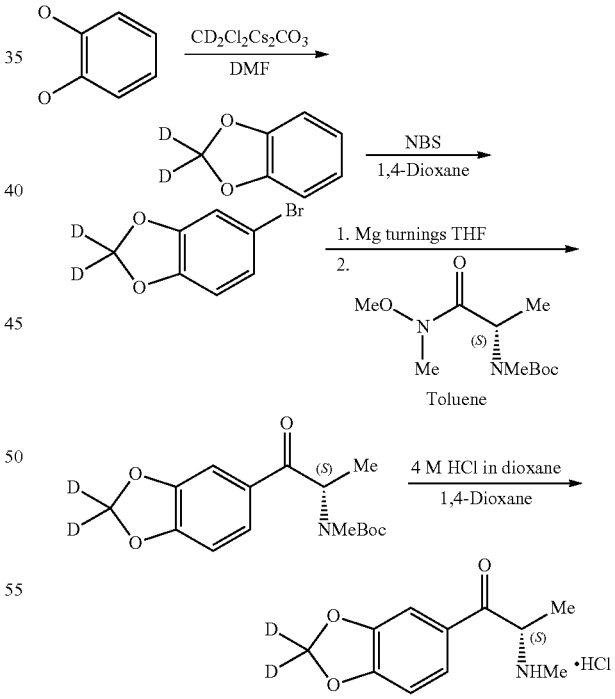

Step 1: Synthesis of Benzo[d][1,3]dioxole-2,2-d₂

To a suspension of Cs₂CO₃ (10.7 g, 32.9 mmol) and D₂O (0.69 g, 0.63 mL, 34.5 mmol) in anhydrous DMF (26 mL) under an atmosphere of N₂ at 110° C. was added a solution of catechol-d2 (3×D₂O exchanges as detailed above, 1.84 g, 16.4 mmol) and dichloromethane-d2 (4.28 g, 3.14 mL, 49.2 mmol) in anhydrous DMF (11 mL) dropwise. The mixture was stirred at 110° C. for 2 h, then cooled and the mixture was filtered through Celite, rinsing the filter cake with EtOAc (2×20 mL). H$_2$O (30 mL) was added and the layers were separated. The aqueous layer was extracted with EtOAc (2×30 mL) and the combined organic layers were washed with H$_2$O (5×50 mL), saturated brine (50 mL), dried (MgSO$_4$) and concentrated to give an oil. This material was purified by column chromatography on silica gel (DCM/PE, 0:1 to 1:0) to give benzo[d][1,3]dioxole-2,2-d2 (1.42 g, 70%) as an oil. TLC: R$_f$=0.51 (DCM/PE, 1:4 v/v); $^1$H NMR (300 MHz, CDCl$_3$) δ 6.83 (s, 4H, 4×ArH).

Step 2: Synthesis of 5-bromobenzo[d][1,3]dioxole-2,2-d$_2$

To a mixture of benzo[d][1,3]dioxole-2,2-d$_2$ (1.74 g, 14.0 mmol) in anhydrous 1,4-dioxane (30 mL) under an atmosphere of N$_2$ was added N-bromosuccinimide (2.62 g, 14.7 mmol) and the mixture was heated at reflux and stirred overnight. The mixture was cooled, saturated sodium bicarbonate (50 mL) was added and the mixture was extracted with EtOAc (3×50 mL). The combined organic layers were washed with saturated brine (75 mL), dried (MgSO$_4$) and concentrated under reduced pressure to give an oil. This material was purified by column chromatography on silica gel eluting (DCM/PE, 0:1 to 1:0) to give 5-bromobenzo[d][1,3]dioxole-2,2-d2 (1.72 g, 60%) as an oil. The sample also contained approximately 33% of starting material. TLC: R$_f$=0.61 (DCM/PE, 1:4 v/v); $^1$H NMR (300 MHz, CDCl$_3$) δ 6.96 (m, 2H, ArH), 6.69 (m, 1H, ArH).

Step 3: Synthesis of tert-butyl (S)-(1-(benzo[d][1,3]dioxol-5-yl-2,2-d2)-1-oxopropan-2-yl)(methyl)carbamate An oven-dried flask was charged with Mg turnings (307 mg, 12.8 mmol), placed under an atmosphere of N$_2$, then 1,2-dibromoethane (160 mg, 74 µL, 0.85 mmol), anhydrous THF (18 mL) and 5-bromobenzo[d][1,3]dioxole-2,2-d2 (1.73 g, 8.52 mmol) were added. The mixture was heated to 51° C. and stirred for 1 h to give an ~0.5M solution of (benzo[d][1,3]dioxol-5-yl-2,2-d2) magnesium bromide in THF as an amber solution.

An oven-dried flask was charged with tert-butyl (S)-(1-(methoxy(methyl)amino)-1-oxopropan-2-yl)(methyl)carbamate (0.54 g, 2.13 mmol) in anhydrous toluene (8 mL) at 0° C. under an atmosphere of N$_2$. (Benzo[d][1,3]dioxol-5-yl-2,2-d2) magnesium bromide, ~0.5M in THF (9 mL, 4.26 mmol) was added and the mixture was stirred at 0° C. for 1 h. A further aliquot of (benzo[d][1,3]dioxol-5-yl-2,2-d2) magnesium bromide, ~0.5M in THF (9 mL, 4.26 mmol) was added and the mixture was stirred at 0° C. for a further 1 h. The mixture was quenched with saturated aqueous NH$_4$Cl (30 mL) and extracted with EtOAc (3×20 mL). The combined organic layers were washed with saturated sodium bicarbonate (30 mL), saturated brine (20 mL), dried (MgSO$_4$) and concentrated to give an oil. This material was purified by column chromatography on silica gel (Et$_2$O/PE, 0:1 to 1:0) to give a 6:4 mixture of tert-butyl (S)-(1-(benzo[d][1,3]dioxol-5-yl-2,2-d$_2$)-1-oxopropan-2-yl)(methyl)carbamate and benzo[d][1,3]dioxol-2,2-d$_2$-5-ol (296 mg) as an oil. TLC: R$_f$=0.34 (Et$_2$O/PE, 1:4 v/v); $^1$H NMR (300 MHz, CDCl$_3$) δ 7.67 (d, J=8.8 Hz, 0.60H, ArH), 7.55 (d, J=8.1 Hz, 0.36H, ArH), 7.47 (s, 0.6H, ArH), 7.41 (s, 0.4H, ArH), 6.80 (d, 1H, J=8.2 Hz, ArH), 5.63 (q, J=7.4 Hz, 0.6H, α-CH), 5.18 (m, 0.4H, α-CH), 2.75 (s, 1.1H, NMe), 2.62 (s, 1.8H, NMe), 1.46 (s, 9H, t-Bu), 1.32 (m, 3H, Me).

Step 4: Synthesis of (S)-1-(benzo[d][1,3]dioxol-5-yl-2,2-d2)-2-(methylamino)propan-1-one HCl To the above mixture (296 mg) in anhydrous 1,4-dioxane (3.1 mL) was added 4 M HCl in 1,4-dioxane (1.70 mL, 6.71 mmol) and the mixture was stirred at rt for 7.5 h (a white precipitate appeared after 30 min). The white precipitate was collected by filtration to give (S)-1-(benzo[d][1,3]dioxol-5-yl-2,2-d2)-2-(methylamino)propan-1-one hydrochloride (144 mg, 27% over 2 steps) as a solid.

This material (144 mg) was crystallized using MeOH/Et$_2$O (2 mL/8 mL; vapor diffusion) at rt overnight to give (S)-methylone-d$_2$ (86 mg) as a solid in 97.8% ee. $^1$H NMR (300 MHz, CD$_3$OD) δ7.70 (dd, J=8.2 and 1.8 Hz, 1H, ArH), 7.49 (d, J=1.8 Hz, 1H, ArH), 7.01 (d, J=8.2 Hz, 1H, ArH), 5.00 (q, J=7.2 Hz, 1H, α-CH), 2.74 (s, 3H, NMe), 1.56 (d, J=7.2 Hz, 3H, Me); $^{13}$C NMR (75.5 MHz, CD$_3$OD) δ195.0, 155.0, 150.2, 128.7, 127.2, 109.4, 108.9, 60.4, 31.8, 16.6.

Example 1-3: Synthesis of (S)-methylone-d$_3$ from the Weinreb amide of tert-butyl (R)-(1-(methoxy(methyl)amino)-1-oxopropan-2-yl)(methyl-d$_3$)carbamate

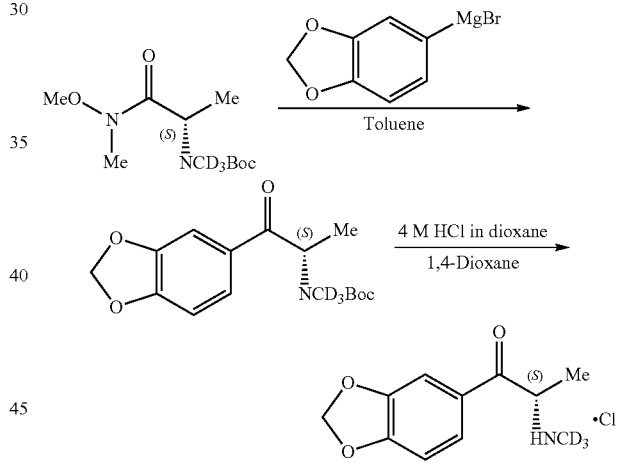

Step 1: Synthesis of tert-butyl (S)-(1-(benzo[d][1,3]dioxol-5-yl)-1-oxopropan-2-yl) (methyl-d$_3$)carbamate An oven-dried flask was charged with a mixture of tert-butyl (S)-(1-(methoxy(methyl)amino)-1-oxopropan-2-yl)(methyl-d3)carbamate (0.50 g, 2.01 mmol) in anhydrous toluene (6.5 mL) at 0° C. under an atmosphere of N$_2$ was added 3,4-(methylenedioxy)phenylmagnesium bromide, 0.5M in THF (8.03 mL, 4.02 mmol) and the mixture was stirred for 2 h. The mixture was quenched with saturated aqueous NH$_4$Cl (15 mL) and extracted with EtOAc (3×20 mL). The combined organic layers were washed with saturated sodium bicarbonate (30 mL), saturated brine (30 mL), dried (MgSO$_4$) and concentrated to give an oil. This material was purified by column chromatography on silica gel (Et$_2$O/PE 0:1 to 1:0) to give tert-butyl (S)-(1-(benzo[d][1,3]dioxol-5-yl)-1-oxopropan-2-yl) (methyl-d3)carbamate (0.57 g, 92% yield) as an oil that solidified upon standing. TLC: $R_f$=0.34 (Et$_2$O/PE, 2:8 v/v); $^1$H NMR (300 MHz, CDCl$_3$) δ 7.65 (dd, J=8.3, 1.7 Hz, 0.64H, ArH), 7.54 (d, J=8.1 Hz, 0.36H, ArH), 7.46 (s, 0.64H, ArH), 7.40 (s, 0.36H, ArH), 6.82 (m 1H, ArH), 6.01 (s, 2H, CH$_2$), 5.61 (q, J=6.9 Hz, 0.64H, α-CH), 5.17 (q, J=6.8 Hz, 0.36H, α-CH), 1.44 (s, 9H, t-Bu), 1.32 (m, 3H, Me); $^{13}$C NMR (75.5 MHz, CDCl$_3$) δ 198.1, 156.0, 152.0, 148.6, 130.1, 125.0, 124.4, 108.4, 108.0, 101.9, 81.2, 80.3, 56.3, 54.1, 41.0, 28.5, 23.9, 14.0, 13.6.

Step 2: Synthesis of (S)-1-(benzo[d][1,3]dioxol-5-yl)-2-((methyl-d$_3$)amino)propan-1-one HCl To a mixture of tert-butyl (S)-(1-(benzo[d][1,3]dioxol-5-yl)-1-oxopropan-2-yl) (methyl-d3)carbamate (0.52 g, 1.67 mmol) in anhydrous 1,4-dioxane (5.4 mL) was added 4M HCl in 1,4-dioxane (2.91 mL, 11.7 mmol) and the mixture was stirred at rt for 7.5 h (a white precipitate appeared after 30 min). The precipitate was collected by filtration to give (S)-1-(benzo[d][1,3]dioxol-5-yl)-2-(methylamino)propan-1-one hydrochloride (365 mg, 88%) as a solid. Part of this material (335 mg) was crystalized using MeOH/Et$_2$O (4 mL/12 mL; vapor diffusion) at rt overnight to give (S)-methylone-d3 (210 mg) as a solid in 97.8% ee. $^1$H NMR (300 MHz, CD$_3$OD) δ7.70 (dd, J=8.2, 1.8 Hz, 1H, ArH), 7.49 (d, J=1.8 Hz, 1H, ArH), 7.01 (d, J=8.2 Hz, 1H, ArH), 6.12 (s, 2H, CH$_2$), 5.00 (q, J=7.2 Hz, 1H, α-CH), 1.56 (d, J=7.2 Hz, 3H, Me); $^{13}$C NMR (75.5 MHz, CD$_3$OD) δ195.0, 155.0, 150.2, 128.7, 127.2, 109.4, 108.9, 104.0, 60.3, 31.8, 16.6.

Example 1-4: Synthesis of (S)-methylone-d$_5$ from the Weinreb amide of N-Boc-N-CD$_3$-L-alanine

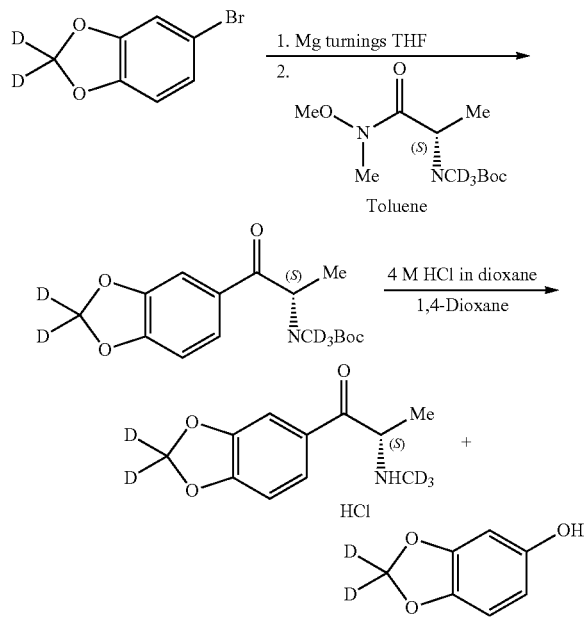

Step 1: Synthesis of tert-butyl (S)-(1-(benzo[d][1,3]dioxol-5-yl-2,2-d$_2$)-1-oxopropan-2-yl)(methyl-d$_3$)carbamate To an oven-dried flask was added a suspension of Mg turnings (337 mg, 14.0 mmol) and 1,2-dibromoethane (176 mg, 81 µL, 0.94 mmol) in anhydrous THF (20 mL) under an atmosphere of N$_2$ was added 5-bromobenzo[d][1,3]dioxole-2,2-d2 (1.90 g, 9.36 mmol). The mixture was heated to 51° C. and stirred for 1.5 h to give a ~0.5 M solution of (benzo[d][1,3]dioxol-5-yl-2,2-d2) magnesium bromide in THF (amber in color).

An oven-dried flask was charged with a solution of tert-butyl (S)-(1-(methoxy(methyl)amino)-1-oxopropan-2-yl)(methyl-d3)carbamate (0.54 g, 2.13 mmol) in anhydrous toluene (9 mL) at 0° C. under an atmosphere of N$_2$ was added (benzo[d][1,3]dioxol-5-yl-2,2-d2) magnesium bromide (~0.5 M in THF, 10 mL, 4.7 mmol) and the mixture was stirred at 0° C. for 1 h. (Benzo[d][1,3]dioxol-5-yl-2,2-d2) magnesium bromide (~0.5 M in THF, 10 mL, 4.7 mmol) was added and the mixture was stirred at 0° C. for a further 1 h, then quenched with saturated NH$_4$Cl (20 mL) and extracted with EtOAc (3×20 mL). The combined organic extracts were washed with H$_2$O (20 mL), saturated aqueous sodium bicarbonate (20 mL), saturated brine (20 mL), dried (MgSO$_4$) and concentrated to give a crude oil. This material was purified by normal phase column chromatography on silica gel (0 to 100% diethyl ether in petrol) to give a 6:4 mixture of tert-butyl (S)-(1-(benzo[d][1,3]dioxol-5-yl-2,2-d2)-1-oxopropan-2-yl)(methyl-d$_3$)carbamate and benzo[d][1,3]dioxol-2,2-d$_2$-5-ol (435 mg) as an oil. TLC: $R_f$=0.34 (diethyl ether-petrol, 2:8 v/v); $^1$H NMR (300 MHz, CDCl$_3$) δ 7.67 (dd, J=8.1 Hz, 0.6H, ArH), 7.55 (d, J=8.0 Hz, 0.4H, ArH), 7.47 (s, 0.6H, ArH), 7.41 (s, 0.4H, ArH), 6.82 (m 1H, ArH), 6.01 (s, 2H, CH$_2$), 5.63 (q, J=7.0 Hz, 0.6H, α-CH), 5.18 (q, 0J=7.3 Hz, 0.4H, α-CH), 1.46 (s, 9H, t-Bu), 1.34 (m, 3H, Me).

Data for benzo[d][1,3]dioxol-2,2-d$_2$-5-ol

TLC: $R_f$=0.30 (diethyl ether-petrol, 2:8 v/v); $^1$H NMR (300 MHz, CDCl$_3$) δ 6.64 (d, 1H, J=8.3 Hz, ArH), 6.43 (d, 1H, J=2.5 Hz, ArH), 6.25 (dd, 1H, J=8.3 and 2.5 MHz, ArH), 4.78 (s, 1H, OH).

Step 2: Synthesis of (S)-1-(benzo[d][1,3]dioxol-5-yl-2,2-d$_2$)-2-((methyl-d$_3$)amino)propan-1-one hydrochloride To the above mixture (435 mg) in 1,4-dioxane (4.5 mL) was added 4 M HCl in 1,4-dioxane (2.44 mL, 9.76 mmol) and the mixture was stirred at rt for 7.5 h (a white precipitate appeared after 30 min). The suspension was diluted with diethyl ether (30 mL) and the solid was collected by filtration to give (S)-1-(benzo[d][1,3]dioxol-5-yl-2,2-d2)-2-((methyl-d3)amino)propan-1-one hydrochloride (220 mg, 38% over 2 steps) as a solid.

This material (220 mg) was crystallized using MeOH/Et$_2$O (2.8 mL/8.0 mL) (vapor diffusion) at rt overnight to give (S)-methylone-d$_5$ (110 mg) as a solid, >99.9% ee. Melting point 232.8° C.; [α]$_D$=−28.0; $^1$H NMR (300 MHz, CD$_3$OD) δ7.69 (dd, J=8.2, 1.8 Hz, 1H, ArH), 7.49 (d, 1H, J=1.8 Hz, ArH), 7.01 (d, J=8.2 Hz, 1H, ArH), 4.99 (q, J=7.2 Hz, 1H, α-CH), 2.74 (s, 3H, NMe), 1.56 (d, J=7.1 Hz, 3H, Me); $^{13}$C NMR (75.5 MHz, CD$_3$OD) δ 195.0, 155.0, 150.3, 128.7, 127.1, 109.4, 108.9, 60.3, 16.6.

Example 1-5: Synthesis of (R)-methylone-d$_2$ from the Weinreb amide of N-Boc N-Methyl-D-alanine

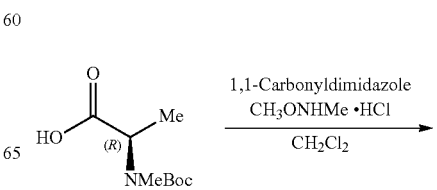

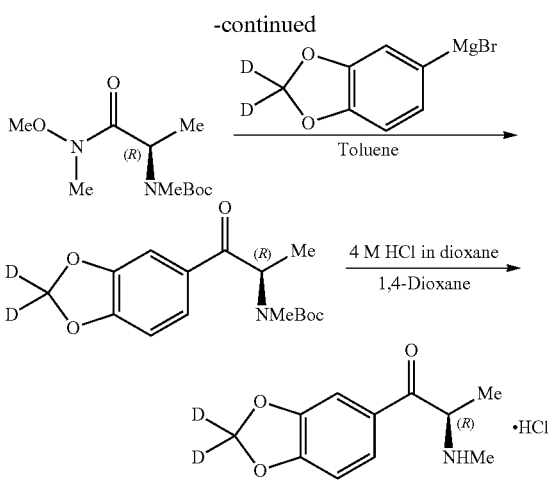

Step 1: Synthesis of tert-butyl (R)-(1-(methoxy (methyl)amino)-1-oxopropan-2-yl)(methyl)carbamate To a solution of N-Boc-(N-methyl)-D-alanine (1.00 g, 4.93 mmol) in DCM (25 mL) under an atmosphere of $N_2$ was added 1,1-carbonyldiimidazole (0.88 g, 5.42 mmol) and the mixture was stirred at rt for 40 min. N,O-dimethylhydroxylamine HCl (0.53 g, 5.42 mmol) was added in one portion and the suspension was stirred at rt overnight. The reaction was quenched with 1M HCl (20 mL) and the layers were separated. The aqueous layer was extracted with DCM (2×20 mL) and the combined organics were washed with $H_2O$ (20 mL), saturated aqueous sodium bicarbonate (20 mL), saturated brine (20 mL), dried ($MgSO_4$) and concentrated to give an oil. This material was purified by normal phase column chromatography on silica gel, eluting with 0 to 100% EtOAc in petrol to give tert-butyl (R)-(1-(methoxy (methyl)amino)-1-oxopropan-2-yl)(methyl)carbamate (0.91 g, 76%) as a colorless oil. TLC: $R_f$=0.49 (EtOAc-petrol, 3:7 v/v); $^1$H NMR (300 MHz, $CDCl_3$) δ 5.17 (m, 0.60H, α-CH), 4.87 (m, 0.40H, α-CH), 3.67 (m, 3H, OMe), 3.13 (s, 3H, NMe amide), 2.80 (s, 3H, NMe). 1.41 (s, 9H, t-Bu), 1.26 (d, J=7.1 Hz, 3H, Me); $^{13}$C NMR (75.5 MHz, $CDCl_3$) δ 173.0, 155.8, 155.2, 80.0, 79.7, 61.5, 61.3, 51.7, 49.9, 32.1, 29.9, 28.5, 14.7.

Step 2: Synthesis of tert-butyl (R)-(1-(benzo[d][1,3]dioxol-5-yl-2,2-d2)-1-oxopropan-2-yl)(methyl)carbamate An oven-dried flask was charged with a suspension of Mg turnings (231 mg, 9.61 mmol) and 1,2-dibromoethane (120 mg, 56 µL, 0.64 mmol) in anhydrous THF (14 mL) under an atmosphere of $N_2$, then 5-bromobenzo[d][1,3]dioxole-2,2-d2 (1.30 g, 6.40 mmol) was added and the mixture was heated to 51° C. and stirred for 1.5 h to give a ~0.5 M solution of (benzo[d][1,3]dioxol-5-yl-2,2-d2) magnesium bromide in THF (amber in color).

An oven-dried flask was charged with a solution of tert-butyl (R)-(1-(methoxy(methyl)amino)-1-oxopropan-2-yl)(methyl) carbamate (399 mg, 1.60 mmol) in anhydrous toluene (6 mL) at 0° C. under an atmosphere of $N_2$ was added (benzo[d][1,3]dioxol-5-yl-2,2-d2) magnesium bromide (~0.5 M in THF, 7.0 mL, 3.2 mmol) and the mixture was stirred at 0° C. for 1 h. (Benzo[d][1,3]dioxol-5-yl-2,2-d2) magnesium bromide (~0.5 M in THF, 7.0 mL, 3.2 mmol) was added and the mixture was stirred at 0° C. for a further 1 h. The reaction was quenched with saturated $NH_4Cl$ (20 mL) and extracted with EtOAc (3×20 mL). The combined organic extracts were washed with $H_2O$ (20 mL), saturated aqueous sodium bicarbonate (20 mL), saturated brine (20 mL), dried ($MgSO_4$), filtered and concentrated to give an oil. This material was purified by normal phase column chromatography on silica gel, eluting with 0 to 100% $Et_2O$ in petrol to give a 7:3 mixture of tert-butyl (R)-(1-(benzo[d][1,3]dioxol-5-yl-2,2-d2)-1-oxopropan-2-yl)(methyl-d3)carbamate and benzo[d][1,3]dioxol-2,2-d2-5-ol (442 mg) as a pale yellow oil. TLC: $R_f$=0.34 (diethyl ether-petrol, 2:8 v/v); $^1$H NMR (300 MHz, $CDCl_3$) δ 7.67 (d, J=8.0 Hz, 0.60H, ArH), 7.55 (d, J=7.3 Hz, 0.40H, ArH), 7.47 (s, 0.60H, ArH), 7.41 (s, 0.40H, ArH), 6.82 (m 1H, ArH), 6.01 (s, 2H, $CH_2$), 5.63 (q, J=6.7 Hz, 0.60H, α-CH), 5.18 (q, J=7.0 Hz, 0.40H, α-CH), 2.75 (s, 1.2H, NMe), 2.62 (s, 1.8H, NMe), 1.46 (s, 9H, t-Bu), 1.34 (m, 3H, Me).

Data for benzo[d][1,3]dioxol-2,2-d2-5-ol: TLC: $R_f$=0.30 (diethyl ether-petrol, 2:8 v/v); $^1$H NMR (300 MHz, $CDCl_3$) δ 6.64 (d, J=8.3 Hz, 1H, ArH), 6.43 (d, J=2.5 Hz, 1H, ArH), 6.25 (dd, J=8.3, 2.5 MHz, 1H, ArH), 4.78 (s, 1H, OH).

Step 3: Synthesis of (R)-1-(benzo[d][1,3]dioxol-5-yl-2,2-d2)-2-((methyl)amino)propan-1-one HCl To the above mixture (442 mg) in 1,4-dioxane (4.6 mL) was added a 4 M HCl in 1,4-dioxane (2.50 mL, 10.0 mmol) and the mixture was stirred at rt for 7.5 h (a white precipitate appeared after 30 min). The suspension was diluted with $Et_2O$ (30 mL) and the solid was collected by filtration to give (R)-1-(benzo[d][1,3]dioxol-5-yl-2,2-d2)-2-((methyl)amino) propan-1-one HCl (270 mg, 68% over 2 steps) as a white solid.

This material (270 mg) was crystallized using MeOH/ $Et_2O$ (3.5 mL/9.8 mL) (vapor diffusion) at rt overnight to give (R)-methylone-d2 (138 mg) as a white solid, >98.6% ee. $^1$H NMR (300 MHz, $CD_3OD$) δ 7.69 (dd, J=8.2, 1.8 Hz, 1H, ArH), 7.49 (d, J=1.8 Hz, 1H, ArH), 7.01 (d, J=8.2 Hz, 1H, ArH), 4.99 (q, J=7.2 Hz, 1H, α-CH), 2.74 (s, 3H, NMe), 1.56 (d, J=7.2 Hz, 3H, Me); $^{13}$C NMR (75.5 MHz, $CD_3OD$) δ 195.0, 155.0, 150.3, 128.7, 127.1, 109.4, 108.9, 60.4, 31.7, 16.6.

Example 1-6: Synthesis of (R)-methylone-d3 from the Weinreb amide of tert-butyl (R)-(1-(methoxy (methyl)amino)-1-oxopropan-2-yl)(methyl-d3)carbamate

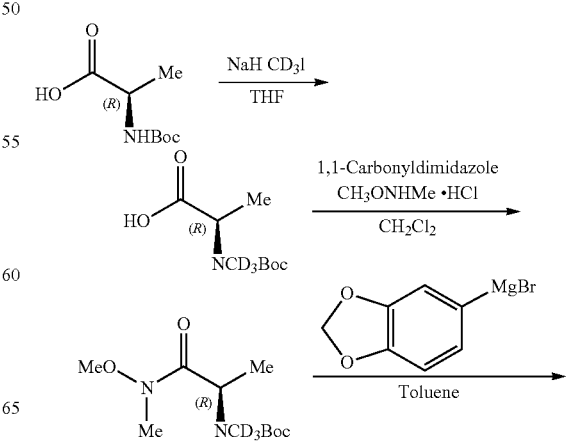

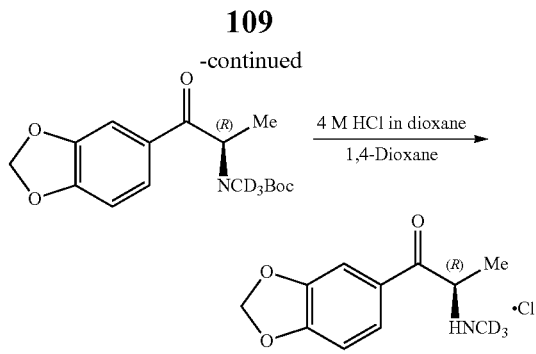

Step 1: Synthesis of N-Boc-(N-methyl-d₃)-D-alanine

To an ice-cold mixture of N-Boc-D-alanine (0.73 g, 3.85 mmol) and iodomethane-d3 (5.59 g, 2.40 mL, 38.5 mmol) in anhydrous THF (30 mL) was added sodium hydride, 60% dispersion in oil (1.54 g, 38.5 mmol) portion-wise. The mixture was warmed to rt and stirred overnight (a white suspension forms). The mixture was diluted with Et₂O (15 mL) and cautiously quenched with H₂O (20 mL). The layers were separated and the aqueous layer was washed with Et₂O (30 mL). The aqueous layer was acidified to pH ~ 3 with 10% citric acid and extracted with EtOAc (3×30 mL). The combined organic layers were washed with saturated brine (50 mL), dried (MgSO₄) and concentrated to give N-Boc-(N-methyl-d₃)-D-alanine (0.77 g) as a solid that was used without further purification. $^1$H NMR (300 MHz, CDCl₃) δ 4.81 (m, 0.65H, α-CH), 4.47 (m, 0.35H, α-CH), 1.46 (s, 12H, t-Bu and Me).

Step 2: Synthesis of tert-butyl (R)-(1-(methoxy (methyl)amino)-1-oxopropan-2-yl)(methyl-d3)carbamate To a mixture of N-Boc-(N-methyl-d₃)-D-alanine (0.77 g, 3.71 mmol) in DCM (19 mL) under an atmosphere of N₂ was added 1,1-carbonyldiimidazole (0.66 mg, 4.08 mmol) and the mixture was stirred at rt for 40 min. N,O-dimethylhydroxylamine HCl (399 mg, 4.08 mmol) was added in one portion and the suspension was stirred at rt overnight. The mixture was quenched with 1M HCl (15 mL) and the layers were separated. The aqueous layer was extracted with DCM (2×15 mL) and the combined organic layers were washed with H₂O (20 mL), saturated aqueous sodium bicarbonate (20 mL), saturated brine (20 mL), dried (MgSO₄) and concentrated to give an oil. This material was purified by column chromatography on silica gel (EtOAc/PE 0:1 to 1:0) to give tert-butyl (R)-(1-(methoxy(methyl)amino)-1-oxopropan-2-yl)(methyl-d₃)carbamate (0.62 g, 64% over 2 steps) as an oil. TLC: R$_f$=0.49 (EtOAc/PE, 3:7 v/v); $^1$H NMR: (300 MHz, CDCl₃) δ 5.20 (m, 0.60H, α-CH), 4.91 (m, 0.40H, α-CH), 3.72 (m, 3H, OMe), 3.18 (s, 3H, NMe amide), 1.46 (s, 9H, t-Bu), 1.30 (d, J=7.1 Hz, 3H, Me).

Step 3: Synthesis of tert-butyl (R)-(1-(benzo[d][1,3]dioxol-5-yl)-1-oxopropan-2-yl) (methyl-d₃)carbamate To an oven-dried flask charged with a mixture of tert-butyl (R)-(1-(methoxy(methyl)amino)-1-oxopropan-2-yl)(methyl-d₃)carbamate (0.61 g, 2.45 mmol) in anhydrous toluene (8 mL) at 0° C. under an atmosphere of N₂ was added 3,4-(methylenedioxy)phenylmagnesium bromide, 0.5M in THF (9.80 mL, 4.90 mmol) and the mixture was stirred at 0° C. for 2 h. The mixture was quenched with saturated aqueous NH₄Cl (15 mL) and extracted with EtOAc (3×20 mL). The combined organics were washed with saturated sodium bicarbonate (30 mL), saturated brine (30 mL), dried (MgSO₄) and concentrated to give an oil. This material was purified by column chromatography on silica gel (Et₂O/PE 0:1 to 1:0) to give tert-butyl (R)-(1-(benzo[d][1,3]dioxol-5-yl)-1-oxopropan-2-yl) (methyl-d₃)carbamate (0.67 g, 88% yield) as an oil that solidified upon standing. TLC: R$_f$=0.34 (Et₂O/PE, 2:8 v/v); $^1$H NMR (300 MHz, CDCl₃) δ 7.65 (d, J=8.1 Hz, 0.65H, ArH), 7.54 (d, J=8.1 Hz, 0.35H, ArH), 7.45 (s, 0.65H, ArH), 7.40 (s, 0.35H, ArH), 6.81 (d, J=8.2, 1H, ArH), 6.01 (s, 2H, CH₂), 5.61 (q, J=6.8 Hz, 0.65H, α-CH), 5.17 (q, J=6.4 Hz, 0.35H, α-CH), 1.44 (s, 9H, t-Bu), 1.32 (m, 3H, Me); $^{13}$C NMR (75.5 MHz, CDCl₃) δ 197.7, 155.6, 152.0, 148.2, 130.1, 125.0, 124.4, 108.4, 108.1, 101.9, 80.8, 80.3, 56.3, 54.1, 41.0, 28.5, 23.9, 14.0, 13.6.

Step 4: Synthesis of (R)-1-(benzo[d][1,3]dioxol-5-yl)-2-((methyl-d₃)amino)propan-1-one HCl To a mixture of tert-butyl (R)-(1-(benzo[d][1,3]dioxol-5-yl)-1-oxopropan-2-yl) (methyl-d₃)carbamate (0.62 g, 2.01 mmol) in anhydrous 1,4-dioxane (6.5 mL) was added 4M HCl in 1,4-dioxane (3.52 mL, 14.0 mmol) and the mixture was stirred at rt for 7.5 h (a white precipitate appeared after 30 min). The precipitate was collected by filtration to give (R)-1-(benzo[d][1,3]dioxol-5-yl)-2-(methylamino)propan-1-one hydrochloride (408 mg, 83%) as a solid. This material (400 mg) was crystalized using MeOH/Et₂O (5 mL/14.5 mL; vapor diffusion) at rt overnight to give (R)-methylone-d₃ (255 mg) as a solid in 97.8% ee. $^1$H NMR (300 MHz, CD₃OD) δ 7.70 (dd, J=8.2, 1.8 Hz, 1H, ArH), 7.49 (d, J=1.8 Hz, 1H, ArH), 7.01 (d, J=8.2 Hz, 1H, ArH), 6.12 (s, 2H, CH₂), 4.99 (q, J=7.2 Hz, 1H, α-CH), 1.56 (d, J=7.2 Hz, 3H, Me).

Example 1-7: Synthesis of (R)-methylone-d₅ from the Weinreb amide of N-Boc N-CD₃-D-alanine

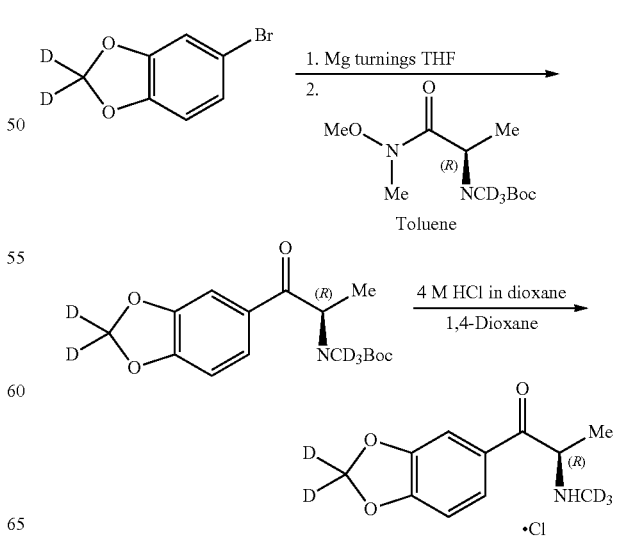

Step 1: Synthesis of tert-butyl (R)-(1-(benzo[d][1,3]dioxol-5-yl-2,2-$d_2$)-1-oxopropan-2-yl)(methyl-$d_3$)carbamate An oven-dried flask was charged with a suspension of Mg turnings (231 mg, 9.61 mmol) and 1,2-dibromoethane (120 mg, 56 µL, 0.64 mmol) in anhydrous THF (14 mL) under an atmosphere of $N_2$ was added 5-bromobenzo[d][1,3]dioxole-2,2-$d_2$ (1.30 g, 6.40 mmol) and the mixture was heated at 51° C. and stirred for 1.5 h to give a ~0.5 M solution of (benzo[d][1,3]dioxol-5-yl-2,2-$d_2$) magnesium bromide in THF (amber in color).

An oven-dried flask was charged with a solution of tert-butyl (R)-(1-(methoxy(methyl)amino)-1-oxopropan-2-yl)(methyl-$d_3$)carbamate (399 mg, 1.60 mmol) in anhydrous toluene (6 mL) at 0° C. under an atmosphere of $N_2$ was added (benzo[d][1,3]dioxol-5-yl-2,2-$d_2$) magnesium bromide (~0.5 M in THF, 7.0 mL, 3.20 mmol) and the mixture was stirred at 0° C. for 1 h. (Benzo[d][1,3]dioxol-5-yl-2,2-$d_2$) magnesium bromide (~0.5 M in THF, 7.0 mL, 3.20 mmol) was added and the mixture was stirred at 0° C. for a further 1 h. The reaction was quenched with saturated $NH_4Cl$ (20 mL) and extracted with EtOAc (3×20 mL). The combined organic layers were washed with $H_2O$ (20 mL), saturated aqueous sodium bicarbonate (20 mL), saturated brine (20 mL), dried ($MgSO_4$), filtered and concentrated to give an oil. This material was purified by normal phase column chromatography on silica gel, eluting with 0 to 100% $Et_2O$ in petrol to give a 6:4 mixture of tert-butyl (R)-(1-(benzo[d][1,3]dioxol-5-yl-2,2-$d_2$)-1-oxopropan-2-yl)(methyl-$d_3$)carbamate and benzo[d] [1,3]dioxol-2,2-$d_2$-5-ol (0.53 g) as an oil. TLC: $R_f$=0.34 (diethyl ether-petrol, 2:8 v/v); $^1$H NMR (300 MHz, $CDCl_3$) δ 7.67 (dd, J=8.1 Hz, 0.60H, ArH), 7.56 (d, J=8.1 Hz, 0.40H, ArH), 7.47 (s, 0.60H, ArH), 7.42 (s, 0.40H, ArH), 6.82 (m 1H, ArH), 6.01 (s, 2H, $CH_2$), 5.63 (q, 0.60H, J=6.9 Hz, α-CH), 5.18 (m, 0.40H, α-CH), 1.46 (s, 9H, t-Bu), 1.34 (m, 3H, Me).

Data for benzo[d][1,3]dioxol-2,2-$d_2$-5-ol
TLC: $R_f$=0.30 (diethyl ether-petrol, 2:8 v/v); $^1$H NMR (300 MHz, $CDCl_3$) δ 6.64 (d, J=8.3 Hz, 1H, ArH), 6.43 (d, J=2.5 Hz, 1H, ArH), 6.25 (dd, J=8.3, 2.5 Hz, 1H, ArH), 4.78 (s, 1H, OH).

Step 2: Synthesis of (R)-1-(benzo[d][1,3]dioxol-5-yl-2,2-$d_2$)-2-((methyl-$d_3$)amino)propan-1-one hydrochloride (25)

To the above mixture (0.53 g) in 1,4-dioxane (5.5 mL) was added a 4 M HCl in 1,4-dioxane (2.97 mL, 11.9 mmol) and the mixture was stirred at rt for 7.5 h (a white precipitate appeared after 30 min). The suspension was diluted with $Et_2O$ (30 mL) and the solid was collected by filtration to give (R)-1-(benzo[d][1,3]dioxol-5-yl-2,2-$d_2$)-2-((methyl-$d_3$)amino)propan-1-one HCl (250 mg, 62% over 2 steps) as a solid.

This material (250 mg) was crystallized using MeOH/$Et_2O$ (3.2 mL/9.1 mL) (vapor diffusion) at rt overnight to give (R)-methylone-$d_5$ (120 mg) as a solid, >98.6% ee. Melting point 232.2° C.; $[α]_D$=+25.4; $^1$H NMR (300 MHz, $CD_3OD$) δ 7.69 (dd, J=8.2, 1.8 Hz, 1H, ArH), 7.49 (d, J=1.8 Hz, 1H, ArH), 7.01 (d, J=8.2 Hz, 1H, ArH), 4.99 (q, J=7.2 Hz, 1H, α-CH), 2.74 (s, 3H, NMe), 1.56 (d, J=7.1 Hz, 3H, Me); $^{13}$C NMR (75.5 MHz, $CD_3OD$) δ 195.0, 155.0, 150.3, 128.7, 127.1, 109.5, 108.9, 60.3, 16.6.

Example 1-8: Synthesis of rac.-methylone-$d_2$ from the Weinreb amide of N-Boc N-Me-DL-alanine

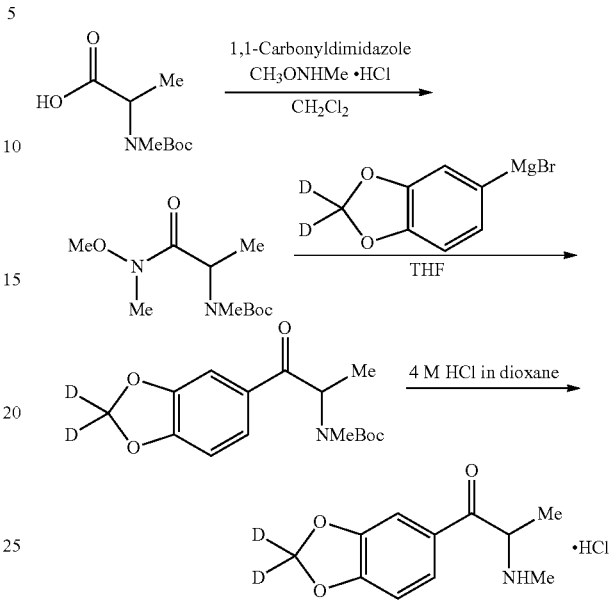

Step 1: Synthesis of tert-butyl (1-(methoxy(methyl)amino)-1-oxopropan-2-yl)methyl)carbamate To a solution of N-Boc-(N-methyl)-DL-alanine (1.00 g, 4.93 mmol) in DCM (25 mL) under an atmosphere of $N_2$ was added 1,1-carbonyldiimidazole (0.88 g, 5.42 mmol) and the mixture was stirred at rt for 40 min. N,O-dimethylhydroxylamine HCl (0.53 g, 5.42 mmol) was added in one portion and the suspension was stirred at rt for 3 days. The reaction was quenched with 1M HCl (20 mL) and the layers were separated. The aqueous layer was extracted with DCM (2×20 mL) and the combined organics were washed with $H_2O$ (20 mL), saturated aqueous sodium bicarbonate (20 mL), saturated brine (20 mL), dried ($MgSO_4$), filtered and concentrated to give an oil. This material was purified by normal phase column chromatography on silica gel, eluting with 0 to 100% EtOAc in petrol to give tert-butyl 1-(methoxy(methyl)amino)-1-oxopropan-2-yl)(methyl)carbamate (1.03 g, 85%) as an oil. TLC: $R_f$=0.49 (ethyl acetate-petrol, 3:7 v/v); $^1$H NMR (300 MHz, $CDCl_3$) δ 5.12 (m, 0.60H, α-CH), 4.82 (m, 0.40H, α-CH), 3.61 (m, 3H, OMe), 3.08 (s, 3H, NMe amide), 2.75 (s, 3H, NMe), (1.36 (s, 9H, t-Bu), 1.20 (d, J=7.1 Hz, 3H, Me); $^{13}$C NMR (75.5 MHz, $CDCl_3$) δ 172.9, 172.2, 155.6, 155.0, 79.8, 79.6, 61.4, 61.2, 51.6, 49.8, 32.0, 29.8, 28.4, 14.5.

Step 2: Synthesis of tert-butyl (1-(benzo[d][1,3]dioxol-5-yl-2,2-$d_2$)-1-oxopropan-2-yl)(methyl)carbamate An oven-dried flask was charged with a solution of tert-butyl (1-(methoxy(methyl)amino)-1-oxopropan-2-yl)(methyl) carbamate (339 mg, 1.38 mmol) in anhydrous toluene (5.5 mL) at 0° C. under an atmosphere of $N_2$ was added (benzo[d][1,3]dioxol-5-yl-2,2-$d_2$) magnesium bromide (~0.5 M in THF, 6.2 mL, 2.8 mmol) and the mixture was stirred at 0° C. for 1 h. (Benzo[d][1,3]dioxol-5-yl-2,2-$d_2$) magnesium bromide (~0.5 M in THF, 6.2 mL, 2.8 mmol)

was added and the mixture was stirred at 0° C. for a further 1 h. The reaction was quenched with saturated NH$_4$Cl (20 mL) and extracted with EtOAc (3×20 mL). The combined organic layers were washed with H$_2$O (20 mL), saturated aqueous sodium bicarbonate (20 mL), saturated brine (20 mL), dried (MgSO$_4$), filtered and concentrated to give an oil. This material was purified by normal phase column chromatography on silica gel, eluting with 0 to 100% Et$_2$O in petrol to give a 64:36 mixture of tert-butyl (1-(benzo[d][1,3]dioxol-5-yl-2,2-d$_2$)-1-oxopropan-2-yl)(methyl)carbamate and benzo[d] [1,3]dioxol-2,2-d$_2$-5-ol (297 mg) as a pale yellow oil. TLC: R$_f$=0.34 (diethyl ether-petrol, 2:8 v/v); $^1$H NMR (300 MHz, CDCl$_3$) δ 7.67 (d, J=8.5 Hz, 0.60H, ArH), 7.56 (d, J=8.7 Hz, 0.40H, ArH), 7.47 (s, 0.60H, ArH), 7.41 (s, 0.40H, ArH), 6.83 (d, J=8.2 Hz, 1H, ArH), 5.63 (q, J=7.1 Hz, 0.60H, α-CH), 5.19 (m, 0.40H, α-CH), 2.76 (s, 1.10H, NMe), 2.62 (s, 1.80H, NMe), 1.46 (s, 9H, t-Bu), 1.34 (m, 3H, Me).

Step 3: Synthesis of 1-(benzo[d][1,3]dioxol-5-yl-2,2-d$_2$)-2-((methyl)amino)propan-1-one HCl To the above mixture (295 mg) in 1,4-dioxane (3.1 mL) was added 4 M HCl in 1,4-dioxane (1.67 mL, 6.68 mmol) and the mixture was stirred at rt for 7.5 h (a white precipitate appeared after 30 min). The suspension was diluted with Et$_2$O (30 mL) and the solid was collected by filtration to give 1-(benzo[d][1,3]dioxol-5-yl-2,2-d$_2$)-2-((methyl-d$_3$)amino) propan-1-one HCl (151 mg, 45% over 2 steps) as a solid. Melting point 236.1° C.; $^1$H NMR (300 MHz, CD$_3$OD) δ 7.70 (dd, J=8.2, 1.7 Hz, 1H, ArH), 7.49 (d, J=1.8 Hz, 1H, ArH), 7.01 (d, J=8.2 Hz, 1H, ArH), 5.00 (q, J=7.2 Hz, 1H, α-CH), 2.74 (s, 3H, NMe), 1.57 (d, J=7.2 Hz, 3H, Me); 13C NMR (75.5 MHz, CD$_3$OD) δ 195.0, 155.0, 150.2, 128.6, 127.1, 109.5, 108.9, 60.4, 31.7, 16.6.

Example 1-9: Synthesis of rac.-methylone-d$_3$ from the Weinreb amide of N-Boc N-CD$_3$-DL-alanine

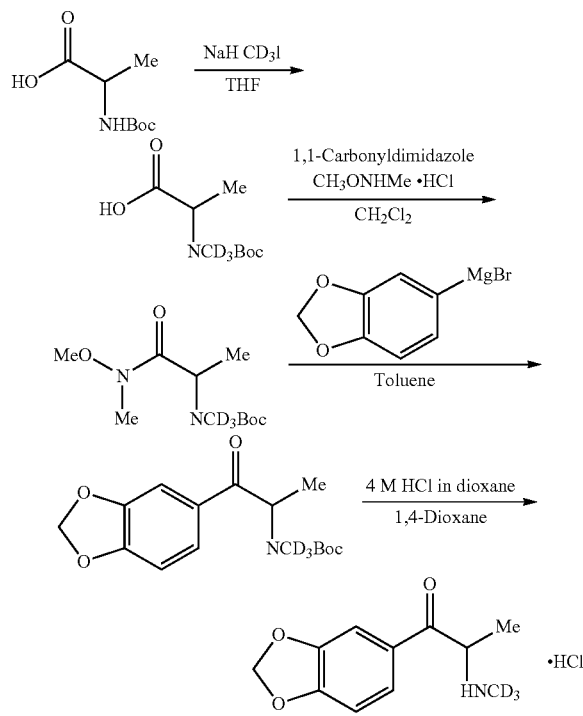

Step 1: Synthesis of N-Boc-(N-methyl-d$_3$)-L-alanine

To an ice-cold solution of N-Boc-DL-alanine (2.00 g, 10.6 mmol) and iodomethane-d$_3$ (15.3 g, 6.59 mL, 106 mmol) in anhydrous THF (70 mL) was added sodium hydride (60% dispersion in oil, 4.23 g, 106 mmol) portion-wise and the mixture was stirred at rt overnight. The mixture was diluted with Et$_2$O (30 mL) and cautiously quenched with H$_2$O (50 mL). The layers were separated, and the aqueous phase was washed with Et$_2$O (40 mL). The aqueous layer was acidified to pH ~ 3 with 20% citric acid and extracted with EtOAc (3×40 mL). The combined organic layers were washed with saturated brine (60 mL), dried (MgSO$_4$), filtered and concentrated to give N-Boc-(N-methyl-d$_3$)-DL-alanine (2.12 g) as a solid that was used without further purification.

Step 2: Synthesis of tert-butyl (1-(methoxy(methyl) amino)-1-oxopropan-2-yl)(methyl-d$_3$)carbamate To a solution of N-Boc-(N-methyl-d$_3$)-DL-alanine (2.12 g, 10.3 mmol) in DCM (52 mL) under an atmosphere of N$_2$ was added 1,1-carbonyldiimidazole (1.84 g, 11.3 mmol) and the mixture was stirred at rt for 40 min. N,O-dimethylhydroxylamine HCl (1.10 g, 11.3 mmol) was added in one portion and the suspension was stirred at rt overnight. The reaction was quenched with 1 M HCl (50 mL) and the layers were separated. The aqueous layer was extracted with DCM (2×40 mL) and the combined organic layers were washed with H$_2$O (50 mL), saturated aqueous sodium bicarbonate (50 mL), saturated brine (50 mL), dried (MgSO$_4$), filtered and concentrated to give an oil. This material was purified by normal phase column chromatography on silica gel, eluting with 0 to 100% EtOAc in petrol to give tert-butyl 1-(methoxy(methyl)amino)-1-oxopropan-2-yl)(methyl-d$_3$) carbamate (2.12 g, 80% over 2 steps) as an oil. TLC: R$_f$=0.49 (ethyl acetate-petrol, 3:7 v/v); $^1$H NMR (300 MHz, CDCl$_3$) δ 5.20 (m, 0.60H, α-CH), 4.92 (m, 0.40H, α-CH), 3.71 (m, 3H, OMe), 3.18 (s, 3H, NMe amide), 1.46 (s, 9H, t-Bu), 1.30 (d, J=7.1 Hz, 3H, Me); $^{13}$C NMR (75.5 MHz, CDCl$_3$) δ 173.2, 155.7, 155.1, 80.0, 79.7, 61.5, 61.3, 51.6, 49.9, 32.1, 14.7.

Step 3: Synthesis of tert-butyl (1-(benzo[d][1,3] dioxol-5-yl)-1-oxopropan-2-yl)(methyl-d$_3$)carbamate An oven-dried flask was charged with a solution of tert-butyl 1-(methoxy(methyl)amino)-1-oxopropan-2-yl) (methyl-d$_3$)carbamate (0.50 g, 2.00 mmol) in anhydrous toluene (6.5 mL) at 0° C. under an atmosphere of N$_2$ was added 3,4-(methylenedioxy)phenylmagnesium bromide (0.5 M in THF, 8.03 mL, 4.0 mmol) and the mixture was stirred at 0° C. for 2 h. The mixture was quenched with saturated aqueous NH$_4$Cl (15 mL) and extracted with EtOAc (3×20 mL). The combined organic layers were washed with saturated sodium bicarbonate (30 mL), saturated brine (30 mL), dried (MgSO$_4$), filtered and concentrated to give an oil. This material was purified by normal phase column chromatography on silica gel, eluting with 0 to 100% Et$_2$O in petrol to give a 9:1 mixture of tert-butyl (1-(benzo[d][1,3]dioxol-5-yl)-1-oxopropan-2-yl)(methyl-d$_3$)carbamate and benzo[d] [1,3]dioxol-5-ol (459 mg) as a pale yellow oil. TLC: R$_f$=0.34 (diethyl ether-petrol, 2:8 v/v); $^1$H NMR (300 MHz, CDCl$_3$) δ 7.67 (d, J=8.1 Hz, 0.60H, ArH), 7.55 (d, J=7.7 Hz, 0.40H, ArH), 7.47 (s, 0.60H, ArH), 7.41 (s, 0.40H, ArH), 6.82 (d, J=8.2 Hz, 1H, ArH), 6.03 (s, 2H, CH$_2$), 5.63 (q, J=6.8 Hz, 0.60H, α-CH), 5.18 (q, J=7.0 Hz, 0.40H, α-CH), 1.46 (s, 9H, t-Bu), 1.34 (m, 3H, Me).

Step 4: Synthesis of 1-(benzo[d][1,3]dioxol-5-yl)-2-((methyl-d$_3$)amino)propan-1-one HCl To a solution of tert-butyl 1-(benzo[d][1,3]dioxol-5-yl)-1-oxopropan-2-yl)(methyl-d$_3$)carbamate (482 mg, 1.55 mmol) in anhydrous 1,4-dioxane (5.1 mL) was added a 4 M HCl in 1,4-dioxane (2.72 mL, 10.9 mmol) and the mixture was stirred at rt for 7.5 h (a white precipitate appeared after 30 min). The suspension was diluted with Et$_2$O (30 mL) and the solid was collected by filtration to give 1-(benzo[d][1,3]dioxol-5-yl)-2-((methyl-d$_3$)amino)propan-1-one HCl (307 mg, 62% over 2 steps) as a solid. Melting point 229.0-231.5° C.; $^1$H NMR (300 MHz, CD$_3$OD) δ 7.70 (dd, J=8.2, 1.8 Hz, 1H, ArH), 7.49 (d, J=1.7 Hz, 1H, ArH), 7.01 (d, J=8.2 Hz, 1H, ArH), 6.12 (s, 2H, CH$_2$), 5.00 (q, J=7.2 Hz, 1H, α-CH), 1.56 (d, J=7.2 Hz, 3H, Me); 13C NMR (75.5 MHz, CD$_3$OD) δ 195.0, 155.0, 150.2, 128.6, 127.2, 109.5, 109.0, 104.0, 60.3, 16.6.

Synthesis of rac.-methylone-d$_5$ from the Weinreb amide of N-Boc N-CD$_3$-DL-alanine

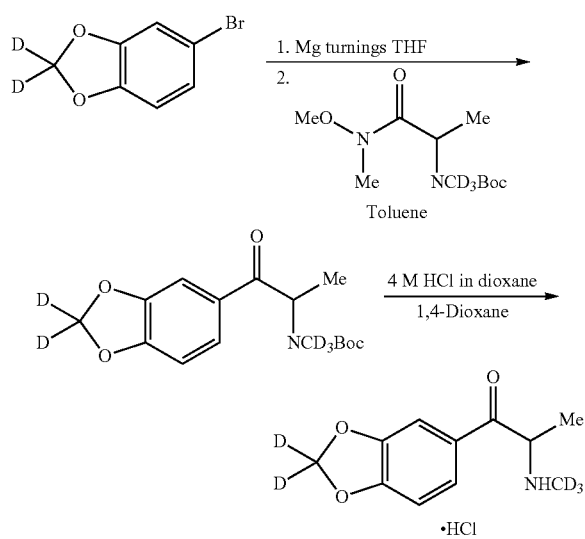

Step 1: Synthesis of tert-butyl 1-(benzo[d][1,3]dioxol-5-yl-2,2-d$_2$)-1-oxopropan-2-yl)(methyl-d$_3$)carbamate An oven-dried flask was charged with a solution of tert-butyl (1-(methoxy(methyl)amino)-1-oxopropan-2-yl)(methyl-d$_3$)carbamate (460 mg, 1.85 mmol) in anhydrous toluene (6.9 mL) at 0° C. under an atmosphere of N$_2$ was added (benzo[d][1,3]dioxol-5-yl-2,2-d$_2$) magnesium bromide (~0.5 M in THF, 7.5 mL, 3.7 mmol) and the mixture was stirred at 0° C. for 1 h. (Benzo[d][1,3]dioxol-5-yl-2,2-d$_2$) magnesium bromide (~0.5 M in THF, 7.5 mL, 3.7 mmol) was added and the mixture was stirred at 0° C. for a further 1 h. The reaction was quenched with saturated NH$_4$Cl (15 mL) and extracted with EtOAc (3×15 mL). The combined organic layers were washed with H$_2$O (20 mL), saturated aqueous sodium bicarbonate (20 mL), saturated brine (20 mL), dried (MgSO$_4$), filtered and concentrated to give an oil. This material was purified by normal phase column chromatography on silica gel, eluting with 0 to 100% Et$_2$O in petrol to give a tert-butyl (1-(benzo[d][1,3]dioxol-5-yl-2,2-d$_2$)-1-oxopropan-2-yl)(methyl-d$_3$)carbamate and only traces of benzo[d][1,3]dioxol-2,2-d$_2$-5-ol (459 mg) as a yellow oil. TLC: R$_f$=0.34 (diethyl ether-petrol, 2:8 v/v); $^1$H NMR (300 MHz, CDCl$_3$) δ 7.67 (d, J=8.0 Hz, 0.60H, ArH), 7.55 (d, J=8.1 Hz, 0.40H, ArH), 7.47 (s, 0.60H, ArH), 7.41 (s, 0.40H, ArH), 6.83 (d, J=8.2 Hz, 1H, ArH), 5.63 (q, J=6.9 Hz, 0.60H, α-CH), 5.18 (q, J=6.8 Hz, 0.40H, α-CH), 1.46 (s, 9H, t-Bu), 1.34 (m, 3H, Me).

Step 2: Synthesis of 1-(benzo[d][1,3]dioxol-5-yl-2,2-d$_2$)-2-((methyl-d$_3$)amino)propan-1-one HCl To the above mixture (459 mg) in 1,4-dioxane (4.9 mL) was added 4 M HCl in 1,4-dioxane (2.58 mL, 10.3 mmol) and the mixture was stirred at rt for 7.5 h (a white precipitate appeared after 30 min). The suspension was diluted with Et$_2$O (30 mL) and the solid was collected by filtration to give 1-(benzo[d][1,3]dioxol-5-yl-2,2-d$_2$)-2-((methyl-d$_3$)amino)propan-1-one HCl (343 mg, 75% over 2 steps) as a solid. Melting point 228.5-231.0° C.; $^1$H NMR (300 MHz, CD$_3$OD) δ 7.70 (dd, J=8.2, 1.8 Hz, 1H, ArH), 7.49 (d, J=1.8 Hz, 1H, ArH), 7.01 (d, J=8.2 Hz, 1H, ArH), 5.00 (q, J=7.2 Hz, 1H, α-CH), 1.56 (d, J=7.2 Hz, 3H, Me); $^{13}$C NMR: (75.5 MHz, CD$_3$OD) δ 195.0, 155.0, 150.3, 128.7, 127.1, 109.5, 108.9, 60.3, 16.6.

Example 1-A: Evaluation of Metabolic Stability in Human Liver Microsomes

Pooled liver microsomes are purchased from a reputable commercial supplier. Microsomes are stored at 80° C. prior to use. Microsomes (final protein concentration 0.5 mg/mL), 0.1 M phosphate buffer pH 7.4 and test compound (final substrate concentration 1 μM; final DMSO concentration 0.25%) are preincubated at 37° C. prior to the addition of NADPH (final concentration 1 mM) to initiate the reaction. A minus cofactor control incubation is included for each compound tested where 0.1 M phosphate buffer pH 7.4 is added instead of NADPH (minus NADPH). Two control compounds are included with each species. All incubations are performed singularly for each test compound. Each compound is incubated for 0, 5, 15, 30 and 45 min. The control (minus NADPH) is incubated for 45 min only. The reactions are stopped by transferring incubate into acetonitrile at the appropriate time points, in a 1:3 ratio. The termination plates are centrifuged at 3,000 rpm for 20 min at 4° C. to precipitate the protein.

Data Analysis

From a plot of ln peak area ratio (compound peak area/internal standard peak area) against time, the gradient of the line is determined. Subsequently, half-life and intrinsic clearance are calculated using the equations below:

Elimination rate constant (k)=(−gradient)

Half-life (t½)(min)=0.693/k

Intrinsic clearance (CLint)(μL/min/mg protein)=V× 0.693/t½ where V=Incubation volume (μL)/Microsomal protein (mg)

Relevant control compounds were assessed, ensuring intrinsic clearance values fall within the specified limits (if available).

The following values were obtained from the above experiment,

Metabolic stability Human Liver Microsomes

| Compound ID | $CL_{int}$ (μL/min/mg protein) | SE $CL_{int}$ | $t_{1/2}$ (min) | n |
|---|---|---|---|---|
| (S)-Methylone-d2 hydrochloride | 9.41 | 3.55 | 147 | 5 |
| (S)-Methylone-d3 hydrochloride | 9.60 | 3.66 | 144 | 5 |
| (S)-Methylone-d5 hydrochloride | 9.07 | 3.05 | 153 | 5 |
| (S)-Methylone Hydrochloride | 10.1 | 3.18 | 137 | 5 |
| (R)-Methylone-d2 hydrochloride | 7.00 | 2.99 | 198 | 5 |
| (R)-Methylone-d3 hydrochloride | 6.49 | 2.00 | 214 | 5 |
| (R)-Methylone-d5 hydrochloride | 6.27 | 3.20 | 221 | 5 |
| (R)-Methylone Hydrochloride | 6.82 | 3.29 | 203 | 5 |
| (rac)-Methylone-d2 hydrochloride | 9.46 | 3.31 | 147 | 5 |
| (rac)-Methylone-d3 hydrochloride | 8.02 | 3.31 | 173 | 5 |
| (rac)-Methylone-d5 hydrochloride | 7.59 | 2.78 | 183 | 5 |
| (rac)-Methylone Hydrochloride | 8.84 | 3.54 | 157 | 5 |

Based on the results above, (S)-methylone-$d_5$ hydrochloride demonstrated the most significant difference in half-life and intrinsic clearance compared with (S)-methylone hydrochloride. (R)-Methylone-$d_5$ hydrochloride demonstrated the most significant difference in half-life and intrinsic clearance compared with (R)-methylone hydrochloride. (rac)-methylone-$d_5$ hydrochloride demonstrated the most significant difference in half-life and intrinsic clearance compared with (rac)-methylone hydrochloride. Additionally, (S)-methylone-$d_2$ hydrochloride, (S)-methylone-$d_3$ hydrochloride, (R)-methylone-$d_2$ hydrochloride, (R)-methylone-$d_3$ hydrochloride, (rac)-methylone-$d_2$ hydrochloride, and (rac)-methylone-$d_3$ hydrochloride demonstrated differences in half-life and intrinsic clearance compared to the relevant control compounds.

Example 1-B: Evaluation of Oral Bioavailability of Deuterated Methylones in Rats Pharmacokinetics of Test Articles Following a Single Intravenous or Oral Administration in Rats:

A pharmacokinetic (PK) study is performed in three male Sprague-Dawley (SD) rats following intravenous (IV) and oral (PO) administration of methylone, or test deuterated-methylone, at 1 mg/kg (IV) and 10 (PO) mg/kg. Test compounds, or methylone, are measured in plasma.

In Vivo Methods

Rat Strain

Rats used in these studies are supplied by Charles River (Margate UK) and are specific pathogen free. The strain of rats is Sprague Dawley. Male rats are 175-225 g on receipt and are allowed to acclimatise for 5-7 days.

Animal Housing

Rats are group housed in sterilized individual ventilated cages that expose the animals at all times to HEPA filtered sterile air. Animals will have free access to food and water (sterile) and will have sterile aspen chip bedding (at least once weekly). The room temperature is 22° C.+/−1° C., with a relative humidity of 60% and maximum background noise of 56 dB. Rats are exposed to 12 hour light/dark cycles.

Treatment

Test article is diluted 10% v/v DMSO, 40% v/v PEG-400, 50% v/v Water. The test articles are administered in a dose volume of 2 mL/kg for intravenous (IV) and 5 mL/kg (PO) for oral routes of administration.

Single IV/PO Dose Pharmacokinetics Study in Rats

Each test article is administered as a single IV bolus (via a lateral tail-vein) or a single oral gavage in cohorts of 3 rats per route. Following dose administrations, a 100 μL whole blood sample (EDTA) is collected via the tail-vein at timepoints described in Table 2. The blood is centrifuged to separate plasma. Approximately 40 μL of plasma is dispensed per time-point, per rat, in a 96 well plate and frozen until analysis. Bioanalysis is carried out on plasma samples.

TABLE 2

Single IV and oral dose pharmacokinetics profile of test articles in rat plasma

| Group | Test article | Route | Dose (mg/kg) | Blood sample collection (post dose) | No. of rats |
|---|---|---|---|---|---|
| 1 | Methylone | IV | 1 | 5 min, 15 min, 30 min, 1 h, 2 h, 4 h, 7 h, 24 h | 3 |
| 2 | Methylone | PO | 10 | 15 min, 30 min, 45 min, 1 h, 2 h, 4 h, 7 h, 24 h | 3 |
| 3 | Test Article | IV | 1 | 5 min, 15 min, 30 min, 1 h, 2 h, 4 h, 7 h, 24 h | 3 |
| 4 | Test Article | PO | 10 | 15 min, 30 min, 45 min, 1 h, 2 h, 4 h, 7 h, 24 h | 3 |

Dose Formulation Samples

Dose formulation samples are diluted in two steps with 50:50 (v/v) methanol/water to an appropriate concentration, then diluted 10:90 (v/v) with control matrix to match to the calibration standard in plasma.

Sample Extraction Procedure

Calibration and QC standards, incurred samples, blank matrix and dose formulation samples are extracted by protein precipitation, via the addition of a bespoke acetonitrile (ACN)-based Internal Standard (IS) solution, containing several compounds and including Metoprolol and Rosuvastatin, both of which are monitored for during analysis. Following centrifugation, a 40 μL aliquot of supernatant is diluted by the addition of 80 μL water. The prepared sample extracts are analysed by LC-MS/MS.

Example of Bioanalytical Method and Assay Information Document:

1 According to the plate layout, aliquot to wells in 0.8 mL 96-well plate (Abgene). 30 μL for Calibration, QC standards, blanks and dose formulation check.
2 Prepare Calibration and QC standards according to the assay information. Dilute dose formulation according to the assay information. Aliquot incurred samples according to the plate layout & assay information.
3 Add 90 μL of ACN internal standard and vortex mix for 5 minutes at 850 rpm
4 Centrifuge at nominally 4000 rpm for 10 minutes
6 Transfer 40 μL of supernatant into a new 0.8 mL Abgene plate.
6 Add 80 μL of water to all transferred supernatant.
7 Vortex mix for 30 seconds at 1400 rpm
8 Analyse immediately by LC-MS/MS or store at +4° C. until analysis.

Example 1-C: Biological Assays and Methods for Evaluating Methylone and Ethylone Derivatives and Solid Forms Thereof 1. Head-Twitch Response (HTR)

The head-twitch response assay is performed as is known to those of skill in the art using both male and female C57BL/6J mice (2 per treatment). The mice are obtained and were approximately 8 weeks old at the time of the experiments. Compounds were administered via intraperitoneal injection (5 mL/kg) using 0.9% saline as the vehicle. As a positive control, 5-MeO-DMT fumarate (2:1 amine/acid) was utilized. Behavior was videotaped, later scored by two blinded observers, and the results were averaged (Pearson correlation coefficient=0.93).

2. Serotonin and Opioid Receptor Functional Assays.

Functional assay screens at 5-HT and opioid receptors are performed in parallel using the same compound dilutions and 384-well format high-throughput assay platforms. Assays assess activity at all human isoforms of the receptors, except where noted for the mouse 5-HT2A receptor. Receptor constructs in pcDNA vectors were generated from the Presto-Tango GPCR library with minor modifications. All compounds were serially diluted in drug buffer (HBSS, 20 mM HEPES, pH 7.4 supplemented with 0.1% bovine serum albumin and 0.01% ascorbic acid) and dispensed into 384-well assay plates using a FLIPR$^{TETRA}$ (Molecular Devices). Every plate included a positive control such as 5-HT (for all 5-HT receptors), DADLE (DOR), salvinorin A (KOR), and DAMGO (MOR). For measurements of 5-HT$_{2A}$, 5-HT2B, and 5-HT2C Gq-mediated calcium flux function, HEK Flp-In 293 T-Rex stable cell lines (Invitrogen) were loaded with Fluo$_{-4}$ dye for one hour, stimulated with compounds and read for baseline (0-10 seconds) and peak fold-over-basal fluorescence (5 minutes) at 25° C. on the FLIPR$^{TETRA}$. For measurement of 5-HT6 and 5-HT7a functional assays, Gs-mediated cAMP accumulation was detected using the split-luciferase GloSensor assay in HEKT cells measuring luminescence on a Microbeta Trilux (Perkin Elmer) with a 15 min drug incubation at 25° C. For 5-HT1A, 5-HT1B, 5-HT1F, MOR, KOR, and DOR functional assays, Gi/o-mediated cAMP inhibition was measured using the split-luciferase GloSensor assay in HEKT cells, conducted similarly as above, but in combination with either 0.3 µM isoproterenol (5-HT1A, 5-HT1B, 5-HT1F) or 1 µM forskolin (MOR, KOR, and DOR) to stimulate endogenous cAMP accumulation. For measurement of 5-HT1D, 5-HT1E, 5-HT4, and 5-HT5A functional assays, P-arrestin2 recruitment was measured by the Tango assay utilizing HTLA cells expressing TEV fused-P-arrestin2, as described previously with minor modifications. Data for all assays were plotted and non-linear regression was performed using "log(agonist) vs. response" in Graphpad Prism to yield Emax and EC$_{50}$ parameter estimates.

3. 5HT$_{2A}$ Sensor Assays

HEK293T (ATCC) 5HT$_{2A}$ sensor stable line (sLight1.3s) is generated via lentiviral transduction of HIV-EF1α-sLight1.3 and propagated from a single colony. Lentivirus is produced using $2^{nd}$ generation lentiviral plasmids pHIV-EF1α-sLight1.3, pHCMV-G, and pCMV-deltaR8.2.

For the screening of the compounds, sLight1.3s cells are plated in 96-well plates at a density of 40000 24-hours prior to imaging. On the day of imaging, compounds solubilized in DMSO are diluted from the 100 mM stock solution to working concentrations of 1 mM, 100 mM and 1 µM with a DMSO concentration of 1%. Immediately prior to imaging, cells growing in DMEM (Gibco) are washed 2× with HBSS (Gibco) and in agonist mode 180 µL of HBSS or in antagonist mode 160 µL of HBSS is added to each well after the final wash. For agonist mode, images are taken before and after the addition of the 20 µL compound working solution into the wells containing 180 µL HBSS. This produces final compound concentrations of 100 mM, 10 mM and 100 nM with a DMSO concentration of 0.1%. For antagonist mode, images are taken before and after addition of 20 µL of 900 nM 5-HT and again after 20 µL of the compound working solutions to produce final concentrations of 100 nM for 5HT and 100 mM, 10 mM and 100 nM for the compounds with a DMSO concentration of 0.1%. Each compound is tested in triplicate (3 wells) for each concentration (100 mM, 10 mM and 100 nM). Additionally, within each plate, 100 nM 5HT and 0.1% DMSO controls are also imaged.

Imaging is performed using the Leica DMi8 inverted microscope with a 40× objective using the FITC preset with an excitation of 460 nm and emission of 512-542 nm. For each well, the cellular membrane where the 5HT2A sensor is targeted is autofocused using the adaptive focus controls and 5 images from different regions within the well were taken with each image processed from a 2×2 binning.

For data processing, the membranes from each image are segmented and analyzed using a custom algorithm written in MATFAB producing a single raw fluorescence intensity value. For each well the 5 raw fluorescence intensity values generated from the 5 images are averaged and the change in fluorescence intensity (dFF) is calculated as:

$$dFF=(F_{sat}-F_{apo})/F_{apo}$$

For both agonist and antagonist modes, the fluorescence intensity values before compound addition in FIBSS only are used as the $F_{apo}$ values while the fluorescence intensity values after compound addition are used as the $F_{sat}$ values.

For agonist mode, data are as percent activation relative to 5HT, where 0 is the average of the DMSO wells and 100 is the average of the 100 µM 5HT wells. For antagonist mode, the inactivation score is calculated as:

$$\text{Inactivation score}=(dFFF(\text{Compound}+5HT)-dFF(5HT))/dFF(5HT)$$

4. Plasticity Effects

Treatment of rat embryonic cortical neurons with compounds of Formula I is evaluated for increased dendritic arbor complexity at 6 days in vitro (DIV6) as measured by Sholl analysis. The effect of the present compounds on dendritic growth can be determined to be 5-HT2A-dependent, if pretreatment with ketanserin—a 5-HT2A antagonist—inhibits their effects.

In addition to promoting dendritic growth, the present compounds also are evaluated for increased dendritic spine density to a comparable extent as ibogaine in mature cortical cultures (DIV20). The effects of the compounds on cortical dendritic spine dynamics in vivo using transcranial 2-photon imaging is assessed. First, spines are imaged on specific dendritic loci defined by their relation to blood vessel and dendritic architectures. Next, the animals are systemically administered vehicle, a compound of the present disclosure, or the hallucinogenic 5-HT2A agonist 2,5-dimethoxy-4-iodoamphetamine (DOI). After 24 h, the same dendritic segments are re-imaged, and the number of spines gained or lost is quantified. Examples of the presently disclosed compounds increase spine formation in mouse primary sensory cortex, suggesting that the present compounds support neuronal plasticity.

As increased cortical structural plasticity in the anterior parts of the brain mediates the sustained (>24 h) antidepressant-like effects of ketamine and play a role in the therapeutic effects of 5-HT2A agonists, the impact of the present compounds on forced swim test (FST) behavior is evaluated. First, a pretest is used to induce a depressive phenotype. Compounds are administered 24 h after the pre-test, and the FST is performed 24 h and 7 d post compound administration. Effective compounds of the invention, like ketamine, significantly reduced immobility 24 h after administration.

5. Dendritogenesis Assays.

Compounds disclosed herein are evaluated for their ability to increase dendritic arbor complexity in cultures of cortical neurons using a phenotypic assay. Following treatment, neurons are fixed and visualized using an antibody against MAP2—a cytoskeletal protein localized to the somatodendritic compartment of neurons. Sholl analysis is then performed, and the maximum number of crossings ($N_{max}$) was used as a quantitative metric of dendritic arbor complexity. For statistical comparisons between specific compounds, the raw $N_{max}$ values are compared. Percent efficacies are determined by setting the $N_{max}$ values for the vehicle (DMSO) and positive (ketamine) controls equal to 0% and 100%, respectively.

Animals. For the dendritogenesis experiments, timed pregnant Sprague Dawley rats are obtained. For the head-twitch response assay, male and female C57BL/6J mice are obtained.

6. Dendritogenesis—Sholl Analysis.

Dendritogenesis experiments are performed following a previously published methods with slight modifications. Neurons are plated in 96-well format (200 μL of media per well) at a density of approximately 15,000 cells/well in Neurobasal (Life Technologies) containing 1% penicillin-streptomycin, 10% heat-inactivated fetal bovine serum, and 0.5 mM glutamine. After 24 h, the medium is replaced with Neurobasal containing 1× B27 supplement (Life Technologies), 1% penicillin-streptomycin, 0.5 mM glutamine, and 12.5 pM glutamate. After 3 days in vitro (DIV3), the cells are treated with compounds. All compounds tested in the dendritogenesis assays are treated at 10 pM. Stock solutions of the compounds in DMSO are first diluted 100-fold in Neurobasal before an additional 10-fold dilution into each well (total dilution=1:1000; 0.10% DMSO concentration). Treatments are randomized. After 1 h, the media is removed and replaced with new Neurobasal media containing 1× B27 supplement, 1% penicillin-streptomycin, 0.5 mM glutamine, and 12.5 mM glutamate. The cells are allowed to grow for an additional 71 h. At that time, neurons are fixed by removing 80% of the media and replacing it with a volume of 4% aqueous paraformaldehyde (Alfa Aesar) equal to 50% of the working volume of the well. Then, the cells are incubated at room temperature for 20 min before the fixative is aspirated and each well washed twice with DPBS. Cells are permeabilized using 0.2% Triton X-100 (ThermoFisher) in DPBS for 20 minutes at room temperature without shaking. Plates are blocked with antibody diluting buffer (ADB) containing 2% bovine serum albumin (BSA) in DPBS for 1 h at room temperature. Then, plates are incubated overnight at 4° C. with gentle shaking in ADB containing a chicken anti-MAP2 antibody (1:10,000; EnCor, CPCA-MAP2). The next day, plates are washed three times with DPBS and once with 2% ADB in DPBS. Plates are incubated for 1 h at room temperature in ADB containing an anti-chicken IgG secondary antibody conjugated to Alexa Fluor 488 (Life Technologies, 1:500) and washed five times with DPBS. After the final wash, 100 μL of DPBS is added per well and imaged on an ImageXpress Micro XL High-Content Screening System (Molecular Devices, Sunnyvale, CA) with a 20× objective. Images are analyzed using ImageJ Fiji (version 1.51 W). First, images corresponding to each treatment are sorted into individual folders that are then blinded for data analysis. Plate controls (both positive and negative) are used to ensure that the assay is working properly as well as to visually determine appropriate numerical values for brightness/contrast and thresholding to be applied universally to the remainder of the randomized images. Next, the brightness/contrast settings are applied, and approximately 1-2 individual pyramidal-like neurons per image (i.e., no bipolar neurons) are selected using the rectangular selection tool and saved as separate files. Neurons are selected that do not overlap extensively with other cells or extend far beyond the field of view.

7. In Vivo Spine Dynamics.

Male and female Thy1-GFP-M line mice (n=5 per condition) are purchased from The Jackson Laboratory (JAX #007788) and maintained. In vivo transcranial two-photon imaging and data analysis are performed as previously described. Briefly, mice are anesthetized with an intraperitoneal (i.p.) injection of a mixture of ketamine (87 mg/kg) and xylazine (8.7 mg/kg). A small region of the exposed skull is manually thinned down to 20-30 pm for optical access. Spines on apical dendrites in mouse primary sensory cortices are imaged using a Bruker Ultima IV two-photon microscope equipped with an Olympus water-immersion objective (40×, NA=0.8) and a Ti:Sapphire laser (Spectra-Physics Mai-Tai, excitation wavelength 920 nm). Images are taken at a zoom of 4.0 (pixel size 0.143×0.143 pm) and Z-step size of 0.7 pm. The mice receive an i.p. injection (injection volume=5 mL/kg) of DOI (10 mg/kg) or TBG (50 mg/kg) immediately after they recovered from anesthesia given prior to the first imaging session. The animals are re-imaged 24 h after drug administration. Dendritic spine dynamics were analyzed using ImageJ. Spine formation and elimination were quantified as percentages of spine number on day 0.

8. Forced Swim Test (FST).

Male C57/BL6J mice (9-10 weeks old at time of experiment) are obtained. After 1 week in the vivarium each mouse is handled for approximately 1 minute by the experimenter for 3 consecutive days leading up to the first FST. All experiments are carried out by the same experimenter who performs handling. During the FST, mice undergo a 6 min swim session in a clear Plexiglas cylinder 40 cm tall, 20 cm in diameter, and filled with 30 cm of 24±1° C. water. Fresh water is used for every mouse. After handling and habituation to the experimenter, drug-naive mice first undergo a pretest swim to more reliably induce a depressive phenotype in the subsequent FST sessions. Immobility scores for all mice are determined after the pre-test and mice are randomly assigned to treatment groups to generate groups with similar average immobility scores to be used for the following two FST sessions. The next day, the animals receive intraperitoneal injections of experimental compounds (20 mg/kg), a positive control (ketamine, 3 mg/kg), or vehicle (saline). The animals were subjected to the FST 30 mins after injection and then returned to their home cages. All FSTs are performed between the hours of 8 am and 1 pm. Experiments are video-recorded and manually scored offline. Immobility time—defined as passive floating or remaining motionless with no activity other than that needed to keep the mouse's head above water—is scored for the last 4 min of the 6 min trial.

Statistical analysis. Treatments are randomized, and data are analyzed by experimenters blinded to treatment conditions. Statistical analyses are performed using GraphPad Prism (version 8.1.2). The specific tests are, F-statistics and degrees of freedom. All comparisons are planned prior to performing each experiment. For dendritogenesis experiments a one way ANOVA with Dunnett's post hoc test is deemed most appropriate. Ketamine was included as a positive control to ensure that the assay is working properly.

9. Alcohol Use Disorder Model

To assess the anti-addictive potential of the present compounds, an alcohol drinking paradigm that models heavy alcohol use and binge drinking behavior in humans is employed. Using a 2-bottle choice setup (20% ethanol (v/v), EtOH vs. water, $H_2O$), mice are subjected to repeated cycles of binge drinking and withdrawal over the course of 7 weeks.

This schedule results in heavy EtOH consumption, binge drinking-like behavior, and generates blood alcohol content equivalent to that of human subjects suffering from alcohol use disorder (AUD). Next, compounds of the invention are administered via intraperitoneal injection 3 h prior to a drinking session, and EtOH and $H_2O$ consumption is monitored. Effective compounds of the invention, such as those of Formula I, robustly reduce binge drinking during the first 4 h, decreasing EtOH consumption. With exemplary compounds, consumption of ethanol is lower for at least two days following administration with no effect on water intake. Efficacy in this assay suggests the present compounds are useful for the treatment of AUD.

Example 2-1: Preparation and Characterizations of Polymorphs of Methylone Hydrochloride The active pharmaceutical ingredient (API), methylone hydrochloride, was characterized to evaluate its physical properties. The evaluation performed included X-ray powder diffraction (XRPD), polarized light microscopy (PLM), differential scanning calorimetry (DSC), thermogravimetry (TG), dynamic vapor sorption/desorption (DVS), and/or solubility testing in organic solvents, water, and mixed solvent systems. XRPD data are used to assess crystallinity. PLM data are used to evaluate crystallinity and particle size/morphology. DSC data are used to evaluate melting point, thermal stability, and crystalline form conversion. TG data are used to evaluate if the API is a solvate or hydrate, and to evaluate thermal stability. DVS data are used to evaluate hygroscopicity of the API and if hydrates can be formed at high relative humidity. About 10 to 15 solvents may be selected from the list shown in Table 3 below, based on their properties (polarity, dielectric constant and dipole moment).

TABLE 3

| Solvents | |
|---|---|
| acetic acid | n-heptane |
| acetone | n-hexane |
| acetonitrile | 1,1,1,3,3,3-hexafluoro-2-propanol |
| benzyl alcohol | isobutanol (2-methyl-1-propanol) |
| 1-butanol | isopentanol (3-methyl-1-butanol) |
| 2-butanol | isopropyl alcohol (2-propanol) |
| butyl acetate | isopropylbenzene (cumene) |
| t-butyl methyl ether | methanol |
| chlorobenzene | methoxybenzene (anisole) |
| chloroform | methyl acetate |
| di(ethylene glycol) | methyl ethyl ketone (2-butanone) |
| dichloromethane | methyl isobutyl ketone |
| diethyl ether | nitromethane |
| diethylamine | N-methyl-2-pyrrolidone (NMP) |
| Dimethylacetamide (DMA) | 1-octanol |
| diisopropyl ether | 1-pentanol |
| N,N-dimethyl-formamide (DMF) | 1-propanol |
| dimethyl sulfoxide | perfluorohexane |
| 1,4-dioxane | propyl acetate |
| 1,2-ethanediol (ethylene glycol) | 1,1,2,2-tetrachloroethane |
| ethanol | tetrahydrofuran |
| ethanolamine | toluene |
| 2-ethoxyethanol (Cellusolve) | 1,1,1-trichloroethane |

TABLE 3-continued

| Solvents | |
|---|---|
| ethyl acetate | 2,2,2-trifluoroethanol |
| ethyl formate | water |
| formic acid | o-xylene (1,2-dimethylbenzene) |
| glycerol | p-xylene (1,4-dimethylbenzene) |

The results of a solubility screen are shown in Table 4. The experiments were carried out by adding the test solvent in aliquots to weighed portions of solid. Whether dissolution had occurred was judged by visual inspection after addition of each solvent aliquot. Solubility numbers recorded in Table 4 were calculated by dividing the weight of the sample by the total amount of solvent used to dissolve the sample. The actual solubilities may be greater than the numbers calculated because of the use of solvent aliquots that were too large or because of slow dissolution rates. All solubility measurements were carried out at room temperature unless noted otherwise.

TABLE 4

| Solvent | Solubility (mg/mL) |
|---|---|
| Acetone | <1 |
| ACN | <1 |
| $CHCl_3$ | <1 |
| DMF | 5 |
| EtOAc (wet) | 9 |
| EtOH | 8 |
| $H_2O$ | 47 |
| MeOH | 48 |
| MeOH/$CHCl_3$ 50/50 | 45 |
| THF | <1 |

The information obtained was used for designing the subsequent polymorph screen. Solvents were used as a single solvent or as solvent mixtures, some containing water. The techniques used for the polymorph screen were chosen based on the solvent selected and properties of the API. The following techniques (or a combination of techniques) may be used for the polymorph screening:

API is dissolved in a solvent or mixture of solvents, and the solvents are evaporated at different rates (slow evaporation or fast evaporation) and at different temperatures (ambient or elevated).

API is dissolved in a solvent or mixture of solvents (at ambient temperature or an elevated temperature), and the final solution is cooled (between −78° C. to 20° C.). The cooling method can be a fast cooling (by plunging the sample to an ice bath or a dry ice/acetone bath), or slow cooling. The solids formed will be recovered by filtration and dried (air dried or vacuum dried).

API is dissolved in a solvent or mixture of solvents, and an antisolvent is added to precipitate the salt. The solids formed will be recovered by filtration and dried (air dried or vacuum dried).

API is added to a solvent or mixture of solvents, where the API is not fully dissolved. The slurry will be agitated at different temperatures for a number of days. The solids formed will be recovered by filtration and (air dried or vacuum dried).

API is milled (by mechanical milling or by mortar and pestle), with a drop of solvent, or without any solvent.

API is melted and cooled (at different cooling rates, fast and slow, and cooled to different temperatures) to obtain solids.

API is suspended in a solvent or mixture of solvents, and the slurry is placed in a heating/cooling cycle for multiple cycles. The remaining solids after the final cooling cycle will be filtered and (air dried or vacuum dried).

API is processed to obtain an amorphous form (by melting, milling, solvent evaporation, spray drying or lyophilization). The amorphous form will then be exposed to elevated humidity (or elevated temperature, or combination thereof), or to solvent vapors for extended period of days.

API is exposed to elevated humidity (or elevated temperature, or combination thereof), or to solvent vapors for extended period of days.

Two or more polymorphs of the API are mixed in a solvent or solvent systems (some solvent mixtures containing variable amount of water) to obtain a slurry, and the slurry will be agitated (at various temperatures) for an extended period of time (days). The solvent system used can be pre-saturated with the API. The final solids will be filtered and dried (air dried or vacuum dried).

API is heated to a specific temperature and cooled (at ambient conditions or in a dry box).

The solids obtained were analyzed by XRPD to determine if they are crystalline and, if so, by DSC to see the melting point and by TG to see if they are hydrated/solvated, and by $^1$H NMR spectroscopy to ensure chemical integrity. KF water titration is performed on forms that are hydrated. DVS analysis is performed to evaluate hygroscopicity of the form and if hydrated form is present. In particular variable temperature analyses, including variable temperature XRPD, are performed to assess the stability of each physical form as well as its crystallinity.

Differential scanning calorimetry (DSC) thermograms were obtained using a DSC Q 100 (TA Instruments, New Castle, DE). The temperature axis and cell constant of the DSC cell are calibrated with indium (10 mg, 99.9% pure, melting point 156.6° C., heat of fusion 28.4 J/g). Samples (2.0-5.0 mg) are weighed in aluminum pans on an analytical balance. Aluminum pans without lids are used for the analysis. The samples are equilibrated at 25° C. and heated to 250-300° C. at a heating rate of 10° C./min under continuous nitrogen flow. TG analysis of the samples is performed with a Q 50 (TA Instruments, New Castle, DE). Samples (2.0-5.0 mg) are analyzed in open aluminum pans under a nitrogen flow (50 mL/min) at 25° C. to 210° C. with a heating rate of 10° C./min.

The sample for moisture analysis was allowed to dry at 25° C. for up to 4 hours under a stream of dry nitrogen. The relative humidity is then increased stepwise from 10 to 90% relative humidity (adsorption scan) allowing the sample to equilibrate for a maximum of four hours before weighing and moving on to the next step. The desorption scan is measured from 85 to 0% relative humidity with the same equilibration time. The sample is then dried under a stream of dry nitrogen at 80° C. for 2 hours or until no weight loss is observed.

X-ray powder diffraction data were collected using a Rigaku Smart-Lab X-ray diffraction system was configured for reflection Bragg-Brentano geometry using a line source X-ray beam. The X-ray source is a Cu Long Fine Focus tube that was operated at 40 kV and 44 ma. That source provides an incident beam profile at the sample that changes from a narrow line at high angles to a broad rectangle at low angles. Beam conditioning slits are used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1 °2θ or less. The axial divergence of the X-ray beam is controlled by 5.0-degree Soller slits in both the incident and diffracted beam paths.

Powder samples were prepared in a low background Si holder using light manual pressure to keep the sample surfaces flat and level with the reference surface of the sample holder. Each sample was analyzed from 2 to 40 °2θ using a continuous scan of 6 °2θ per minute with an effective step size of 0.02 °2θ.

Variable temperature XRPD data are collected using a Huber Imaging Plate Guinier Camera 670 employing Ni-filtered Cu Kα1 radiation (λ=1.5405981 Å) produced at 40 kV and 20 mA by a Philips PW1120/00 generator fitted with a Huber long fine-focus tube PW2273/20 and a Huber Guinier Monochromator Series 611/15. The original powder is packed into a Lindemann capillary (Hilgenberg, Germany) with an internal diameter of 1 mm and a wall thickness of 0.01 mm. The sample is heated at an average rate of 5 Kmin$^{-1}$ using a Huber High Temperature Controller HTC 9634 unit with the capillary rotation device 670.2. The temperature is held constant at selected intervals for 10 min while the sample is exposed to X-rays and multiple scans are recorded. A 2θ-range of 4.00-100.0° is used with a step size of 0.0050 2θ.

Exemplary samples generated and analyzed are listed in Table 5.

TABLE 5

Samples Generated and Analyzed

Figure 3:
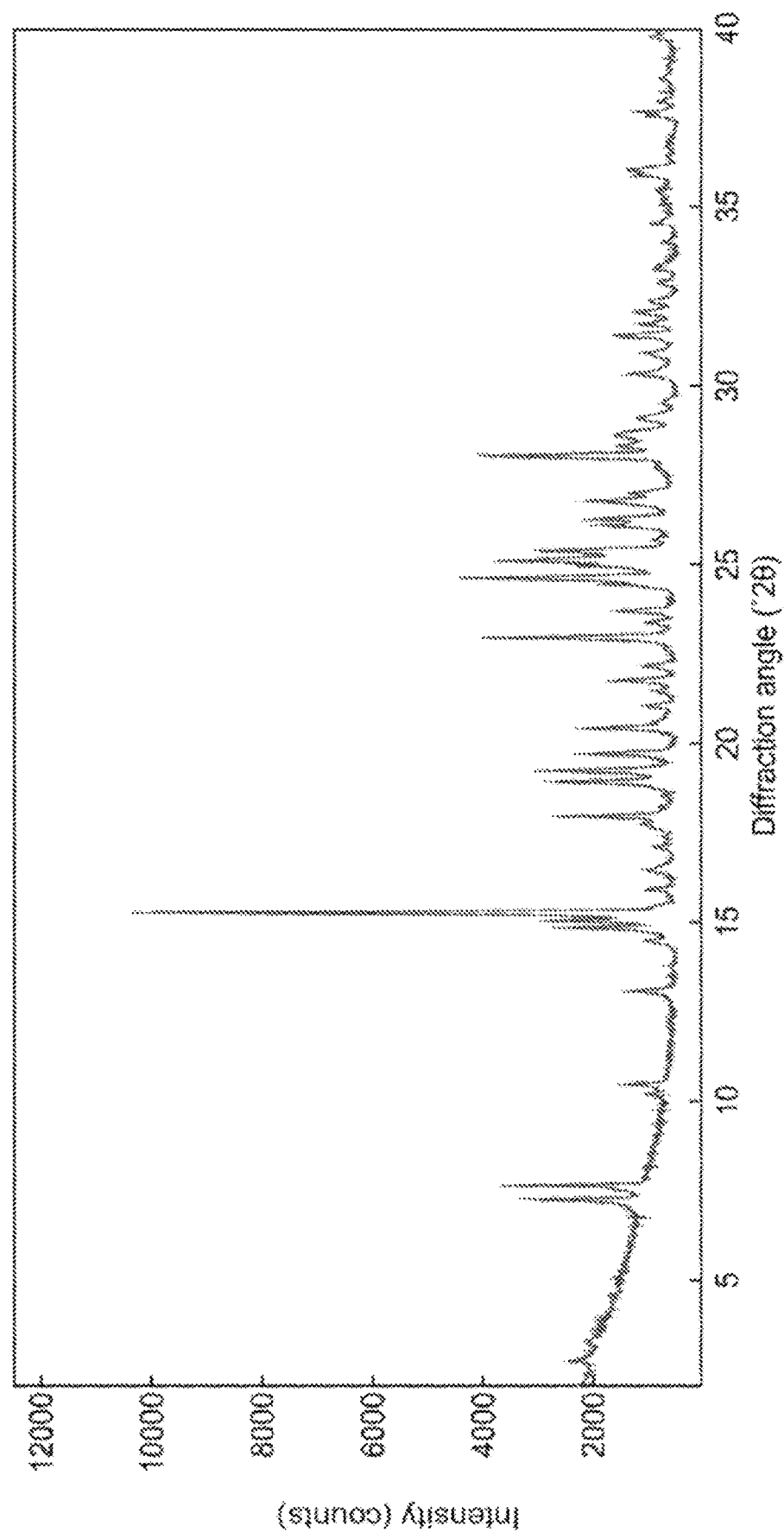
FIG. 3 illustrates an XRPD diffractogram of methylone hydrochloride (racemate) comprising a mixture of Forms A and C, prepared by evaporation of ethanol.
Figure 4:
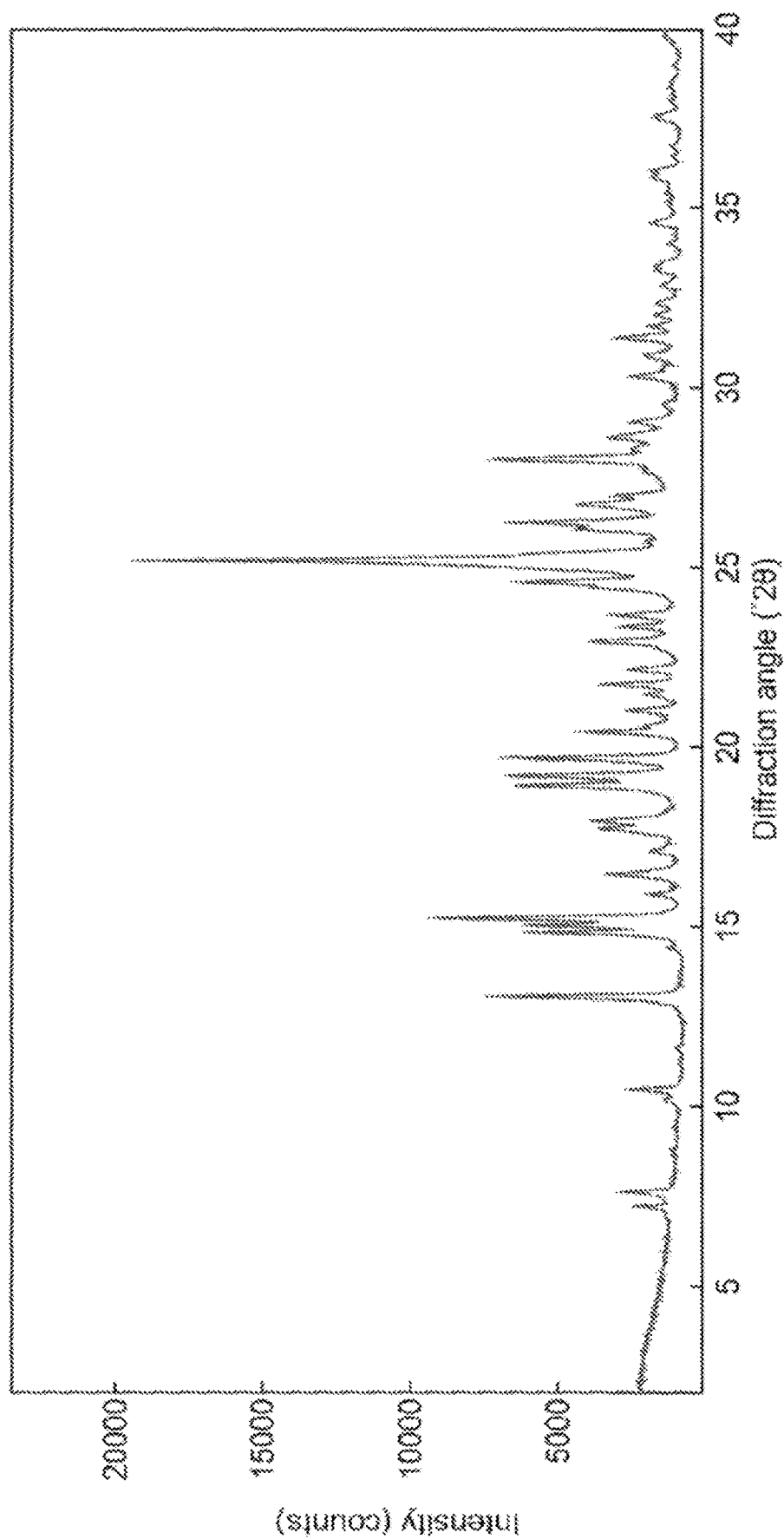
FIG. 4 illustrates an XRPD diffractogram of methylone hydrochloride (racemate) comprising a mixture of Forms A and C, prepared by evaporation of water.
Figure 5:
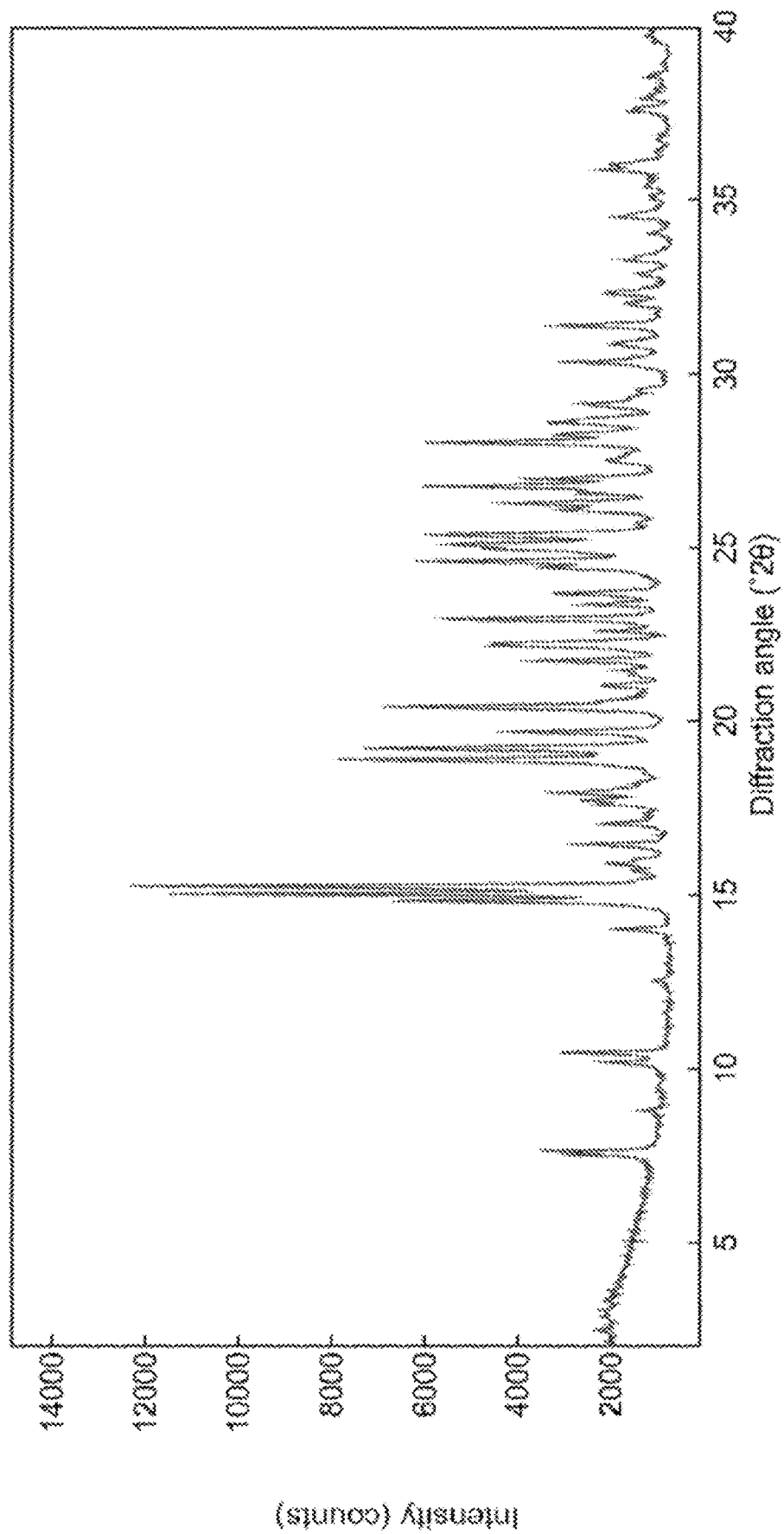
FIG. 5 illustrates an XRPD diffractogram of methylone hydrochloride (racemate) comprising a crystalline Form A and D, prepared by evaporation of methanol.
Figure 6:
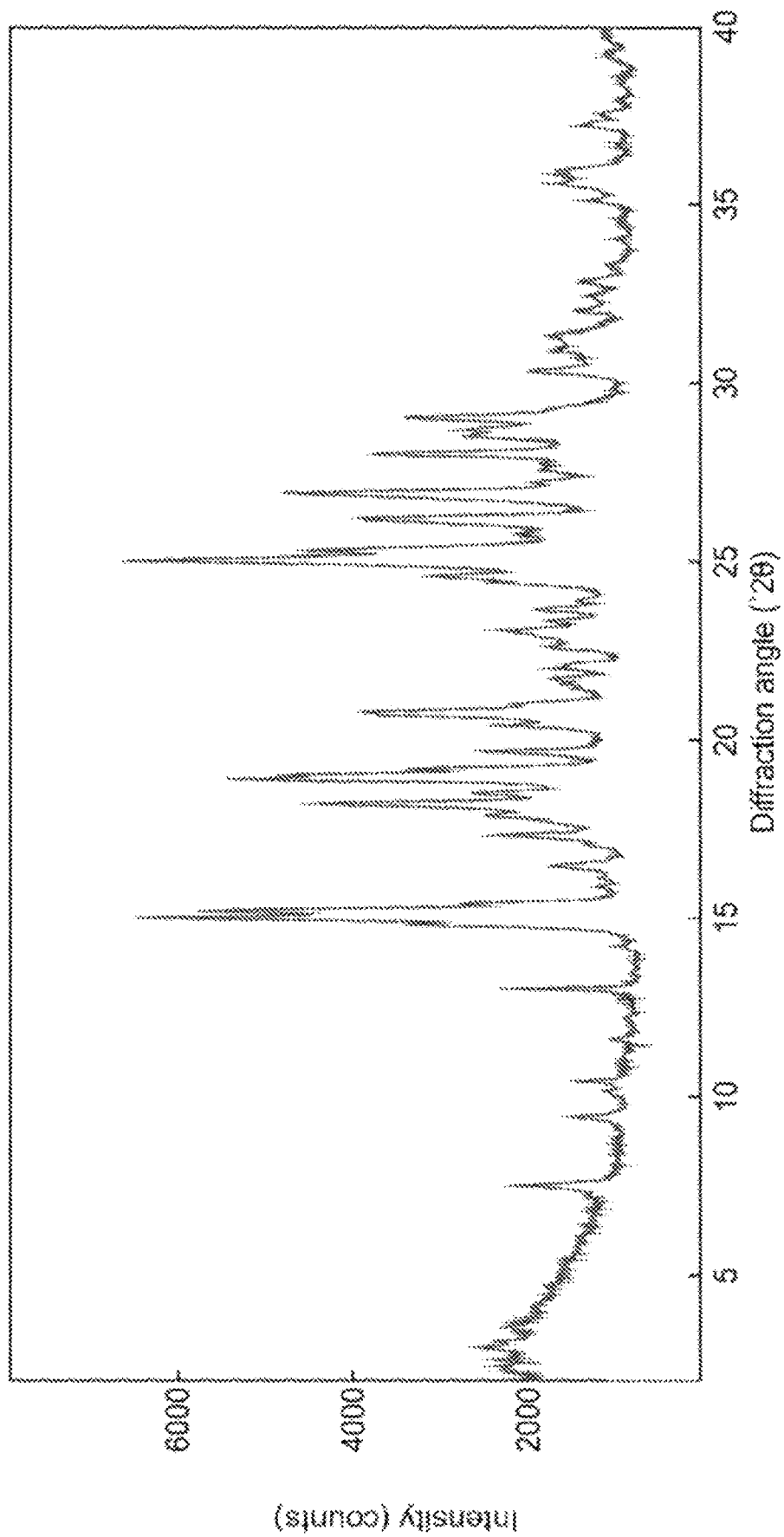
FIG. 6 illustrates an XRPD diffractogram of methylone hydrochloride (racemate) comprising a mixture of Forms A, B and C, prepared by evaporation of a methanol/chloroform mixture.
Figure 7:
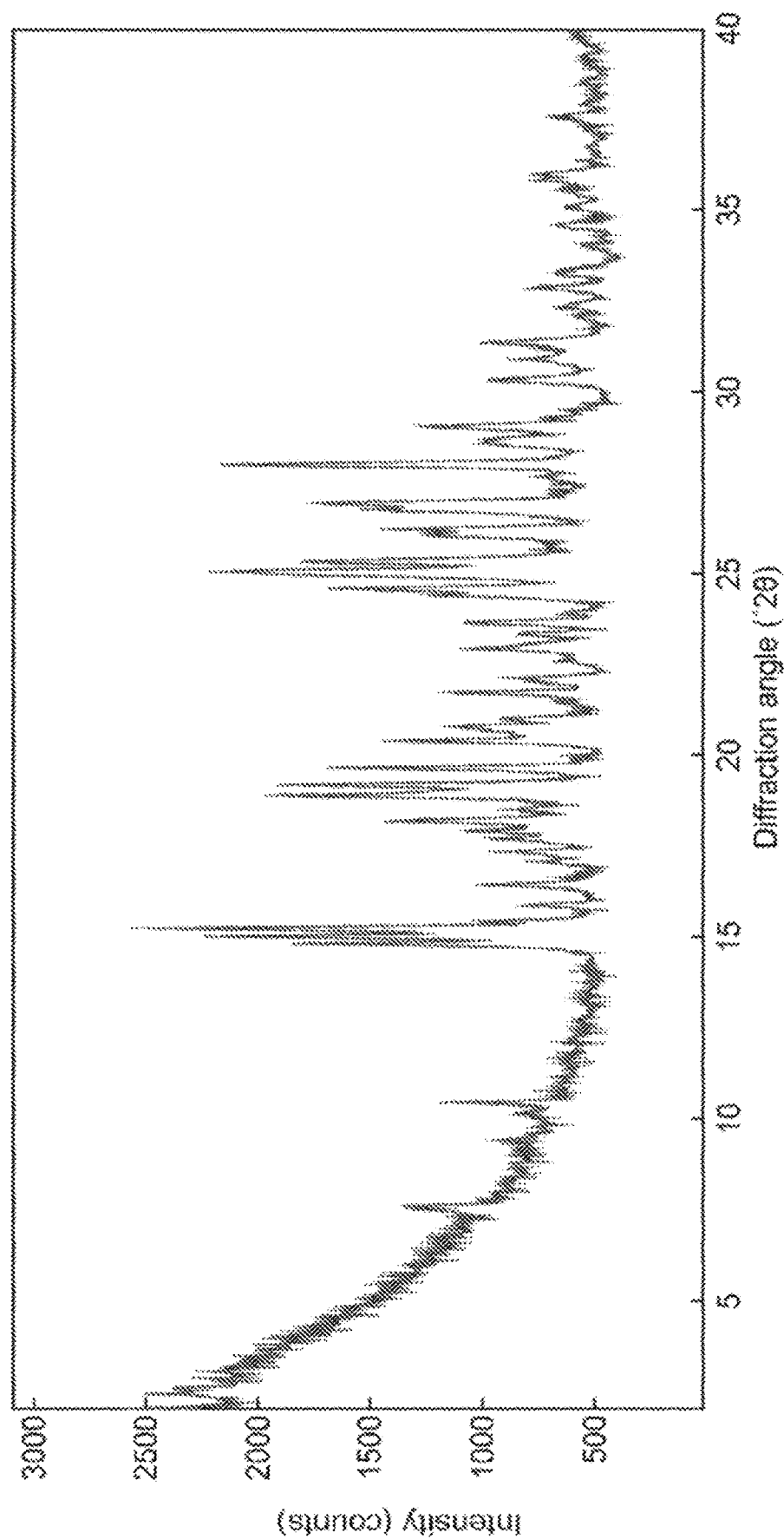
FIG. 7 illustrates an XRPD diffractogram of methylone hydrochloride (racemate) comprising a mixture of Forms A and B, prepared by cooling of a 98:2 chloroform:methanol mixture.
Figure 8:
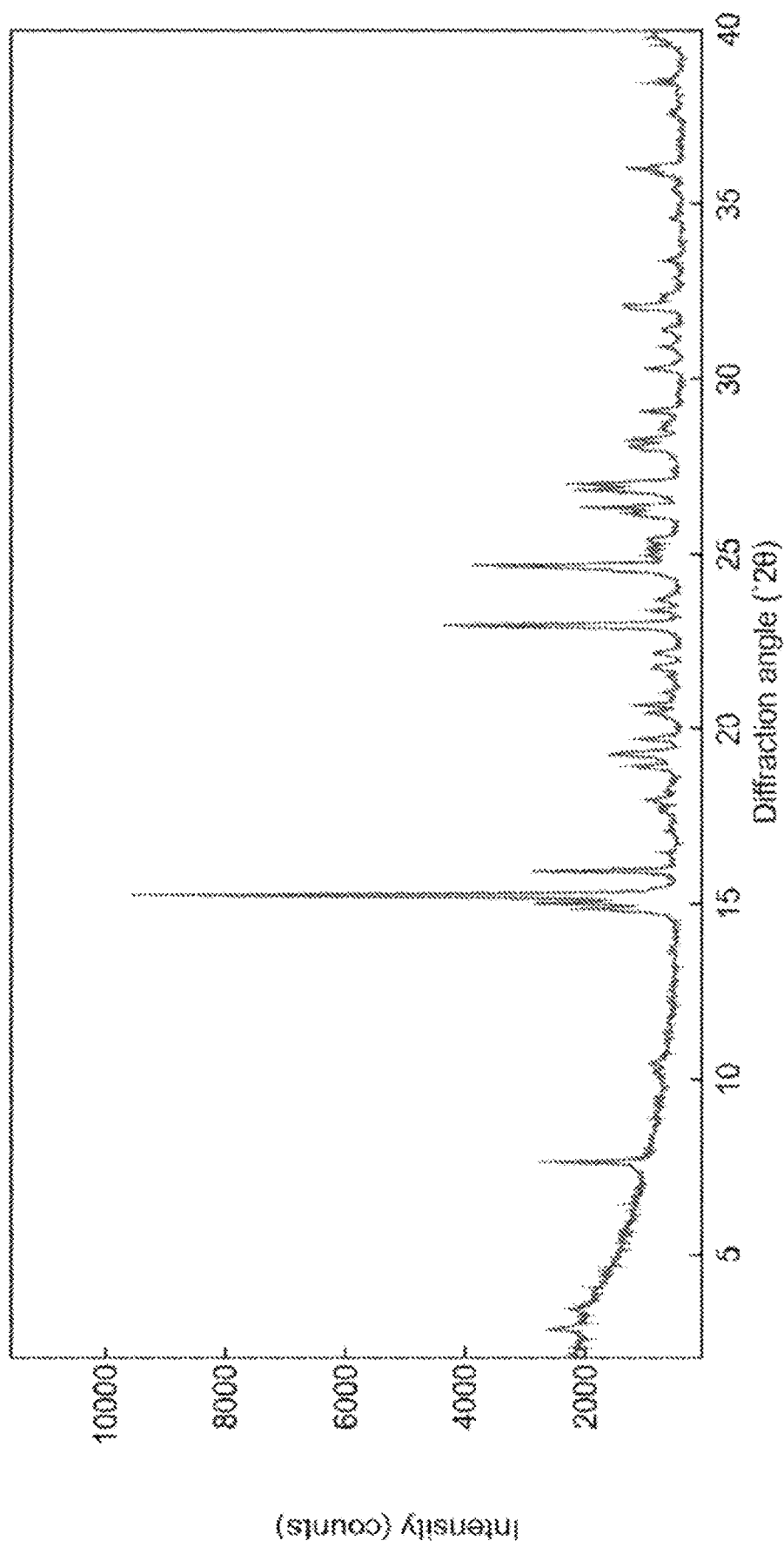
FIG. 8 illustrates an XRPD diffractogram of methylone hydrochloride (racemate) comprising Form A, prepared by cooling of a methylone hydrochloride solution in an ethyl acetate/methanol mixture.
Figure 9:
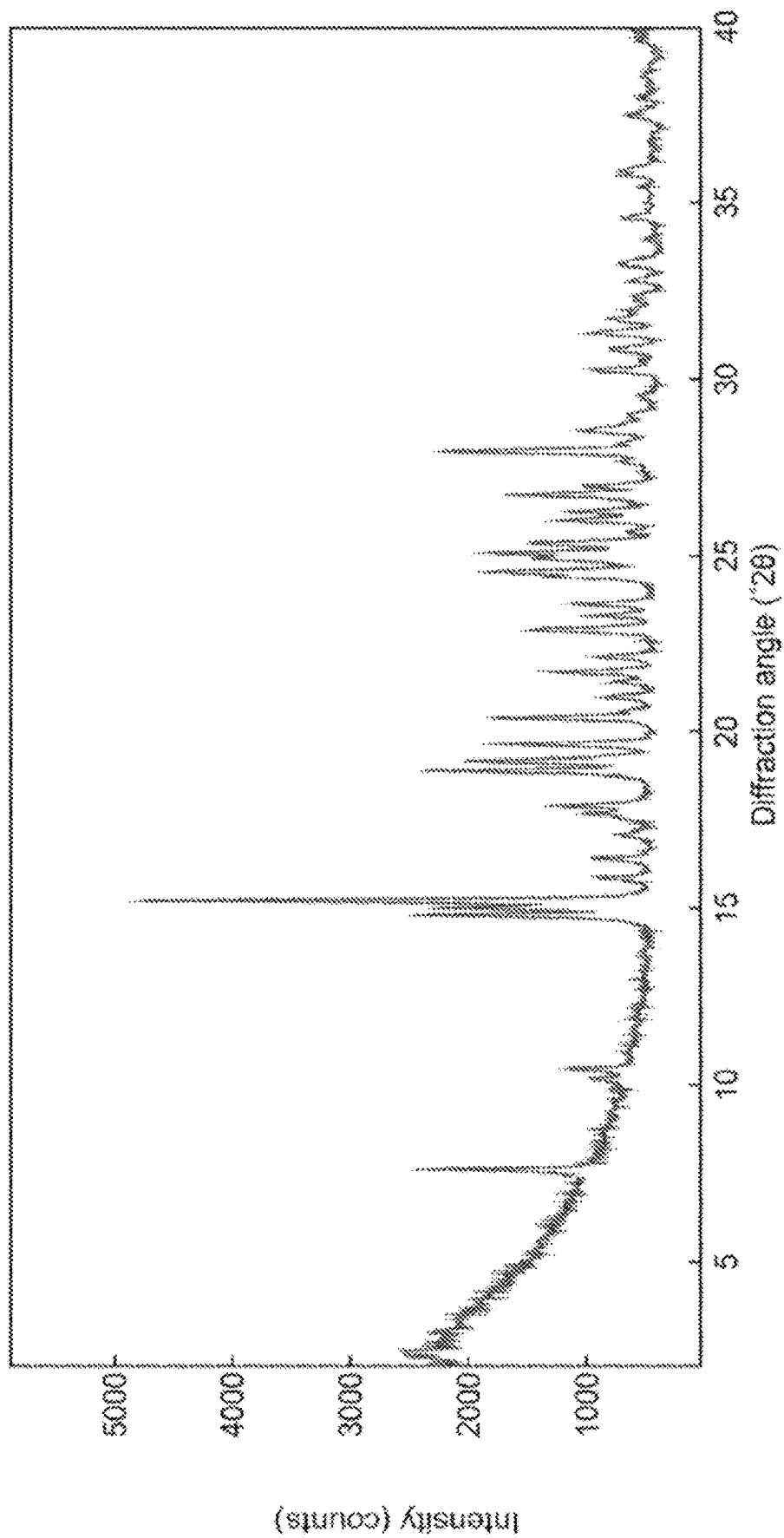
FIG. 9 illustrates an XRPD diffractogram of methylone hydrochloride (racemate) comprising Form A, prepared by cooling of cooling of a methylone hydrochloride solution in ethanol.
Figure 10:
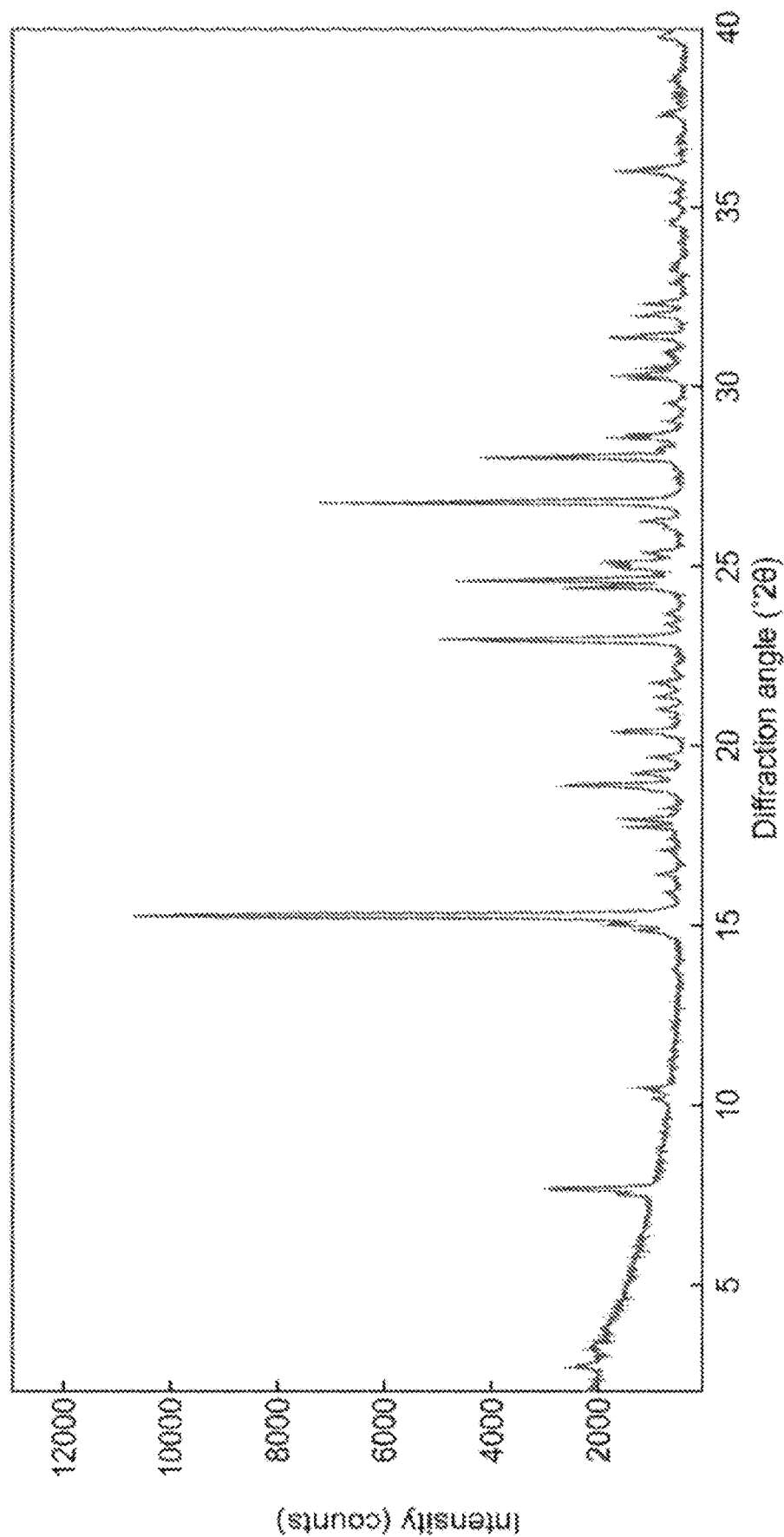
FIG. 10 illustrates an XRPD diffractogram of methylone hydrochloride (racemate) comprising Form A, prepared by cooling of a methylone hydrochloride solution in a diisopropyl ether/methanol mixture.
Figure 11:
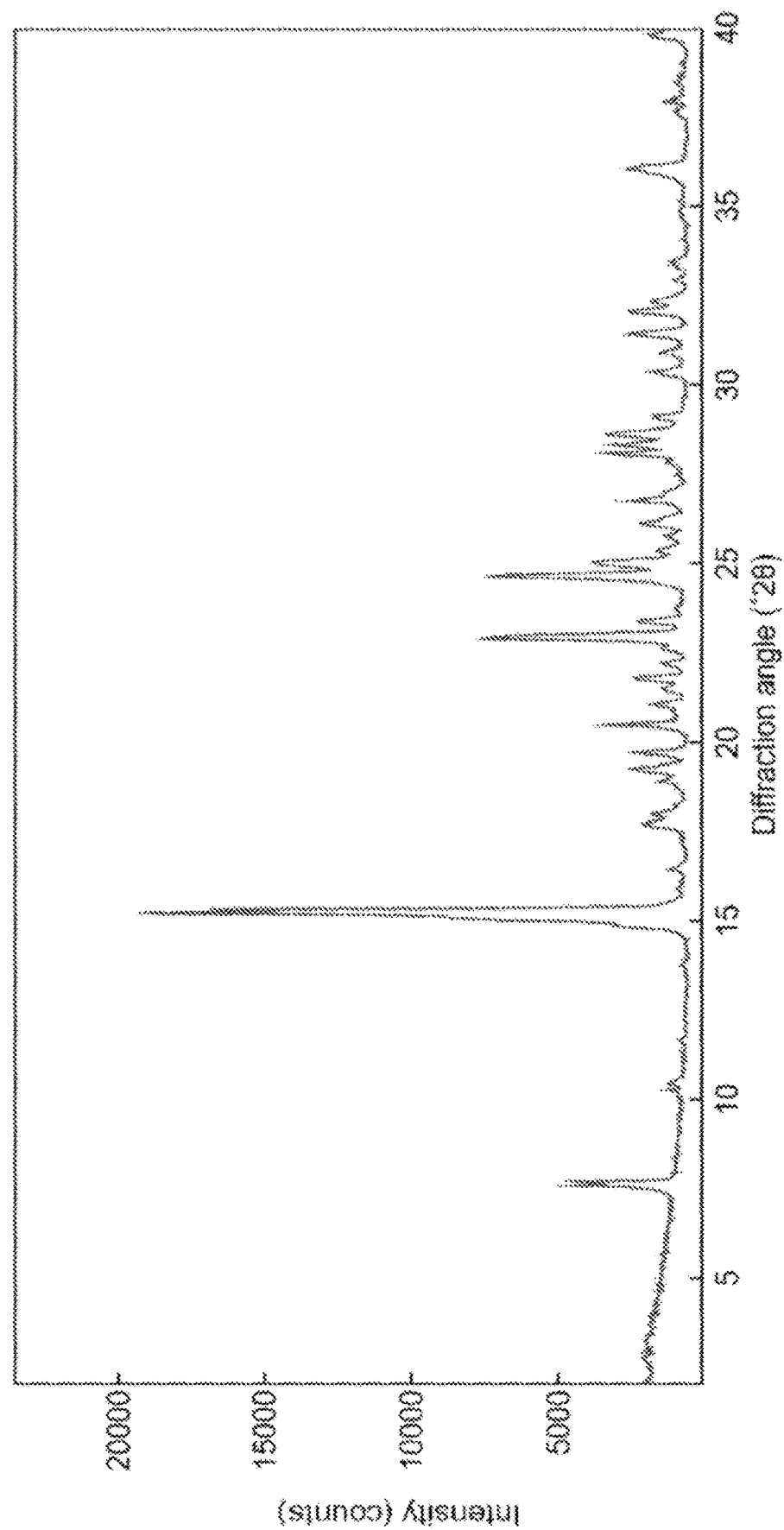
FIG. 11 illustrates an XRPD diffractogram of methylone hydrochloride (racemate) comprising Form A, prepared by cooling of a methylone hydrochloride solution in a methyl tert-butyl ether/methanol mixture.
Figure 12:
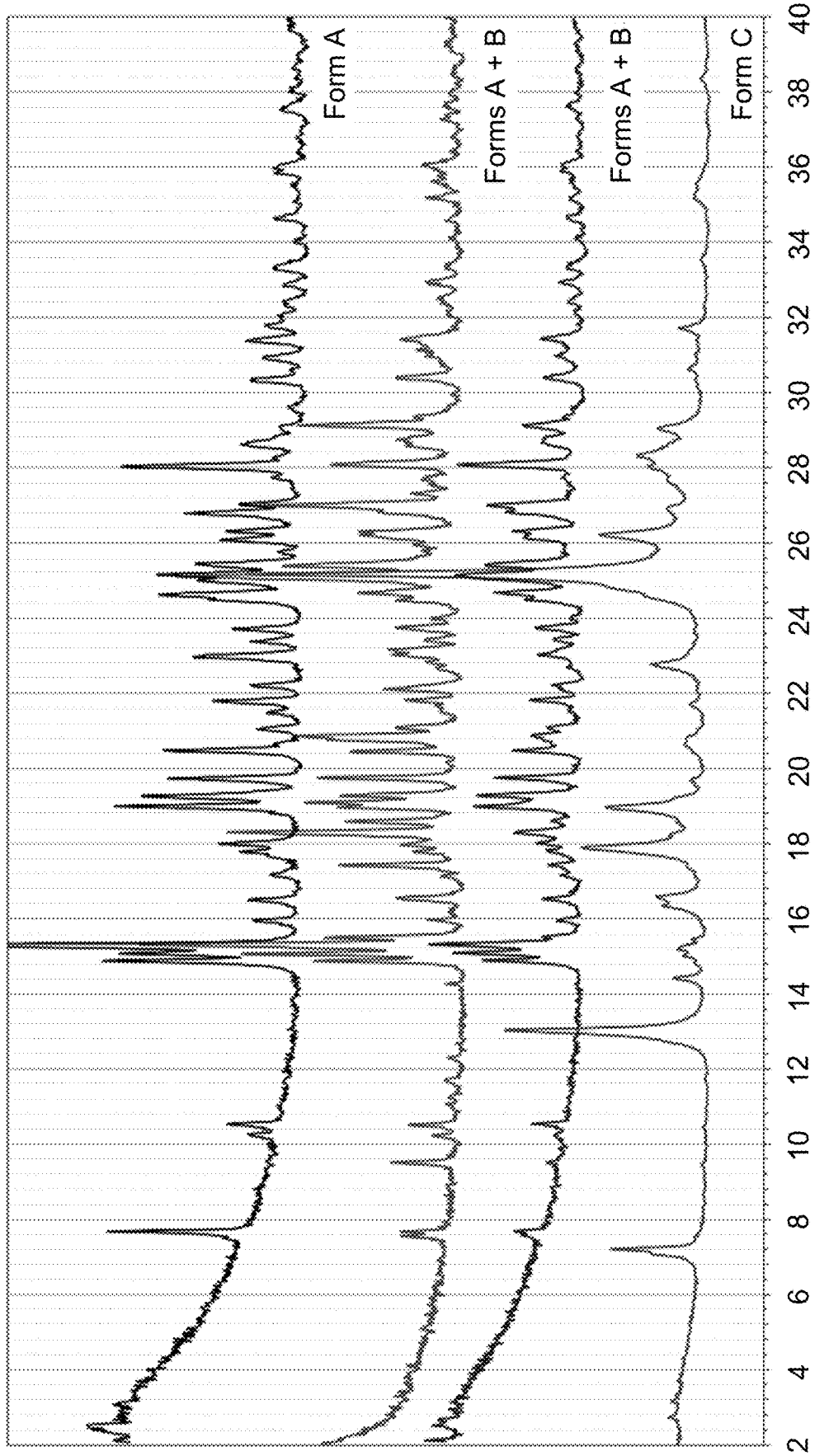
FIG. 12 provides an overlay of XRPD diffractograms of methylone hydrochloride (racemate) Form A alone (diffractogram on top), Forms A+B (middle two diffractogram), and Form C (diffractogram at the bottom).

| Technique | Solvent | Conditions | XRPD Pattern | FIG. |
|---|---|---|---|---|
| Evaporation | EtOAc (wet) | Foil w/1 pinhole, RT | C | FIG. 2 |
| | EtOH | Foil w/1 pinhole, RT | A + C | FIG. 3 |
| | H$_2$O | Foil w/1 pinhole, RT | C + A | FIG. 4 |
| | MeOH | Foil w/1 pinhole, RT | A + D + pks | FIG. 5 |
| | MeOH/ CHCl$_3$ | Foil w/1 pinhole, RT | A + B + C | FIG. 6 |
| Cooling | CHCl$_3$/ MeOH 98/2 | 60° C. → 5° C.; NS. (crushed sample) | A + B Partial E, RT | FIG. 7 |
| | EtOAc/ MeOH | 60° C.→RT | A | FIG. 8 |
| | EtOH | 60° C. → 5° C. | A | FIG. 9 |
| | IPE/MeOH | 60° C. → 5° C. (crushed sample) | A | FIG. 10 |
| | MTBE/ MeOH | 60° C. → 5° C. (crushed sample) | A | FIG. 11 |

Additional crystalline methylone hydrochloride samples were prepared by other techniques set forth above, including precipitation, slurry, vapor diffusion and by cooling from various solvent systems. These techniques produced crystalline materials of forms A, B, and/or C. For example, precipitation of methylone hydrochloride from ethanol/heptane yielded methylone hydrochloride of Form B.

Methylone free base also was used as a starting material for the production of methylone hydrochloride via in situ addition of HCl to methylone free base in various solvents. Table 6 summarizes the production of crystalline methylone hydrochloride in situ from the addition of HCl to methylone in solvent slurries as is known to those of skill in the art.

Methylone free base was prepared by adding 1.4 mL of 1N NaOH to a solution of 300.3 mg of methylone HCl in 3 mL of water (cloudy, then oiling observed). The mixture was stirred for 30 minutes at room temperature, and then extracted w/EtOAc (3×). The organic layers were combined and dried over MgSO4. Evaporation with a stream of air yielded methylone free base as an oil (Free base sample 1).

Alternatively methylone free base was prepared by adding 6.9 mL of 1N NaOH to a solution of 1.1 g of methylone HCl in 10 mL of water (cloudy, then oiling observed). The resulting mixture was stirred at room temperature for one day and then extracted with EtOAc (3×). The organic layers were combined and dried over MgSO4. Evaporation with a stream of air yielded methylone free base as an oil (Free base sample 2).

TABLE 6

Methylone Hydrochloride Forms Generated from Free Base

| Solvent | Conditions[a] | Crystalline form via XRPD |
|---|---|---|
| Acetone | SL, RT | B |
| ACN | SL, RT | B |
| CHCl3 | SL, RT | A |
| EtOH | SL, RT | A + NC |
| IPA | SL, RT | D (FIG. 13) |
| IPE | SL, 50° C. | B + A |
| iPrOAc | SL, 50° C. | B + trace A |
| MEK | SL, 50° C. | A + B + D |
| 2-Me THF | SL, 50° C. | B + trace A |
| MTBE | SL, 50° C. | B + trace A |

With reference to Table 6, an XRPD diffractogram of crystalline methylone hydrochloride isolated from isopropyl alcohol is provided as FIG. 13.

In certain embodiments, the XRPD pattern of a sample of solid form, including the solid forms characterized in Tables 4 and 5, indicates that the sample has a well-defined crystal structure and a high degree of crystallinity.

Exemplary methylone hydrochloride samples were further characterized as summarized in Table 7.

TABLE 7

Figure 15:
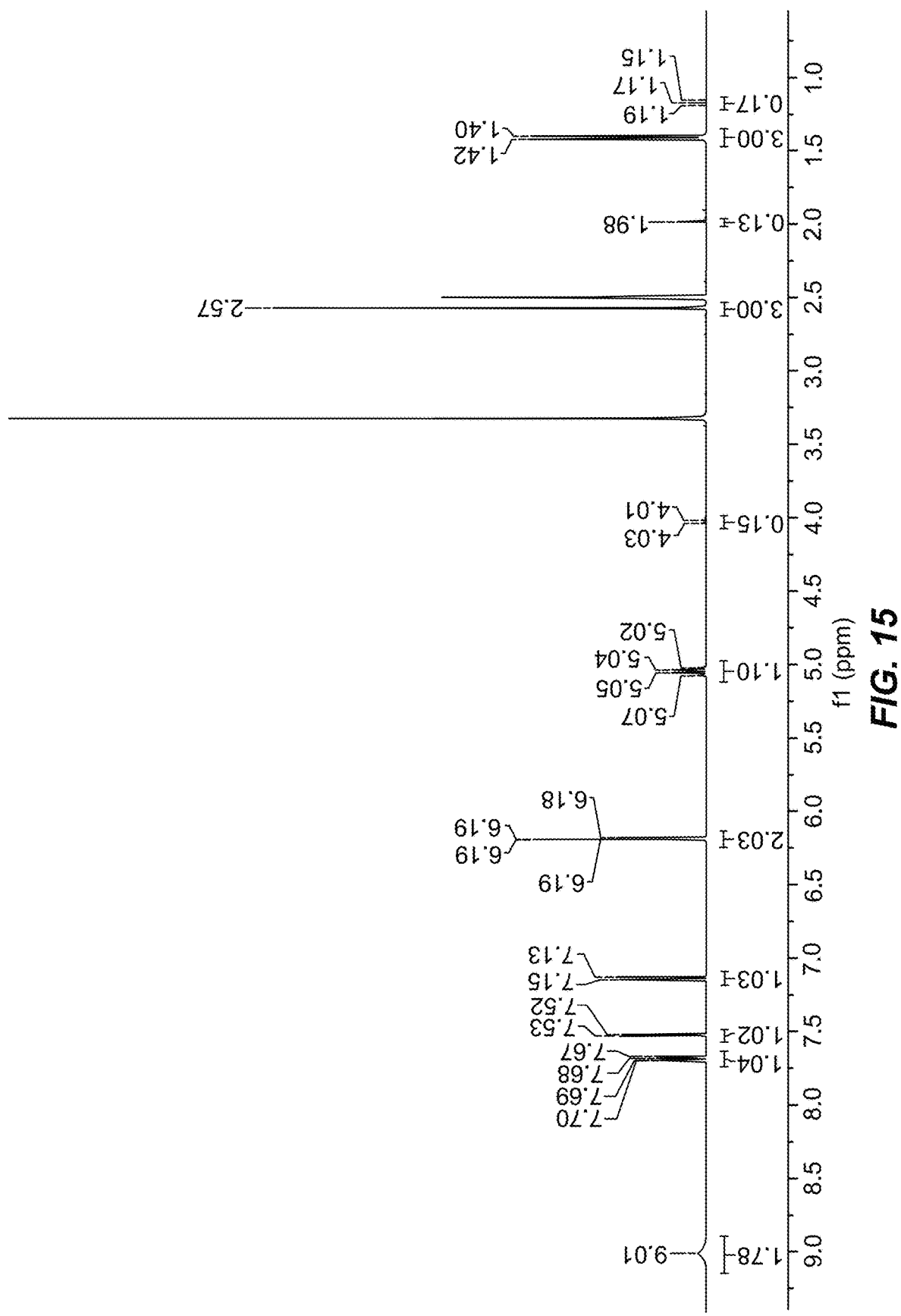
FIG. 15 provides a $^1$H NMR spectrum of a sample of methylone hydrochloride (racemate) prepared from the crystalline methylone hydrochloride Form A having the XRPD pattern provided in FIG. 14.
Figure 18:
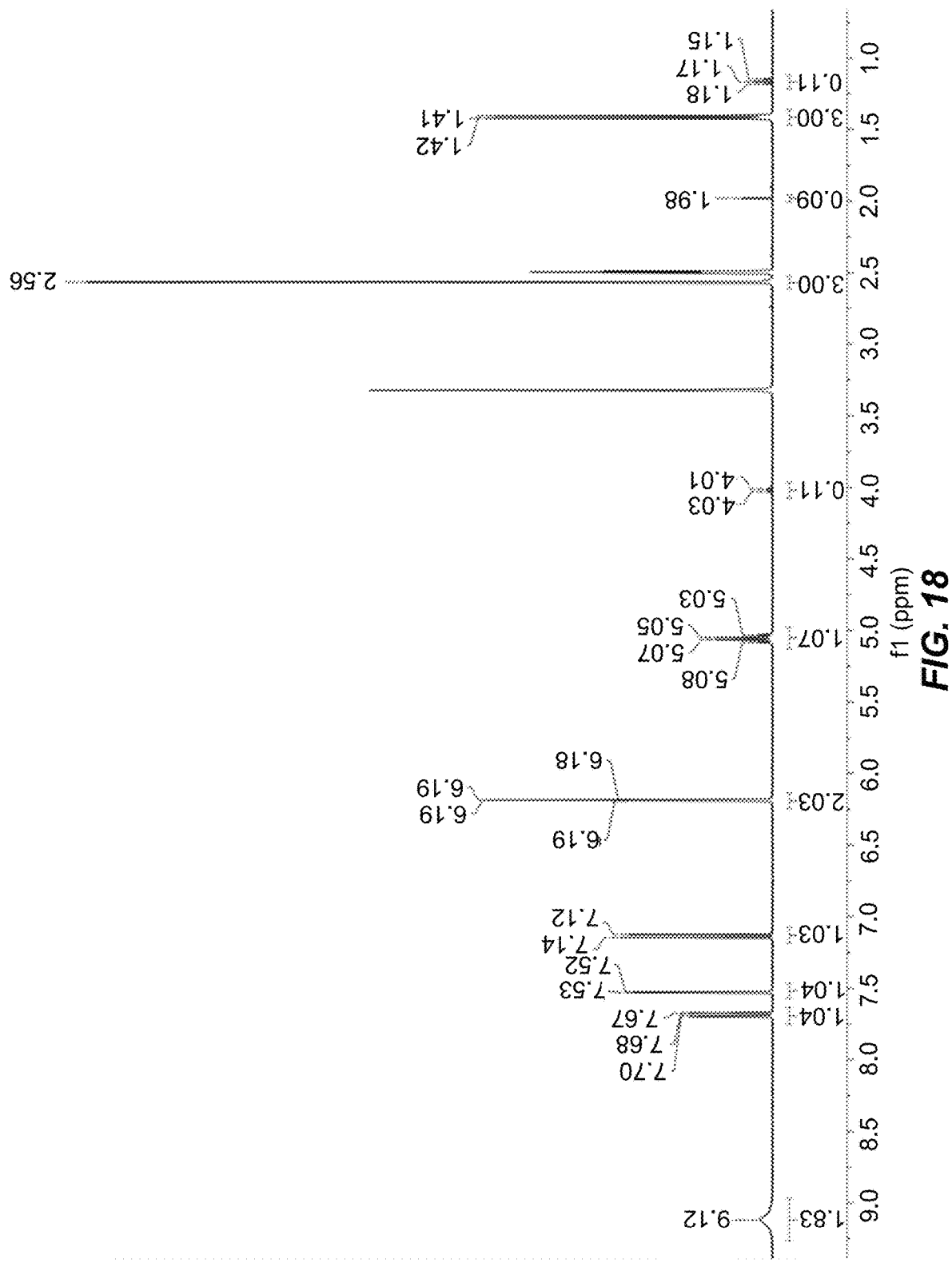
FIG. 18 provides a $^1$H NMR spectrum of a sample of methylone hydrochloride prepared from the crystalline methylone hydrochloride (racemate) Form B having the XRPD pattern provided in FIG. 17.
Figure 19:
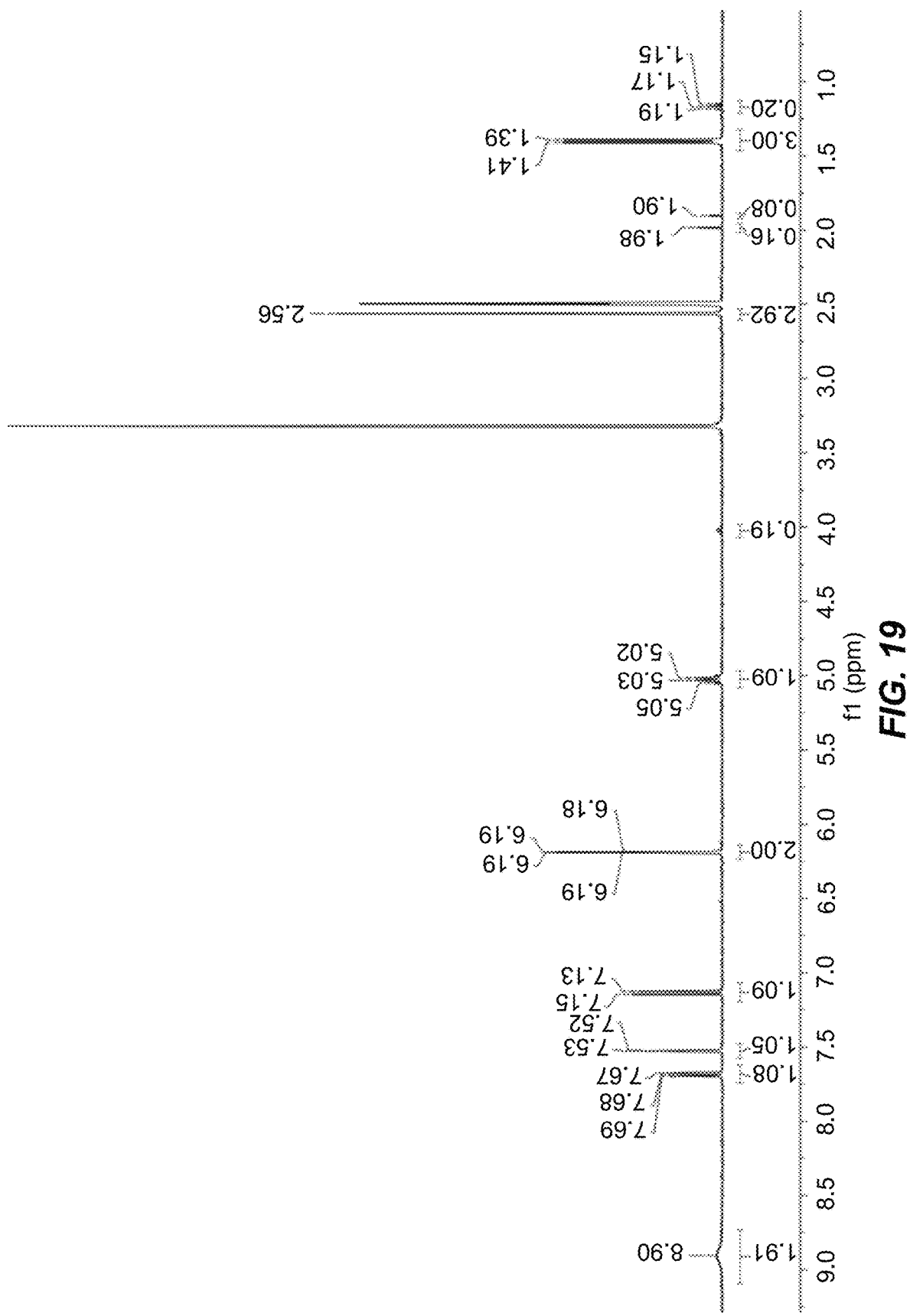
FIG. 19 provides a $^1$H NMR spectrum of a sample of methylone hydrochloride prepared from the crystalline methylone hydrochloride (racemate) Form C having the XRPD pattern provided in FIG. 2.
Figure 22:
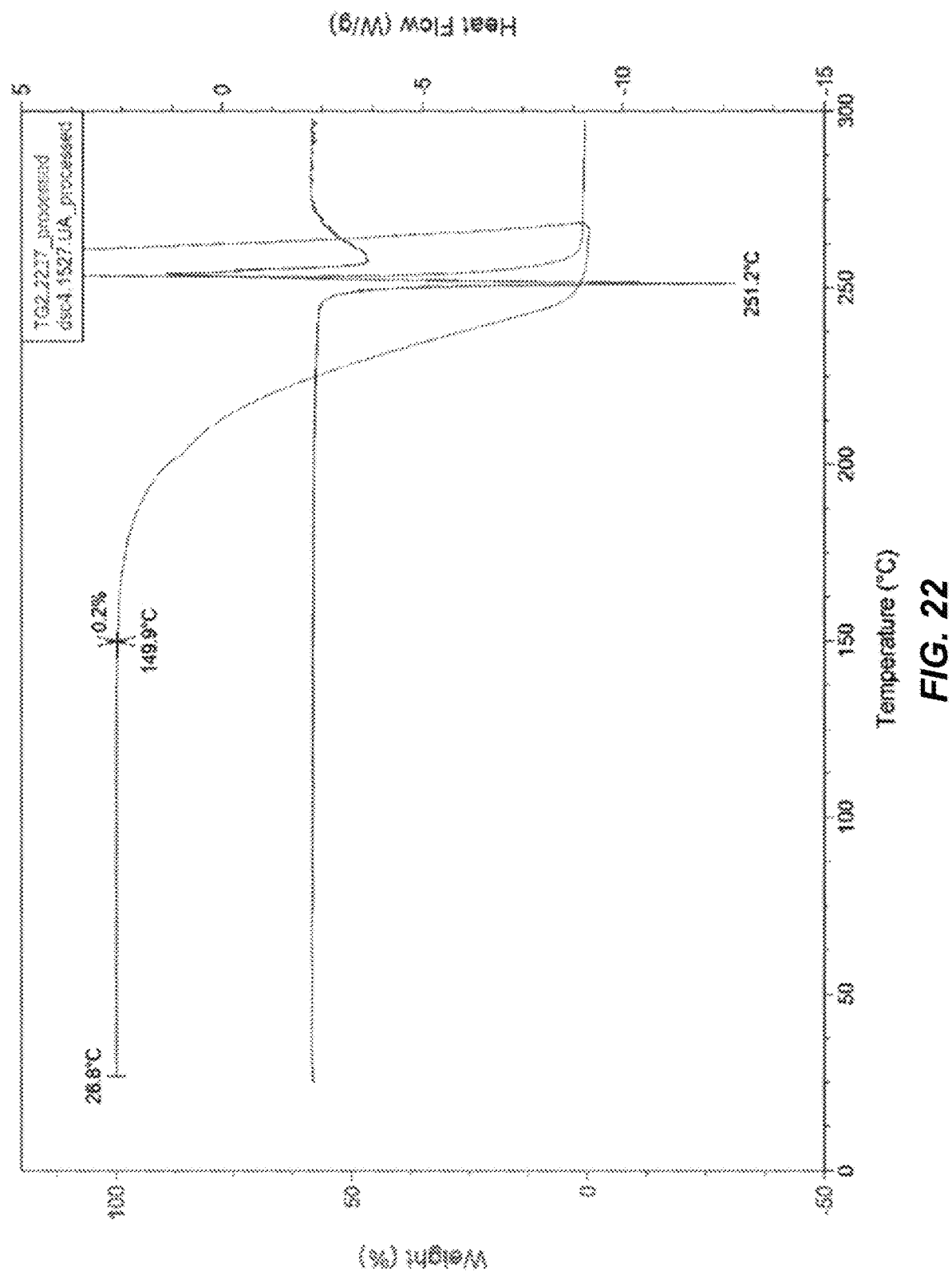
FIG. 22 illustrates a thermogravimetric analysis (TGA) thermogram and a differential scanning calorimetry (DSC) thermogram of crystalline methylone hydrochloride (racemate), Form A.
Figure 23:
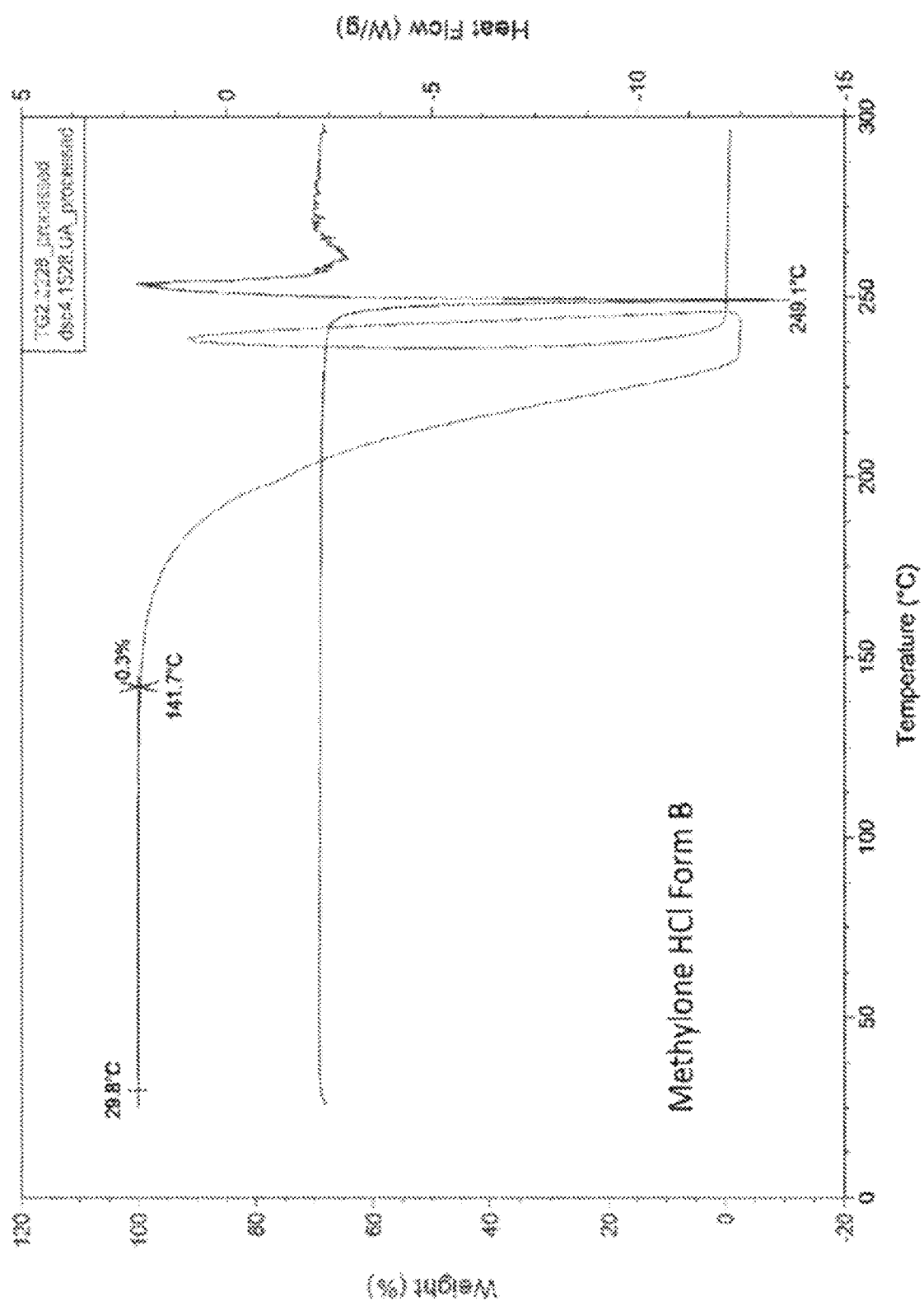
FIG. 23 illustrates a thermogravimetric analysis (TGA) thermogram and a differential scanning calorimetry (DSC) thermogram of crystalline methylone hydrochloride (racemate), Form B.
Figure 24:
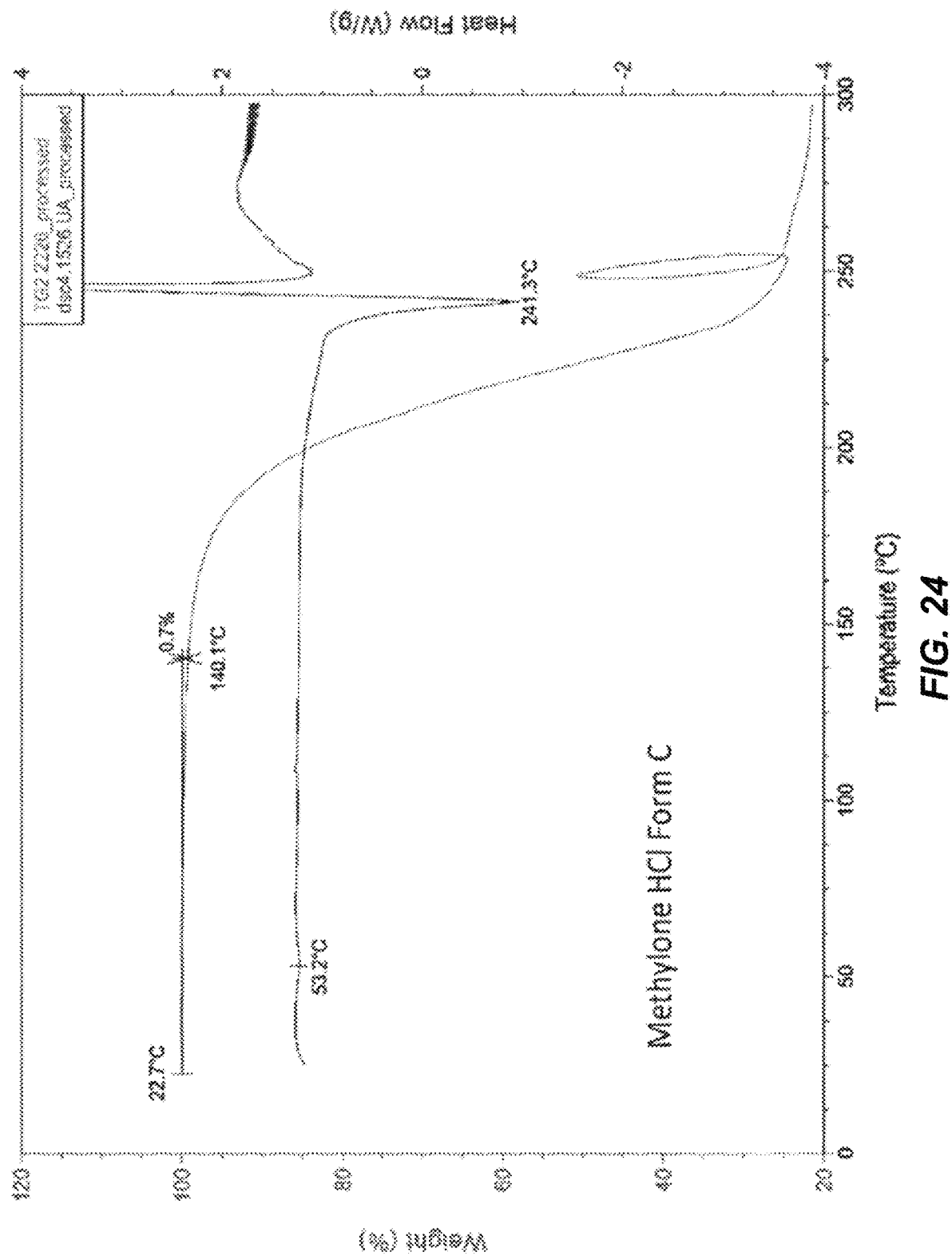
FIG. 24 illustrates a thermogravimetric analysis (TGA) thermogram and a differential scanning calorimetry (DSC) thermogram of crystalline methylone hydrochloride (racemate), Form C.

| Sample | Analytical Technique | Results |
|---|---|---|
| 1 (Form A) | $^1$H NMR | Consistent with structure No organic solvents FIG. 15 |
| | TGA | 0.2%, start to 150° C. FIG. 22 |
| | DSC | Endo: 251° C. FIG. 22 |
| | XRPD | FIG. 14 and FIG. 21 |
| 2 (Form B) | $^1$H NMR | Consistent with structure No organic solvents FIG. 18 |
| | TGA | 0.3%, start to 142° C. FIG. 23 |
| | DSC | Endo: 249° C. FIG. 23 |
| | XRPD | FIG. 17 |
| 3 (Form C) | $^1$H NMR | Consistent with structure No organic solvents FIG. 19 |
| | TGA | 0.7%, start to 140° C. FIG. 24 |
| | DSC | Endo: 53° C. (minor), 241° C. FIG. 24 |
| | XRPD | FIG. 2 |

TABLE 7-continued

Figure 16:
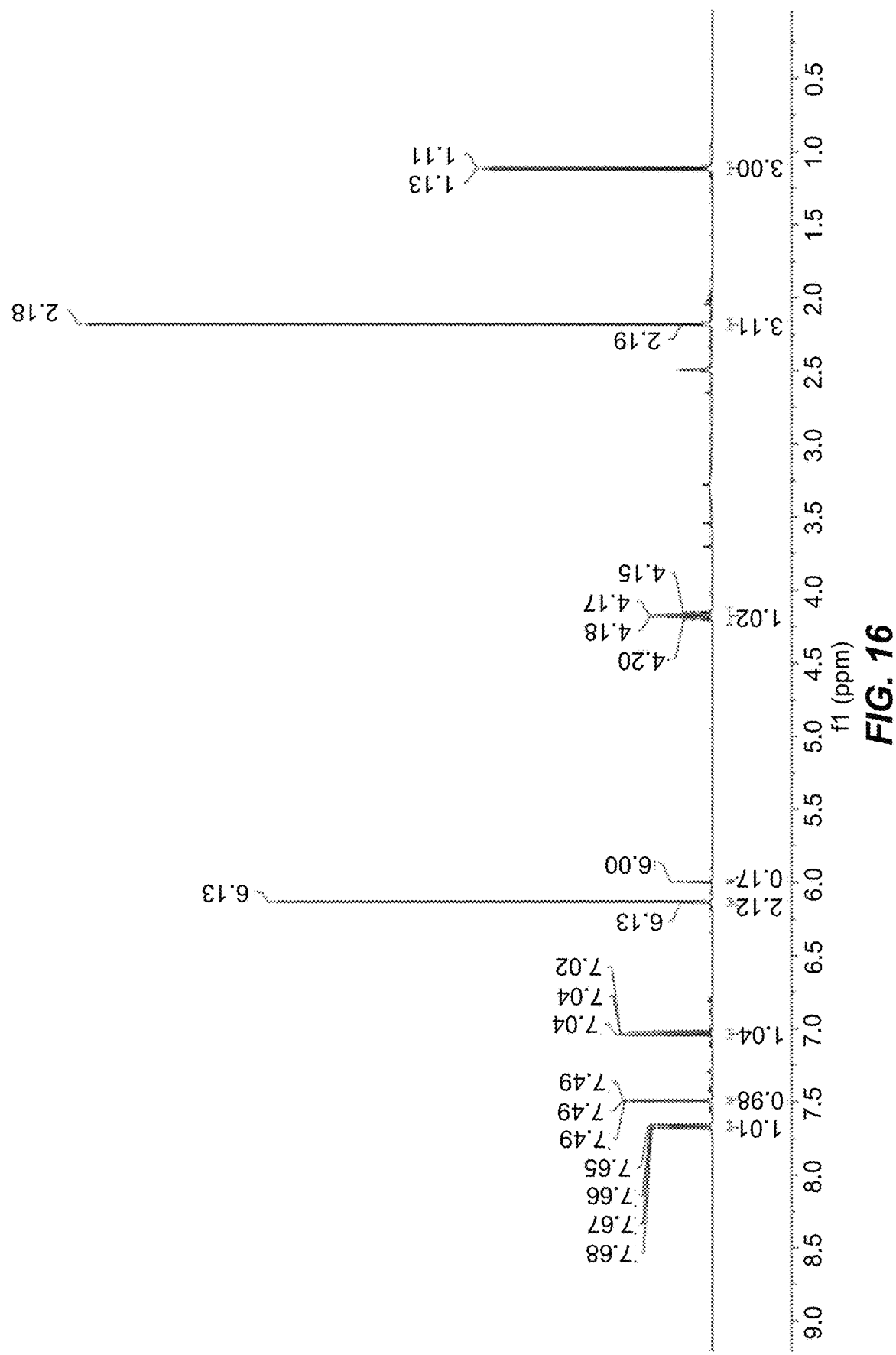
FIG. 16 provides a $^1$H NMR spectrum of a sample of methylone free base (racemate).
Figure 20:
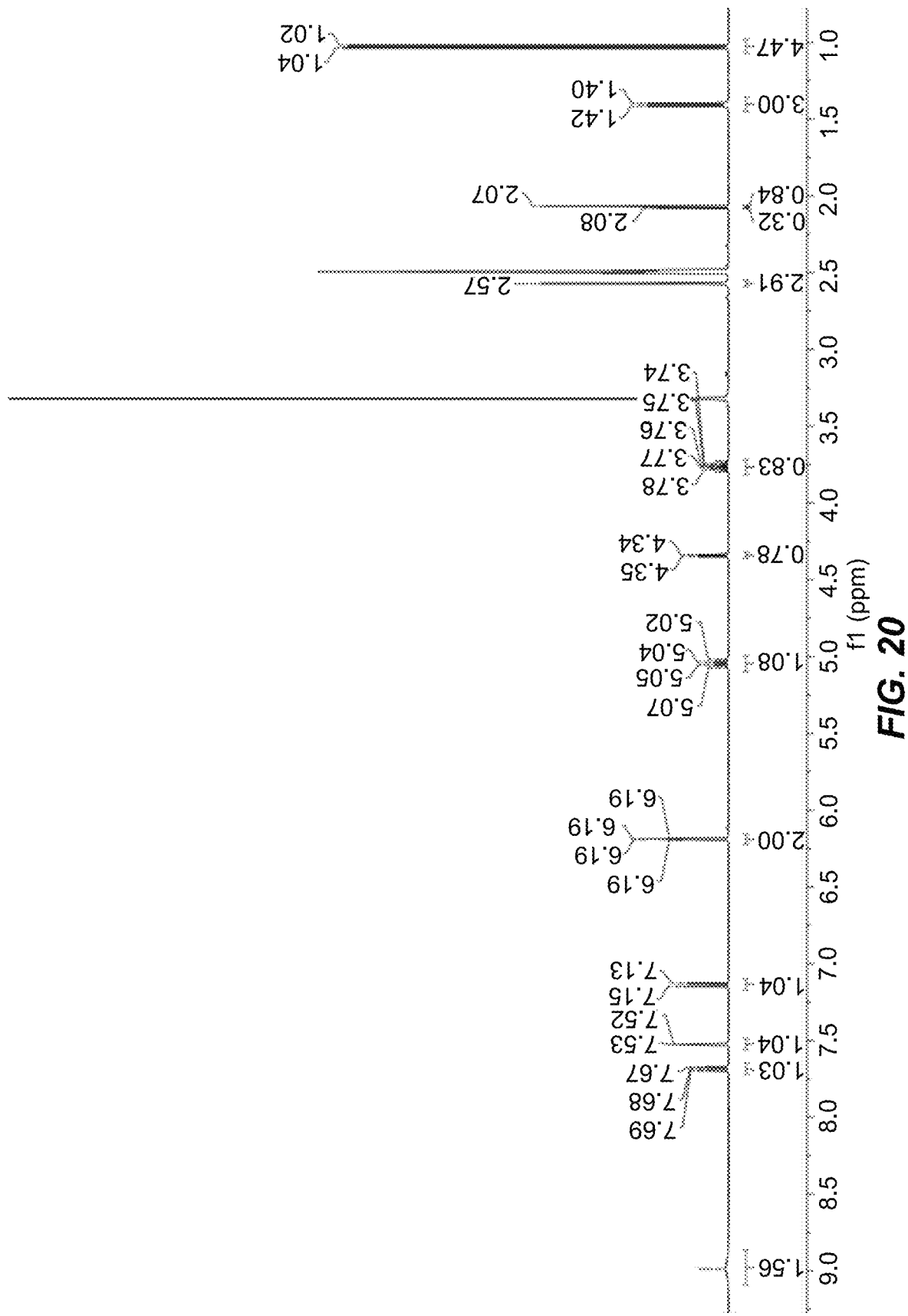
FIG. 20 provides a $^1$H NMR spectrum of a sample of methylone hydrochloride prepared from the crystalline methylone hydrochloride (racemate) Form D having the XRPD pattern provided in FIG. 13.
Figure 25:
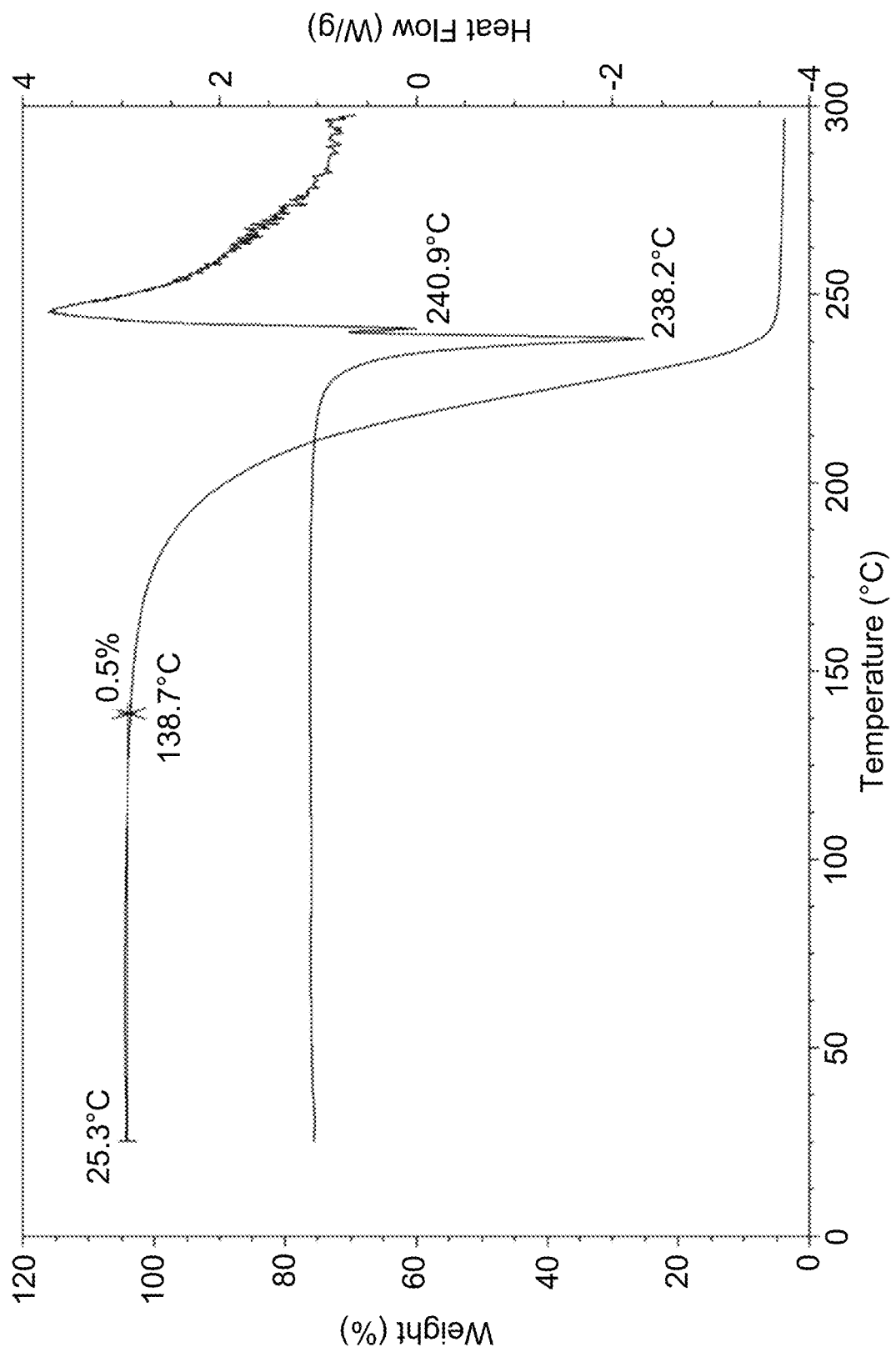
FIG. 25 illustrates a thermogravimetric analysis (TGA) thermogram and a differential scanning calorimetry (DSC) thermogram of methylone hydrochloride (racemate), Form D.

| Sample | Analytical Technique | Results |
|---|---|---|
| 4 (Form D) | $^1$H NMR | Consistent with structure, 0.75 moles IPA FIG. 20 |
| | TGA | 0.5%, start to 139° C. FIG. 25 |
| | DSC | Endo: 238° C., 241° C. FIG. 25 |
| | XRPD | FIG. 13 |
| Free Base Sample 2 sample | $^1$H NMR | Consistent with structure. Significant peak shifts compared to spectrum of HCl salt FIG. 16 |
| | TGA | — |
| | DSC | — |
| | XRPD | — |

With reference to Table 7, the symbol "--" means that data were not collected for a given entry. With continued reference to Table 7, Sample 1 (Form A) was prepared by cooling of an isopropyl acetate/methanol solution of methylone hydrochloride from 60° C. to 5° C. Sample 2 (Form B) was prepared by precipitation of methylone hydrochloride from methanol and diethyl ether. Sample 3 (Form C) was prepared as set forth in Table 5 for the sample with the XRPD diffractogram provided in FIG. 2. Sample 4 (Form D) was prepared as set forth in Table 6 from a slurry of methylone in isopropyl alcohol.

X-Ray Powder Diffraction (XRPD)

Although the following diffractometers were used, other types of diffractometers could be used. Furthermore, other wavelengths could be used and converted to the Cu Kα. In some embodiments, Synchrotron Radiation X-Ray Powder Diffraction (SR-XRPD) can be used to characterize the crystalline forms.

"Characteristic peaks", to the extent they exist, are a subset of observed peaks and are used to differentiate one crystalline polymorph from another crystalline polymorph (polymorphs being crystalline forms having the same chemical composition). Characteristic peaks are determined by evaluating which observed peaks, if any, are present in one crystalline polymorph of a compound against all other known crystalline polymorphs of that compound to within ±0.2 °2-Theta.

STOE Stadi-P Transmission Diffractometer

X-ray powder diffractions were performed with STOE Stadi-P transmission diffractometers using Cu-Kα1 radiation. Linear position sensitive detectors were used for capillary measurements and for samples in flat preparation, while image plate position sensitive detectors (IP-PSDs) were used for temperature-resolved XRPD, humidity-resolved XRPD and for robot samples in 96-well plates. The measured data was visualized and evaluated with the Software WinXPOW V2.12.

The 2-Theta peak values that are provided for the XRPD are within ±0.2° 2-Theta.

XRPD patterns were identified with an Rigaku SmartLab X-Ray Diffractometer configured in Bragg-Brentano reflection geometry equipped with a beam stop and knife edge to reduce incident beam and air scatter. Data collection parameters are shown in the following table.

| Parameter | Value | Parameter | Value |
|---|---|---|---|
| Geometry | Bragg-Brentano | Receiving Slit 1 (mm) | 18 |
| Tube Anode | Cu | Receiving Slit 2 (mm) | open |
| Tube Type | Long Fine Focus | Start Angle 2θ (°) | 2 |
| Tube Voltage (kV) | 40 | End Angle 2θ (°) | 40 |
| Tube Current (mA) | 44 | Step Size (°) | 0.02 |
| Detector | D/teX Ultra 250 (RX1, RX3) HyPix-3000 (XR4) | Scan Speed (°/min) | 6 |
| Monochromator | Ni foil Cu Kβ Filter | Spinning (rpm) | 11 |
| Incident Slit (°) | 1/3 | Sample Holder | Low-background Si |

Figure 46:
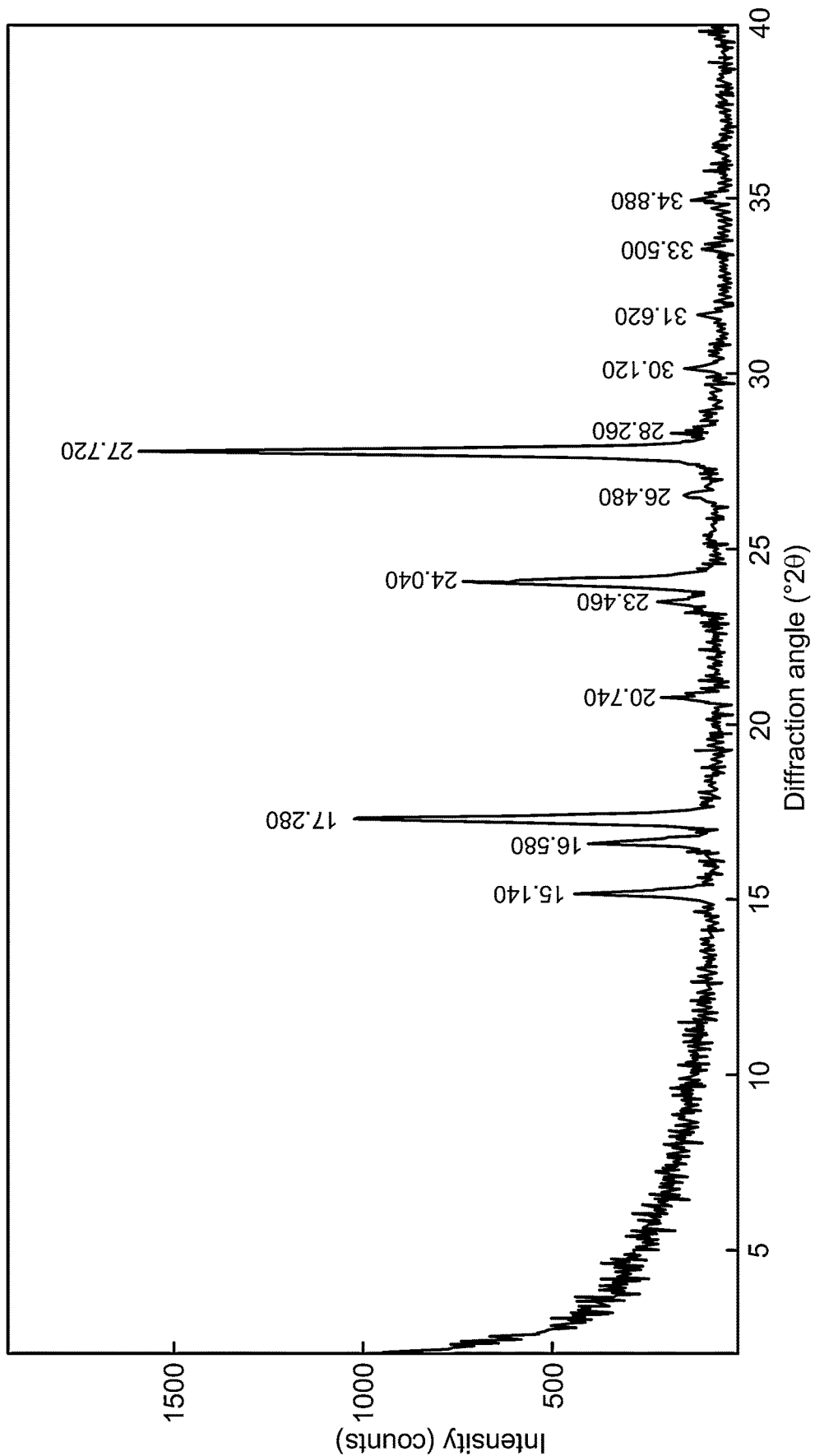
FIG. 46 provides an XRPD diffractogram of a crystalline methylone freebase (racemate).

XRPD analysis of methylone freebase (racemate) (FIG. 46) showed it to be crystalline with characteristic peaks at 15.1° 2-Theta, 16.6° 2-Theta, 17.3° 2-Theta, 20.7° 2-Theta, 23.5° 2-Theta, 24.0° 2-Theta, 26.5° 2-Theta, 27.7° 2-Theta, and 28.3° 2-Theta as measured with Cu Kα radiation.

XRPD analysis of methylone hydrochloride (racemate) Form A (FIG. 14) showed it to be crystalline with characteristic peaks at 7.7° 2-Theta, 10.5° 2-Theta, 14.9° 2-Theta, 15.1° 2-Theta, 15.3° 2-Theta, 18.9° 2-Theta, 19.3° 2-Theta, 19.7° 2-Theta, 20.4° 2-Theta, 23.0° 2-Theta, 24.6° 2-Theta, 25.1° 2-Theta, and 28.0° 2-Theta.

XRPD analysis of methylone hydrochloride (racemate) Form A (FIG. 21) showed it to be crystalline with characteristic peaks at 7.6° 2-Theta, 10.5° 2-Theta, 14.8° 2-Theta, 15.0° 2-Theta, 15.3° 2-Theta, 18.9° 2-Theta, 19.2° 2-Theta, 19.7° 2-Theta, 20.4° 2-Theta, 23.0° 2-Theta, 24.6° 2-Theta, 25.1° 2-Theta, and 28.0° 2-Theta.

XRPD analysis of methylone hydrochloride (racemate) Form B (FIG. 17) showed it to be crystalline with characteristic peaks at 7.5° 2-Theta, 9.5° 2-Theta, 14.8° 2-Theta, 15.0° 2-Theta, 15.3° 2-Theta, 15.5°-Theta, 17.4° 2-Theta, 18.3° 2-Theta, 18.5° 2-Theta, 19.0° 2-Theta, 19.7° 2-Theta, 20.8° 2-Theta, 22.1° 2-Theta, 23.1° 2-Theta, 25.1° 2-Theta, 25.4° 2-Theta, 26.2° 2-Theta, 27.0° 2-Theta, and 29.1° 2-Theta.

XRPD analysis of methylone hydrochloride (racemate) Form C (FIG. 2) showed it to be crystalline with characteristic peaks at 7.2° 2-Theta, 13.0° 2-Theta, 14.4° 2-Theta, 17.9° 2-Theta, 19.0° 2-Theta, 25.2° 2-Theta, and 26.2° 2-Theta.

XRPD analysis of methylone hydrochloride (racemate) Form D (FIG. 13) showed it to be crystalline with characteristic peaks at 12.5° 2-Theta, 14.0° 2-Theta, 15.7° 2-Theta, 16.0° 2-Theta, 22.3° 2-Theta, 27.5° 2-Theta, 28.2° 2-Theta, 29.1° 2-Theta, and 29.3° 2-Theta.

Differential Scanning Calorimetry (DSC)

In certain embodiments wherein the solid form is a solvate, such as a hydrate, the DSC thermogram reveals endothermic transitions.

DSC analyses were carried out using a TA Instruments Q2500 Discovery Series instrument. The instrument temperature calibration was performed using indium. The DSC cell was kept under a nitrogen purge of ~50 mL per minute during each analysis. The sample was placed in a standard, crimped, aluminum pan and was heated from approximately 25° C. to 300° C. at a rate of 10° C. per minute.

The DSC results are summarized in Table 7 above.

DSC analysis of methylone hydrochloride (racemate) Form A (FIG. 22) showed a single endothermic peak at about 251° C.

DSC analysis of methylone hydrochloride (racemate) Form B (FIG. 23) showed a single endothermic peak at about 249° C.

DSC analysis of methylone hydrochloride (racemate) Form C (FIG. 24) showed a first endotherm at about 53° C. and a second endothermic peak at about 241° C.

DSC analysis of methylone hydrochloride (racemate) Form D (FIG. 25) showed a first endothermic peak at about 238° C., a second endothermic peak at about 241° C.

Thermogravimetric Analysis (TGA)

In accordance with the observed DSC transitions, TGA analysis indicates stages of weight change corresponding to desolvation or dehydration and/or melting of the sample. In the case of hydrates, these results are in harmony with Karl Fischer titration data which indicate the water content of the sample.

The TG analysis was carried out using a TA Instruments Q50 instrument. The instrument balance was calibrated using class M weights and the temperature calibration was performed using alumel. The nitrogen purge was ~10 mL per minute at the balance and ~90 mL per minute at the furnace. Each sample was placed into a pre-tared platinum pan and heated from approximately 25° C. to 300° C. at a rate of 10° C. per minute.

Alternatively, the TG analysis was carried out using a TA Instruments Q50 instrument. The instrument balance was calibrated using class M weights and the temperature calibration was performed using alumel. The nitrogen purge was ~10 mL per minute at the balance and ~90 mL per minute at the furnace. Each sample was placed into a pre-tared platinum pan and heated from approximately 25° C. to 350° C. at a rate of 10° C. per minute.

The TGA results are summarized in Table 7 above.

TGA of methylone hydrochloride (racemate) Form A (FIG. 22) showed about 0.2% weight loss prior to 150° C.

TGA of methylone hydrochloride (racemate) Form B (FIG. 23) showed about 0.3% weight loss prior to 142° C.

TGA of methylone hydrochloride (racemate) Form C (FIG. 24) showed about 0.7% weight loss prior to 140° C.

TGA of methylone hydrochloride (racemate) Form D (FIG. 25) showed about 0.5% weight loss prior to 139° C.

Dynamic Vapor Sorption (DVS)

The moisture sorption profile of a sample can be generated to assess the stability of a solid form is stable over a range of relative humidity. In certain embodiments, the change in moisture content over 10.0 to 95.0% relative humidity is small. In other embodiments the change in moisture content over 10.0 to 95.0% relative humidity is reversible.

DVS analysis was carried out using a TA Instruments Q5000 Dynamic Vapor Sorption analyzer. The instrument was calibrated with standard weights and a sodium bromide standard for humidity. Approximately 10-25 mg of sample was loaded into a metal-coated quartz pan for analysis. The sample was analyzed at 25° C. with a maximum equilibration time of one hour in 10% relative humidity (RH) steps from 5 to 95% RH (adsorption cycle) and from 95 to 5% RH (desorption cycle). The movement from one step to the next occurred either after satisfying the equilibrium criterion of 0.01% weight change or, if the equilibrium criterion was not met, after one hour. The percent weight change values were calculated.

Figure 26:
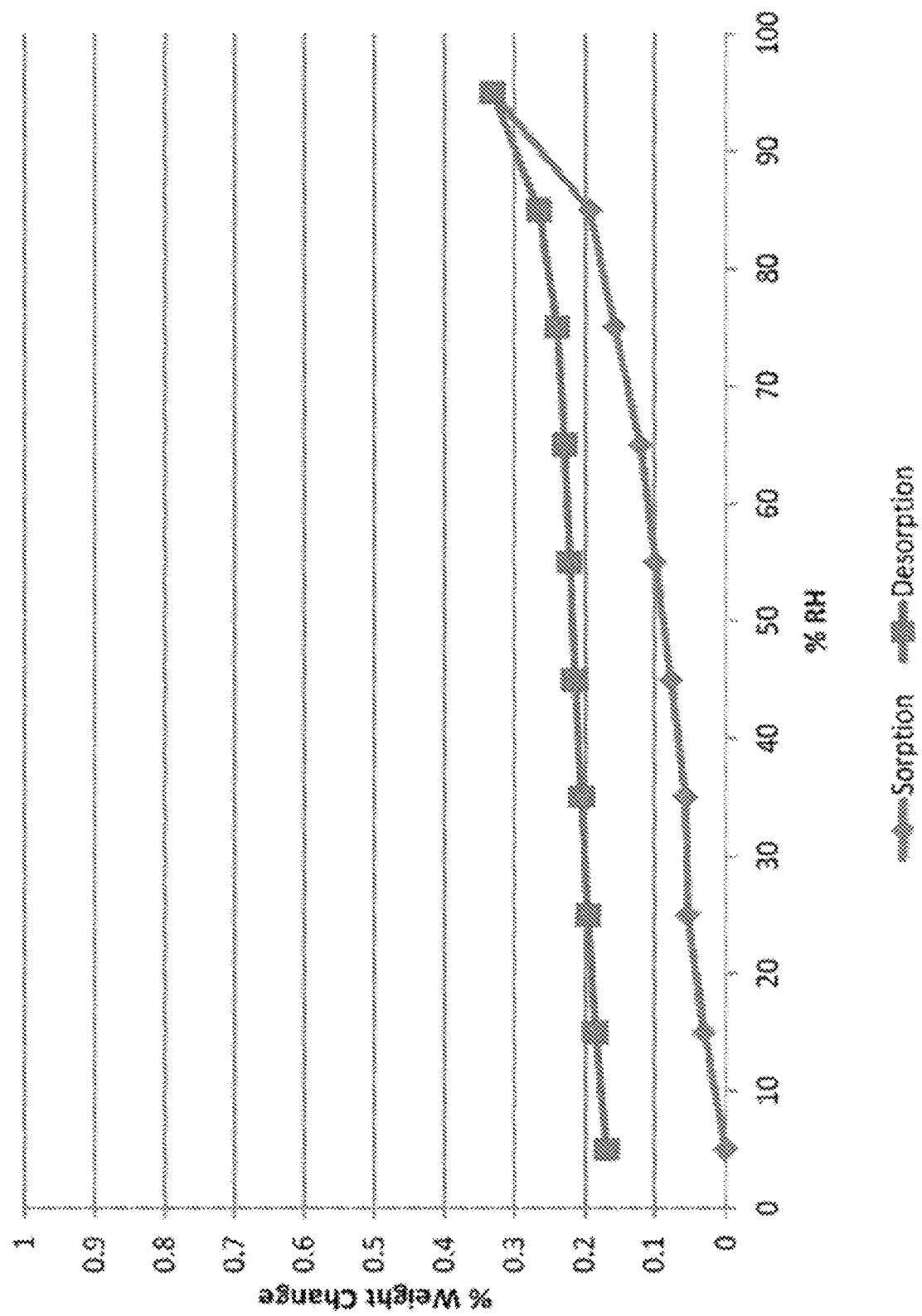
FIG. 26 illustrates a dynamic vapor sorption (DVS) analysis of methylone hydrochloride (racemate).
Figure 27:
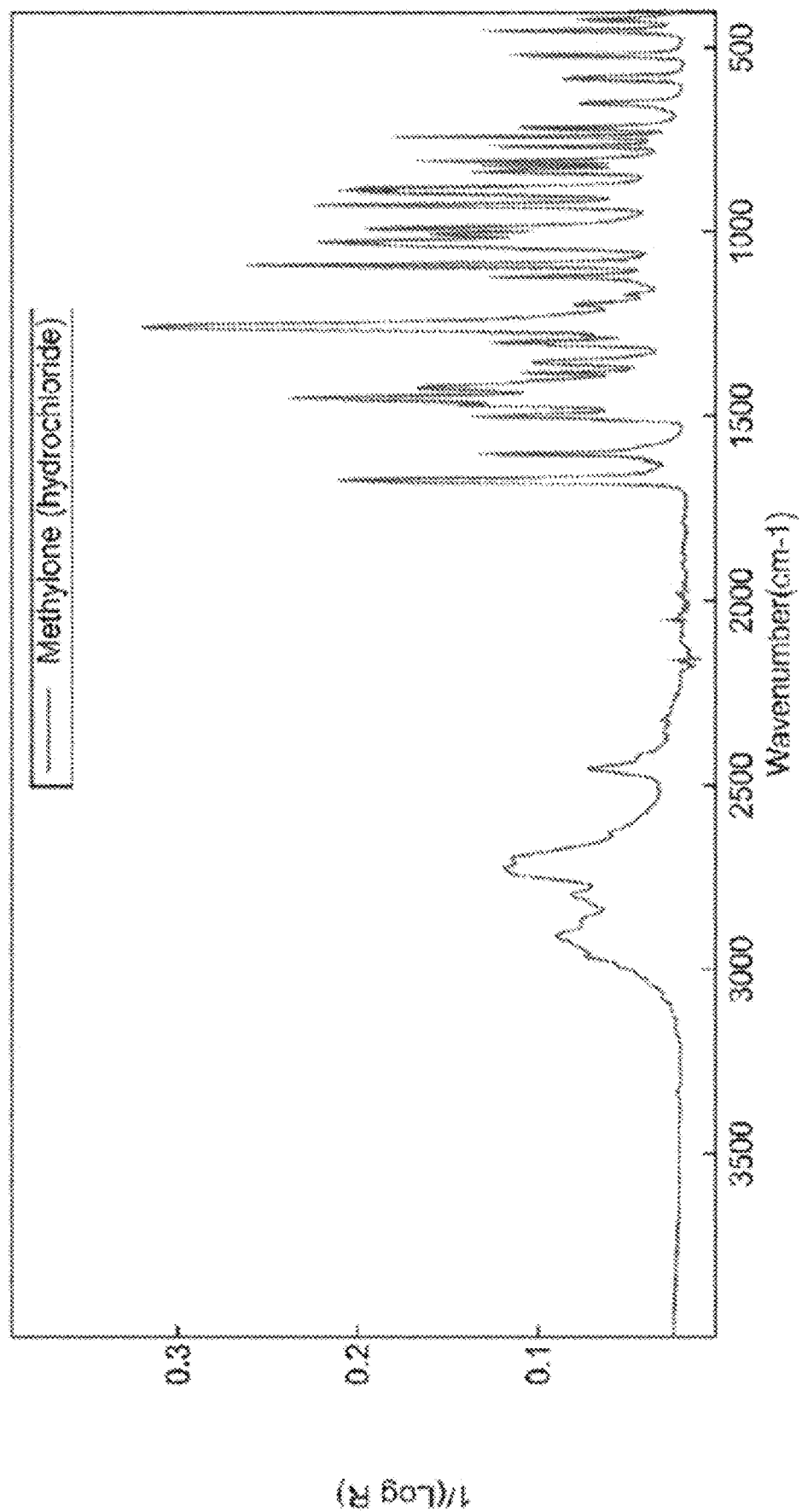
FIG. 27 illustrates an IR analysis of methylone hydrochloride (racemate).

The DVS analysis of methylone hydrochloride (racemate) (FIG. 26) showed that the compound was non-hygroscopic and physically stable after the moisture sorption-desorption analysis between 5% RH and 95% RH. The material showed 0.33% water gain between 5% RH and 95% RH, and 0.15% water loss between 95% RH and 5% RH.

The DVS analysis of methylone hydrochloride (racemate) (FIG. 26) showed water uptake above 75% RH. The material became tacky and stuck to the vial when exposed to 75% RH for 2 hours. The material was moderately hygroscopic.

Example 3-1: Screening of Additional Methylone Salts

Additional Methylone salts were prepare and screened using the solvents and methods similar to those mentioned above in Example 2-1.

The salt screen was performed by reacting the free base with pharmaceutically acceptable acids under various conditions in attempts to generate crystalline salts. Pharmaceutically acceptable acids that may be used are listed below in Table 8. Specific acids are selected based on the pKa of the free base, and typically 15 to 20 acids are selected. Experiments are performed using 0.5 molar equivalent, 1 molar equivalent and/or 2 molar equivalents of the acid.

TABLE 8

Exemplary Acids

| | |
|---|---|
| naphthalene-1,5-disulfonic acid | citric acid |
| sulfuric acid | d-glucuronic acid |
| ethane-1,2-disulfonic acid | lactobionic acid |
| p-toluenesulfonic acid | D-glucoheptonic acid |
| thiocyanic acid | (-)-L-pyroglutamic acid |
| methanesulfonic acid | L-malic acid |
| dodecylsulfuric acid | hippuric acid |
| naphthalene-2-sulfonic acid | D-gluconic acid |
| benzenesulfonic acid | D,L-lactic acid |
| oxalic acid | oleic acid |
| glycerophosphoric acid | succinic acid |
| ethanesulfonic acid, 2-hydroxy | glutaric acid |
| L-aspartic acid | cinnamic acid |
| maleic acid | adipic acid |
| phosphoric acid | sebacic acid |
| ethanesulfonic acid | (+)-camphoric acid |
| glutamic acid | acetic acid |
| pamoic (embonic) acid | nicotinic acid |
| glutaric acid, 2-oxo- | isobutyric acid |
| 2-naphthoic acid, 1-hydroxy | propionic acid |
| malonic acid | lauric acid |
| gentisic acid | stearic acid |
| L-tartaric acid | orotic acid |
| Fumaric acid | carbonic acid |
| galactaric (mucic) acid | |

Solvent systems for the salt crystallization experiments were selected based on the solubility of the free base and the selected acid. Solvents were used as a single solvent or as solvent mixtures, some containing water. The techniques used for salt crystallization were chosen based on the solvent selected and properties of the free base. The following techniques (or combination of techniques) may be used for salt crystallization:

Free base and acid are dissolved in a solvent or mixture of solvents, and the solvents are evaporated at different rates (slow evaporation or fast evaporation) and at different temperatures (ambient or elevated).

Free base and acid are dissolved in a solvent or mixture of solvents (at ambient temperature or an elevated temperature), and the final solution is cooled to a sub-ambient temperature (between −78° C. to 15° C.). The cooling method can be a fast cooling (by plunging the sample into an ice bath or a dry ice/acetone bath), or slow cooling. The solids formed will be recovered by filtration and dried (air dried or vacuum dried).

Free base and acid are dissolved in a solvent or mixture of solvents, and an antisolvent is added to precipitate the salt. The solids formed will be recovered by filtration and dried (air dried or vacuum dried).

Free base and acid are added to a solvent or mixture of solvents, where one or both components are not fully dissolved. The slurry is agitated at different temperatures for a number of days. The solids formed will be recovered by filtration and dried (air dried or vacuum dried). The same experiment can be also performed in solvent systems where the solvents are not miscible.

Free base and acid are milled together (by mechanical milling or by mortar and pestle), with a drop of solvent, or without any solvent.

Free base and acid are melted together, and cooled to various temperatures using various cooling rates.

If an amorphous form of a salt is obtained, the amorphous salt will be exposed to elevated humidity, or elevated temperature (or combination of both), or solvent vapors at various temperatures to form crystalline salts.

The stoichiometric ratio of acid to methylone was confirmed by $^1$H NMR, HPLC, or both as is known to those of ordinary skill in the art.

The salts obtained were analyzed by XRPD to determine if they are crystalline and, if so, by DSC to see the melting point and by TG to see if they are hydrated/solvated, and by 1H NMR spectroscopy to ensure chemical integrity. KF water titration is performed on salts that are hydrated. DVS analysis is performed to evaluate hygroscopicity of the salt and if hydrated form is present.

The free base material for the salt screen can be prepared by salt break of a methylone salt, for example methylone hydrochloride, alternatively the free base material can be prepared as is described in Example 3-3. In an exemplary salt break preparation, 6.9 mL of 1N NaOH was added to a solution of 1.1 g of methylone HCl in 10 mL of water (cloudy, then oiling observed), followed by stirring at room temperature for 1 day. The mixture was extracted w/EtOAc (3×), organic layers were combined and dried with MgSO$_4$. Evaporation with a stream of air yielded the free base as an oil.

Materials with unique XRPD patterns were generated with maleic acid, fumaric acid, gentisic acid, and L-tartaric acid during the salt screen. Further characterization suggested that salt formation only occurred with maleic acid. Samples from fumaric and tartaric acid experiments did not contain any counterion and likely represented new forms of the free base. Additional solution NMR peaks were observed for the gentisic and maleic acid samples suggesting possible degradation. Experiments to produce the maleate salt without extra peaks were unsuccessful.

The salts herein, including those described in Table 9, were prepared from methylone free base.

TABLE 9

Figure 28:
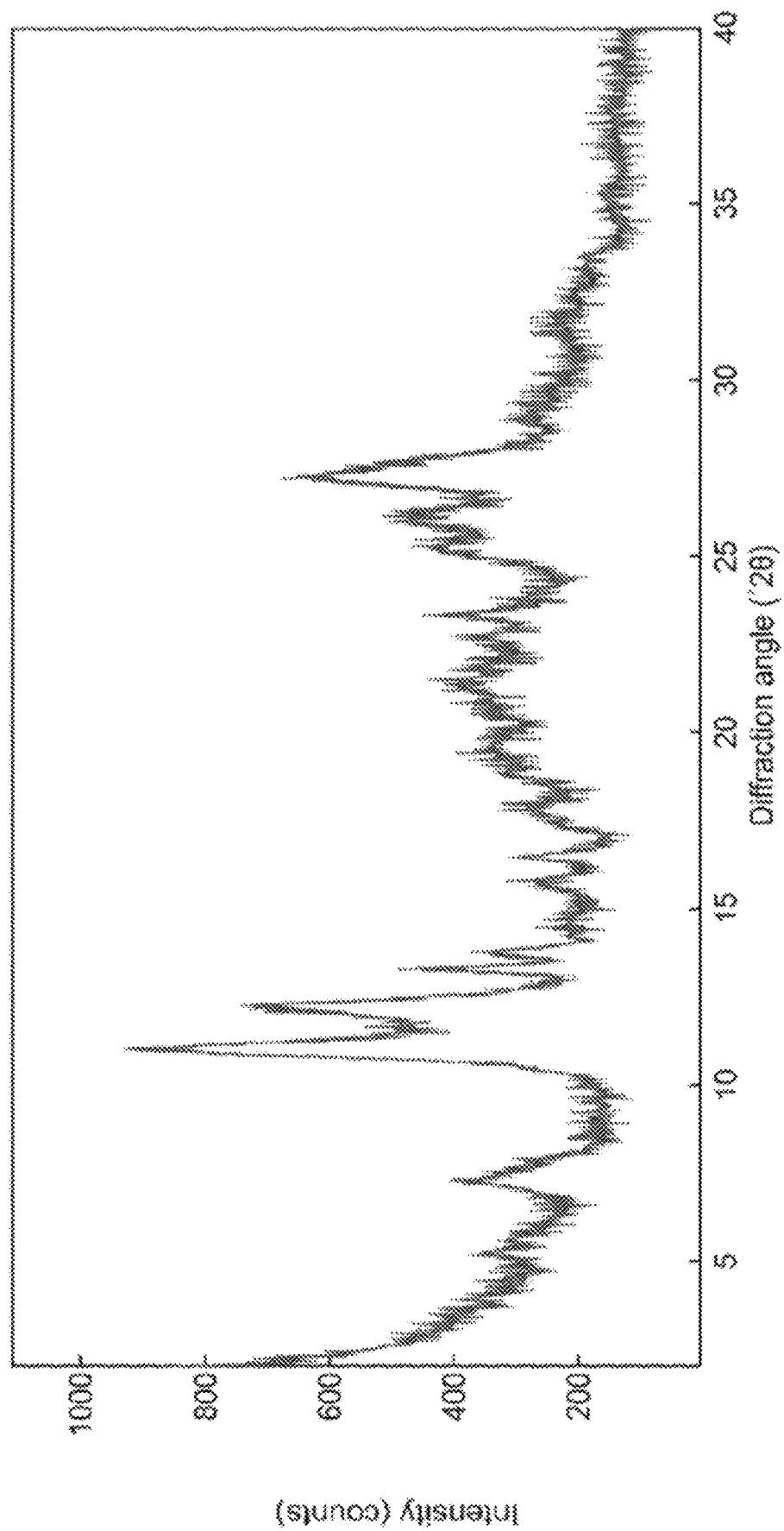
FIG. 28 provides an XRPD diffractogram of a crystalline methylone·fumarate (racemate) Form 1.
Figure 29:
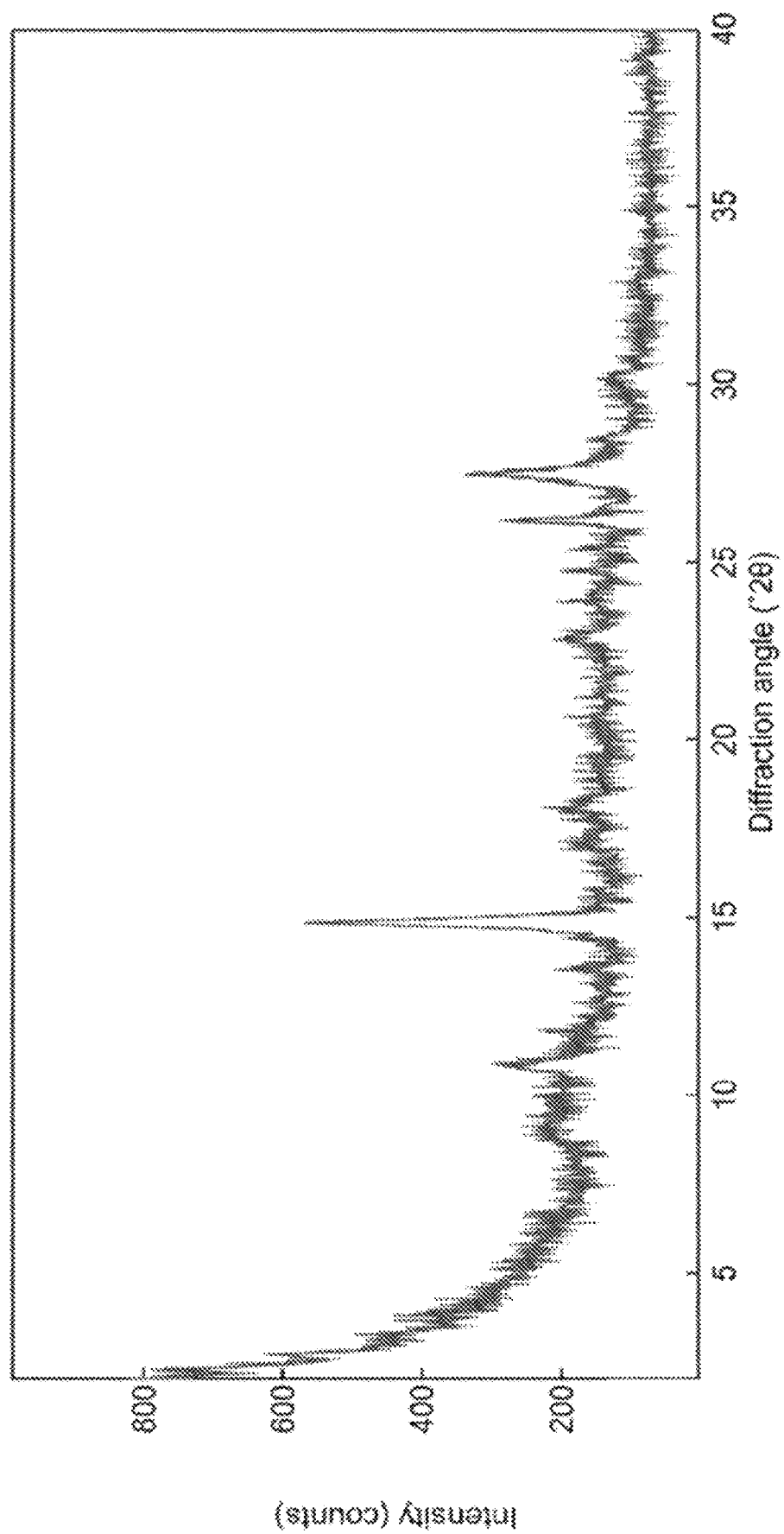
FIG. 29 provides an XRPD diffractogram of a crystalline methylone·gentisate (racemate).
Figure 31:
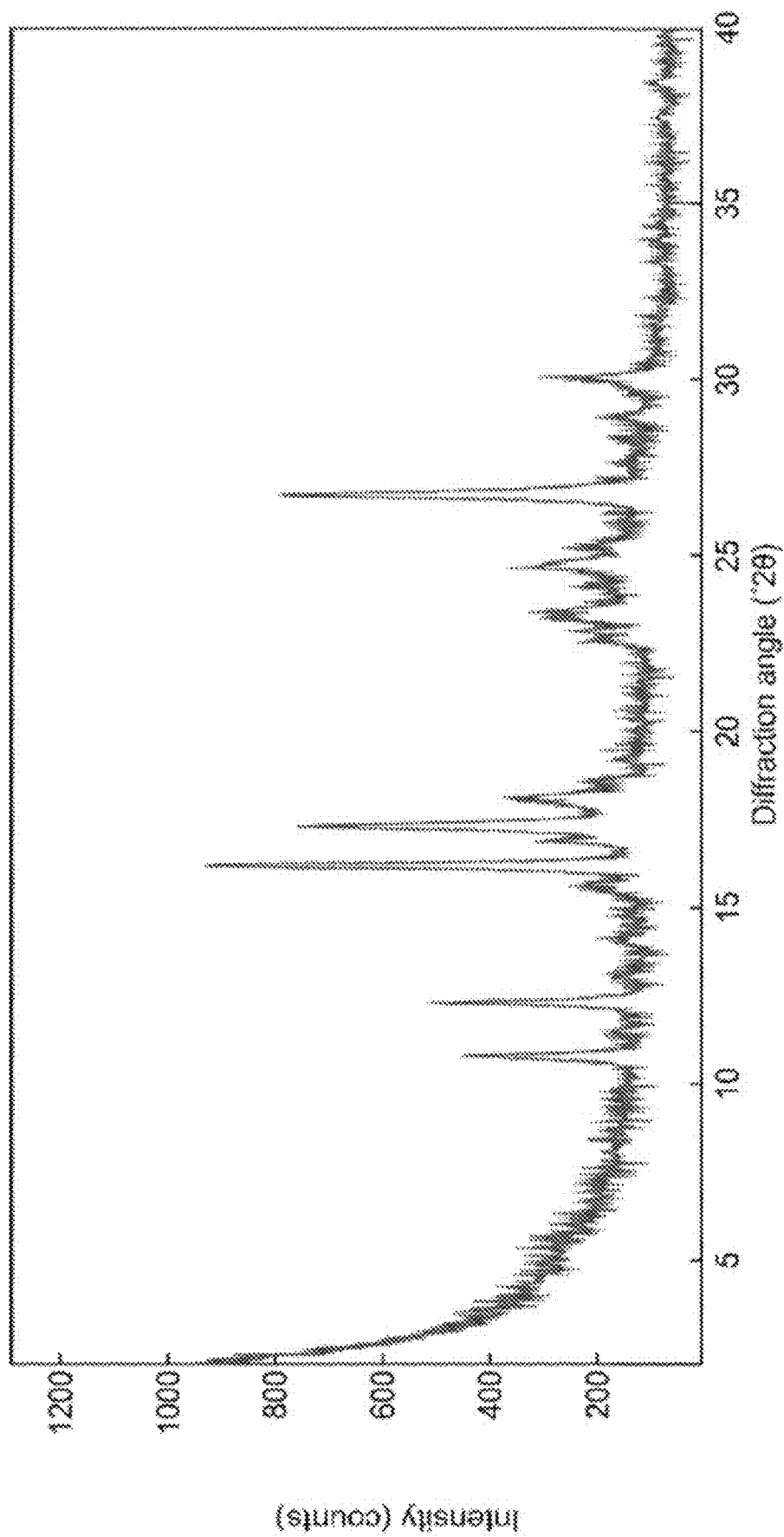
FIG. 31 provides an XRPD diffractogram of methylone·fumarate (racemate) comprising crystalline Forms 2 and 3.
Figure 32:
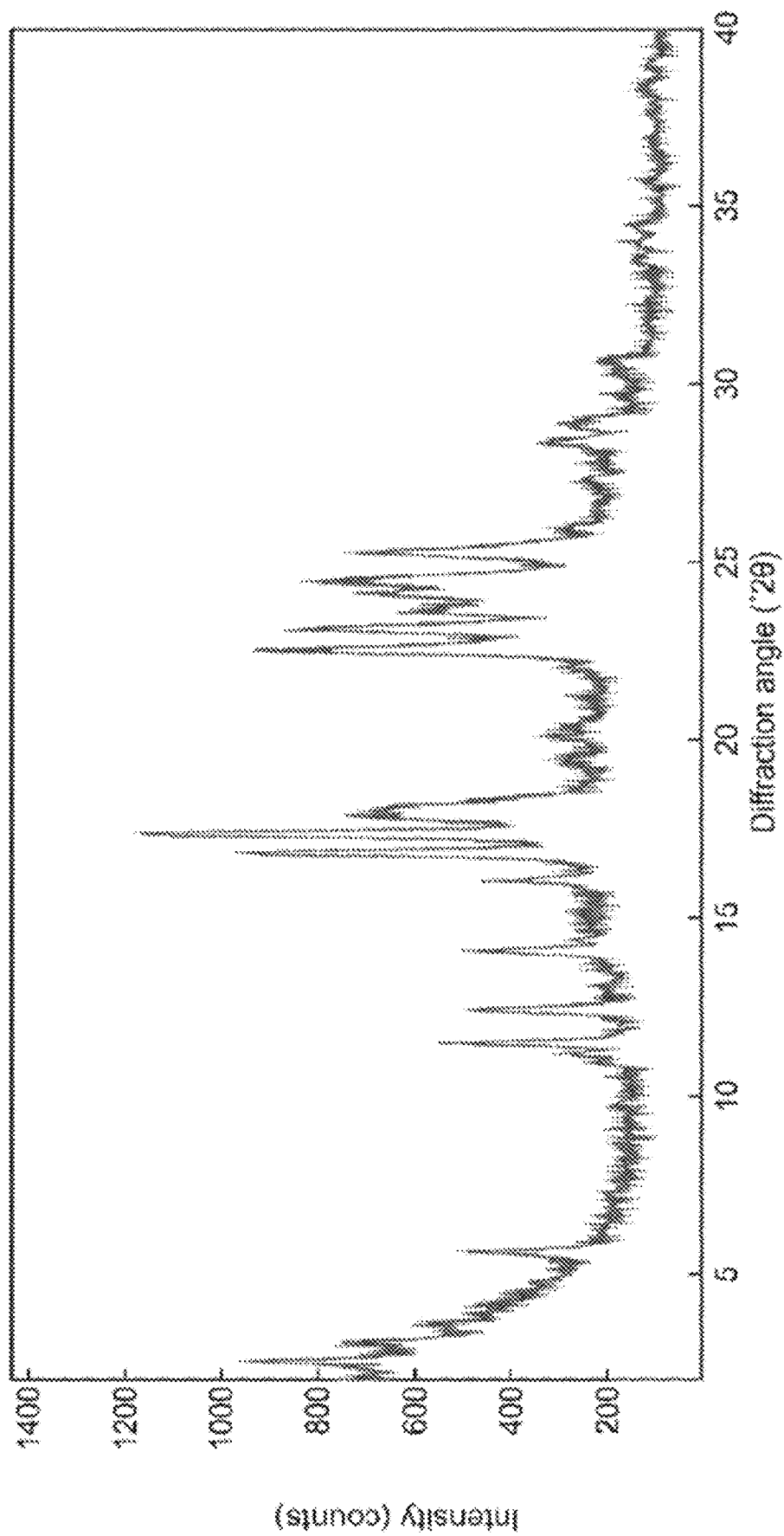
FIG. 32 provides an XRPD diffractogram of a crystalline methylone·fumarate (racemate) Form 2.
Figure 33:
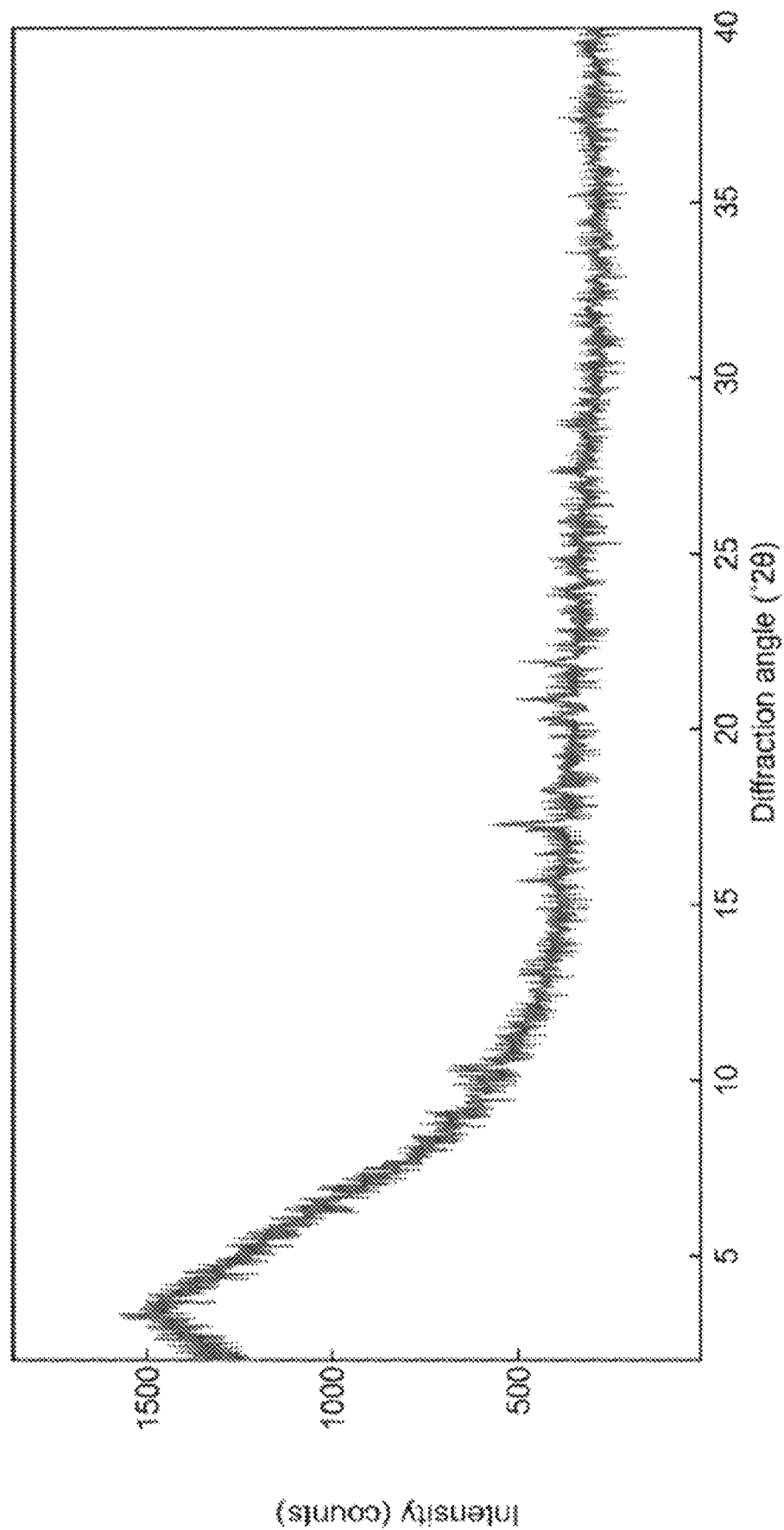
FIG. 33 provides an XRPD diffractogram of a crystalline methylone·citrate (racemate).
Figure 34:
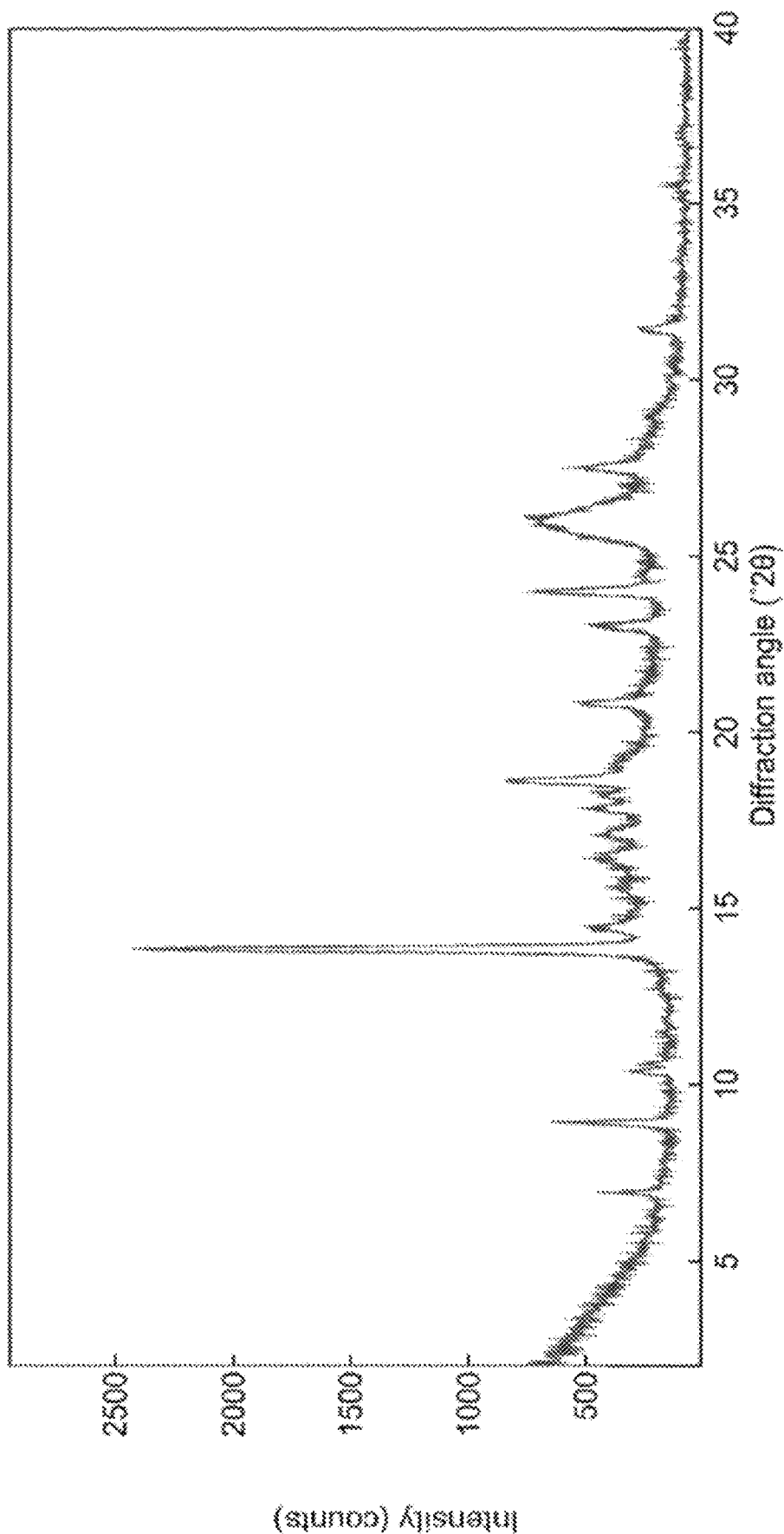
FIG. 34 provides an XRPD diffractogram of a crystalline methylone·gentisate (racemate) Form 2.
Figure 35:
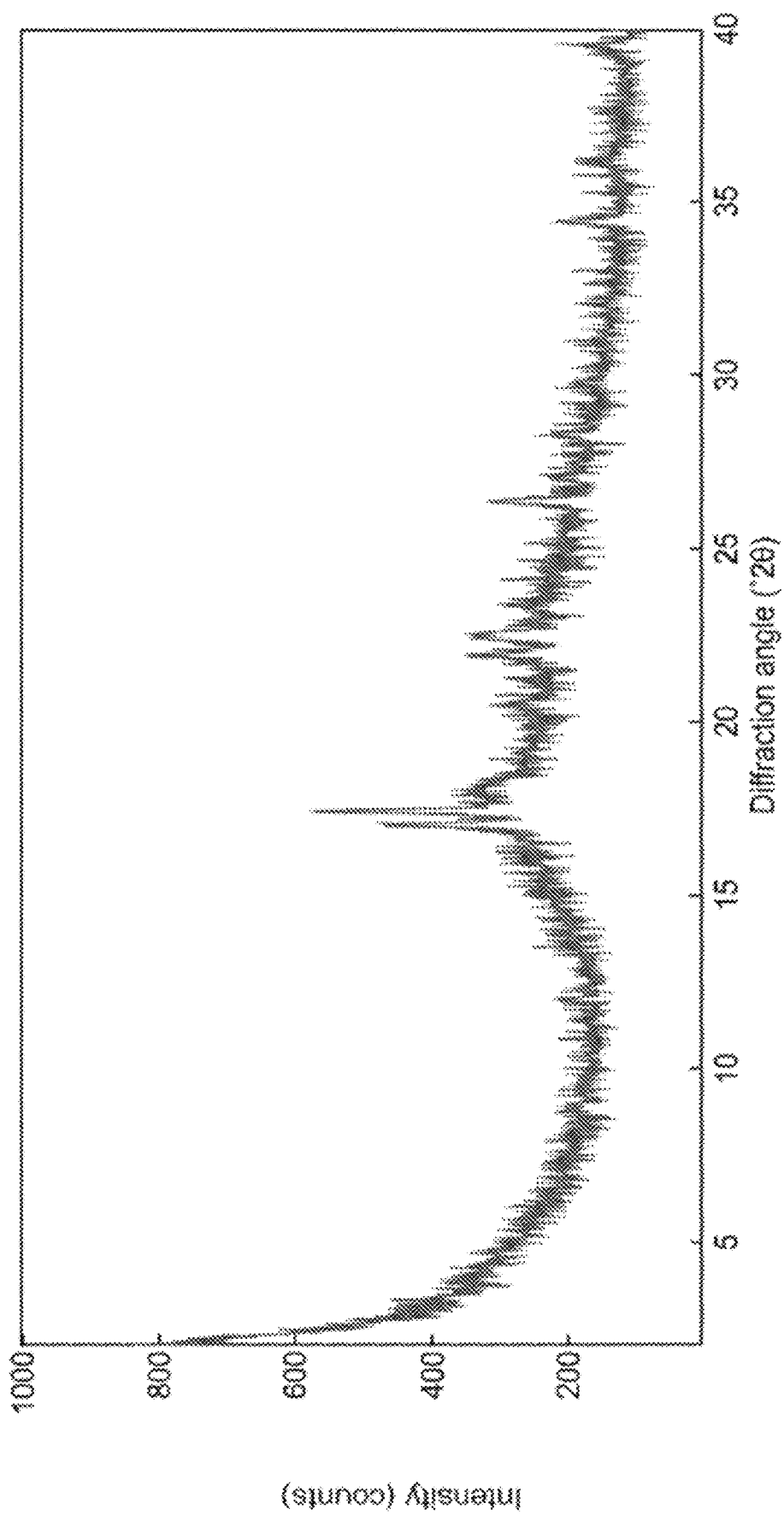
FIG. 35 provides an XRPD diffractogram of a crystalline methylone·tartrate (racemate).

| Methylone Salt formed | Conditions | $^1$H NMR consistent with salt form | XRPD |
|---|---|---|---|
| Fumaric acid | Added acid to sol'n of FB in EtOAc at 50° C.; solids remained. Added H2O at ET; clear. Cooled to RT, stirred at RT; tacky solids. Decanted, triturated w/DEE, scraped solids w/spatula until powdery. SL, RT | No | FIG. 28 Form 1 |
| | Added acid to sol'n of FB in IPE/EtOH; tacky solids. Heated at 50° C., w/stirring; cloudy, flocculent solids slowly formed. | No | FIG. 31 Forms 2 and 3 |
| | Added acid to sol'n of FB in EtOAc at 50° C.; tacky solids pp'd. SL, 50° C., 4 d | No | FIG. 32 Form 2 |
| Gentisic acid | Added acid to sol'n of FB in THF; cloudy + oily residue. Heated at 50° C.; oil began to solidify. SL, 50° C., 2 d→RT | No | FIG. 29 |
| | Added acid to sol'n of FB in EtOAc at 50° C.; tacky solids pp'd. SL, 50° C., 4 d | No | FIG. 34 Crystalline Form 2 and non-crystalline material |
| Maleic acid | Added acid to sol'n of FB in IPE/EtOH at RT; clear. Added DEE until turbid, stirred in freezer | Yes | FIG. 30 |
| Citric acid | Added acid to sol'n of FB in MeOH; clear. Added DEE until turbid; stirred in fridge. | No | FIG. 33 Crystalline and non-crystalline material |
| Tartaric acid | Added acid to sol'n of FB in EtOAc at 50° C.; solids remained. Added MeOH at ET; clear sol'n + oily residue. Cooled to RT; gel/film. Decanted, triturated w/EtOAc and DEE; oily residue. Decanted, triturated w/MTBE; no change. Decanted, triturated w/MTBE; no change. Decanted, triturated w/IPE; no change. Decanted, triturated w/EtOAc; some solids. Stirred in freezer. | No | FIG. 35 |

Notes:
FB = free base;
sol'n = solution;
EtOH = ethanol;
H$_2$O = water;
IPA = isopropanol;
DEE = diethyl ether;
EtOAc = ethyl acetate;
MeOH = methanol;
THF = tetrahydrofuran;
ACN = acetonitrile;
MTBE = methyl tert-butyl ether;
SL = slurry;
E = evaporation;
P = precipitation;
NS = no solids;
RT = room/ambient temperature;
ET = elevated temperature;
pp'd = precipitated;
d = day(s);
sol'n = solution;
DMSO = dimethyl sulfoxide A new crystalline form of methylone was identified from experiments with maleic acid. XRPD analysis of this new crystalline form of methylone maleate is shown in FIG. 30

XRPD analysis of methylone·maleate (FIG. 30) showed it to be crystalline with characteristic peaks at 10.1° 2-Theta, 12.0° 2-Theta, 15.4° 2-Theta, 17.0° 2-Theta, 19.7° 2-Theta, 23.5° 2-Theta, 24.1° 2-Theta, 24.9° 2-Theta, 25.8° 2-Theta, 28.7° 2-Theta, and 29.4° 2-Theta as measured with Cu Kα radiation.

Example 3-2: Polymorph Screen of Additional Methylone Salts

The methylone salts prepared according to Example 3-1, was characterized to evaluate its physical properties using the solvents and methods similar to those mentioned above in Example 2-1.

The information obtained was used for designing the subsequent polymorph screen. Solvents are used as a single solvent or as solvent mixtures, some containing water. The techniques used for the polymorph screen are chosen based on the solvent selected and properties of the API. The following techniques (or a combination of techniques) may be used for the polymorph screening:

- API is dissolved in a solvent or mixture of solvents, and the solvents are evaporated at different rates (slow evaporation or fast evaporation) and at different temperatures (ambient or elevated).
- API is dissolved in a solvent or mixture of solvents (at ambient temperature or an elevated temperature), and the final solution is cooled (between −78° C. to 20° C.). The cooling method can be a fast cooling (by plunging the sample to an ice bath or a dry ice/acetone bath), or slow cooling. The solids formed will be recovered by filtration and dried (air dried or vacuum dried).
- API is dissolved in a solvent or mixture of solvents, and an antisolvent is added to precipitate the salt. The solids formed will be recovered by filtration and dried (air dried or vacuum dried).
- API is added to a solvent or mixture of solvents, where the API is not fully dissolved. The slurry will be agitated at different temperatures for a number of days. The solids formed will be recovered by filtration and (air dried or vacuum dried).
- API is milled (by mechanical milling or by mortar and pestle), with a drop of solvent, or without any solvent.
- API is melted and cooled (at different cooling rates, fast and slow, and cooled to different temperatures) to obtain solids.
- API is suspended in a solvent or mixture of solvents, and the slurry is placed in a heating/cooling cycle for multiple cycles. The remaining solids after the final cooling cycle will be filtered and (air dried or vacuum dried).
- API is processed to obtain an amorphous form (by melting, milling, solvent evaporation, spray drying or lyophilization). The amorphous form will then be exposed to elevated humidity (or elevated temperature, or combination thereof), or to solvent vapors for extended period of days.
- API is exposed to elevated humidity (or elevated temperature, or combination thereof), or to solvent vapors for extended period of days.
- Two or more polymorphs of the API are mixed in a solvent or solvent systems (some solvent mixtures containing variable amount of water) to obtain a slurry, and the slurry will be agitated (at various temperatures) for an extended period of time (days). The solvent system used can be pre-saturated with the API. The final solids will be filtered and dried (air dried or vacuum dried).
- API is heated to a specific temperature and cooled (at ambient conditions or in a dry box).

The solids obtained were analyzed by XRPD to determine if they are crystalline and, if so, by DSC to see the melting point and by TG to see if they are hydrated/solvated, and by $^1$H NMR spectroscopy to ensure chemical integrity. KF water titration was performed on forms that are hydrated. DVS analysis was performed to evaluate hygroscopicity of the form and if hydrated form is present. In particular variable temperature analyses, including variable temperature XRPD, were performed to assess the stability of each physical form as well as its crystallinity.

Differential scanning calorimetry (DSC) thermograms were obtained using a DSC Q 100 (TA Instruments, New Castle, DE). The temperature axis and cell constant of the DSC cell were calibrated with indium (10 mg, 99.9% pure, melting point 156.6° C., heat of fusion 28.4 J/g). Samples (2.0-5.0 mg) are weighed in aluminum pans on an analytical balance. Aluminum pans without lids were used for the analysis. The samples were equilibrated at 25° C. and heated to 250-300° C. at a heating rate of 10° C./min under continuous nitrogen flow. TG analysis of the samples was performed with a Q 50(TA Instruments, New Castle, DE). Samples (2.0-5.0 mg) were analyzed in open aluminum pans under a nitrogen flow (50 mL/min) at 25° C. to 210° C. with a heating rate of 10° C./min.

The sample for moisture analysis was allowed to dry at 25° C. for up to 4 hours under a stream of dry nitrogen. The relative humidity was then increased stepwise from 10 to 90% relative humidity (adsorption scan) allowing the sample to equilibrate for a maximum of four hours before weighing and moving on to the next step. The desorption scan was measured from 85 to 0% relative humidity with the same equilibration time. The sample was then dried under a stream of dry nitrogen at 80° C. for 2 hours or until no weight loss is observed.

X-ray powder diffraction data are collected using a Miniflex Tabletop XRD system (Rigaku/MSC, The Woodlands, TX) from 5° to 45° 2θ with steps of 0.1°, and the measuring time is 1.0 second/step. All samples are ground to similar size before exposure to radiation. The powder samples are illuminated using Cu Kα radiation (λ=1.54056 Å) at 30 kV and 15 mA.

Variable temperature XRPD data were collected using a Huber Imaging Plate Guinier Camera 670 employing Ni-filtered Cu Kαi radiation (λ=1.5405981 Å) produced at 40 kV and 20 mA by a Philips PW1120/00 generator fitted with a Huber long fine-focus tube PW2273/20 and a Huber Guinier Monochromator Series 611/15. The original powder is packed into a Lindemann capillary (Hilgenberg, Germany) with an internal diameter of 1 mm and a wall thickness of 0.01 mm. The sample is heated at an average rate of 5 Kmin$^{-1}$ using a Huber High Temperature Controller HTC 9634 unit with the capillary rotation device 670.2. The temperature is held constant at selected intervals for 10 min while the sample is exposed to X-rays and multiple scans were recorded. A 2θ-range of 4.00-100.0° is used with a step size of 0.005° 2θ.

In certain embodiments wherein the solid form is a solvate, such as a hydrate, the DSC thermogram reveals endothermic transitions. In accordance with the observed DSC transitions, TGA analysis indicates stages of weight change corresponding to desolvation or dehydration and/or melting of the sample. In the case of hydrates, these results are in harmony with Karl Fischer titration data which indicate the water content of the sample.

The moisture sorption profile of a sample can be generated to assess the stability of a solid form is stable over a range of relative humidities. In certain embodiments, the change in moisture content over 10.0 to 95.0% relative humidity is small. In other embodiments the change in moisture content over 10.0 to 95.0% relative humidity is reversible.

In certain embodiments, the XRPD pattern of a sample of solid form indicates that the sample has a well-defined crystal structure and a high degree of crystallinity.

Example 3-3: Synthesis of Methylone

Materials and Methods

Chemicals were purchased primarily from Sigma-Aldrich (Merck Life Science U.K. Ltd, The Old Brickyard, New Rd, Gillingham, Dorset SP8 4XT, U.K.); Alfa Aesar, Heysham, Morecambe, Lancashire LA3 2XY and were used without further purification. Solvents were purchased as anhydrous. Petrol (pet ether) was the alkane fraction boiling between 40-60° C.

TLC was carried out using aluminum plates pre-coated with silica gel (Kieselgel 60 F254, 0.2 mm, Merck, Darmstadt, Germany). Visualization was by UV light.

$^1$H NMR spectra were recorded on a Bruker Avance BVT3200 spectrometer using the residual proton(s) in the deuterated solvents as internal standards.

HPLC analyses were performed with a Shimadzu Prominence instrument (Shimadzu UK Ltd., Unit 1A Mill Court, Featherstone Road, Milton Keynes MK12 5RD, U.K.) with diode array detection and a Kinetex EVO C18, 5 µm, 250 mm×4.6 mm column.

LC-MS analyses were performed on a Shimadzu 2020 instrument operating in positive or negative ESI mode with UV detection at 254 nm.

Automated chromatography was performed on a Biotage Selekt purification system (Biotage GB Limited, Distribution Way, Dyffryn Business Park, Ystrad Mynach, Hengoed, Mid Glamorgan CF82 7TS, Wales).

Synthesis of Rac.-Methylone

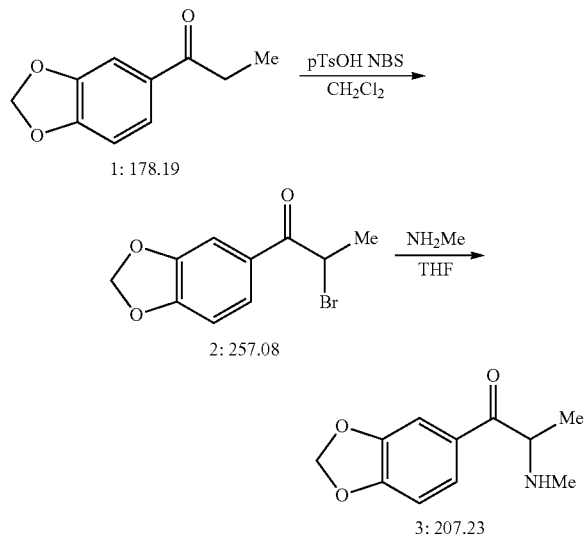

Scheme 2: Synthesis of rac.-methylone via bromination with p-toluenesulfonic acid Step 1: Synthesis of rac.-1-(benzo[d][1,3]dioxol-5-yl)-2-bromopropan-1-one (2)

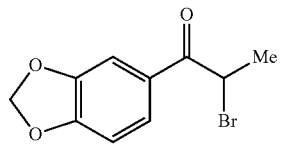 [SMILES: CC(Br)C(=O)c1ccc2c(c1)OCO2]

To a solution of 1-(benzo[d][1,3]dioxol-5-yl)propan-1-one (10.0 g, 56.1 mmol) in anhydrous acetonitrile (84 mL) and anhydrous dichloromethane (21 mL) were added p-toluenesulfonic acid (2.14 g, 11.2 mmol) followed by N-bromosuccinimide (20.0 g, 112.2 mmol) and the mixture was heated in the dark at 40° C. under a nitrogen atmosphere for 6 h. The resulting dark orange solution was cooled to room temperature and quenched with saturated sodium bicarbonate solution (70 mL) and extracted with diethyl ether (3×100 mL). The combined organic extracts were washed with saturated brine (50 mL), dried (MgSO$_4$) and concentrated to give a brown oil. The crude material was purified by normal phase chromatography, eluting with 0 to 100% diethyl ether in petrol to give rac.-1-(benzo[d][1,3]dioxol-5-yl)-2-bromopropan-1-one (13.5 g, 93% yield) as a pale yellow oil that solidified to a waxy solid upon standing. $^1$H NMR: (CDCl$_3$) δ 7.70 (dd, 1H, J=8.2 and 1.7 Hz, ArH), 7.49 (d, 1H, J=1.7 Hz, ArH), 6.87 (d, 1H, J=8.2 Hz, ArH), 6.06 (s, 2H, CH$_2$), 5.21 (q, 1H, J=6.6 Hz, α-CH), 1.88 (d, 3H, J=6.6 Hz, Me). TLC: R$_f$=0.43 (diethyl ether-petrol, 1:3 v/v)

Step 2: Synthesis of rac.-1-(benzo[d][1,3]dioxol-5-yl)-2-(methylamino)propan-1-one (3)

To a solution of 1-(benzo[d][1,3]dioxol-5-yl)-2-bromopropan-1-one (5.87 g, 22.84 mmol) in anhydrous THF (30 mL) was added methylamine dropwise (2.0 M in THF, 22.8 mL, 45.68 mmol) and the mixture was stirred at room temperature under a nitrogen atmosphere for 5 h. The resulting pale orange cloudy suspension was concentrated, 1 M hydrochloric acid (100 ml) was added to the residue and the mixture was washed with diethyl ether (3×50 mL). The aqueous phase was basified to pH 10-11 with aqueous sodium hydroxide (3.0 M) and extracted with dichloromethane (3×50 mL). The combined organics extracts were dried (Na$_2$SO$_4$) and concentrated to give a golden oil. This material was purified under normal phase conditions eluting with 0 to 100% methanol in dichloromethane to give rac.-1-(benzo[d][1,3]dioxol-5-yl)-2-(methylamino)propan-1-one (3.36 g, 71% yield) as a clear oil that solidified to a waxy solid upon standing. $^1$H NMR: (CDCl$_3$) δ 7.58 (dd, 1H, J=8.2 and 1.7 Hz, ArH), 7.46 (d, 1H, J=1.7 Hz, ArH), 6.87 (d, 1H, J=8.2 Hz, ArH), 6.05 (s, 2H, CH$_2$), 4.11 (q, 1H, J=7.0 Hz, α-CH), 2.35 (s, 3H, NMe), 1.28 (d, 3H, J=7.0 Hz, Me). TLC: R$_f$=0.37 (methanol —CH$_2$Cl$_2$, 1:9 v/v)

Example 3-4: Chiral HPLC Methods for Separating Enantiomers of Methylone

As will be appreciated by those of skill in the art, methylone exists as two mirror image compounds, enantiomers. The enantiomers are (R)-methylone and (S)-methylone. (R)-methylone and (S)-methylone can be isolated from a racemic mixture of the two isomers as described herein to provide a compound that is substantially enantiomerically pure. For example, using chiral HPLC as described herein, the two enantiomers can be separated to greater than a ratio of 85:15 (S)-methylone:(R)-methylone, such as 90:10 (S)-methylone:(R)-methylone, such as 95:5, 97:3, 98:2, 99:1 or greater. Thus, in certain embodiments the disclosed salts, solid forms and salts thereof are substantially pure (S)-methylone. In other embodiments, the disclosed salts solid forms and salts thereof are optically active (meaning they have more (S)-methylone than (R)-methylone, such as in a ratio of from about 85:15, 90:10, 95:5, 97:3, 98:2 or about 99:1.

Exemplary conditions useful to separate (R)-methylone and (S)-methylone into the purified optically active compositions described above are described in Protocols 1 and 2 below:

Protocol-1:
   HPLC: Waters 2695 Alliance
   Diode array detector (210-400 nm)
   Column: Phenomenex Lux Amylose-2; 5 micron, 4.6× 250 mm
   Mobil phase (isocratic): 20% acetonitrile, 40% aqueous, 20 mM monobasic potassium
   phosphate buffer
   Flow rate: 0.5 ml/min
   Injection volume: 3 µL
   Concentration: approximate 5 mg/ml
   Detection: UV at 254 nm
   Run Time: 30 minutes Protocol-2:
   Column: Daicel Chemical Industries, Chiralcel OJ, 4.6× 250 mm
   Mobile phase: 1:1 Methanol Ethanol 0.10% diethylamine (isocratic)
   Flow rate: 0.5 ml/min
   Run time: 15 minutes
   Temperature: room temperature
   Detection: Water 996 PDA
   HPLC: Waters 2690 Separations Module Example 3-5: Salt Screen (S)-methylone was characterized to evaluate its physical properties using the solvents and methods similar to those mentioned above in Example 2-1. Likewise, (R)-methylone is characterized to evaluate its physical properties using the solvents and methods similar to those mentioned above in Example 2-1.

The information obtained was used for subsequent polymorph screen. The salt screen was performed by reacting the free base (S)-methylone with pharmaceutically acceptable acids under various conditions in attempts to generate crystalline salts. In a similar manner, the salt screen is performed by reacting the free base (R)-methylone with pharmaceutically acceptable acids under various conditions in attempts to generate crystalline salts. Pharmaceutically acceptable acids that may be used are listed below. Specific acids are selected based on the pKa of the free base, and typically 15 to 20 acids are selected. Experiments are performed using 0.5 molar equivalent, 1 molar equivalent and/or 2 molar equivalents of the acid.

Solvent systems for the salt crystallization experiments were selected based on the solubility of the free base and the selected acid. Solvents were used as a single solvent or as solvent mixtures, some containing water. The techniques that are used for salt crystallization are chosen based on the solvent selected and properties of the free base. The following techniques (or combination of techniques) may be used for salt crystallization:

Free base and acid are dissolved in a solvent or mixture of solvents, and the solvents are evaporated at different rates (slow evaporation or fast evaporation) and at different temperatures (ambient or elevated).

Free base and acid are dissolved in a solvent or mixture of solvents (at ambient temperature or an elevated temperature), and the final solution is cooled to a sub-ambient temperature (between −78° C. to 15° C.). The cooling method can be a fast cooling (by plunging the sample into an ice bath or a dry ice/acetone bath), or slow cooling. The solids formed will be recovered by filtration and dried (air dried or vacuum dried).

Free base and acid are dissolved in a solvent or mixture of solvents, and an antisolvent is added to precipitate the salt. The solids formed will be recovered by filtration and dried (air dried or vacuum dried).

Free base and acid are added to a solvent or mixture of solvents, where one or both components are not fully dissolved. The slurry is agitated at different temperatures for a number of days. The solids formed will be recovered by filtration and dried (air dried or vacuum dried). The same experiment can be also performed in solvent systems where the solvents are not miscible.

Free base and acid are milled together (by mechanical milling or by mortar and pestle), with a drop of solvent, or without any solvent.

Free base and acid are melted together, and cooled to various temperatures using various cooling rates.

If an amorphous form of a salt is obtained, the amorphous salt will be exposed to elevated humidity, or elevated temperature (or combination of both), or solvent vapors at various temperatures to form crystalline salts.

The stoichiometric ratio of acid to methylone free base was confirmed by $^1$H NMR, HPLC, or both as is known to those of ordinary skill in the art.

The salts obtained were analyzed by XRPD to determine if they are crystalline and, if so, by DSC to see the melting point and by TG to see if they are hydrated/solvated, and by $^1$H NMR spectroscopy to ensure chemical integrity. KF water titration is performed on salts that are hydrated. DVS analysis is performed to evaluate hygroscopicity of the salt and if hydrated form is present.

Preparation of (S)-Methylone Free Base

Added 6.3 mL of 1N NaOH to a solution of 1.02 g of (S)-methylone HCl in 10 mL of water (cloudy, then oiling observed). Stirring, RT, 3 d. Extracted w/EtOAc (3×). Combined organic layers and dried w/MgSO4. Evaporated w/stream of air (oil).

Added 12.4 mL of 1N NaOH to a solution of 2.00 g of (S)-methylone HCl in 20 mL of water (cloudy, then oiling observed). Stirring, RT, 1 d. Extracted w/EtOAc (3×). Combined organic layers and dried w/MgSO4. Evaporated w/stream of air (oil).

The as-received lot of (S)-methylone HCl was a mixture of forms, designated as Forms A+C.

Materials with unique XRPD patterns were generated with fumaric acid, gentisic acid, hydrochloric acid (HCl 2), and L-tartaric acid during the salt screen with (S)-methylone. Solution NMR data showed impurities in the fumaric acid, gentisic acid, sulfuric acid, and HCl 2 samples with (S)-methylone. L-tartaric acid could not be analyzed due to the solid being insoluble in the deuterated solvent. With the exception of HCl, the materials obtained from this salt screen were not composed of (S)-methylone by 1H NMR. The HCl salt experiment in Table 10 produced another form of the HCl salt, which was designated as Form B. Based on these data, HCl was a viable salt produced in the screening.

The salts in Table 10 were formed from the (S)-methylone free base using one molar equivalent of acid, unless otherwise noted.

TABLE 10

Figure 37:
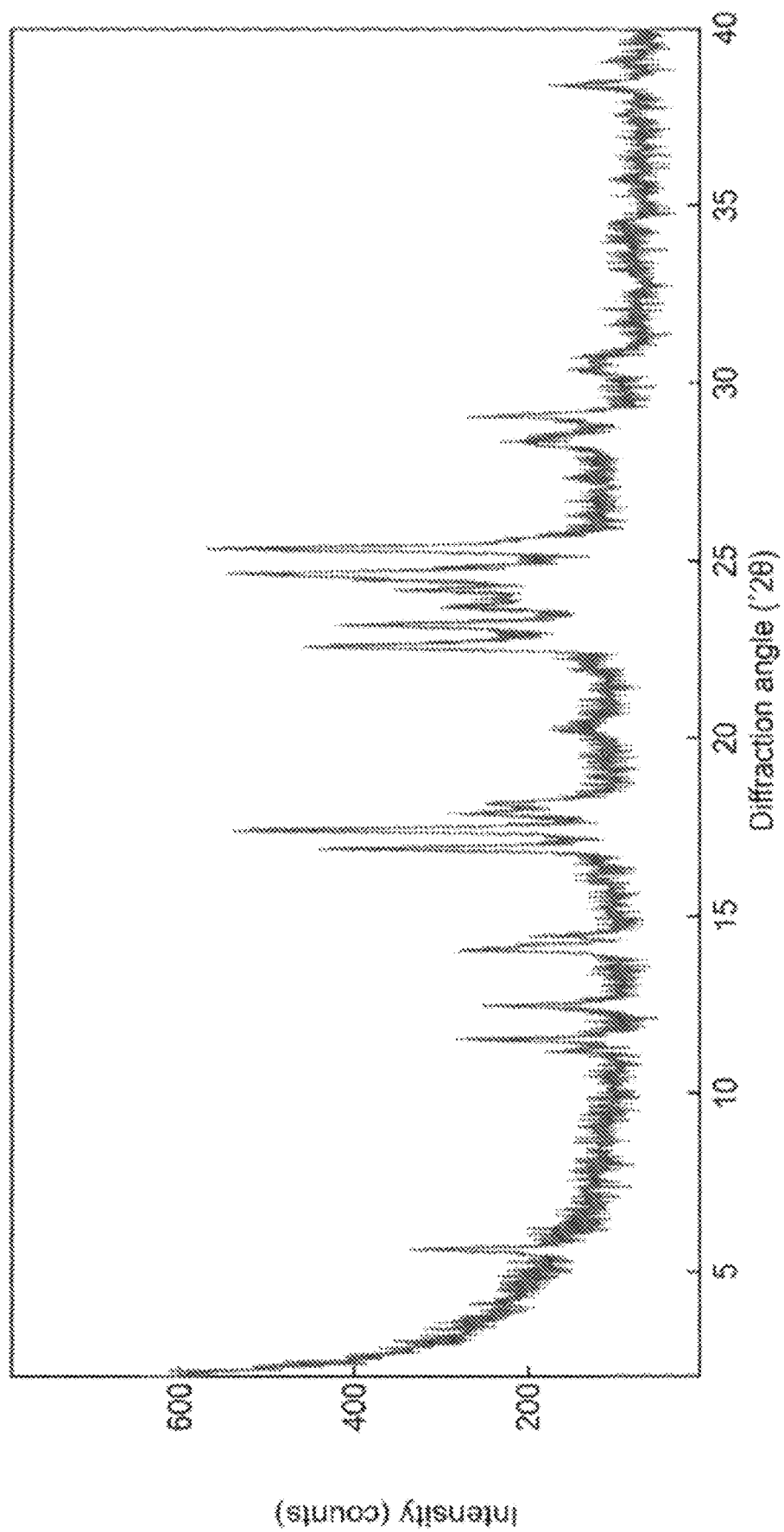
FIG. 37 provides an XRPD diffractogram of crystalline (S)-methylone·fumarate, Form 1.
Figure 38:
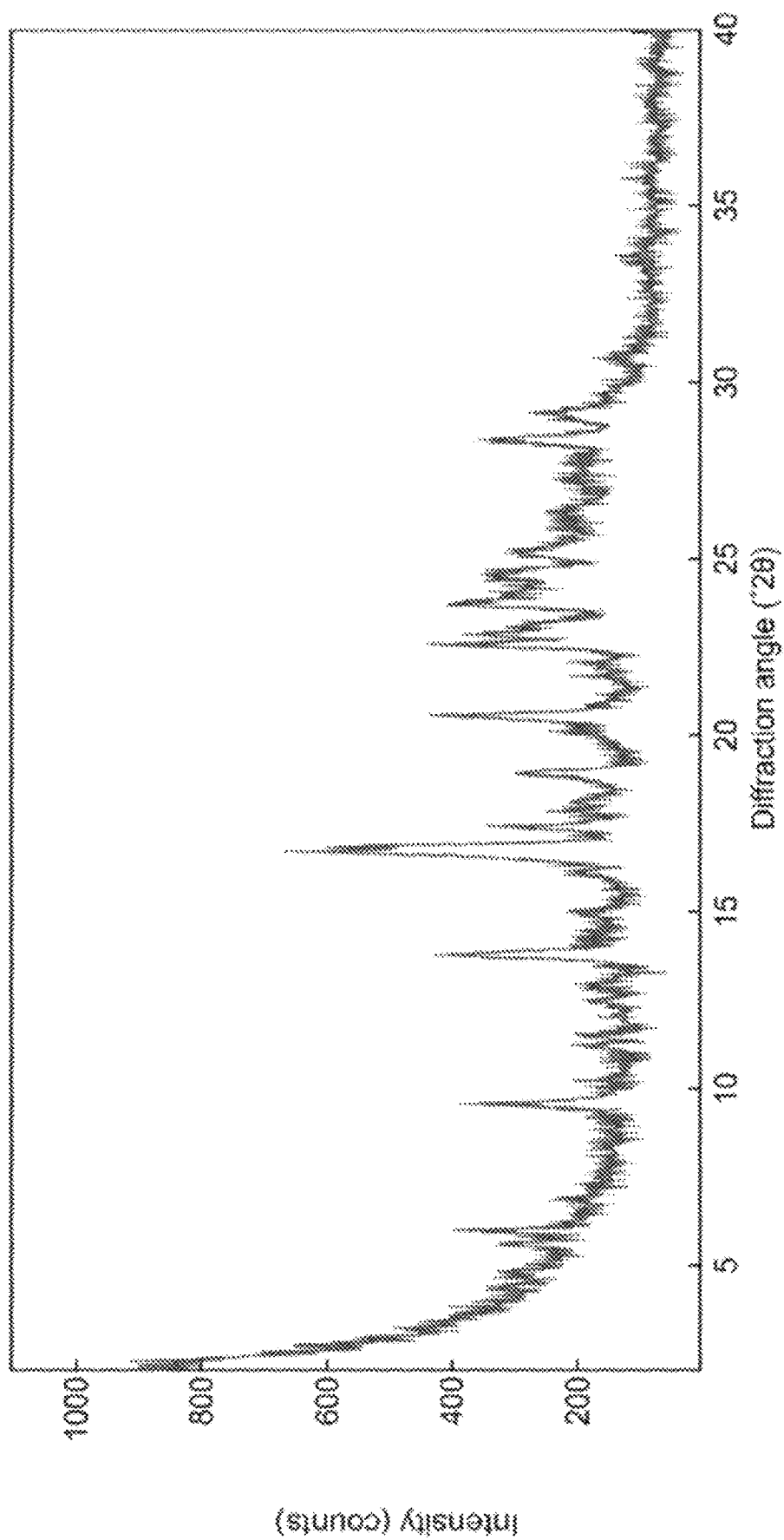
FIG. 38 provides an XRPD diffractogram of crystalline (S)-methylone·fumarate comprising (S)-methylone·fumarate crystalline Forms 1 and 2.
Figure 39:
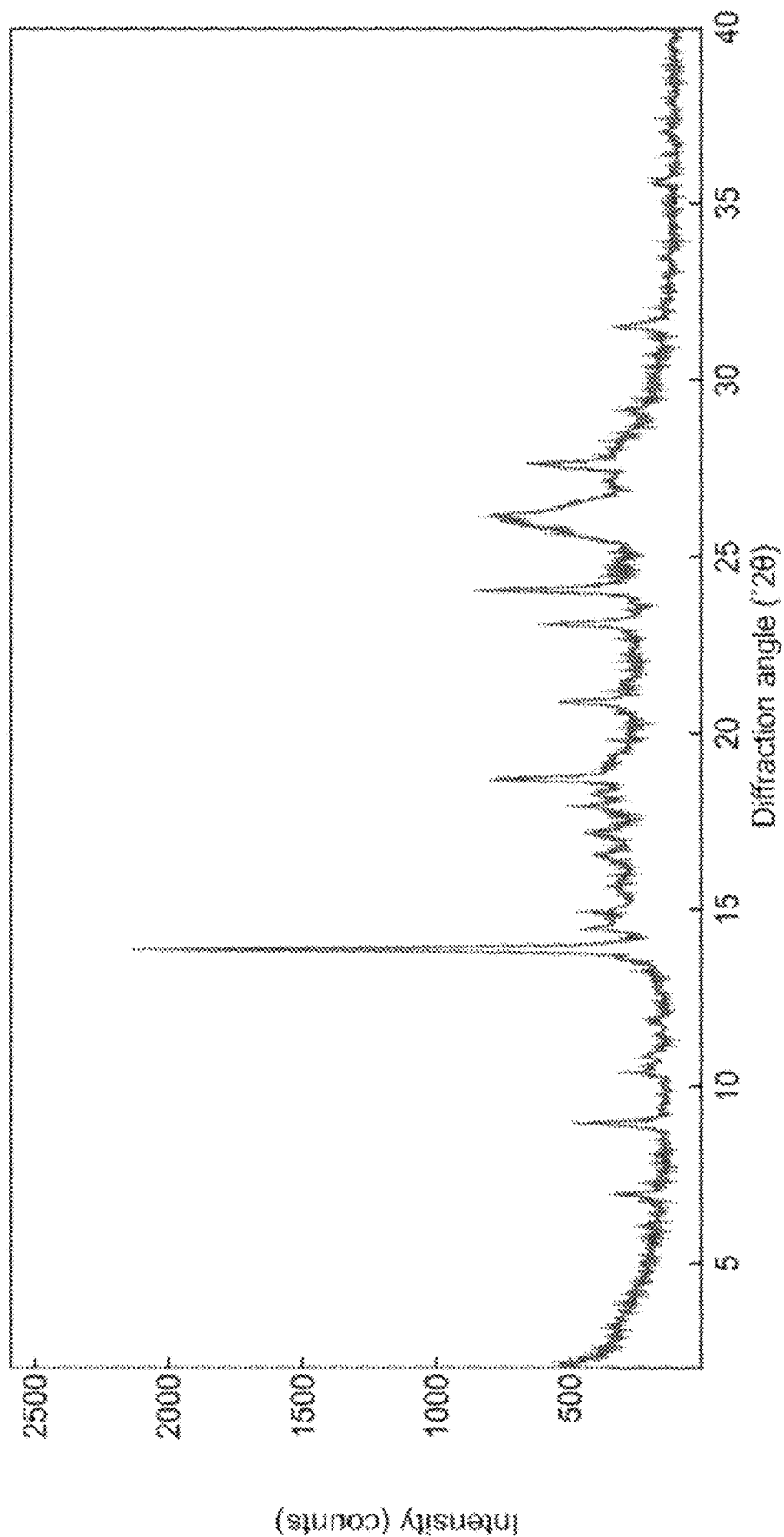
FIG. 39 provides an XRPD diffractogram of a crystalline (S)-methylone·gentisate.
Figure 41:
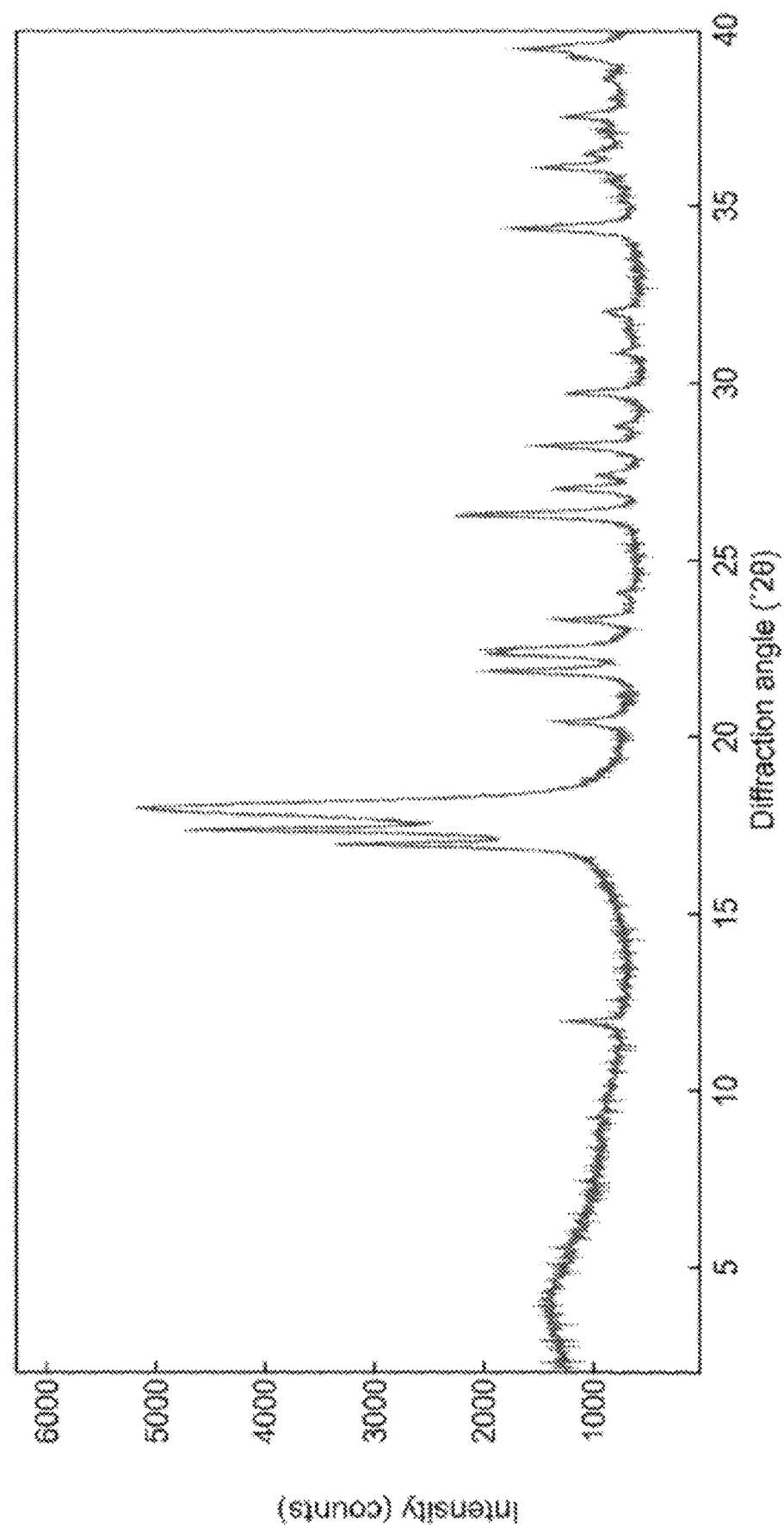
FIG. 41 provides an XRPD diffractogram of a crystalline (S)-methylone L-tartrate.

| Salt formed | Conditions | XRPD |
|---|---|---|
| Fumaric acid | Added acid to sol'n of FB in EtOAc at 50° C.; flocculent solids. SL, 50° C. | FIG. 37 |
| Fumaric acid | Added sol'n of FB in MEK to suspension of acid in MEK at 50° C.; cloudy. Stirring, 50° C., 1 d→RT | FIG. 38 |
| Gentisic acid | Added acid to sol'n of FB in EtOAc at 50° C.; tacky solids. Stirring, 50° C. | FIG. 39 |
| Hydrochloric acid | P, IPA, RT; NS. Added MTBE until turbid. Stirring, RT; solids pp'd. | FIG. 40 |
| L-tartaric | Added acid to sol'n of FB in IPA. Heated at 50° C.; some solids remained. Added MeOH at ET; clear. Stirring, 50° C.→RT. Added MTBE until turbid. Stirring, RT, 9 d; solids pp'd. | FIG. 41 |
| Sulfuric acid | P, IPA, RT; NS. Added DEE; solids initially pp'd, then clear. Stirring, RT; NS, E, RT; oil. Added DCM. Stirring, RT, 1 d; some solids. Stirred in fridge; solids pp'd. | FIG. 42 |

Notes:
FB = free base;
sol'n = solution;
EtOH = ethanol;
H$_2$O = water;
IPA = isopropanol;
IPE = di-isopropyl ether;
DEE = diethyl ether;
EtOAc = ethyl acetate;
MeOH = methanol;
ACN = acetonitrile;
THF; tetrahydrofuran;
MTBE = methyl tert-butyl ether;
MEK = methyl ethyl ketone;
CHCl$_3$ = chloroform;
SL = slurry;
E = evaporation;
P = precipitation;
NS = no solids;
RT = room/ambient temperature;
ET = elevated temperature;
pp'd = precipitated;
d = day(s)

Example 3-6: Salt Screen of (S)-Methylone with Hydrochloric Acid

Figure 36:
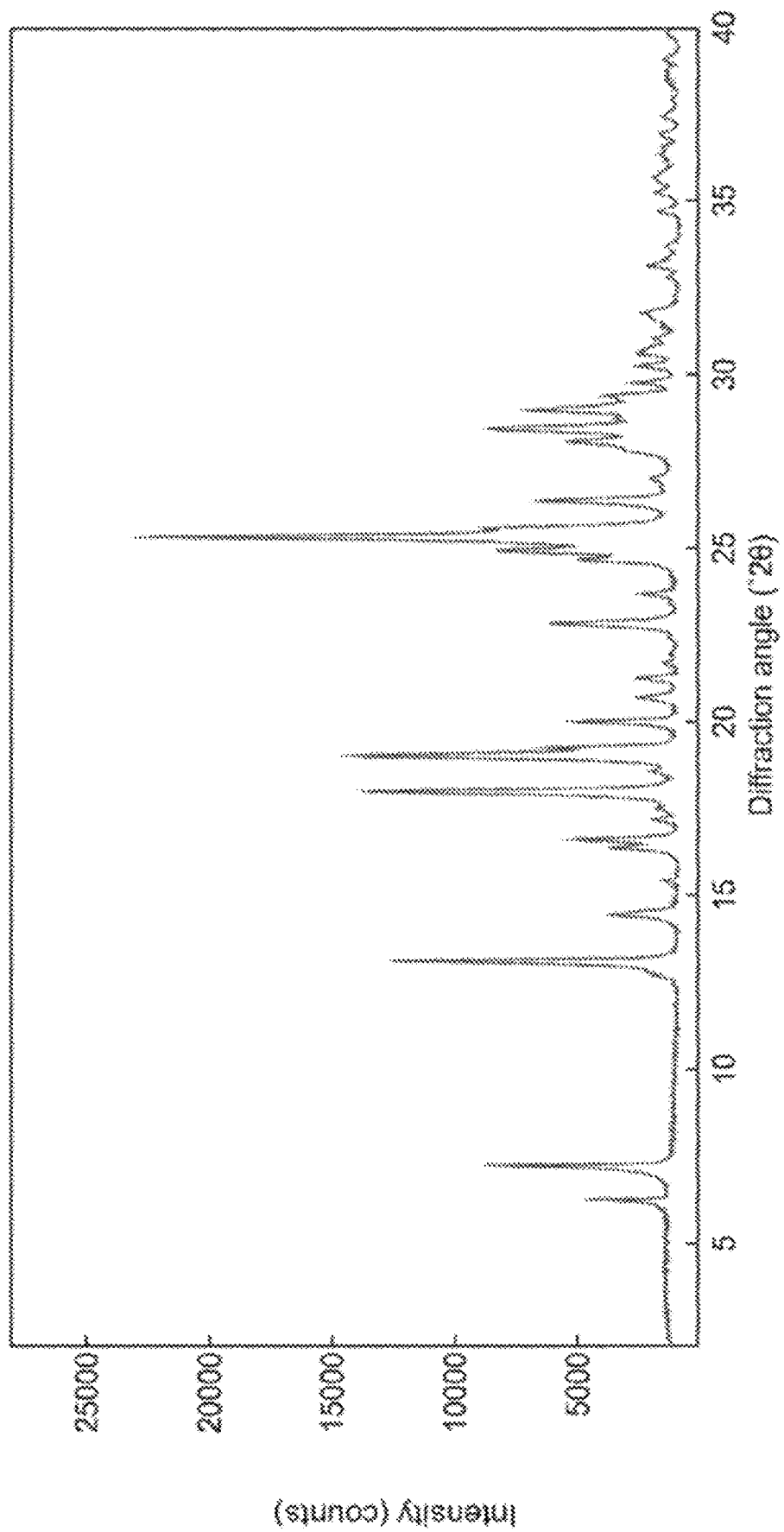
FIG. 36 provides an XRPD diffractogram of (S)-methylone·hydrochloride comprising crystalline Form A and Form C.

A mixture of new crystalline form of (S)-methylone was produced from experiments with HCl and analyzed with XRPD. XRPD analysis of a sample comprising new crystalline (S)-methylone hydrochloride Form A and Form C is shown in FIG. 36. XRPD analysis of (S)-methylone hydrochloride (mixture of Form A and Form C) (FIG. 36) showed it to be comprising crystalline with peaks at 6.2° 2-Theta, 7.2° 2-Theta, 13.1° 2-Theta, 14.4° 2-Theta, 14.5° 2-Theta, 17.2° 2-Theta, 18.0° 2-Theta, 20.0° 2-Theta, 21.3° 2-Theta, and 25.3° 2-Theta as measured with Cu Kα radiation. XRPD analysis (FIG. 36) also showed it to also have additional peaks at 19.0° 2-Theta, 24.9° 2-Theta, 25.6° 2-Theta, 28.4° 2-Theta, and 29.0° 2-Theta as measured with Cu Kα radiation. The 2-Theta peak values that are provided for the XRPD are within ±0.2° 2-Theta.

XRPD analysis of a sample comprising crystalline (S)-methylone hydrochloride Form C showed it have peaks at 6.2° 2-Theta, 14.4° 2-Theta, 17.2° 2-Theta, 19.2° 2-Theta, 20.0° 2-Theta, 21.3° 2-Theta, 24.7° 2-Theta, 24.9° 2-Theta, 28.7° 2-Theta, 29.0° 2-Theta, 29.4° 2-Theta, and 29.8° 2-Theta as measured with Cu Kα radiation.

XRPD analysis of a sample comprising crystalline (S)-methylone hydrochloride Form A only is shown in FIG. 45. XRPD analysis of (S)-methylone hydrochloride (Form A) (FIG. 45) showed it to have peaks at 7.2° 2-Theta, 13.1° 2-Theta, 14.5° 2-Theta, 16.6° 2-Theta, 18.0° 2-Theta, 19.0° 2-Theta, 25.3° 2-Theta, 25.6° 2-Theta, 26.4° 2-Theta, and 28.5° 2-Theta as measured with Cu Kα radiation.

A new crystalline form of (S)-methylone was identified from experiments with HCl. XRPD analysis of a sample comprising this new crystalline form of (S)-methylone hydrochloride Form 2 (Form B) is shown in FIG. 40. XRPD analysis of (S)-methylone hydrochloride Form 2 (Form B) (FIG. 40) showed it to have peaks at 12.6° 2-Theta, 14.0° 2-Theta, 15.8° 2-Theta, 16.1° 2-Theta, 21.5° 2-Theta, 22.2° 2-Theta, 24.2° 2-Theta, 27.5° 2-Theta, 28.2° 2-Theta, and 29.2° 2-Theta as measured with Cu Kα radiation.

Figure 42:
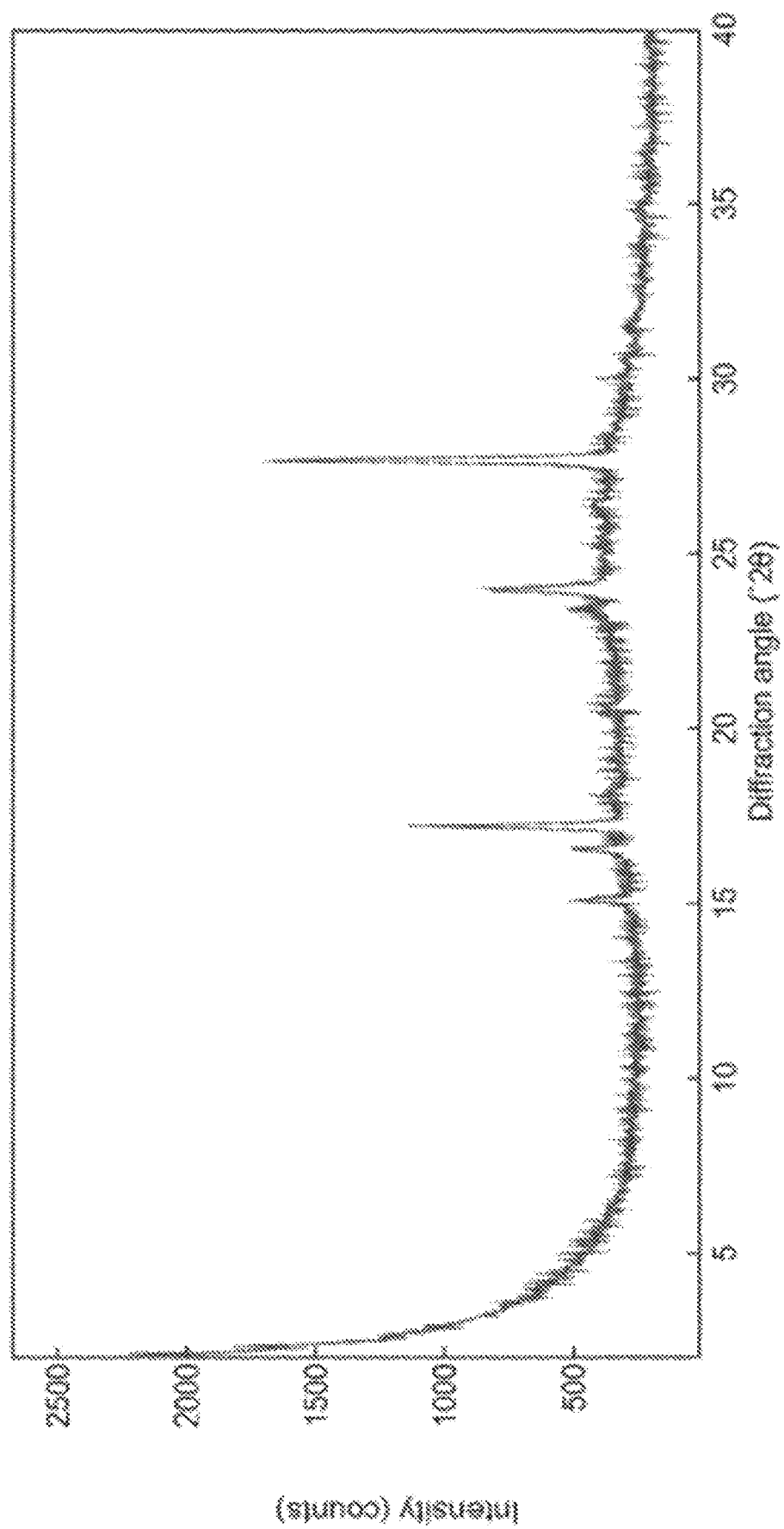
FIG. 42 illustrates an XRPD diffractogram of a crystalline prepared from (S)-methylone with sulfuric acid ($H_2SO_4$).

A new crystalline form of (S)-methylone was identified from experiments with H$_2$SO$_4$. XRPD analysis of this new crystalline form sulfate is shown in FIG. 42. Experimental conditions. P, IPA, RT; NS. Added DEE; solids initially precipitated, then clear. Stirring, RT; NS, E, RT; oil. Added DCM. Stirring, RT, 1 d; some solids. Stirred in fridge; solids precipitated.

Example 3-7: Cocrystal Screens Using Methylone HCl Racemate and (S)-Methylone HCl Cocrystal screen experiments were performed using methylone HCl racemate resulted in Forms A, Form B, or a mixture of Forms A and B. The experimental conditions and XRPDs are summarized in examples herein above.

One unique crystalline produced with (S)-methylone HCl and gentisic acid was identified. Gentisate CC1 was characterized by NMR and TGA/DSC. NMR analysis showed that it has 1:1 (S)-methylone:gentisic acid stoichiometry and is structurally intact. XRPD analysis of this new crystalline form of (S)-methylone is shown in FIGS. 43 and 44.

XRPD analysis of co-crystalline of (S)-methylone and gentisic acid (1:1 stoichiometry) (FIG. 43) showed it to be crystalline with peaks at 7.5° 2-Theta, 8.7° 2-Theta, 10.8° 2-Theta, 14.7° 2-Theta, 15.6° 2-Theta, 16.1° 2-Theta, 19.3° 2-Theta, 23.9° 2-Theta, 26.3° 2-Theta, 26.6° 2-Theta, and 27.4° 2-Theta as measured with Cu Kα radiation.

XRPD analysis of co-crystalline of (S)-methylone and gentisic acid (1:1 stoichiometry) (FIG. 44) showed it to be crystalline with peaks at 7.5° 2-Theta, 8.6° 2-Theta, 10.8° 2-Theta, 14.7° 2-Theta, 15.6° 2-Theta, 16.0° 2-Theta, 19.2° 2-Theta, 23.8° 2-Theta, 26.2° 2-Theta, 26.5° 2-Theta, 27.3° 2-Theta, and 27.5° 2-Theta as measured with Cu Kα radiation.

This co-crystal of (S)-methylone:gentisic acid (1:1 stoichiometry) was also obtained via a solution-based method. See Example 3-10. XRPD analysis of this new crystalline form of (S)-methylone obtained via the solution-based method is shown in FIG. 47.

XRPD analysis of co-crystalline of (S)-methylone and gentisic acid (1:1 stoichiometry) (FIG. 47) showed it to be crystalline with peaks at 7.6° 2-Theta, 8.7° 2-Theta, 10.8° 2-Theta, 14.7° 2-Theta, 15.6° 2-Theta, 16.1° 2-Theta, 19.3° 2-Theta, 23.9° 2-Theta, 26.3° 2-Theta, 26.6° 2-Theta, 27.0° 2-Theta, and 27.5° 2-Theta as measured with Cu Kα radiation.

The 2-Theta peak values that are provided for the XRPD are within ±0.2° 2-Theta.

Thermal data (e.g., TGA) shows a 3.8% weight loss, which is accompanied by a broad endotherm at 103° C. in the DSC thermogram. Because organic solvents were not present in the NMR spectrum, this is likely due to water and would be equivalent to approximately 0.8%.

Example 3-8: Polymorph Screen

The salts of (S)-methylone or (R)-methylone according to Example 3-5 were characterized to evaluate its physical properties using the solvents and methods similar to those mentioned in the above examples.

The information obtained is used for designing the subsequent polymorph screen. Solvents are used as a single solvent or as solvent mixtures, some containing water. The techniques used for the polymorph screen are chosen based on the solvent selected and properties of the API. The following techniques (or a combination of techniques) may be used for the polymorph screening:

- API is dissolved in a solvent or mixture of solvents, and the solvents are evaporated at different rates (slow evaporation or fast evaporation) and at different temperatures (ambient or elevated).
- API is dissolved in a solvent or mixture of solvents (at ambient temperature or an elevated temperature), and the final solution is cooled (between −78° C. to 20° C.). The cooling method can be a fast cooling (by plunging the sample to an ice bath or a dry ice/acetone bath), or slow cooling. The solids formed will be recovered by filtration and dried (air dried or vacuum dried).
- API is dissolved in a solvent or mixture of solvents, and an antisolvent is added to precipitate the salt. The solids formed will be recovered by filtration and dried (air dried or vacuum dried).
- API is added to a solvent or mixture of solvents, where the API is not fully dissolved. The slurry will be agitated at different temperatures for a number of days. The solids formed will be recovered by filtration and (air dried or vacuum dried).
- API is milled (by mechanical milling or by mortar and pestle), with a drop of solvent, or without any solvent.
- API is melted and cooled (at different cooling rates, fast and slow, and cooled to different temperatures) to obtain solids.
- API is suspended in a solvent or mixture of solvents, and the slurry is placed in a heating/cooling cycle for multiple cycles. The remaining solids after the final cooling cycle will be filtered and (air dried or vacuum dried).
- API is processed to obtain an amorphous form (by melting, milling, solvent evaporation, spray drying or lyophilization). The amorphous form will then be exposed to elevated humidity (or elevated temperature, or combination thereof), or to solvent vapors for extended period of days.
- API is exposed to elevated humidity (or elevated temperature, or combination thereof), or to solvent vapors for extended period of days.
- Two or more polymorphs of the API are mixed in a solvent or solvent systems (some solvent mixtures containing variable amount of water) to obtain a slurry, and the slurry will be agitated (at various temperatures) for an extended period of time (days). The solvent system used can be pre-saturated with the API. The final solids will be filtered and dried (air dried or vacuum dried).
- API is heated to a specific temperature and cooled (at ambient conditions or in a dry box).

The solids obtained were analyzed by XRPD to determine if they are crystalline and, if so, by DSC to see the melting point and by TG to see if they are hydrated/solvated, and by 1H NMR spectroscopy to ensure chemical integrity. KF water titration was performed on forms that are hydrated. DVS analysis was performed to evaluate hygroscopicity of the form and if hydrated form is present. In particular variable temperature analyses, including variable temperature XRPD, were performed to assess the stability of each physical form as well as its crystallinity.

Differential scanning calorimetry (DSC) thermograms are obtained using a DSC Q 100 (TA Instruments, New Castle, DE). The temperature axis and cell constant of the DSC cell are calibrated with indium (10 mg, 99.9% pure, melting point 156.6° C., heat of fusion 28.4 J/g). Samples (2.0-5.0 mg) are weighed in aluminum pans on an analytical balance. Aluminum pans without lids are used for the analysis. The samples are equilibrated at 25° C. and heated to 250-300° C. at a heating rate of 10° C./min under continuous nitrogen flow. TG analysis of the samples is performed with a Q 50(TA Instruments, New Castle, DE). Samples (2.0-5.0 mg) are analyzed in open aluminum pans under a nitrogen flow (50 mL/min) at 25° C. to 210° C. with a heating rate of 10° C./min.

The sample for moisture analysis is allowed to dry at 25° C. for up to 4 hours under a stream of dry nitrogen. The relative humidity is then increased stepwise from 10 to 90% relative humidity (adsorption scan) allowing the sample to equilibrate for a maximum of four hours before weighing and moving on to the next step. The desorption scan is measured from 85 to 0% relative humidity with the same equilibration time. The sample is then dried under a stream of dry nitrogen at 80° C. for 2 hours or until no weight loss is observed.

X-ray powder diffraction data are collected using a Miniflex Tabletop XRD system (Rigaku/MSC, The Woodlands, TX) from 5° to 45° 2θ with steps of 0.1°, and the measuring time is 1.0 second/step. All samples are ground to similar size before exposure to radiation. The powder samples are illuminated using Cu Kα radiation ($\lambda$=1.54056 Å) at 30 kV and 15 mA.

Variable temperature XRPD data are collected using a Huber Imaging Plate Guinier Camera 670 employing Ni-filtered Cu Kαi radiation ($\lambda$=1.5405981 Å) produced at 40 kV and 20 mA by a Philips PW1120/00 generator fitted with a Huber long fine-focus tube PW2273/20 and a Huber Guinier Monochromator Series 611/15. The original powder is packed into a Lindemann capillary (Hilgenberg, Germany) with an internal diameter of 1 mm and a wall thickness of 0.01 mm. The sample is heated at an average rate of 5 Kmin$^{-1}$ using a Huber High Temperature Controller HTC 9634 unit with the capillary rotation device 670.2. The temperature is held constant at selected intervals for 10 min while the sample is exposed to X-rays and multiple scans were recorded. A 2θ-range of 4.00-100.0° is used with a step size of 0.005° 2θ.

In certain embodiments wherein the solid form is a solvate, such as a hydrate, the DSC thermogram reveals endothermic transitions. In accordance with the observed DSC transitions, TGA analysis indicates stages of weight change corresponding to desolvation or dehydration and/or melting of the sample. In the case of hydrates, these results are in harmony with Karl Fischer titration data which indicate the water content of the sample.

The moisture sorption profile of a sample can be generated to assess the stability of a solid form is stable over a range of relative humidity. In certain embodiments, the change in moisture content over 10.0 to 95.0% relative humidity is small. In other embodiments the change in moisture content over 10.0 to 95.0% relative humidity is reversible.

In certain embodiments, the XRPD pattern of a sample of solid form indicates that the sample has a well-defined crystal structure and a high degree of crystallinity.

Example 3-9: Chiral Synthesis of (S)-Methylone

This example describes the synthesis of the active pharmaceutical ingredient (API), (S)-methylone, in homochiral fashion.

Materials and Methods

Chemicals were purchased primarily from Sigma-Aldrich (Merck Life Science U.K. Ltd, The Old Brickyard, New Rd, Gillingham, Dorset SP8 4XT, U.K.); Alfa Aesar, Heysham, Morecambe, Lancashire LA3 2XY and were used without further purification. Solvents were purchased as anhydrous. Petrol (pet ether) was the alkane fraction boiling between 40-60° C.

TLC was carried out using aluminum plates pre-coated with silica gel (Kieselgel 60 F254, 0.2 mm, Merck, Darmstadt, Germany). Visualization was by UV light.

$^1$H NMR spectra were recorded on a Bruker Avance BVT3200 spectrometer using the residual proton(s) in the deuterated solvents as internal standards.

HPLC analyses were performed with a Shimadzu Prominence instrument (Shimadzu UK Ltd., Unit TA Mill Court, Featherstone Road, Milton Keynes MK12 5RD, U.K.) with diode array detection and a Kinetex EVO C18, 5 µm, 250 mm×4.6 mm column. Chiral HPLC analysis were performed using a Phenomenex Lux Cellulose 2, 250 mm×4.6 mm column.

For separating (S)-methylone and (R)-methylone, the following conditions were used:

| Parameter | Conditions |
|---|---|
| Column: | Phenomenex Lux Cellulose 2, 250 mm × 4.6 mm |
| Flow rate: | 1.5 mL/min |
| Detection: | 275 nm |
| Column Temperature | 30° C. |
| Mobile Phase: | A: n-Hexane + 0.1 % diethylamine. |
| | B: Ethanol + 0.1 % diethylamine |

| Time (min) | % A | % B |
|---|---|---|
| Isocratic | 0 | 99.5 | 0.5 |
| | 90 | 99.5 | 0.5 |

Under these conditions (S)-methylone had a retention time of ~55 min, while the retention time of (R)-methylone was 80 min.

LC-MS analyses were performed on a Shimadzu 2020 instrument operating in positive or negative ESI mode with UV detection at 254 nm.

Automated chromatography was performed on a Biotage Selekt purification system (Biotage GB Limited, Distribution Way, Dyffryn Business Park, Ystrad Mynach, Hengoed, Mid Glamorgan CF82 7TS, Wales).

Synthesis of (S)-1-(Benzo[d][1,3]dioxol-5-yl)-2-(methylamino)propan-1-one Hydrochloride [(S)-Methylone Hydrochloride]

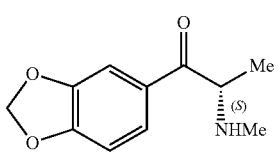

Synthesis of (S)-methylone from the Weinreb amide of Boc N-methyl-L-alanine

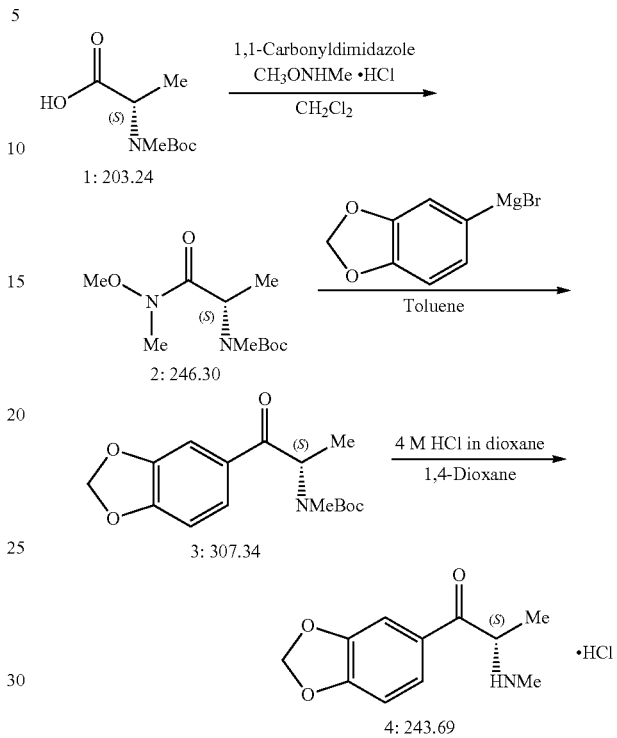

Scheme 1: Synthesis of (S)-methylone hydrochloride via a Weinreb amide

Step 1: Synthesis of tert-butyl (S)-(1-(methoxy(methyl)amino)-1-oxopropan-2-yl)(methyl)carbamate (2)

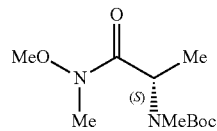

To a solution of N-methyl-N-Boc-L-alanine (5.00 g, 24.6 mmol) in anhydrous dichloromethane (125 mL) under a nitrogen atmosphere was added 1,1-carbonyldiimidazole (4.39 g, 27.1 mmol) and the mixture was stirred at room temperature for 40 min. N,O-dimethylhydroxylamine hydrochloride (2.64 g, 27.1 mmol) was added in one portion and the suspension was stirred at room temperature overnight. The reaction was quenched with 1 M hydrochloric acid (100 mL) and the layers were separated. The aqueous layer was extracted with dichloromethane (2×70 mL) and the combined organics were washed with water (100 mL), saturated sodium bicarbonate (100 mL), saturated brine (100 mL), dried (MgSO$_4$) and concentrated to give a colorless oil. This material was purified by normal phase chromatography, eluting with 0 to 100% ethyl acetate in petrol to give tert-butyl (S)-(1-(methoxy(methyl)amino)-1-oxopropan-2-yl)(methyl)carbamate (5.50 g, 91%) as a colorless oil.

$^1$H NMR: (CDCl$_3$) δ 5.17 (m, 0.64H, α-CH), 4.88 (m, 0.36H, α-CH), 3.70 (s, 1.92H, OMe), 3.66 (s, 1.08H, OMe), 3.14 (s, 3H, NMe amide), 2.82 (s, 3H, NMe), 1.42 (s, 9H, t-Bu), 1.27 (d, 3H, J=7.1 Hz, Me). $^{13}$C NMR: (CDCl$_3$) δ 173.0, 155.8, 155.1, 80.1, 79.7, 61.3, 51.7, 50.0, 32.4, 29.9, 28.5, 14.7. TLC: $R_f$=0.49 (ethyl acetate-petrol, 3:7 v/v) Step 2: Synthesis of tert-butyl (S)-(1-(benzo[d][1,3]dioxol-5-yl)-1-oxopropan-2-yl) (methyl)carbamate (3)

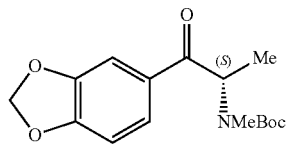

To a solution of tert-butyl (S)-(1-(methoxy(methyl) amino)-1-oxopropan-2-yl)(methyl)carbamate (4.10 g, 16.2 mmol) in anhydrous toluene (50 mL) in an oven-dried flask at 0° C. was added 3,4-(methylenedioxy)phenylmagnesium bromide (0.5 M in THF, 67.0 mL, 33.3 mmol) and the mixture was stirred at 0° C. under a nitrogen atmosphere for 2 h. The reaction was quenched with saturated NH$_4$Cl (50 mL) and extracted with ethyl acetate (3×50 mL). The combined organics were washed with saturated brine (100 mL), dried (MgSO$_4$) and concentrated to give a pale-yellow oil. This material was purified by normal phase chromatography, eluting with 0 to 100% diethyl ether in petrol to give tert-butyl (S)-(1-(benzo[d][1,3]dioxol-5-yl)-1-oxopropan-2-yl)(methyl)carbamate (4.67 g, 94% yield) as a white solid. $^1$H NMR: (CDCl$_3$) δ 7.65 (d, 0.64H, J=8.0 Hz, ArH), 7.53 (d, 0.36H, J=7.8 Hz, ArH), 7.45 (s, 0.64H, ArH), 7.39 (s, 0.36H, ArH), 6.80 (d, 1H, J=8.2 Hz, ArH), 6.01 (s, 2H, CH$_2$), 5.61 (q, 0.64H, J=6.7 Hz, α-CH), 5.16 (q, 0.36H, J=6.3 Hz, α-CH), 2.73 (s, 1.08H, NMe), 2.60 (s, 1.92H, NMe), 1.44 (s, 9H, t-Bu), 1.32 (m, 3H, Me). $^{13}$C NMR: (CDCl$_3$) δ 198.1, 156.0, 152.4, 148.6, 130.5, 125.4, 124.8, 108.8, 108.5, 102.3, 81.2, 80.8, 56.8, 54.6, 30.7, 29.9, 28.9, 14.4, 14.0. TLC: $R_f$=0.34 (diethyl ether-petrol, 2:8 v/v)
Step 3: Synthesis of (S)-1-(benzo[d][1,3]dioxol-5-yl)-2-(methylamino)propan-1-one hydrochloride (4)

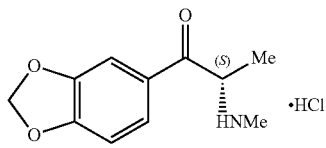

To a solution of tert-butyl (S)-(1-(benzo[d][1,3]dioxol-5-yl)-1-oxopropan-2-yl)(methyl)carbamate (4.46 g, 14.5 mmol) in 1,4-dioxane (45 mL) was added 4 M hydrogen chloride in anhydrous 1,4-dioxane (21.8 mL, 87.2 mmol) and the mixture was stirred at room temperature for 8 h (a white precipitate appeared after 30 min). The white precipitate was collected by suction filtration to give (S)-1-(benzo [d][1,3]dioxol-5-yl)-2-(methylamino)propan-1-one hydrochloride (3.27 g, 93%) as a white solid. $^1$H NMR: (CD$_3$OD) δ 7.70 (dd, 1H, J=8.2 and 1.8 Hz, ArH), 7.49 (d, 1H, J=1.7 Hz, ArH), 7.01 (d, 1H, J=8.2 Hz, ArH), 6.12 (s, 2H, CH$_2$), 5.00 (q, 1H, J=7.2 Hz, α-CH), 2.75 (s, 3H, NMe), 1.56 (d, 3H, J=7.2 Hz, Me). $^{13}$C NMR: (CDCl$_3$) δ 195.0, 155.0, 150.3, 128.7, 127.1, 109.5, 108.9, 104.0, 60.4, 31.7, 16.6. Chiral HPLC ratio of the hydrochloride salt (S/R)-96.8:3.8
Crystallization of (S)-methylone hydrochloride
Crystallization of (S)-methylone hydrochloride (50 mg, 92.4% ee) using vapor diffusion with methanol (1 mL) and methyl tert-butyl ether (MTBE) (5 mL) gave 39 mg of colorless needles (97.2% ee).

Crystallization of (S)-methylone hydrochloride (1.50 g, 92.4% ee) using vapor diffusion with methanol (20 mL) and MTBE (35 mL) gave 0.53 g of colorless needles (97.0% ee). The filtrate was concentrated to give an off-white solid (0.92 g). This material was crystallized as above using vapor diffusion with methanol (10 mL) and MTBE (20 mL), with the set-up being left at ~ 5° C. overnight. The solvent was decanted and the crystals were washed with cold MTBE (3×10 mL) to give (S)-methylone hydrochloride (460 mg, 96.6% ee) as colorless needles.

Synthesis of racemic (rac.) methylone was performed to prepare optically active methylone compositions via resolution, for example, using diastereomeric salt formation with chiral acids.

Example 3-10: Synthesis of Co-Crystal of (S)-Methylone HCl and Gentisic Acid

To a PEEK grinding cup was added 40.5 mg of S-methylone HCl, 25.8 mg of gentisic acid, 20 µL of wet ethyl acetate, and a stainless-steel ball. The internal volume of the grinding cup is about 2 mL. The grinding cup was placed on a Retsch mill and milled at 25 Hz for 30 minutes. Co-crystal of (S)-methylone HCl and gentisic acid (1:1 stoichiometry) was obtained. XRPD analysis of this new crystalline form of (S)-methylone is shown in FIGS. 43 and 44.

Alternatively, co-crystal of (S)-methylone HCl and gentisic acid (1:1 stoichiometry) was also obtained via a solution-based method.

To a wet ethyl acetate solution that was pre-saturated with gentisic acid, was added (S)-methylone HCl until solids persisted. The mixture was seeded with a small amount of gentisic acid CC1 and slurried at ambient temperature for one week.

The sample was then centrifuged and the mother liquor was decanted. Isolated solids were briefly dried with an air purge and analyzed by XRPD. XRPD analysis of this new crystalline form of (S)-methylone obtained from this solution-based method is shown in FIG. 47.

Example 3-11: Chiral Synthesis of (R)-Methylone

This example describes the synthesis of the active pharmaceutical ingredient (API), (R)-methylone, in homochiral fashion.
Materials and Methods
Chemicals were purchased primarily from Sigma-Aldrich (Merck Life Science U.K. Ltd, The Old Brickyard, New Rd, Gillingham, Dorset SP8 4XT, U.K.); Alfa Aesar, Heysham, Morecambe, Lancashire LA3 2XY and were used without further purification. Solvents were purchased as anhydrous. Petrol (pet ether) was the alkane fraction boiling between 40-60° C.

TLC was carried out using aluminum plates pre-coated with silica gel (Kieselgel 60 F254, 0.2 mm, Merck, Darmstadt, Germany). Visualization was by UV light.

$^1$H NMR spectra were recorded on a Bruker Avance BVT3200 spectrometer using the residual proton(s) in the deuterated solvents as internal standards.

HPLC analyses were performed with a Shimadzu Prominence instrument (Shimadzu UK Ltd., Unit 1A Mill Court, Featherstone Road, Milton Keynes MK12 5RD, U.K.) with diode array detection and a Kinetex EVO C18, 5 µm, 250 mm×4.6 mm column. Chiral HPLC analysis were performed using a Phenomenex Lux Cellulose 2, 250 mm×4.6 mm column.

For separating (S)-methylone and (R)-methylone, the following conditions were used:

| Parameter | Conditions | | |
|---|---|---|---|
| Column: | Phenomenex Lux Cellulose 2, 250 mm × 4.6 mm | | |
| Flow rate: | 1.5 mL/min | | |
| Detection: | 275 nm | | |
| Column Temperature | 30° C. | | |
| Mobile Phase: | A: n-Hexane + 0.1 % diethylamine. | | |
| | B: Ethanol + 0.1 % diethylamine | | |
| | Time (min) | % A | % B |
| Isocratic | 0 | 99.5 | 0.5 |
| | 90 | 99.5 | 0.5 |

Under these conditions (S)-methylone had a retention time of ~55 min, while the retention time of (R)-methylone was 80 min.

LC-MS analyses were performed on a Shimadzu 2020 instrument operating in positive or negative ESI mode with UV detection at 254 nm.

Automated chromatography was performed on a Biotage Selekt purification system (Biotage GB Limited, Distribution Way, Dyffryn Business Park, Ystrad Mynach, Hengoed, Mid Glamorgan CF82 7TS, Wales).

Synthesis of (R)-1-(Benzo[d][1,3]dioxol-5-yl)-2-(methylamino)propan-1-one Hydrochloride [(R)-Methylone Hydrochloride]

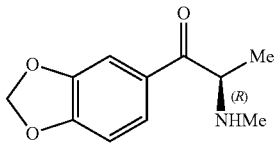

Synthesis of (R)-methylone from the Weinreb amide of Boc N-methyl-L-alanine

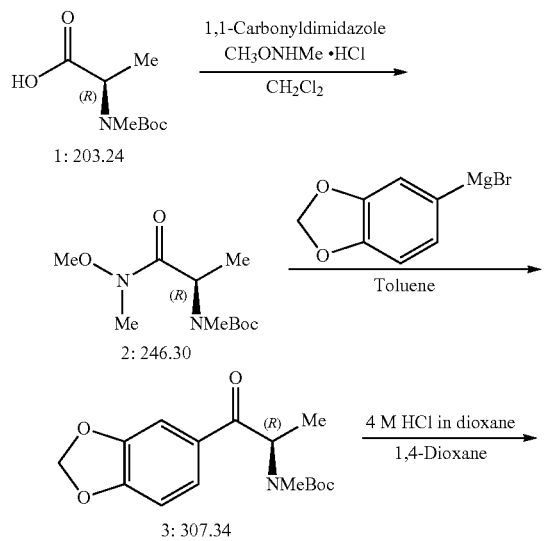

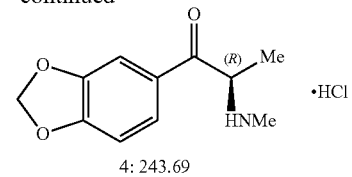

4: 243.69

Scheme 1: Synthesis of (R)-methylone hydrochloride via a Weinreb amide

Step 1: Synthesis of tert-butyl (R)-(1-(methoxy(methyl)amino)-1-oxopropan-2-yl)(methyl)carbamate (2)

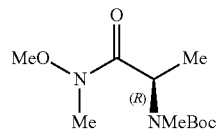

To a solution of N-methyl-N-Boc-D-alanine (5.00 g, 24.6 mmol) in anhydrous dichloromethane (125 mL) under a nitrogen atmosphere is added 1,1-carbonyldiimidazole (4.39 g, 27.1 mmol) and the mixture is stirred at room temperature for 40 min. N,O-dimethylhydroxylamine hydrochloride (2.64 g, 27.1 mmol) is added in one portion and the suspension is stirred at room temperature overnight. The reaction is quenched with 1 M hydrochloric acid (100 mL) and the layers are separated. The aqueous layer is extracted with dichloromethane (2×70 mL) and the combined organics are washed with water (100 mL), saturated sodium bicarbonate (100 mL), saturated brine (100 mL), dried (MgSO$_4$) and concentrated to give a colorless oil. This material is purified by normal phase chromatography, eluting with 0 to 100% ethyl acetate in petrol to give tert-butyl (R)-(1-(methoxy(methyl)amino)-1-oxopropan-2-yl)(methyl)carbamate (5.50 g, 91%) as a colorless oil. $^1$H NMR: (CDCl$_3$) δ 5.17 (m, 0.64H, α-CH), 4.88 (m, 0.36H, α-CH), 3.70 (s, 1.92H, OMe), 3.66 (s, 1.08H, OMe), 3.14 (s, 3H, NMe amide), 2.82 (s, 3H, NMe), 1.42 (s, 9H, t-Bu), 1.27 (d, 3H, J=7.1 Hz, Me). $^{13}$C NMR: (CDCl$_3$) δ 173.0, 155.8, 155.1, 80.1, 79.7, 61.3, 51.7, 50.0, 32.4, 29.9, 28.5, 14.7. TLC: R$_f$=0.49 (ethyl acetate-petrol, 3:7 v/v)

Step 2: Synthesis of tert-butyl (R)-(1-(benzo[d][1,3]dioxol-5-yl)-1-oxopropan-2-yl) (methyl)carbamate (3)

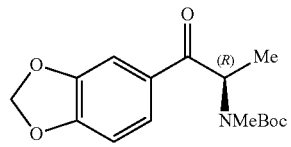

To a solution of tert-butyl (R)-(1-(methoxy(methyl)amino)-1-oxopropan-2-yl)(methyl)carbamate (4.10 g, 16.2 mmol) in anhydrous toluene (50 mL) in an oven-dried flask at 0° C. is added 3,4-(methylenedioxy)phenylmagnesium bromide (0.5 M in THF, 67.0 mL, 33.3 mmol) and the mixture is stirred at 0° C. under a nitrogen atmosphere for 2 h. The reaction is quenched with saturated NH$_4$Cl (50 mL) and extracted with ethyl acetate (3×50 mL). The combined organics are washed with saturated brine (100 mL), dried (MgSO$_4$) and concentrated to give a pale-yellow oil. This material is purified by normal phase chromatography, eluting with 0 to 100% diethyl ether in petrol to give tert-butyl (R)-(1-(benzo[d][1,3]dioxol-5-yl)-1-oxopropan-2-yl)(methyl)carbamate (4.67 g, 94% yield) as a white solid. $^1$H NMR: (CDCl$_3$) δ 7.65 (d, 0.64H, J=8.0 Hz, ArH), 7.53 (d, 0.36H, J=7.8 Hz, ArH), 7.45 (s, 0.64H, ArH), 7.39 (s, 0.36H, ArH), 6.80 (d, 1H, J=8.2 Hz, ArH), 6.01 (s, 2H, CH$_2$), 5.61 (q, 0.64H, J=6.7 Hz, α-CH), 5.16 (q, 0.36H, J=6.3 Hz, α-CH), 2.73 (s, 1.08H, NMe), 2.60 (s, 1.92H, NMe), 1.44 (s, 9H, t-Bu), 1.32 (m, 3H, Me). $^{13}$C NMR: (CDCl$_3$) δ 198.1, 156.0, 152.4, 148.6, 130.5, 125.4, 124.8, 108.8, 108.5, 102.3, 81.2, 80.8, 56.8, 54.6, 30.7, 29.9, 28.9, 14.4, 14.0. TLC: R$_f$=0.34 (diethyl ether-petrol, 2:8 v/v)

Step 3: Synthesis of (R)-1-(benzo[d][1,3]dioxol-5-yl)-2-(methylamino)propan-1-one hydrochloride (4)

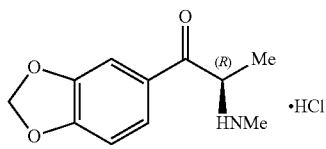

To a solution of tert-butyl (R)-(1-(benzo[d][1,3]dioxol-5-yl)-1-oxopropan-2-yl)(methyl)carbamate (4.46 g, 14.5 mmol) in 1,4-dioxane (45 mL) is added 4 M hydrogen chloride in anhydrous 1,4-dioxane (21.8 mL, 87.2 mmol) and the mixture is stirred at room temperature for 8 h (a white precipitate appeared after 30 min). The white precipitate is collected by suction filtration to give (R)-1-(benzo[d][1,3]dioxol-5-yl)-2-(methylamino)propan-1-one hydrochloride (3.27 g, 93%) as a white solid. $^1$H NMR: (CD$_3$OD) δ 7.70 (dd, 1H, J=8.2 and 1.8 Hz, ArH), 7.49 (d, 1H, J=1.7 Hz, ArH), 7.01 (d, 1H, J=8.2 Hz, ArH), 6.12 (s, 2H, CH$_2$), 5.00 (q, 1H, J=7.2 Hz, α-CH), 2.75 (s, 3H, NMe), 1.56 (d, 3H, J=7.2 Hz, Me). $^{13}$C NMR: (CDCl$_3$) δ 195.0, 155.0, 150.3, 128.7, 127.1, 109.5, 108.9, 104.0, 60.4, 31.7, 16.6.

Crystallization of (R)-Methylone Hydrochloride

Crystallization of (R)-methylone hydrochloride (50 mg, 92.4% ee) using vapor diffusion with methanol (1 mL) and methyl tert-butyl ether (MTBE) (5 mL) gives 39 mg of colorless needles (97.2% ee).

Crystallization of (R)-methylone hydrochloride (1.50 g, 92.4% ee) using vapor diffusion with methanol (20 mL) and MTBE (35 mL) gives 0.53 g of colorless needles (97.0% ee). The filtrate is concentrated to give an off-white solid (0.92 g). This material is crystallized as above using vapor diffusion with methanol (10 mL) and MTBE (20 mL), with the set-up being left at ~ 5° C. overnight. The solvent is decanted and the crystals are washed with cold MTBE (3×10 mL) to give (R)-methylone hydrochloride (460 mg, 96.6% ee) as colorless needles.

Example 3-12: Optical Resolution of rac.-methylone

A variety of chiral acid salts and solvents were screened in combination to determine whether they would be suitable for the resolution of methylone enantiomers. Representative results are provided in Tables 11-14.

TABLE 11

| (MeOH solvent) | | | | |
|---|---|---|---|---|
| rac-Methylone | Resolving Agent | Solvent | Method | Comments Ratio S/R |
| 99 mg (0.48 mmol) | (+)-Dibenzoyl-D-tartaric acid 172 mg (0.48 mmol) | MeOH (1.0 mL) | Slow cooling (55° C. + R.T. O/N) | No crystals |
| 98 mg (0.47 mmol) | (−)-Dibenzoyl-L-tartaric acid 170 mg (0.47 mmol) | MeOH (1.0 mL) | Slow cooling (55° C. + R.T. O/N) | No crystals |
| 109 mg (0.53 mmol) | (S)-(+)-Mandelic acid 80 mg (0.53 mmol) | MeOH (1.0 mL) | Slow cooling (55° C. + R.T. O/N) | No crystals |
| 110 mg (0.53 mmol) | (R)-(−)-Mandelic acid 80 mg (0.53 mmol) | MeOH (1.0 mL) | Slow cooling (55° C. + R.T. O/N) | No crystals |
| 106 mg (0.51 mmol) | L-(+)-Tartaric acid 77 mg (0.51 mmol) | MeOH (1.0 mL) | Slow cooling (55° C. + R.T. O/N) | No crystals |
| 95 mg (0.46 mmol) | D-(−)-Tartaric acid 69 mg (0.46 mmol) | MeOH (1.0 mL) | Slow cooling (55° C. + R.T. O/N) | No crystals |

TABLE 12

| (EtOAc-petrol solvent) | | | | |
|---|---|---|---|---|
| rac-Methylone | Resolving Agent | Solvent | Method | Comments Ratio S/R |
| 53 mg (0.26 mmol) | (S)-(+)-Mandelic acid 39 mg (0.26 mmol) | EtOAc/Petrol (1.9 mL/4.5 mL) | Vapor diffusion | 36:64 |
| 57 mg (0.28 mmol) | (R)-(−)-Mandelic acid 42 mg (0.28 mmol) | EtOAc/Petrol (1.9 mL/4.5 mL) | Vapor diffusion | 50:50 |

TABLE 13

(EtOAc-EtOH solvent)

| rac-Methylone | Resolving Agent | Solvent | Method | Comments Ratio S/R |
|---|---|---|---|---|
| 60 mg (0.29 mmol) | R-(−)-Camphor-10-sulfonic acid 67 mg (0.29 mmol) | EtOAc/ EtOH/Petrol (1 mL/ 0.1 mL/5.0 mL) | Vapor diffusion | 51.2:48.8 (solid after 24 h) 38.8:61.2 (liquid after 5 days) 49.3:50.7 (solid after 5 days) |
| 60 mg (0.29 mmol) | S-(+)-Camphor-10-sulfonic acid 67 mg (0.29 mmol) | EtOAc/ EtOH/Petrol (1 mL/ 0.1 mL/5.0 mL) | Vapor diffusion | 43.5:56.5 (solid after 24 h) 70.7:29.3 (liquid after 5 days) 53.0:47.0 (solid after 5 days) |

TABLE 14

(various solvents)

| rac-Methylone | Resolving Agent | Solvent | Method | Comments Ratio S/R |
|---|---|---|---|---|
| 25 mg (0.12 mmol) | (+)-Dibenzoyl-D-tartaric acid 43 mg (0.12 mmol) | Ethanol (2 mL) | Vapor diffusion | No crystals |
| 25 mg (0.12 mmol) | (+)-Dibenzoyl-D-tartaric acid 43 mg (0.12 mmol) | 2-Propanol (2 mL) | Vapor diffusion | No crystals |
| 25 mg (0.12 mmol) | (−)-Dibenzoyl-L-tartaric acid 43 mg (0.12 mmol) | Ethanol (2 mL) | Vapor diffusion | No crystals |
| 25 mg (0.12 mmol) | (−)-Dibenzoyl-L-tartaric acid 43 mg (0.12 mmol) | 2-Propanol (2 mL) | Vapor diffusion | No crystals |
| 25 mg (0.12 mmol) | (S)-(+)-Mandelic acid 18 mg (0.12 mmol) | EtOAc (2 mL) | Vapor diffusion | 47.9:52.1 |
| 25 mg (0.12 mmol) | (S)-(+)-Mandelic acid 18 mg (0.12 mmol) | Ethanol (2 mL) | Vapor diffusion | No crystals |
| 25 mg (0.12 mmol) | (S)-(+)-Mandelic acid 18 mg (0.12 mmol) | 2-Propanol (2 mL) | Vapor diffusion | No crystals |
| 25 mg (0.12 mmol) | (S)-(+)-Mandelic acid 18 mg (0.12 mmol) | Dimethyl carbonate (2 mL) | Vapor diffusion | 13.1:86.9 (solid) 80.3:19.7 (filtrate) |
| 25 mg (0.12 mmol) | (R)-(−)-Mandelic acid 18 mg (0.12 mmol) | EtOAc (2 mL) | Vapor diffusion | 58.9:41.1 |
| 25 mg (0.12 mmol) | (R)-(−)-Mandelic acid 18 mg (0.12 mmol) | Ethanol (2 mL) | Vapor diffusion | No crystals |
| 25 mg (0.12 mmol) | (R)-(−)-Mandelic acid 18 mg (0.12 mmol) | 2-Propanol (2 mL) | Vapor diffusion | No crystals |
| 25 mg (0.12 mmol) | (R)-(−)-Mandelic acid 18 mg (0.12 mmol) | Dimethyl carbonate (2 mL) | Vapor diffusion | No crystals |
| 25 mg (0.12 mmol) | L-(+)-Tartaric acid 18 mg (0.12 mmol) | Ethanol (2 mL) | Vapor diffusion | No crystals |
| 25 mg (0.12 mmol) | D-(−)-Tartaric acid 18 mg (0.12 mmol) | Ethanol (2 mL) | Vapor diffusion | No crystals |
| 25 mg (0.12 mmol) | R-(−)-Camphor-10-sulfonic acid 28 mg (0.12 mmol) | EtOAc (2 mL) | Vapor diffusion | 49.6:50.4 |
| 25 mg (0.12 mmol) | R-(−)-Camphor-10-sulfonic acid 28 mg (0.12 mmol) | Ethanol (2 mL) | Vapor diffusion | No crystals |
| 25 mg (0.12 mmol) | R-(−)-Camphor-10-sulfonic acid 28 mg (0.12 mmol) | 2-Propanol (2 mL) | Vapor diffusion | No crystals |
| 25 mg (0.12 mmol) | R-(−)-Camphor-10-sulfonic acid 28 mg (0.12 mmol) | Dimethyl carbonate (2 mL) | Vapor diffusion | 66.3:33.7 |
| 25 mg (0.12 mmol) | S-(+)-Camphor-10-sulfonic acid 28 mg (0.12 mmol) | EtOAc (2 mL) | Vapor diffusion | 49.0:51.0 |
| 25 mg (0.12 mmol) | S-(+)-Camphor-10-sulfonic acid 28 mg (0.12 mmol) | Ethanol (2 mL) | Vapor diffusion | No crystals |
| 25 mg (0.12 mmol) | S-(+)-Camphor-10-sulfonic acid 28 mg (0.12 mmol) | 2-Propanol (2 mL) | Vapor diffusion | No crystals |

TABLE 14-continued (various solvents)

| rac-Methylone | Resolving Agent | Solvent | Method | Comments Ratio S/R |
|---|---|---|---|---|
| 25 mg (0.12 mmol) | S-(+)-Camphor-10-sulfonic acid 28 mg (0.12 mmol) | Dimethyl carbonate (2 mL) | Vapor diffusion | No crystals |

Based on the results set forth in Tables 10-13, resolution efforts were scaled up using optically active mandelic acid to selectively crystallize one methylone enantiomer over the other.

Example 3-13: Diastereomeric Salt Formation with (R)-(−)-Mandelic Acid or (S)-(+)-Mandelic Acid General Procedure Via Precipitation To a stirred solution of rac.-methylone 3 (1.0 equiv.) in dimethyl carbonate was added the corresponding mandelic acid (1.0 equiv.) in a glass test tube. After addition of the acid, the initial suspension became a homogeneous solution within seconds, with formation of a white precipitate observed shortly thereafter. The suspension was stirred for 10 min at room temperature. The precipitate was collected by Buchner filtration.

Step 1: Diastereomeric Salt Formation Via Precipitation

To a stirred solution of rac.-methylone 3 (6.44 g, 31.1 mmol) in dimethyl carbonate (250 mL) was added the corresponding mandelic acid (4.73 g, 31.1 mmol) in a glass test tube. After addition of the acid, the initial suspension became a homogeneous solution within seconds, with formation of a white precipitate observed shortly thereafter. The suspension was stirred for 10 min at room temperature. In the case of using (R)-(−)-mandelic acid, the precipitate was collected by Buchner filtration to give 5.85 g of mandelate salt as a white solid (chiral HPLC ratio 83.5:16.5 (S):(R)). An orange gummy solid (5.66 g, chiral HPLC ratio 9.6:90.4 (S):(R)) was isolated from the filtrate after concentration. Accordingly, (R)-(−)-mandelic acid, and its enantiomer can be used to selectively isolate either methylone enantiomer over the other.

Step 2: First Trituration of the Diastereomeric Salt

The mandelate salt (5.85 g, chiral HPLC Ratio 83.5:16.5) was stirred vigorously in dimethyl carbonate (100 mL) giving the mandelate salt as a white solid (5.16 g, chiral HPLC ratio 95.0:5.0). An orange gummy solid (0.86 g, chiral HPLC ratio 18.4:81.6) was isolated from the filtrate after concentration.

Step 3: Second Trituration of the Diastereomeric Salt

A second trituration was carried out on the mandelate salt (5.16 g, chiral HPLC Ratio 95.0:5.0) in dimethyl carbonate (100 mL) giving the mandelate salt (4.86 g, chiral HPLC ratio 96.7:3.3) as a white solid.

Step 4: Free Base Release

The mandelate salt (4.86 g, chiral HPLC ratio 96.7:3.3) was stirred in a 1.0 M aqueous sodium carbonate solution (150 mL) for 5 min at room temperature. The organics were extracted into ethyl acetate (3×50 mL). The combined organics extracts were washed with saturated brine (50 mL), dried ($Na_2SO_4$) and concentrated to give methylone 3 (free base, 2.85 g) as a pale-yellow oil.

Step 5: Diastereomeric Salt Formation Via Precipitation

To a stirred solution of methylone 3 (free base, 2.85 g, 13.8 mmol, 1.0 equiv.) in dimethyl carbonate (75 mL) was added (R)-(−)-mandelic acid (2.09 g, 13.8 mmol, 1.0 equiv.) in a glass test tube. A white precipitate formed seconds after addition of the acid. The suspension was stirred for 10 min at room temperature to give the mandelate salt (4.49 g, chiral HPLC ratio 98.8:1.2 (S):(R)) as a white solid. This experiment was initially started with a solution of methylone 3 (free base) in dimethyl carbonate (50 mL). However, upon formation of the white precipitate, the suspension ceased stirring. Extra dimethyl carbonate (25 mL) was required to resume the stirring].

Step 6: Free Base Release

The mandelate salt (4.49 g, chiral HPLC ratio 98.8:1.2) was stirred in a 1.0 M sodium carbonate aqueous solution (200 mL) for 5 min at room temperature. The organics were extracted into ethyl acetate (3×50 mL). The combined organics extracts were washed with saturated brine (50 mL), dried ($Na_2SO_4$) and concentrated to give methylone 3 (free base, 2.63 g) as a colorless oil.

Step 7: Methylone Hydrochloride Formation

To methylone 3 (free base, 2.63 g, 12.7 mmol, 1.0 equiv.) in anhydrous diethyl ether (190 mL) was added hydrogen chloride (2.0 M solution in diethyl ether) (19.0 mL, 38.1 mmol, 3.0 equiv.) slowly under nitrogen at room temperature. A white precipitate formed immediately. The dense white suspension was vigorously stirred for 15 min to give methylone hydrochloride (2.90 g, 94% yield) as a white solid (chiral HPLC ratio 98.5:1.5).

Example 3-14: Synthesis of rac.-methylone

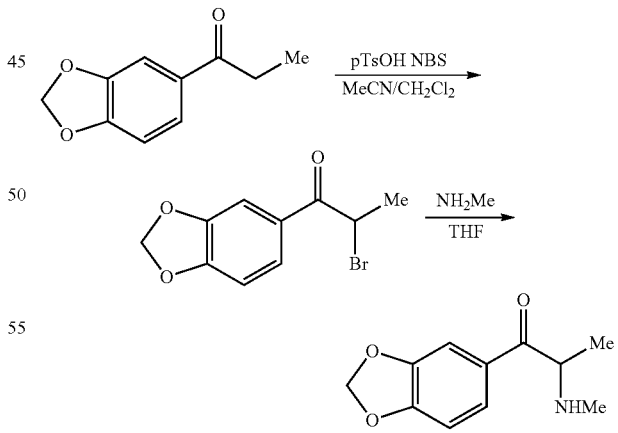

To a solution of 1-(benzo[d][1,3]dioxol-5-yl)propan-1-one (20.0 g, 112 mmol) in MeCN (150 mL) and DCM (38 mL) under an atmosphere of $N_2$ was added p-toluenesulfonic acid hydrate (4.27 g, 22 mmol) and N-bromosuccinimide (29.9 g, 168 mmol). The mixture was stirred in the dark at 40° C. After completion of the reaction, the mixture was cooled to rt, quenched with sat. aqueous $NaHCO_3$ (200 mL)

and extracted with Et₂O (3×100 mL). The combined organic layers were stirred vigorously with 10% aqueous Na₂S2O3 (100 mL) for 5 min and the layers were separated. The organic layer was washed with 10% aqueous Na₂S2O3 (100 mL), brine (150 mL), dried (MgSO₄), filtered and the filtrate was concentrated to afford the product (30.0 g, mass exceed maximum theoretical, 100% yield assumed) as an oil.

To a solution of the above oil in THF (140 mL) under an atmosphere of N₂ was added methylamine, 2M solution in THF (112 mL, 224 mmol, 2 equiv.) dropwise. The mixture was stirred at rt for 5 h, then concentrated under reduced pressure. The resultant residue was dissolved in 1M hydrochloric acid (300 mL) and washed with Et₂O (3×120 mL). The aqueous layer was basified to pH ~11 with 5M NaOH and extracted with EtOAc (3×120 mL). The combined organic layers were washed with brine (200 mL), dried (MgSO₄), filtered and the filtrate was concentrated to afford an oil (15.8 g) which solidified to a beige solid after storage in the freezer. The crude material was subjected to column chromatography on silica gel, eluting with 0 to 50% MeOH in DCM to afford rac.-methylone (11.5 g, 50%) as an oil, which solidified on freezing to a solid.

Example 3-15: Synthesis of (Rac.)-Methylone HCl Salt

To a solution of (rac.)-methylone (7.3 g, 35.2 mmol, 1 equiv.) in Et₂O (400 mL) was added hydrogen chloride, 2M solution in Et₂O (52.8 mL, 105.5 mmol, 3 equiv.) and the resultant suspension was stirred for 15 min under an atmosphere of N₂ at rt. The white solid was collected via filtration, and the filter cake was washed with Et₂O (3×50 mL) to afford (rac.)-methylone hydrochloride (7.8 g, 91%). Analysis by XRPD (PANalytical X'Pert Pro MPD with an XCelerator using Detector Cu Kα radiation) indicated that this was a mixture of polymorph Form A and polymorph Form B (see FIG. 48).

Figure 48:
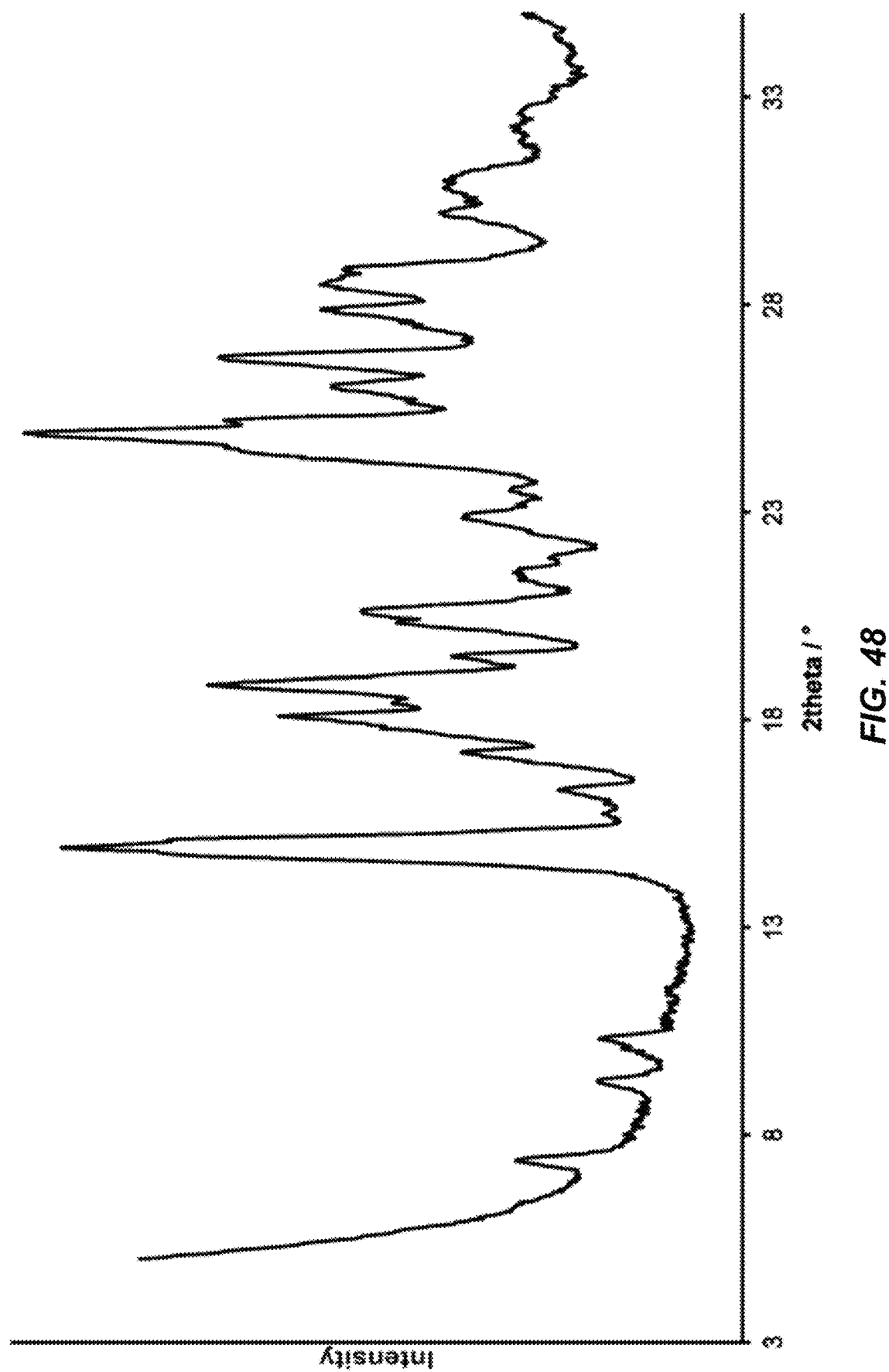
FIG. 48 illustrates an XRPD diffractogram of Methylone HCl (racemate) prepared as outlined in Example 3-15. The representative XRPD diffractogram shows that the sample is a mixture of Form A and Form B.

Comparison of the XRPD in FIG. 48 with the XRPD analysis of a sample of commercially available (rac.)-methylone hydrochloride (available from Cayman Chemical Group, Item No. 10986, prepared February 2018; see the top XRPD diffractogram in FIG. 1) indicated that the two materials are the same, namely a mixture of Form A and a Form B.

Representative peaks of the XRPD from the sample of (rac.)-methylone hydrochloride obtained Cayman Chemical Group, Item No. 10986, prepared February 2018 include those in the following table. The 2-Theta peak values that are provided for the XRPD are within +0.2° 2-Theta.

| Position [°2θ] | Rel. Intensity (%) |
|---|---|
| 9.5 | 27 |
| 14.9 | 49.4 |
| 15.1 | 70.3 |
| 15.3 | 100 |
| 15.5 | 45.9 |
| 16.5 | 25.2 |
| 17.4 | 42.2 |
| 18.3 | 74.4 |
| 18.6 | 40.1 |
| 19 | 42.4 |
| 19.1 | 51.9 |
| 19.3 | 33.3 |
| 19.3 | 41.8 |
| 19.7 | 48.3 |
| 20.4 | 38.8 |
| 20.8 | 45.3 |
| 20.9 | 55.1 |

Representative peaks shown in FIG. 48 are presented in the table below.

| Position [°2θ] | Rel. Intensity (%) |
|---|---|
| 7.4 | 14.5 |
| 9.3 | 11.3 |
| 10.2 | 15.0 |
| 14.7 | 81.2 |
| 16.2 | 26.2 |

The 2-Theta peak values that are provided for the XRPD are within +0.2° 2-Theta. In some embodiments, (R)-methylone hydrochloride is characterized as having an XRPD with representative peaks at 7.3° 2-Theta, 10.2° 2-Theta, and 14.7° 2-Theta, as measured with Cu Kα radiation. In some embodiments, the XRPD further comprises representative peaks at 9.3° 2-Theta and 16.2° 2-Theta, as measured with Cu Kα radiation.

Drug polymorphism requires control over all stages of synthesis, application, and storage. An incident involving the anti-HIV/AIDS drug ritonavir highlighted the need to increase control over drug polymorphism and especially the need to use a single crystalline form over a mixture of crystalline forms. Approximately two years after commercial launch, a batch of ritonavir capsules failed a regulated dissolution test due to the emergence of a slower to dissolve, and previously unknown, polymorph. Worldwide availability of Ritonavir was jeopardized and inventories were quarantined during this time because the drug was forming a different crystalline structure which made it less soluble, so the correct dose of drug was not released inside the patient's body (Newman, A., Wenslow, R. Solid form changes during drug development: good, bad, and ugly case studies. AAPS Open 2, 2 (2016)). Time has shown that the control over the synthesis of new drug polymorphs and the possible transformations of the already-used drug versions are still significant problems.

As disclosed herein, single crystalline forms of (rac.)-methylone hydrochloride are described.

Example 3-16: Attempt to Prepare Form a of (Rac.)-Methylone HCl Form a from a Mixture of Form a and Form B (rac.)-Methylone hydrochloride (200 mg, 0.82 mmol) was suspended in EtOH (1.0 mL) and the mixture was stirred at rt overnight. The solid was collected by filtration, and the filter cake was rinsed with EtOH (3 mL, 2×1 mL) and dried under high vacuum (1 h) to afford (rac.)-methylone hydrochloride (143 mg, 0.59 mmol, 72% recovery). This material was a mixture of polymorph Form A with a small quantity of polymorph Form B. Two samples of this material were analyzed by XRPD (Bruker D2 Phaser with a LynxEye detector using Cu Kα radiation) and the representative XRPD patterns are shown in FIG. 49 (Sample 1) and FIG. 50 (Sample 2).

Figure 49:
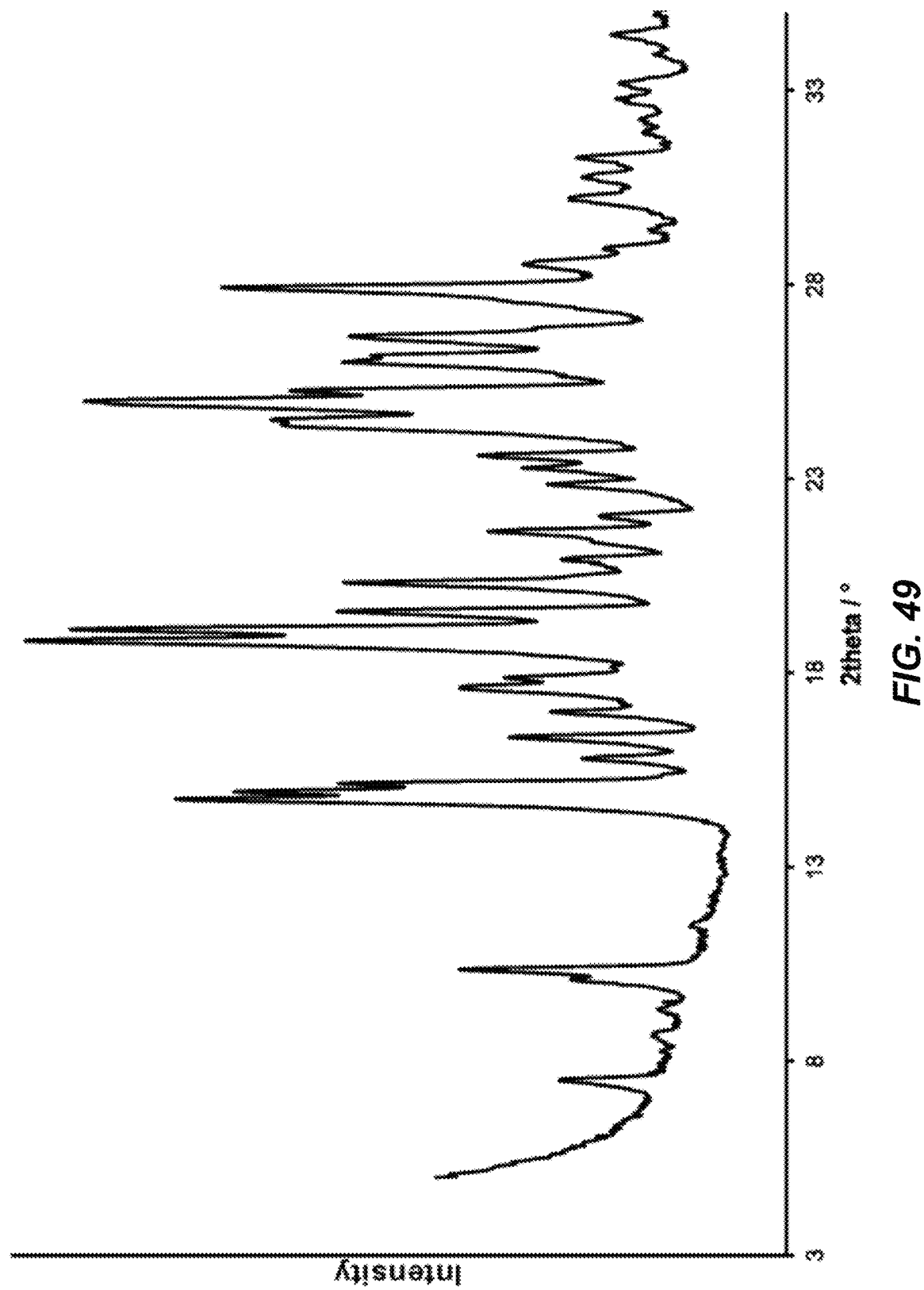
FIG. 49 illustrates an XRPD diffractogram of Methylone HCl (Sample 1) prepared as outlined in Example 3-16. The representative XRPD diffractogram shows that the sample is a mixture of Form A and Form B.

Representative peaks shown in FIG. 49 are presented in the table below.

| Angle [°2θ] | Relative Intensity [%] |
|---|---|
| 7.5 | 10.5 |
| 10.3 | 31.6 |
| 14.7 | 72.0 |
| 14.9 | 53.3 |
| 15.1 | 46.6 |

The 2-Theta peak values that are provided for the XRPD are within +0.2° 2-Theta. In some embodiments, (rac.)-methylone hydrochloride is characterized as having an XRPD with representative peaks at 7.5° 2-Theta, 10.3° 2-Theta, and 14.7° 2-Theta, as measured with Cu Kα radiation. In some embodiments, the XRPD further comprises representative peaks at 14.9° 2-Theta and 15.1° 2-Theta, as measured with Cu Kα radiation.

Figure 50:
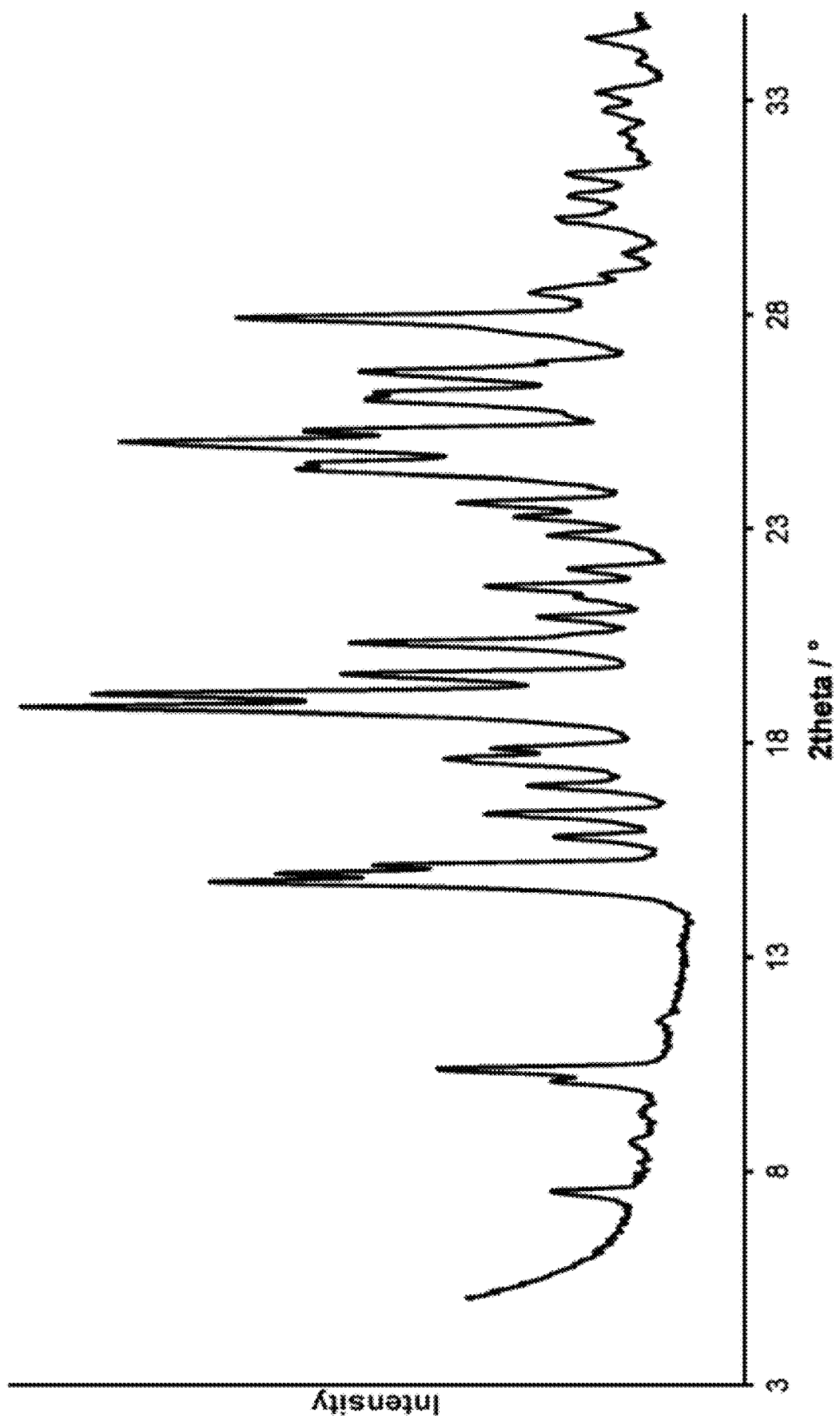
FIG. 50 illustrates an XRPD diffractogram of Methylone HCl (Sample 2) prepared as outlined in Example 3-16. The representative XRPD diffractogram shows that the sample is a mixture of Form A and Form B.

Representative peaks shown in FIG. 50 are presented in the table below.

| Angle [°2θ] | Relative Intensity [%] |
|---|---|
| 7.5 | 10.4 |
| 10.3 | 34.6 |
| 14.7 | 68.9 |
| 14.9 | 50.9 |
| 15.1 | 39.0 |

The 2-Theta peak values that are provided for the XRPD are within +0.2° 2-Theta. In some embodiments, (rac.)-methylone hydrochloride is characterized as having an XRPD with representative peaks at 7.5° 2-Theta, 10.3° 2-Theta, and 14.7° 2-Theta, as measured with Cu Kα radiation. In some embodiments, the XRPD further comprises representative peaks at 14.9° 2-Theta and 15.1° 2-Theta, as measured with Cu Kα radiation.

Example 3-17: Successful Synthesis of (Rac.)-Methylone HCl Polymorph Form A (rac.)-Methylone hydrochloride (200 mg, 0.82 mmol) was suspended in EtOH (1.5 mL) under an atmosphere of N$_2$ and the mixture was heated to 40° C. and stirred overnight. The mixture was cooled to rt and the solid was collected via filtration. The filter cake was rinsed with EtOH (4×1 mL), and dried under high vacuum (1 h) to afford (rac.)-methylone hydrochloride salt, polymorph form A (105 mg, 52% recovery). Analysis by XRPD was performed with a Bruker D2 Phaser with a LynxEye detector using Cu Kα radiation).

Figure 51:
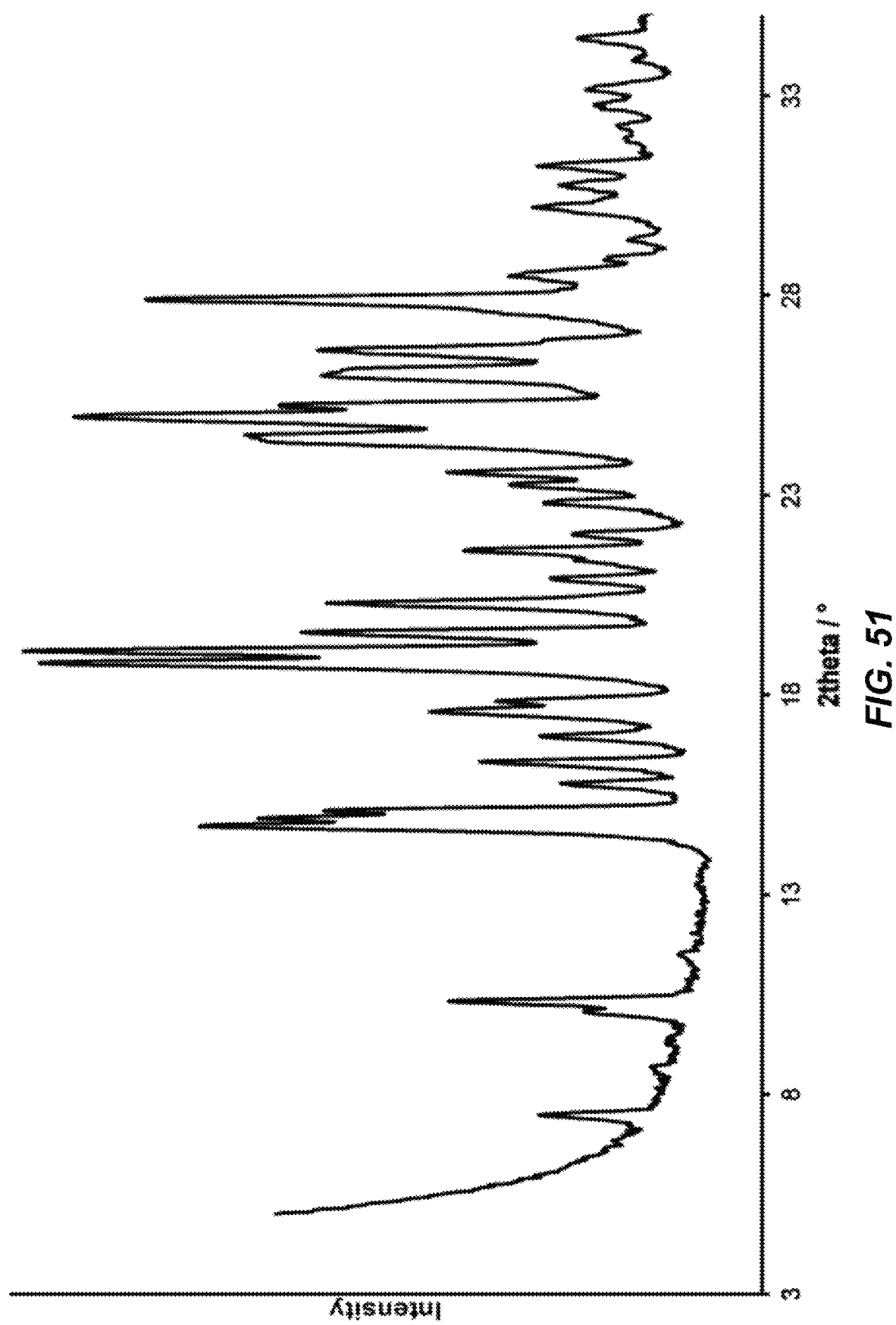
FIG. 51 illustrates an XRPD diffractogram of Methylone HCl (racemate) prepared as outlined in Example 3-17. The representative XRPD diffractogram shows that the sample is Form A.

A representative XRPD pattern of a sample is shown in FIG. 51. Representative peaks shown in FIG. 51 are presented in the table below.

| Angle [°2θ] | Relative Intensity [%] |
|---|---|
| 7.5 | 13.6 |
| 10.3 | 36.3 |
| 14.7 | 79 |
| 14.9 | 50.7 |
| 15.1 | 54.4 |

The 2-Theta peak values that are provided for the XRPD are within +0.2° 2-Theta. In some embodiments, (rac.)-methylone hydrochloride is characterized as having an XRPD with representative peaks at 7.5° 2-Theta, 10.3° 2-Theta, and 14.7° 2-Theta, as measured with Cu Kα radiation. In some embodiments, the XRPD further comprises representative peaks at 14.9° 2-Theta and 15.1° 2-Theta, as measured with Cu Kα radiation.

Example 3-18: Synthesis of Rac-Methylone HCl Form a on a Large 8 g Scale rac-Methylone HCl (11.3 g, 54.4 mmol) was suspended in EtOH (84.5 mL) and the mixture was stirred at 40° C. under nitrogen overnight. The mixture was cooled to room temperature and the solid was collected via Buchner filtration, rinsed with EtOH (4×50 mL), and dried under high vacuum (1 h) to afford rac-methylone HCl (9.03 g, 43.5 mmol, 80% recovery). $^1$H NMR: (300 MHz, CD$_3$OD) δ 7.60 (dd, 1H, J=8.2 and 1.8 Hz, ArH), 7.39 (d, 1H, J=1.8 Hz, ArH), 6.91 (d, 1H, J=8.2 Hz, ArH), 6.02 (s, 2H, CH$_2$), 4.90 (q, 1H, J=7.1 Hz, α-CH), 2.64 (s, 3H, NMe), 1.46 (d, 3H, J=7.1 Hz, Me). LC-MS (+ve mode): R$_f$=2.0 min, m z=208.10 [M+H]$^+$. HPLC: R$_f$=16.1 min, 99.8% purity at 318 nm. Analysis by XRPD was performed with a PANalytical X'Pert Pro MPD with an XCelerator using Detector Cu Kα radiation).

Figure 52:
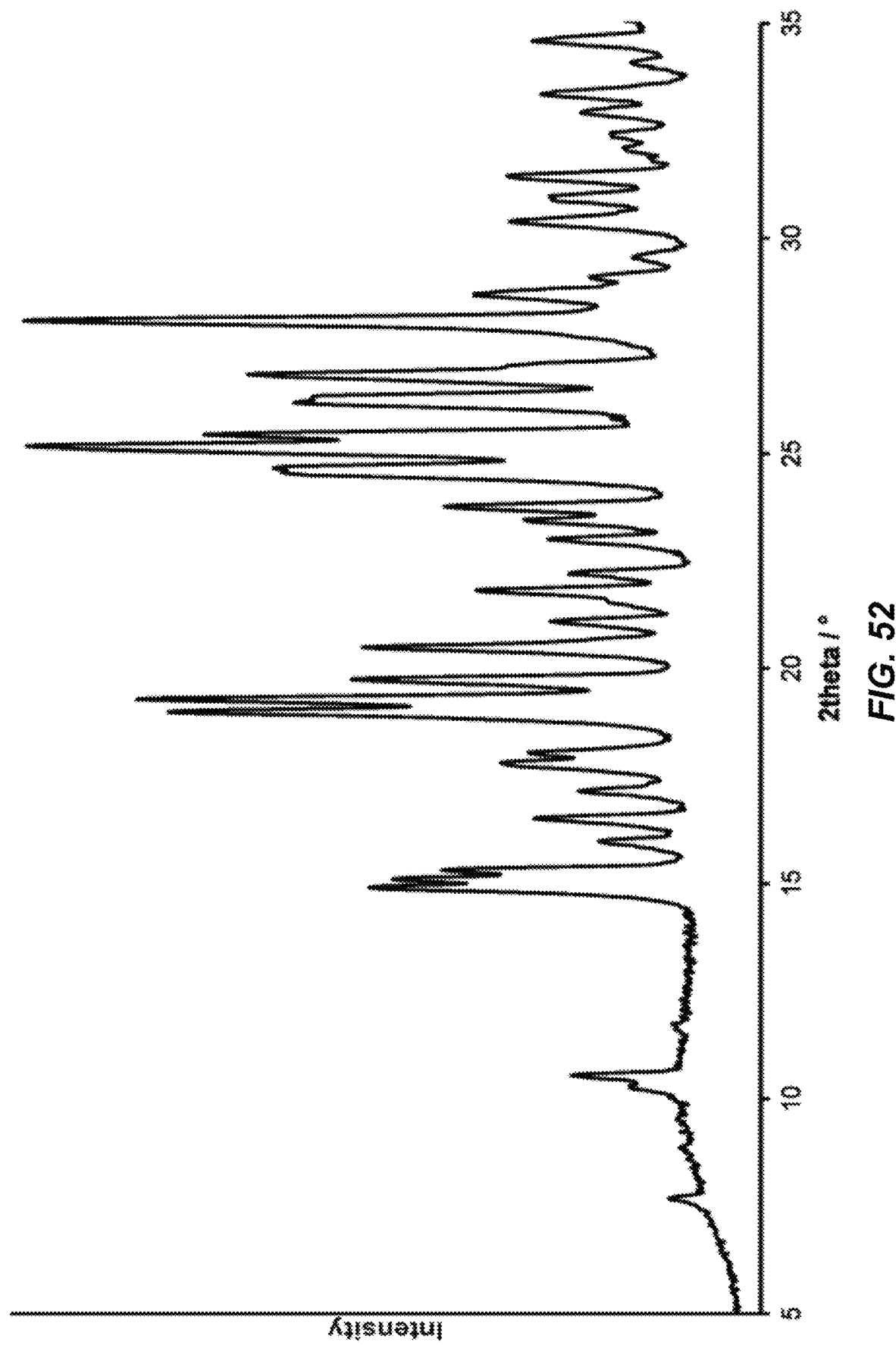
FIG. 52 illustrates an XRPD diffractogram of Scaled-Up Methylone HCl (racemate) prepared as outlined in Example 3-18. The representative XRPD diffractogram shows that the sample is Form A.

A representative XRPD pattern of a sample is shown in FIG. 52. Representative peaks shown in FIG. 52 are presented in the table below.

| Angle [°2θ] | Relative Intensity [%] |
|---|---|
| 10.5 | 14.9 |
| 14.9 | 43.2 |
| 15.1 | 35.1 |
| 15.3 | 33.4 |
| 15.9 | 12.2 |

The 2-Theta peak values that are provided for the XRPD are within ±0.2° 2-Theta. In some embodiments, (rac.)-methylone hydrochloride is characterized as having an XRPD with representative peaks at 10.5° 2-Theta, 14.9° 2-Theta, and 15.1° 2-Theta, as measured with Cu Kα radiation. In some embodiments, the XRPD further comprises representative peaks at 15.3° 2-Theta and 15.9° 2-Theta, as measured with Cu Kα radiation.

Example 3-19: (R)-Methylone HCl—Experiment 1

Isolation of (R)-methylone·HCl using (S)-(+)-mandelic acid

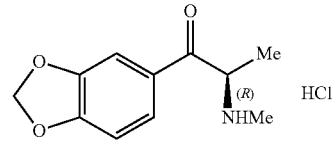

To a stirred solution of rac.-methylone (14.9 g, 72 mmol) in dimethyl carbonate (208 mL) was added (S)-(+)-mandelic acid (10.9 g, 72 mmol). After addition of the acid, the initial suspension became homogeneous within 20 s, with the formation of a white precipitate observed after approximately 4 min. The resulting suspension was stirred for 10 min at room temperature and the precipitate was collected by Buchner filtration, washing with dimethyl carbonate (2×80 mL). The solid was air-dried for 5 min, suspended in dimethyl carbonate (200 mL) and the mixture was stirred for 15 min. The solid was collected by Buchner filtration and air-dried for 5 min. This process was repeated three times to afford the mandelate salt (9.8 g, chiral HPLC S:R ratio 3.1:96.9) as a white solid.

The solid was dissolved in 1 M aqueous Na$_2$CO$_3$ (100 mL) and ethyl acetate (100 mL) was added, followed by brief swirling and separation of the solvent layers. The aqueous phase was extracted with ethyl acetate (3×80 mL). The organic phases were combined, washed with saturated brine (100 mL), dried (MgSO$_4$) and concentrated to obtain methylone free base as a yellow oil (5.80 g, 28.0 mmol). This material was dissolved in dimethyl carbonate (82 mL) and (S)-(+)-mandelic acid (4.30 g, 28.0 mmol) was added. Following the procedure described above, the mandelate salt was obtained (8.1 g, chiral HPLC S:R ratio 1.5:98.5) as a white solid. The resolution was repeated one more time to give the mandelate salt (7.0 g, chiral HPLC S:R ratio 0.6:99.4) as a white solid.

The solid was dissolved in 1 M aqueous Na$_2$CO$_3$ (100 mL) and ethyl acetate (100 mL) was added, followed by brief swirling and separation of the solvent layers. The aqueous phase was extracted with ethyl acetate (3×80 mL). The organic phases were washed with saturated brine (100 mL), dried (MgSO$_4$) and concentrated to obtain methylone free base as a yellow oil (4.1 g, 20 mmol). This material was dissolved in anhydrous diethyl ether (108 mL) and 1 M hydrogen chloride in diethyl ether (5.4 mL, 60 mmol) was added under N$_2$ at room temperature. A white precipitate appeared instantly. Further diethyl ether (30 mL) was added to facilitate stirring. The suspension was stirred for 20 min before the solid was collected by Buchner filtration, washed with diethyl ether (4×15 mL) and air-dried for 20 min to afford an off-white solid (4.7 g). This solid was dried under high vacuum for 2 h to afford (R)-(−)-methylone hydrochloride as an off-white solid (4.58 g, chiral HPLC S:R ratio 0.9:99.1).

$^1$H NMR: (300 MHz, CD$_3$OD) δ 7.70 (dd, 1H, J=8.2 and 1.8 Hz, ArH), 7.52 (d, 1H, J=1.7 Hz, ArH), 7.03 (d, 1H, J=8.2 Hz, ArH), 6.14 (s, 2H, CH$_2$), 5.00 (q, 1H, J=7.1 Hz, α-CH), 2.76 (s, 3H, NMe), 1.58 (d, 3H, J=7.1 Hz, Me). LC-MS (+ve mode): R$_t$=2.1 min, m z=208.10 [M+H]$^+$. HPLC: R$_t$=16.1 min, 100.0% purity (detection at 317 nm).

Example 3-20: (R)-Methylone HCl—Experiment 2

Polymorphism conversion for (R)-methylone HCl to Form A (R)-Methylone HCl (200 mg, 0.82 mmol) was suspended in EtOH (1.5 mL) and the mixture was stirred at 40° C. under nitrogen overnight. The mixture was cooled to room temperature and the solid was collected via Büchner filtration, rinsed with EtOH (4 mL, 4×1 mL), and dried under high vacuum (1 h) to afford (R)-methylone hydrochloride (81 mg, 0.33 mmol, 40% recovery).

Figure 53:
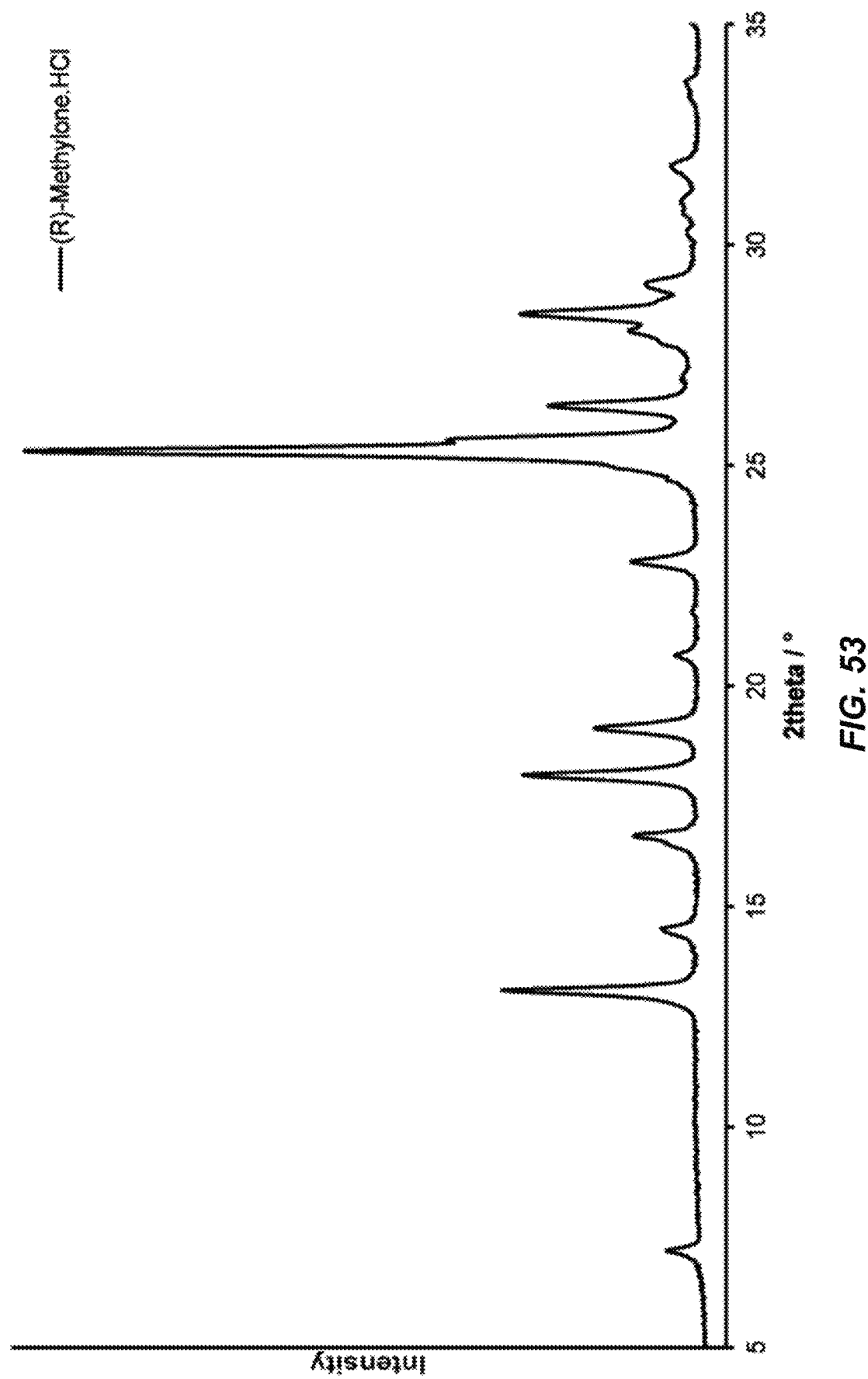
FIG. 53 illustrates an XRPD diffractogram of R-methylone HCl prepared as outlined in Example 3-20.

A representative XRPD pattern of a sample is shown in FIG. 53. Representative peaks shown in FIG. 53 are presented in the table below. Analysis by XRPD was performed with a PANalytical X'Pert Pro MPD with an XCelerator using Detector Cu Kα radiation).

| Angle [°2θ] | Relative Intensity [%] |
|---|---|
| 13.1 | 26.2 |
| 17.9 | 23.2 |
| 19.0 | 13.4 |

-continued

| Angle [°2θ] | Relative Intensity [%] |
|---|---|
| 25.3 | 100 |
| 26.3 | 20.3 |

The 2-Theta peak values that are provided for the XRPD are within +0.2° 2-Theta. In some embodiments, (R)-methylone hydrochloride is characterized as having an XRPD with representative peaks at 13.1° 2-Theta, 17.9° 2-Theta, and 19.0° 2-Theta, as measured with Cu Kα radiation. In some embodiments, the XRPD further comprises representative peaks at 25.3° 2-Theta and 26.3° 2-Theta, as measured with Cu Kα radiation.

Example 3-21: R-Methylone HCl—Experiment 3

Polymorphism Conversion for (R)-Methylone HCl to Form A—Large Scale Batch (R)-Methylone·HCl (10.7 g, 51.5 mmol) was suspended in EtOH (80 mL) and the mixture was stirred at 40° C. under nitrogen overnight. The resulting mixture was cooled to room temperature and the solid was collected via Büchner filtration, washed with EtOH (4×54 mL), and dried under high vacuum (1 h) to afford (R)-methylone hydrochloride (8.83 g, 82% recovery) as a white solid.

$^1$H NMR: (300 MHz, CD$_3$OD) δ 7.59 (dd, 1H, J=8.2 and 1.8 Hz, ArH), 7.39 (d, 1H, J=1.7 Hz, ArH), 6.91 (d, 1H, J=8.2 Hz, ArH), 6.02 (s, 2H, CH$_2$), 4.89 (q, 1H, J=7.1 Hz, α-CH), 2.64 (s, 3H, NMe), 1.46 (d, 3H, J=7.1 Hz, Me). LC-MS (+ve mode): R$_t$=2.1 min, m/z=208.10 [M+H]$^+$. HPLC: R$_t$=16.1 min, 100.0% purity (detection at 318 nm).

Figure 54:
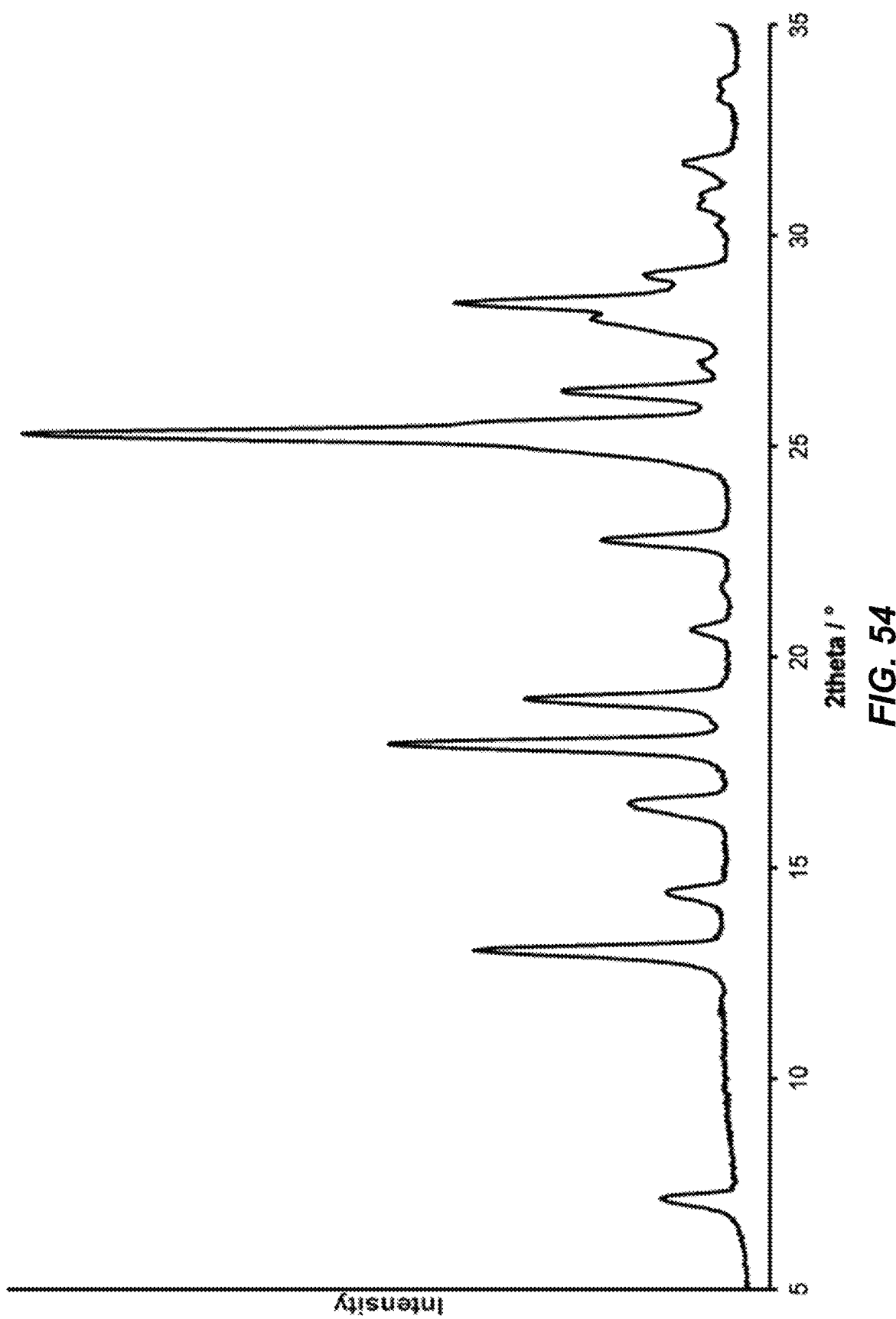
FIG. 54 illustrates an XRPD diffractogram of XRPD pattern of scaled-up batch of R-methylone HCl prepared as outlined in Example 3-21.

A representative XRPD pattern of a sample is shown in FIG. 54. Representative peaks shown in FIG. 54 are presented in the table below. Analysis by XRPD was performed with a PANalytical X'Pert Pro MPD with an XCelerator using Detector Cu Kα radiation).

| Angle [°2θ] | Relative Intensity [%] |
|---|---|
| 7.1 | 10.6 |
| 13.0 | 35.4 |
| 16.4 | 13.9 |
| 17.9 | 49.5 |
| 19.0 | 28.7 |

The 2-Theta peak values that are provided for the XRPD are within +0.2° 2-Theta. In some embodiments, (R)-methylone hydrochloride is characterized as having an XRPD with representative peaks at 7.1° 2-Theta, 13.0° 2-Theta, and 16.4° 2-Theta, as measured with Cu Kα radiation. In some embodiments, the XRPD further comprises representative peaks at 17.9° 2-Theta and 19.0° 2-Theta, as measured with Cu Kα radiation.

Example 3-22: (S)-Methylone HCl—Experiment 1

Isolation of (S)-Methylone·HCl Using (R)-(−)-Mandelic Acid

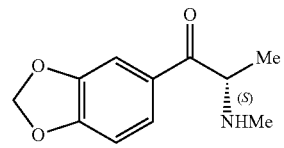

To a stirred solution of rac.-methylone (15.1 g, 73 mmol) in dimethyl carbonate (210 mL) was added (R)-(−)-mandelic acid (11.0 g, 73 mmol). After addition of the acid, the initial suspension became homogeneous within 20 s, with the formation of a white precipitate observed after approximately 4 min. The resulting suspension was stirred for 10 min at room temperature and the precipitate was collected by Buchner filtration, washing with dimethyl carbonate (4×15 mL). The solid was air-dried for 5 min, suspended in dimethyl carbonate (150 mL) and the mixture was stirred for 15 min. The solid was collected by Buchner filtration and air-dried for 5 min. This process was repeated three times to afford the mandelate salt (10.3 g, chiral HPLC S:R ratio 98.1:1.9) as a white solid.

The solid was dissolved in 1M aqueous $Na_2CO_3$ (100 mL) and ethyl acetate (100 mL) was added, followed by brief swirling and separation of the solvent layers. The aqueous phase was extracted with ethyl acetate (3×80 mL). The organic phases were combined, washed with saturated brine (100 mL), dried ($MgSO_4$) and concentrated to obtain methylone free base as a yellow oil (6.10 g, 29 mmol). This material was dissolved in dimethyl carbonate (85 mL) and (R)-(−)-mandelic acid (4.40 g, 29 mmol) was added. Following the procedure described above for the (S)-isomer the mandelate salt of (R)-methylone was obtained (7.0 g, chiral HPLC S:R ratio 99.2:0.8) as a white solid.

The solid was dissolved in 1M aqueous $Na_2CO_3$ (100 mL) and ethyl acetate (100 mL) was added, followed by brief swirling and separation of the solvent layers. The aqueous phase was extracted with ethyl acetate (3×80 mL). The organic phases were combined, washed with saturated brine (100 mL), dried ($MgSO_4$) and concentrated to obtain methylone free base as a yellow oil (6.9 g, 33.6 mmol). This material was dissolved in anhydrous diethyl ether (236 mL) and 2 M hydrogen chloride in diethyl ether (50.5 mL, 100.8 mmol) was added under $N_2$ at room temperature. A white precipitate appeared instantly. Further diethyl ether (40 mL) was added to facilitate stirring. The suspension was stirred for 15 min before the solid was collected by Buchner filtration, washed with diethyl ether (4×15 mL) and air-dried for 20 min to afford an off-white solid (8.2 g). This was dried under high vacuum for 2 h to afford (S)-(+)-methylone hydrochloride as an off-white solid (7.70 g, chiral HPLC S:R ratio 99.3:0.7).

$^1$H NMR: (300 MHz, $CD_3OD$) δ 7.59 (dd, 1H, J=8.2 and 1.8 Hz, ArH), 7.39 (d, 1H, J=1.7 Hz, ArH), 6.91 (d, 1H, J=8.2 Hz, ArH), 6.02 (s, 2H, $CH_2$), 4.89 (q, 1H, J=7.1 Hz, α-CH), 2.64 (s, 3H, NMe), 1.46 (d, 3H, J=7.1 Hz, Me). LC-MS (+ve mode): $R_t$=2.1 min, m z=208.10 $[M+H]^+$. HPLC: $R_t$=16.1 min, 100.0% purity (detection at 317 nm).

Figure 55:
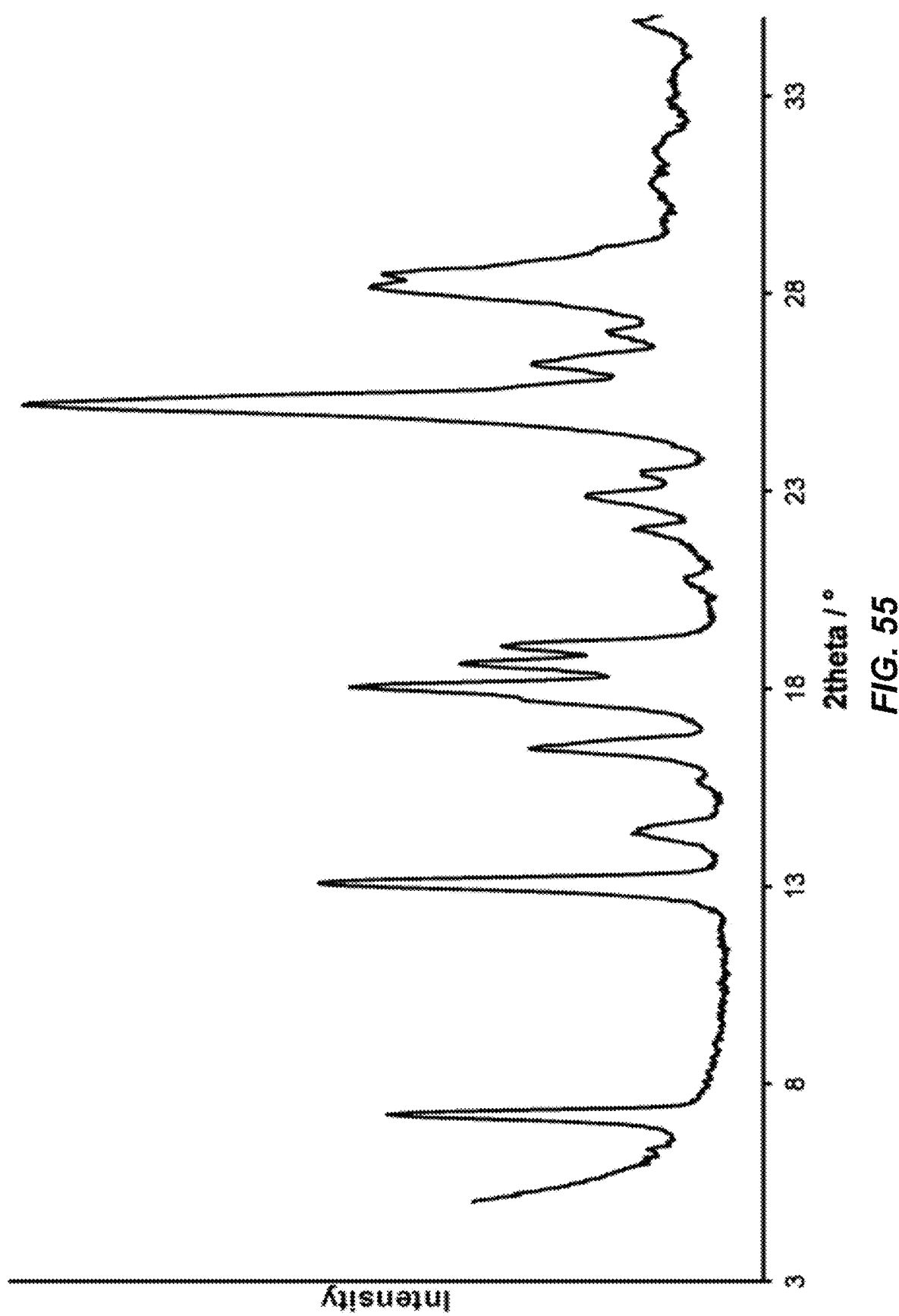
FIG. 55 illustrates an XRPD diffractogram of (S)-methylone HCl prepared as outlined in Example 3-22. The sample appears to comprise mostly Form A with additional peaks in the spectrum, which indicates the sample contains another form.

A representative XRPD pattern of a sample is shown in FIG. 55. Representative peaks shown in FIG. 55 are presented in the table below. Analysis by XRPD was performed with a Bruker D2 Phaser with a LynxEye detector using Cu Kα radiation).

| Angle [°2θ] | Relative Intensity [%] |
|---|---|
| 7.2 | 39.4 |
| 13.0 | 62.3 |
| 14.4 | 13.7 |
| 16.5 | 26.2 |
| 17.7 | 23 |

The 2-Theta peak values that are provided for the XRPD are within ±0.2° 2-Theta. In some embodiments, (S)-methylone hydrochloride is characterized as having an XRPD with representative peaks at 7.2° 2-Theta, 13.0° 2-Theta, and 14.4° 2-Theta, as measured with Cu Kα radiation. In some embodiments, the XRPD further comprises representative peaks at 16.5° 2-Theta and 17.7° 2-Theta, as measured with Cu Kα radiation.

Example 3-23: (S)-Methylone HCl—Experiment 2

Polymorphism Conversion for (S)-Methylone HCl to Form A—Trial Batch (S)-Methylone HCl (200 mg, 0.82 mmol) was suspended in EtOH (1.5 mL) and the mixture was stirred at 40° C. under nitrogen overnight. The mixture was cooled to room temperature and the solid was collected via Buchner filtration, rinsed with EtOH (4 mL, 4×1 mL), and dried under high vacuum (1 h) to afford (S)-methylone hydrochloride (124 mg, 0.59 mmol, 62% recovery).

Figure 56:
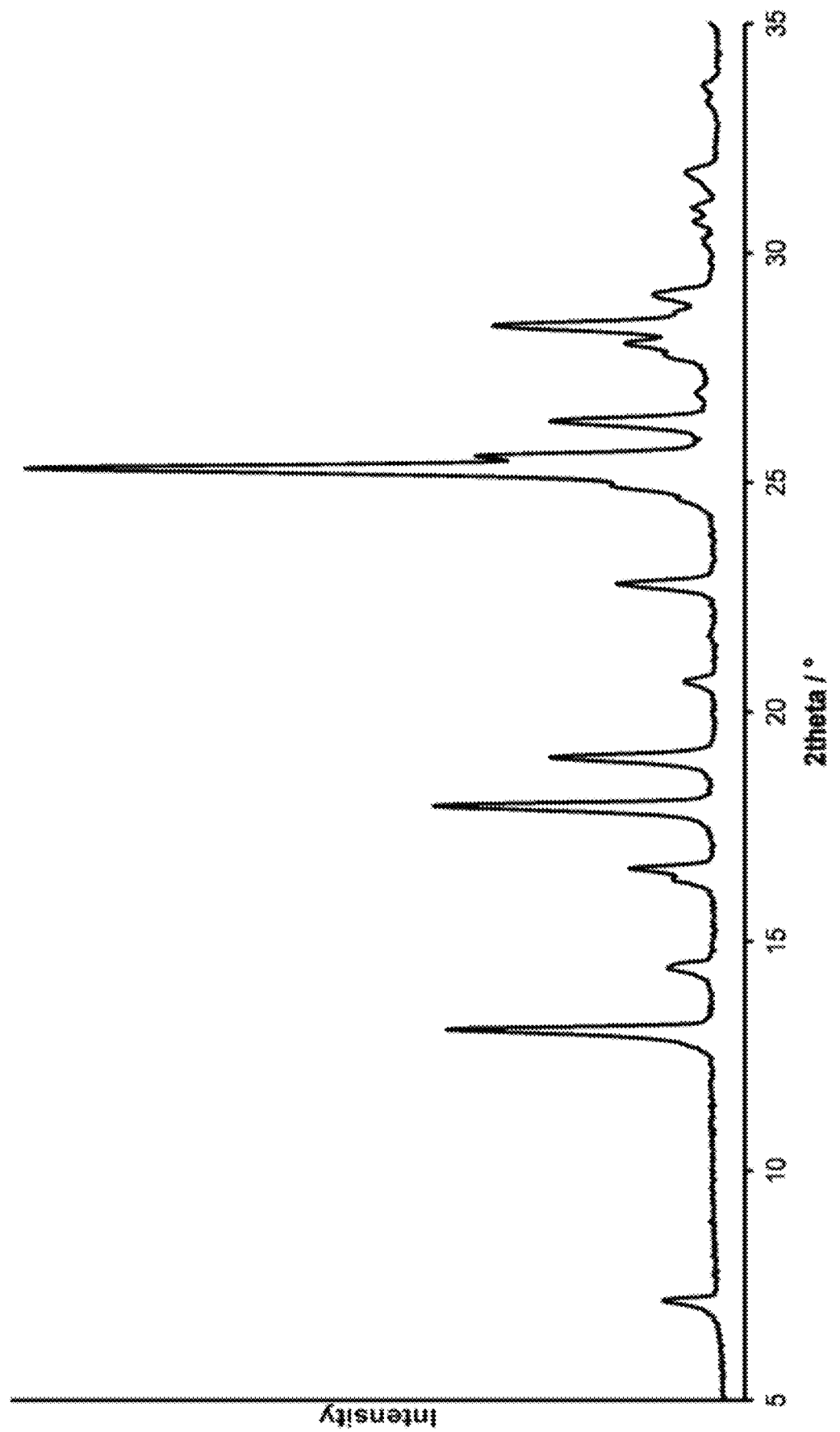
FIG. 56 illustrates an XRPD diffractogram of S-methylone HCl prepared as outlined in Example 3-23. The sample appears to be pure Form A.

A representative XRPD pattern of a sample is shown in FIG. 56. Representative peaks shown in FIG. 56 are presented in the table below. Analysis by XRPD was performed with a PANalytical X'Pert Pro MPD with an XCelerator using Detector Cu Kα radiation).

| Angle [°2θ] | Relative Intensity [%] |
|---|---|
| 13.0 | 37.8 |
| 16.6 | 11.1 |
| 17.9 | 41.2 |
| 19.0 | 23.1 |
| 22.7 | 14.0 |

The 2-Theta peak values that are provided for the XRPD are within +0.2° 2-Theta. In some embodiments, (S)-methylone hydrochloride is characterized as having an XRPD with representative peaks at 13.0° 2-Theta, 16.6° 2-Theta, and 17.9° 2-Theta, as measured with Cu Kα radiation. In some embodiments, the XRPD further comprises representative peaks at 19.0° 2-Theta and 22.7° 2-Theta, as measured with Cu Kα radiation.

Example 3-24: S-Methylone HCl—Experiment 3

Polymorphism conversion for (S)-methylone HCl to Form A—large scale (S)-Methylone·HCl (8.88 g, 42.85 mmol) was suspended in EtOH (67 mL) and the mixture was stirred at 40° C. under nitrogen overnight. The resulting mixture was cooled to room temperature and the solid was collected via Buchner filtration, washed with EtOH (4×45 mL), and dried under high vacuum (1 h) to afford (S)-methylone hydrochloride (7.07 g, 80% recovery) as a white solid.

$^1$H NMR: (300 MHz, $CD_3OD$) δ 7.59 (dd, 1H, J=8.2 and 1.8 Hz, ArH), 7.39 (d, 1H, J=1.7 Hz, ArH), 6.91 (d, 1H, J=8.2 Hz, ArH), 6.02 (s, 2H, $CH_2$), 4.89 (q, 1H, J=7.1 Hz, α-CH), 2.64 (s, 3H, NMe), 1.46 (d, 3H, J=7.1 Hz, Me). LC-MS (+ve mode): $R_t$=2.06 min, m/z=208.10 $[M+H]^+$. HPLC: $R_t$=16.1 min, 100.0% purity (detection at 318 nm).

Figure 57:
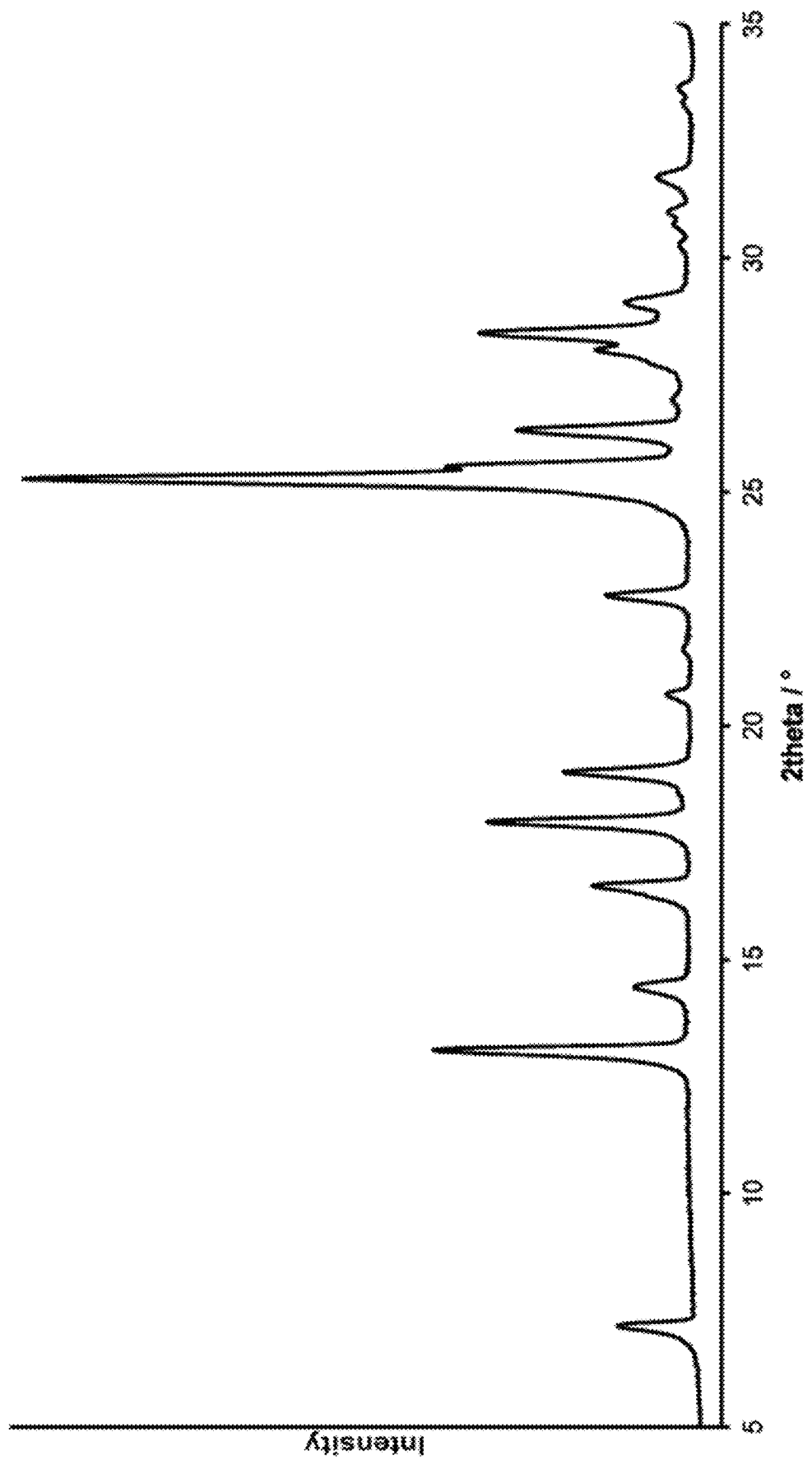
FIG. 57 illustrates an XRPD diffractogram of S-methylone HCl prepared as outlined in Example 3-24. The sample appears to be pure Form A.

A representative XRPD pattern of a sample is shown in FIG. 57. Representative peaks shown in FIG. 57 are presented in the table below. Analysis by XRPD was performed with a PANalytical X'Pert Pro MPD with an XCelerator using Detector Cu Kα radiation).

| Angle [°2θ] | Relative Intensity [%] |
|---|---|
| 7.1 | 11.0 |
| 13.0 | 37.2 |
| 16.5 | 12.6 |
| 17.9 | 29.9 |
| 19.0 | 17.6 |

The 2-Theta peak values that are provided for the XRPD are within ±0.2° 2-Theta. In some embodiments, (S)-methylone hydrochloride is characterized as having an XRPD with representative peaks at 7.1° 2-Theta, 13.0° 2-Theta, 16.5° 2-Theta, and, as measured with Cu Kα radiation. In some embodiments, the XRPD further comprises representative peaks at 17.9° 2-Theta and 19.0° 2-Theta, as measured with Cu Kα radiation.

Example 3-25: Crystallization of Ethylone Hydrochloride

For the crystallization experiments described in this example, the following X-ray Powder Diffraction (XRPD) instrument and conditions were used.

A Rigaku SmartLab X-Ray Diffractometer was configured in Bragg-Brentano reflection geometry equipped with a beam stop and knife edge to reduce incident beam and air scatter. Data collection parameters are shown in the following table. This method has not been validated.

| PXRD Data Collection Parameters | | | |
|---|---|---|---|
| Parameter | Value | Parameter | Value |
| Geometry | Bragg-Brentano | Receiving Slit 1 (mm) | 18 |
| Tube Anode | Cu | Receiving Slit 2 (mm) | 20 |
| Tube Type | Long Fine Focus | Start Angle 2θ (°) | 2 |
| Tube Voltage (kV) | 40 | End Angle 2θ (°) | 40 |
| Tube Current (mA) | 45 | Step Size (°) | 0.02 |
| Detector | HyPix-3000 | Scan Speed (°/min) | 6 |
| Monochromator | Ni foil Cu Kβ Filter | Spinning (rpm) | 11 |
| Incident Slit (°) | 1/3 | Sample Holder | Low-background Si |

Precipitation from N,N-Dimethylformamide (DMF) at Low Temperature 49.8 mg of ethylone hydrochloride was suspended in 5.3 mL of DMF. Stirred on a hotplate set to 60° C. and the solids dissolved. Cooled to room temperature, no solids formed by the next day. Cooled to 5° C., minimal solids formed by the next day. Cooled to −15° C., more solid precipitated. The sample was centrifuged, the mother liquor decanted, and the solids allowed to air dry.

A representative XRPD pattern of a sample is shown in FIG. 58.

Precipitation from 2-Propanol 26.4 mg of ethylone hydrochloride in 10 mL 2-propanol, stirred at 70° C. Solids dissolved. Moved sample to room temperature. No solids formed, placed sample @5° C. for 24 h. Minimal solids formed, placed sample at −15° C. for 24 h. The sample was centrifuged, the mother liquor decanted, and the solids allowed to air dry.

A representative XRPD pattern of a sample is shown in FIG. 59.

Precipitation from N,N-Dimethylformamide (DMF) at Room Temperature 51.3 mg of ethylone hydrochloride in 5 mL DMF, stirred at 60° C. Solids dissolved. Moved sample to room temperature, solids formed. Stirred at room temperature for 1 day. The sample was centrifuged, the mother liquor decanted, and the solids allowed to air dry.

A representative XRPD pattern of a sample is shown in FIG. 60.

The 2-Theta peak values that are provided for the XRPD are within +0.2° 2-Theta. Representative peaks of the XRPD pattern shown in FIG. 60 include 13.0°±0.2 2-Theta, 17.9°±0.2 2-Theta, and 25.3°±0.2 2-Theta, as measured with Cu Kα radiation. Additional peaks include 18.9°±0.2 2-Theta and 28.4°±0.2, as measured with Cu Kα radiation.

All of the experiments produced crystalline material. Of the three samples, the one which appears to have the highest crystallinity was obtained from a cooling experiment involving N,N-dimethylformamide (DMF) which precipitated at room temperature.

Figure 61:
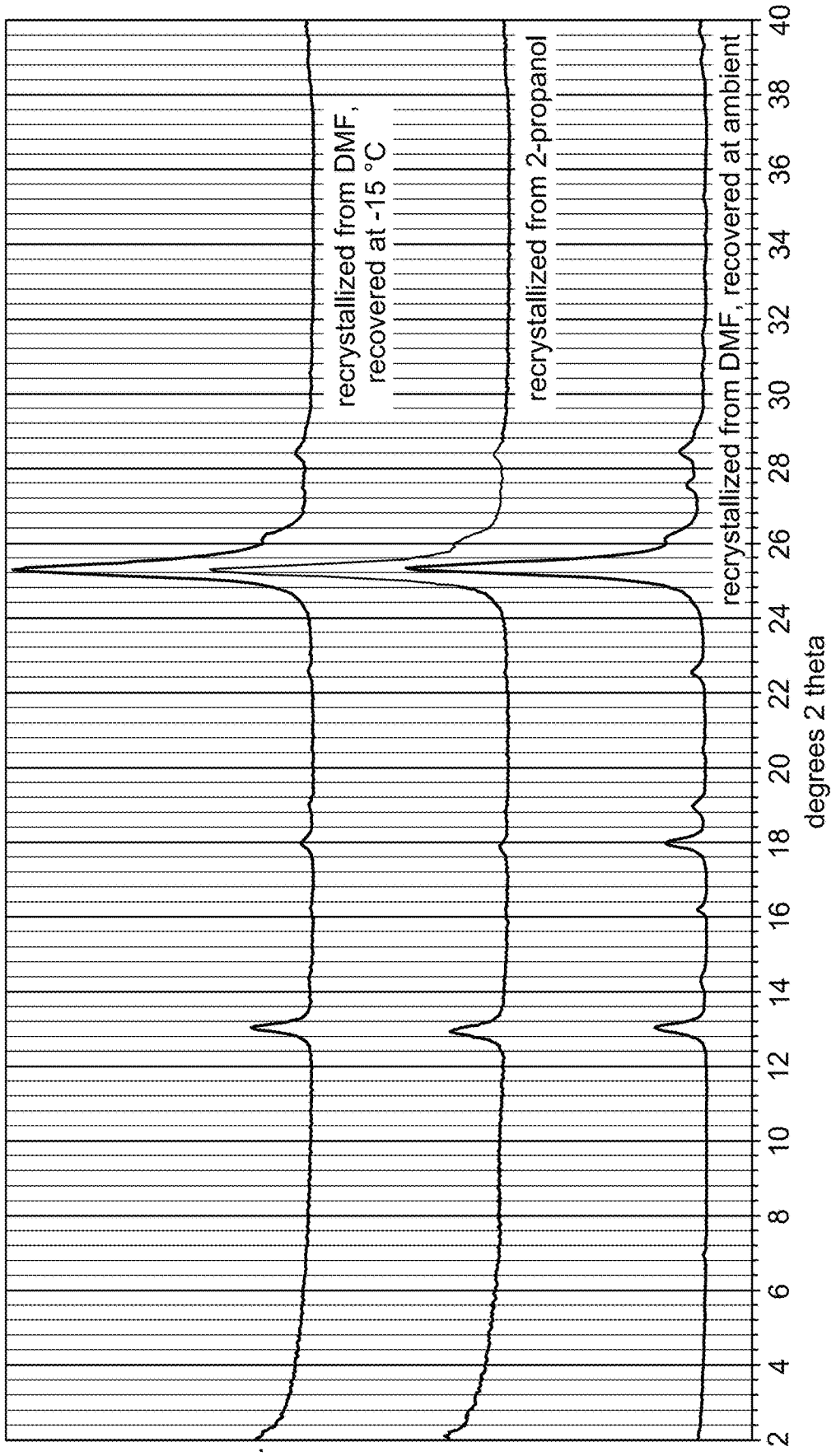
FIG. 61 illustrates an overlay of the XRPD diffractograms of Ethylone HCl isolated from the recrystallization experiments outlined in Example 3-25.

An overlay of the XRPD patterns of these three crystallization experiments is shown in FIG. 61.

Example 3-26: Zero Maze Study

Background

The rat zero-maze model is a refined alternative to the plus-maze, the most widely used animal model of anxiety, and consists of an elevated annular platform, divided equally into four quadrants. Two opposite quadrants are enclosed by Perspex walls on both the inner and the outer edges of the platform, while the remaining two opposite quadrants are open being enclosed only by a Perspex "lip". Animals will show a preference for the closed areas, and avoidance of the open sections is assumed to stem from a rodent's natural aversion to open, exposed spaces. The primary index of anxiety, which reflect changes in open arm preference, is the percentage of time spent on the open areas. A reduction in the amount of activity on the open areas is considered to reflect an increase in anxiety. Other, ethologically-based behaviours are also assessed as indices of anxiety. One of the most important is stretched attend postures (SAP) from closed to open quadrants. Increase in SAPs is indicative of an anxiogenic effect and a decrease in SAPs is indicative of an anxiolytic effect. Shepherd, J K; et al., (1994) Behavioural and pharmacological validation of the elevated "zero-maze" as an animal model of anxiety. Psychopharmacol., 116:56-64.

Animals

Male Sprague-Dawley 200-250 g (Envigo UK) rats were used. Animals were group-housed (5 per cage; cage size: 40×40×20 cm) in a temperature-controlled environment (22±2° C.), under a 12 h light-dark cycle (lights on: 08:00 hours) for one week prior to testing. Food and water were freely available. Number of animals per group=5. Animals were moved into the experimental room 16-24 hours before testing.

Apparatus

The elevated 0-maze comprises a black Perspex annular platform (105 cm diameter, 10 cm width) elevated to 65 cm above ground level, divided equally into four quadrants. Two opposite quadrants are enclosed by clear red Perspex walls (27 cm high) on both the inner and outer edges of the platform, while the remaining two opposite quadrants are surrounded only by a Perspex "lip" (1 cm high) which serves as a tactile guide to animals on these open areas.

Procedure

Subjects were weighed and tail marked before being injected. After a specified pre-treatment time, subjects were placed in a closed quadrant and a 5-min test period were recorded on videotape for subsequent analysis. The maze were cleaned with 5% methanol/water solution and dried thoroughly between test sessions. Behavioural measures comprise percentage time spent on the open areas (% TO) and frequency of stretched attend postures (SAP) from closed to open quadrants. Since the control groups were all treated identically with the same vehicle these were combined to increase power. The Chlordiazepoxide groups were also treated identically with the same dose so these were also combined to increase power. Animals are scored as being in the open area when all four paws were in an open quadrant and in the closed area only when all four paws have passed over the open-closed divide. All testing were carried out between 9.00 and 16.00 hours.

Drug Versus Vehicle Treatments

For each study, a 1-way ANOVA was conducted across vehicle, CDP, and drug treatment groups. Each group was compared to the vehicle group and a p-value for treatment determined by Fishers Least Significant Difference (LSD) test. This analysis was performed in GraphPad Prism (Version 9). Formulations:

Intraperitoneal (IP): Racemic methylone HCl was formulated in Vehicle 1 (Saline) for injection to concentrations of 1, 3 and 6 mg/mL to provide doses of 5, 15 and 30 mg/kg when administered ip in 5 mL/kg dosing volumes.

Intraperitoneal (IP): S-methylone HCl was formulated in Vehicle 1 (Saline) for injection to concentrations of 0.5, 1, 1.5, 3 and 6 mg/mL to provide doses of 2.5, 5, 7.5, 15 and 30 mg/kg when administered ip in 5 mL/kg dosing volumes.

Intraperitoneal (IP): R-methylone HCl was formulated in Vehicle 1 (Saline) for injection to concentrations of 1, 3 and 6 mg/mL to provide doses of 5, 15 and 30 mg/kg when administered ip in 5 mL/kg dosing volumes.

Chlordiazepoxide was formulated in Vehicle 1 (saline) to a concentration of 1.2 mg/mL to provide a dose of 6 mg/kg when administered ip in 5 mL/kg dosing volumes.

Example 3-27: Effect of Administration of Methylone HCl and Chlordiazepoxide on Behavior in a Rat 0-Maze Study Protocol: 25 male Sprague-Dawley rats in treatment groups of 5, were intraperitoneally dosed with either Vehicle 1 (saline) or methylone HCl at 1 of 3 dose levels (5, 15 & 30 mg/kg) or chlordiazepoxide (6 mg/kg) in 5 mL/kg injection volumes. Following injection, each rat was placed in a separate cage with opaque walls in a room adjacent to the study room. Thirty min later at T=0, rats were individually placed in a closed arm of the zero-maze and behaviour assessed by a "blind" observer using remote video monitoring over the subsequent 5 min. The animal was then removed and the maze carefully wiped with 5% methanol/water solution before the next test was begun.

Terminal sampling. At the end of the study, terminal blood was collected from 2 of the vehicle treated rats (>5 mL) and from all methylone HCl treated rats (500 uL) by CP under $CO_2$. Blood samples were placed into Eppendorf tubes on ice containing 22 μL/mL blood (vehicle treated) or 11 μL EDTA (93 mg/mL) (Methylone HCl treated rats) and gently mixed. After no longer than 30 min, blood samples were centrifuged at 10,000 rpm×3 min and plasma samples (>2 mL (vehicle) or 2×100 μL (Methylone HCl treated) placed into Eppendorf tubes (Vehicle) or 96 well plates on dry ice. Immediately after blood sampling, brains were excised, rinsed in saline, blotted, weighed and snap-frozen in liquid $N_2$. All samples were stored at −20° C. until dispatched on dry ice for analysis.

Total number of plasma samples=15+2 vehicle controls.

Total number of brain samples=15+2 vehicle controls.

Synopsis of testing schedule methylone HC and chlordiazepoxide in the rat elevated zero maze model of anxiety.

| n | Rat Strain & sex | 0.5 h Pretest in Veh 1 5 mL/kg ip | T = −0.5 to T = 0 | T = 0 Zero-maze | T = 0.25 Terminal sampling |
|---|---|---|---|---|---|
| 5 | Male SD | Vehicle 1 (Saline) | After dosing, place rats in separate opaque-walled cages in adjacent room | Test | Plasma & brain from 2 rats |
| 5 | Male SD | Methylone HCl 5 mg/kg | | Test | Plasma & brain |
| 5 | Male SD | Methylone HCl 15 mg/kg | | Test | Plasma & brain |
| 5 | Male SD | Methylone HCl 30 mg/kg | | Test | Plasma & brain |
| 5 | Male SD | CDP 6 mg/kg | | Test | n/a |

Example 3-28: Effect of Administration of S-Methylone HC and Chlordiazepoxide on Behavior in a Rat 0-Maze Study Protocol: 35 male Sprague-Dawley rats in treatment groups of 5, were intraperitoneally dosed with either Vehicle 1 (saline) or S-methylone HCl at 1 of 5 dose levels (2.5, 5, 7.5, 15 & 30 mg/kg) or chlordiazepoxide (6 mg/kg) in 5 mL/kg injection volumes. Thirty min later at T=0, rats were individually placed in a closed arm of the zero-maze and behaviour assessed by a "blind" observer using remote video monitoring over the subsequent 5 min. The animal was then removed and the maze carefully wiped with 5% methanol/water solution before the next test was begun.

Terminal sampling. At the end of the study, terminal blood was collected from 2 of the vehicle treated rats (>5 mL) and from all S-methylone HCl treated rats (500 uL) by CP under $CO_2$. Blood samples were placed into Eppendorf tubes on ice containing 22 μL/mL blood (vehicle treated) or 11 μL EDTA (93 mg/mL) (S-methylone HCl treated rats) and gently mixed. After no longer than 30 min, blood samples were centrifuged at 10,000 rpm×3 min and plasma samples (>2 mL (vehicle) or 2×100 μL (S-methylone HCl treated) placed into Eppendorf tubes (Vehicle) or 96 well plates on dry ice. Immediately after blood sampling, brains were excised, rinsed in saline, blotted, weighed and snap-frozen in liquid $N_2$. All samples were stored at −20° C. until dispatched on dry ice for analysis.

Total number of plasma samples=25+2 vehicle controls.

Total number of brain samples=25+2 vehicle controls.

Synopsis of Testing Schedule S-Methylone HC and Chlordiazepoxide in the Rat Elevated Zero Maze Model of Anxiety.

| n | Rat Strain & sex | 0.5 Pretest in Veh 1 5 mL/kg ip | T = 0 Zero-maze | T = 0.25 Terminal sampling |
|---|---|---|---|---|
| 5 | Male SD | Vehicle 1 (Saline) | Test | Plasma & brain from 2 rats |
| 5 | Male SD | S-methylone HCl 2.5 mg/kg | Test | Plasma & brain |
| 5 | Male SD | S-methylone HCl 5 mg/kg | Test | Plasma & brain |
| 5 | Male SD | S-methylone HCl 7.5 mg/kg | Test | Plasma & brain |
| 5 | Male SD | S-methylone HCl 15 mg/kg | Test | Plasma & brain |
| 5 | Male SD | S-methylone HCl 30 mg/kg | Test | Plasma & brain |
| 5 | Male SD | CDP 6 mg/kg | Test | n/a |

Example 3-29: Effect of Administration of R-Methylone HC and Chlordiazepoxide on Behavior in a Rat 0-Maze Study Protocol: 25 male Sprague-Dawley rats in treatment groups of 5, were intraperitoneally dosed with either Vehicle 1 (saline) or R-methylone HCl at 1 of 3 dose levels (5, 15 & 30 mg/kg) or chlordiazepoxide (6 mg/kg) in 5 mL/kg injection volumes. Thirty min later at T=0, rats were individually placed in a closed arm of the zero-maze and behaviour assessed by a "blind" observer using remote video monitoring over the subsequent 5 min. The animal was then removed and the maze carefully wiped with 5% methanol/water solution before the next test is begun.

Terminal sampling. At the end of the study, terminal blood samples were collected from 2 of the vehicle treated rats (>5 mL) and from all R-methylone HCl treated rats (500 uL) by CP under $CO_2$. Blood samples were placed into Eppendorf tubes on ice containing 22 μL/mL blood (vehicle treated) or 11 μL EDTA (93 mg/mL) (R-methylone HCl treated rats) and gently mixed. After no longer than 30 min, blood samples were centrifuged at 10,000 rpm×3 min and plasma samples (>2 mL (vehicle) or 2×100 μL (R-methylone HCl treated) placed into Eppendorf tubes (Vehicle) or 96 well plates on dry ice. Immediately after blood sampling, brains were excised, rinsed in saline, blotted, weighed and snap-frozen in liquid $N_2$. All samples were stored at −20° C. until dispatched on dry ice for analysis.

Total number of plasma samples=15+2 vehicle controls.
Total number of brain samples=15+2 vehicle controls.
Synopsis of Testing Schedule R-Methylone HCl and Chlordiazepoxide in the Rat Elevated Zero Maze Model of Anxiety.

| n | Rat Strain & sex | 0.5 Pretest in Veh 1 5 mL/kg ip | T = 0 Zero-maze | T = 0.25 Terminal sampling |
|---|---|---|---|---|
| 5 | Male SD | Vehicle 1 (Saline) | Test | Plasma & brain from 2 rats |
| 5 | Male SD | R-methylone HCl 5 mg/kg | Test | Plasma & brain |
| 5 | Male SD | R-methylone HCl 15 mg/kg | Test | Plasma & brain |
| 5 | Male SD | R-methylone HCl 30 mg/kg | Test | Plasma & brain |
| 5 | Male SD | CDP 6 mg/kg | Test | n/a |

DISCUSSION

The results show that specific doses of racemic methylone, S-methylone, and R-methylone all increase time in the open arms and decreased the frequency of SAPs as effectively as the benzodiazepine chlordiazepoxide (FIGS. 62-67). This shows that at a sufficient dose, racemic methylone, S-methylone, and R-methylone are all effective anxiolytics and supports their development in these indications. This is the first in vivo data showing methylone is effective in these indications. However, there were some unexpected findings that show they are not equivalent in regard to side effects that further inform dose selection for their therapeutic use in humans.

Figure 62:
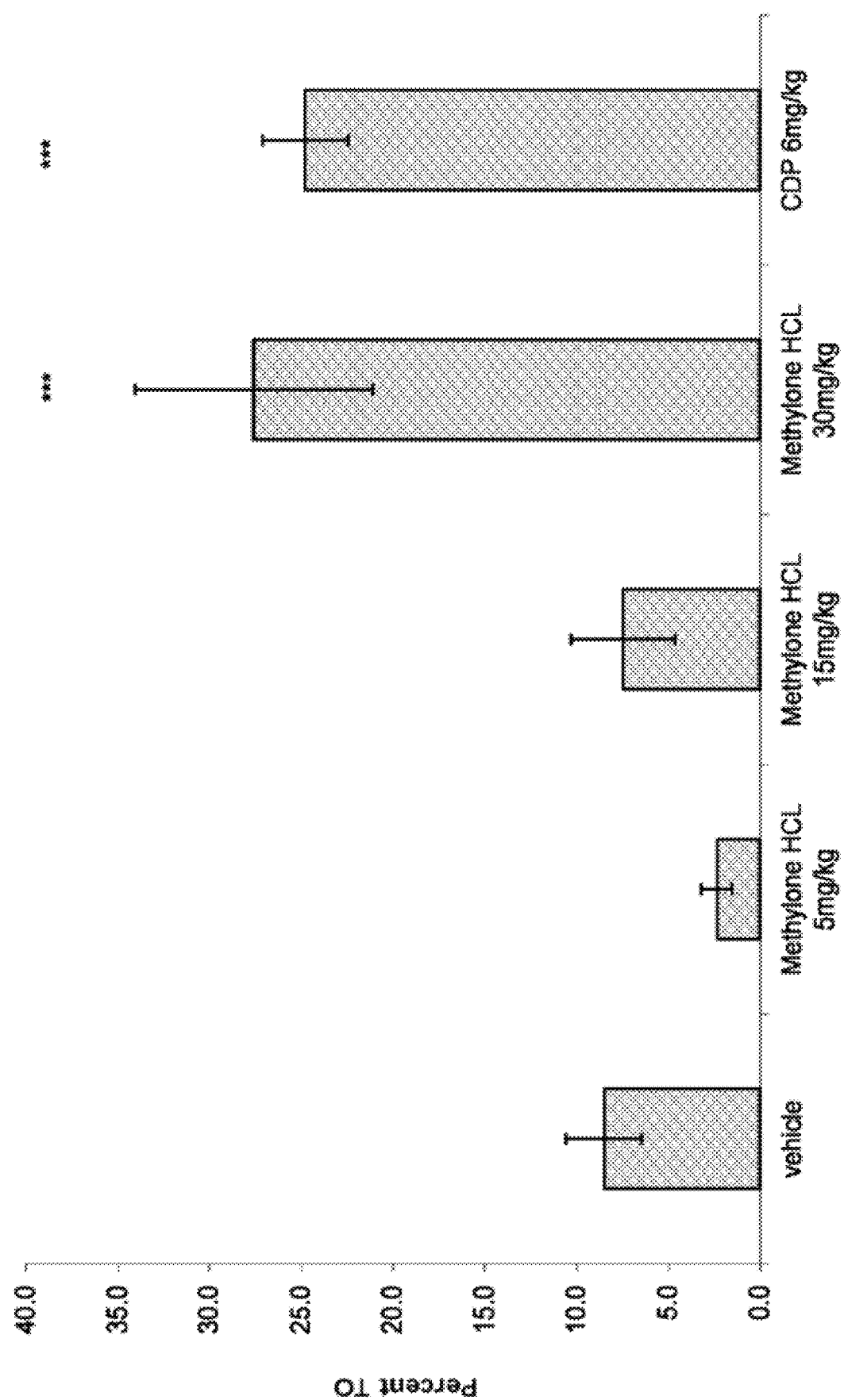
FIG. 62 illustrates the percentage of time spent in the open arms after racemic methylone compared to vehicle and chlordiazepoxide control on the elevated zero maze.
Figure 63:
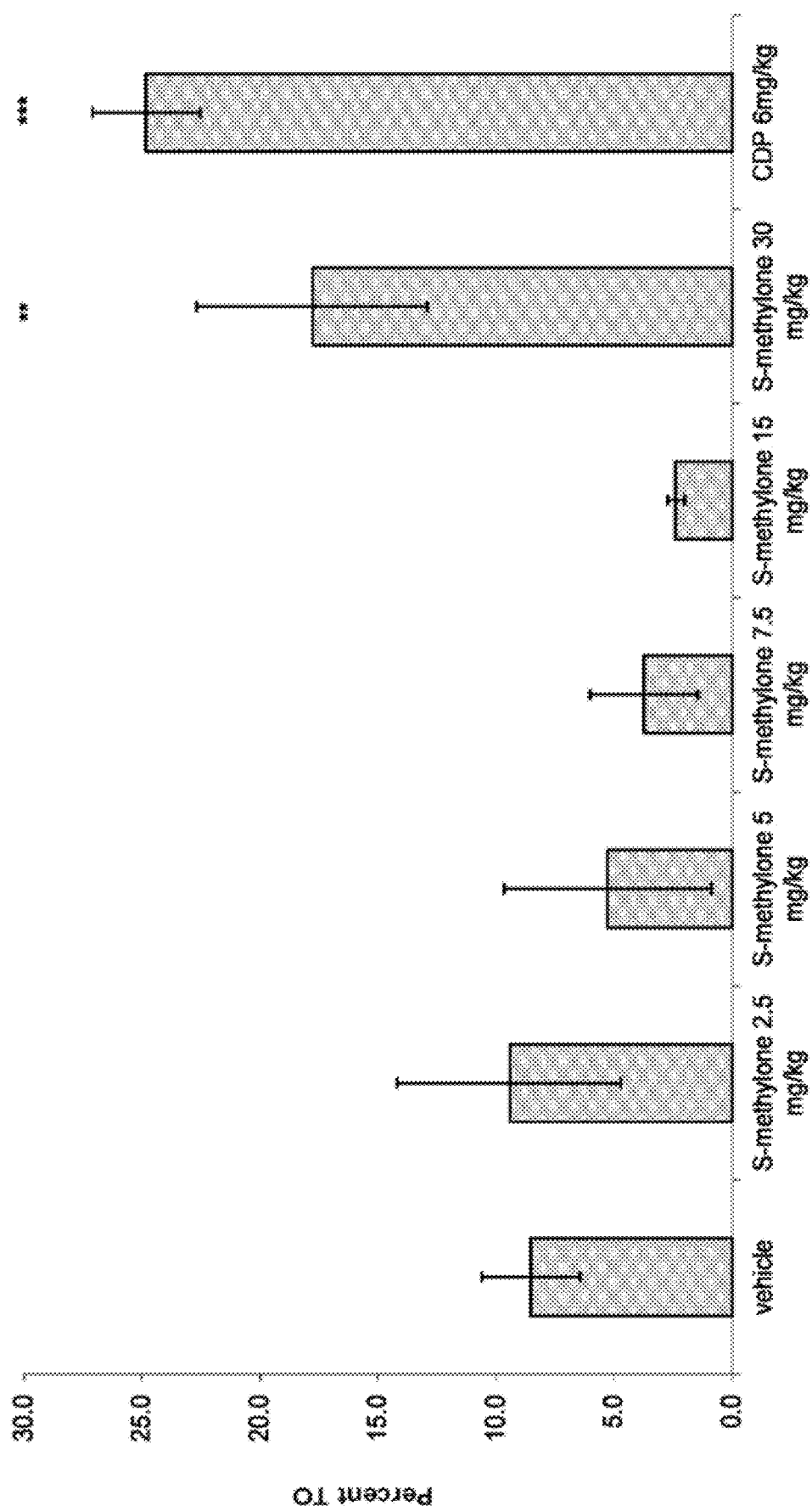
FIG. 63 illustrates the percentage of time spent in the open arms after S-methylone compared to vehicle and chlordiazepoxide control on the elevated zero maze.
Figure 65:
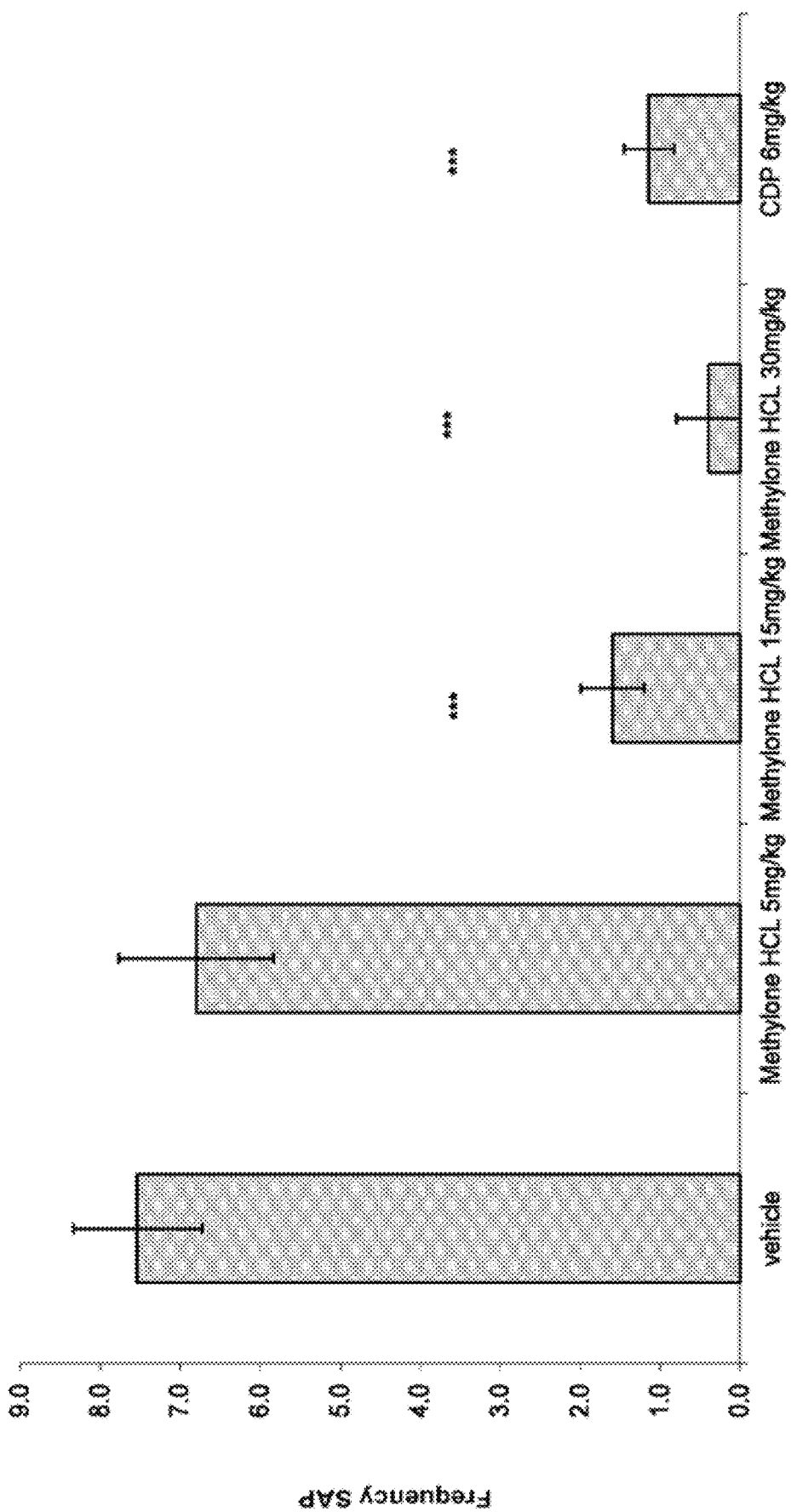
FIG. 65 illustrates the frequency of SAPs after racemic methylone compared to vehicle and chlordiazepoxide control on the elevated zero maze.
Figure 68:
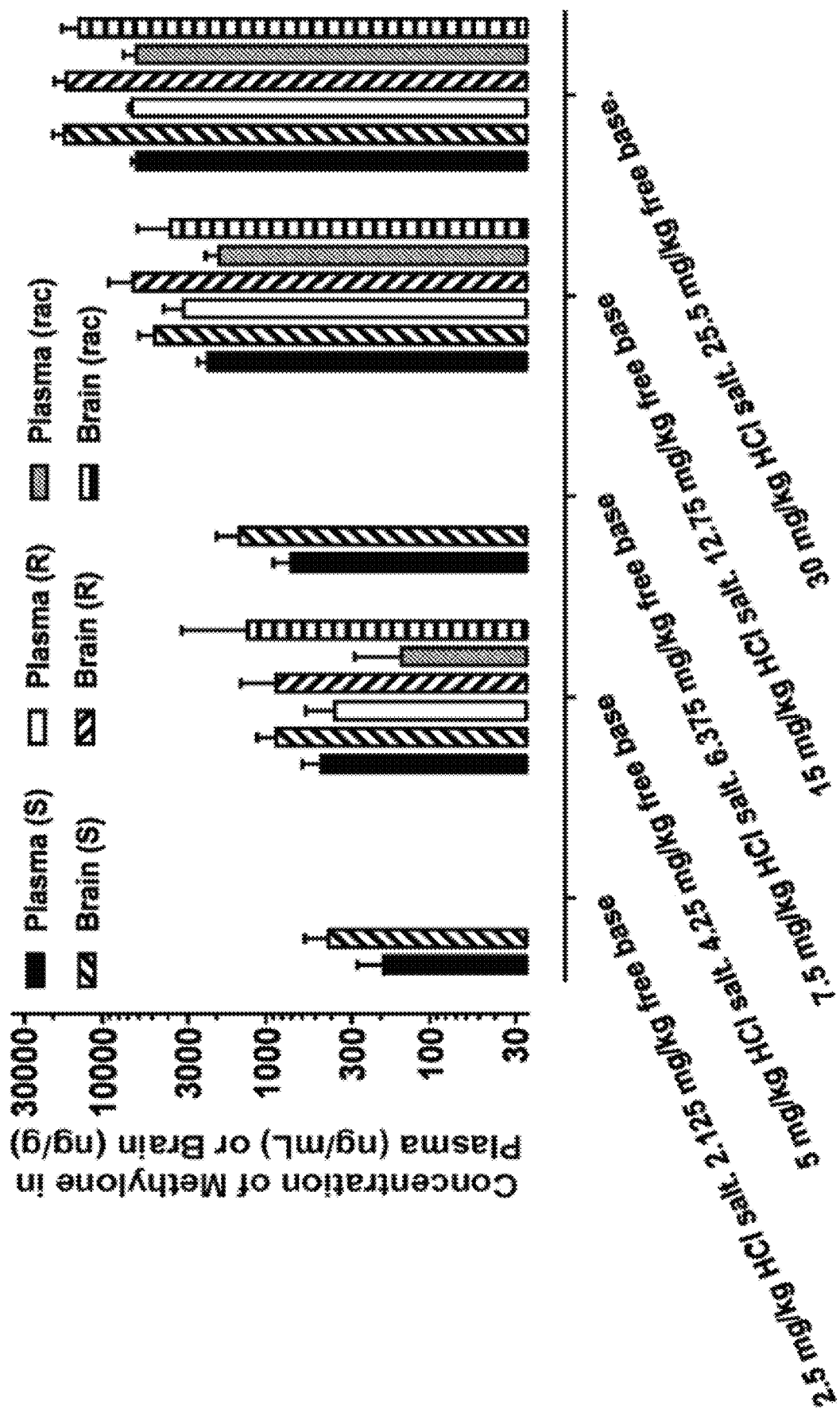
FIG. 68 illustrates a logarithmic graph showing the concentration of racemic methylone, R-methylone, and S-methylone in plasma and brain measured at the end of the zero maze study.
Figure 69:
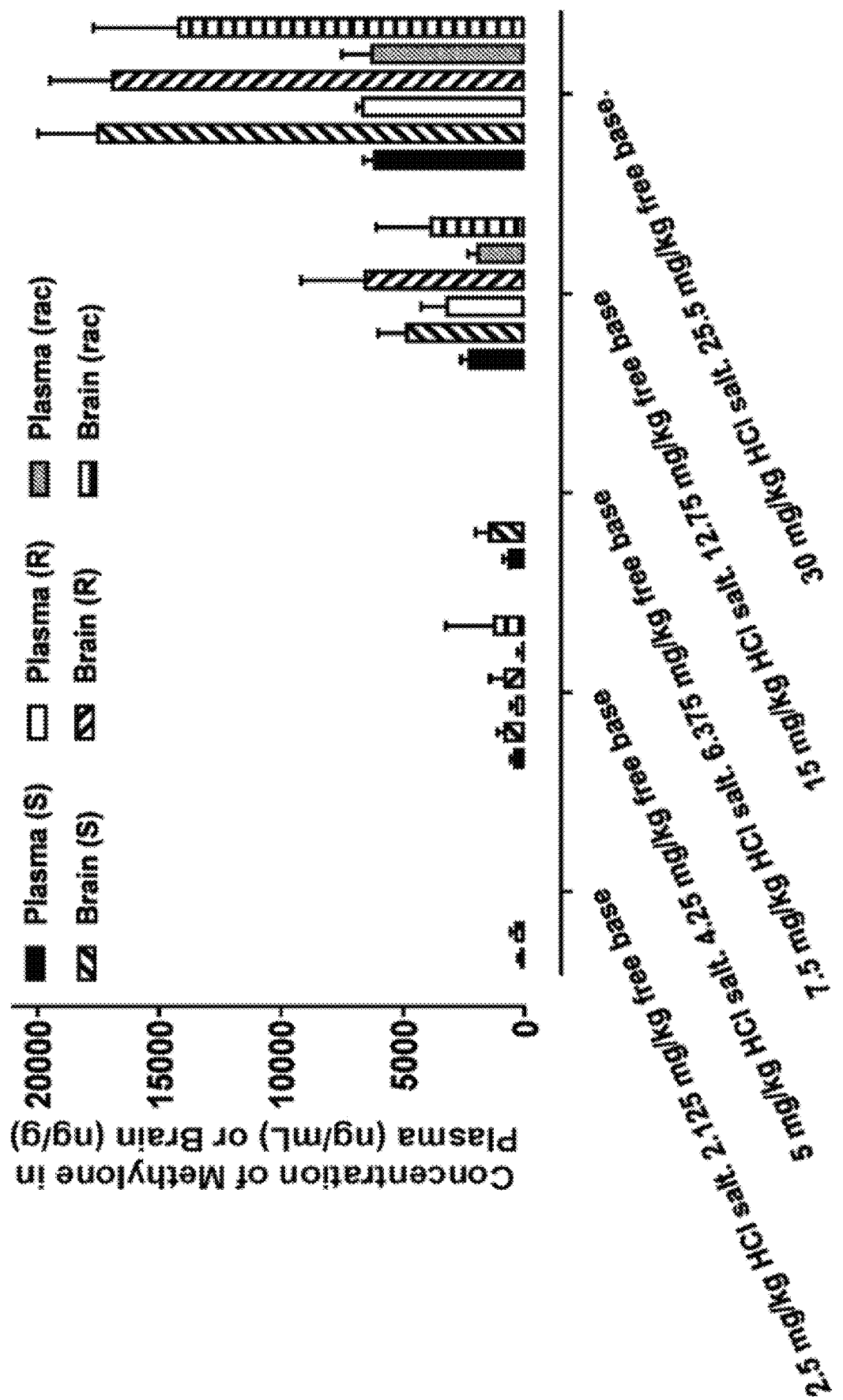
FIG. 69 illustrates a graph showing the concentration of racemic methylone, R-methylone, and S-methylone in plasma and brain measured at the end of the zero maze study.

First, for racemic methylone, the lowest dose tested (5 mg/kg) showed a decrease in time spent in the open arms vs placebo (FIG. 62). This indicates that this low dose of methylone had an anxiogenic effect. Similarly, the middle dose of 15 mg/kg showed no difference from placebo in time spent in the open arms but showed a dose dependent decrease in SAPs indicating a mixed anxiogenic anxiolytic effect at this dose range (FIG. 65). However, the decrease in SAPs was not as effective as chlordiazepoxide at this dose. In contrast, the 30 mg/kg dose showed both a significant decrease in time spent in the open arms as well as a decrease in SAPs. This indicates that for racemic methylone, low doses can paradoxically increase anxiety and that this anxiogenic effect shifts to an anxiolytic effect at doses that are sufficiently high to induce a therapeutic effect. This data is supported by the plasma and brain samples verifying the dose of methylone indeed increased in both brain and plasma at the higher doses (FIG. 68 and FIG. 69).

Figure 66:
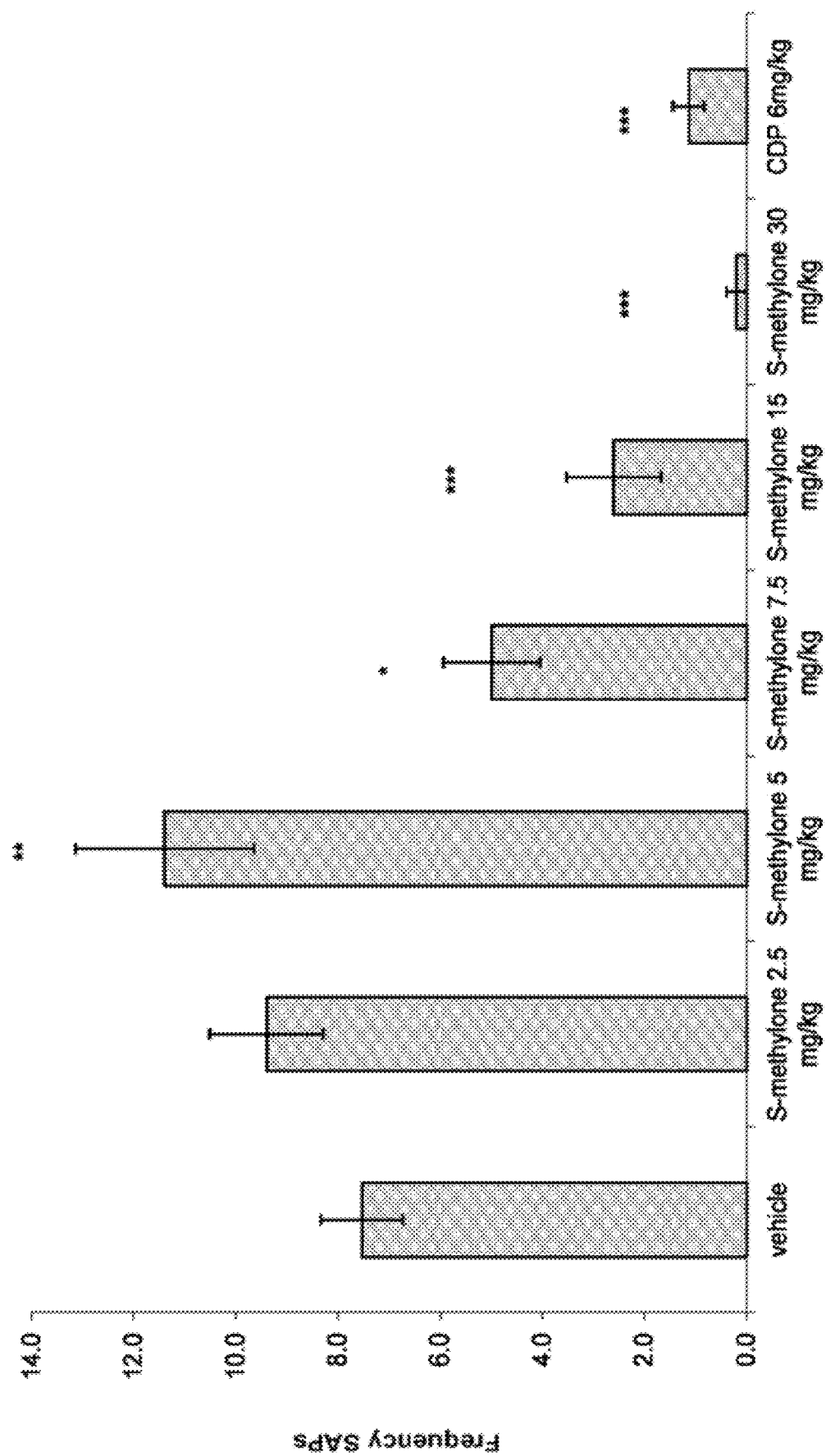
FIG. 66 illustrates the frequency of SAPs after S-methylone compared to vehicle and chlordiazepoxide control on the elevated zero maze.

Since we hypothesized that S-methylone would be the more potent enantiomer, the dose range was expanded to even lower doses to investigate the dose range that may induce anxiogenic effects or mixed effects. There was an even stronger dose dependent anxiogenic effect observed with S-methylone than racemic methylone. For S-methylone, the time spent in the open arms decreased as the dose increased with the 5 mg/kg, 7.5 mg/kg and 15 mg/kg indicating an increasing anxiogenic effect. This was reversed at 30 mg/kg at which point the time in the open arms increased (FIG. 63) and was as effective as chlordiazepoxide at increasing time spent in the open arms. This indicated that this dose level was the most effective anxiolytic dose of S-methylone. Similarly, a dose dependent increase in SAPs at the 2.5 mg/kg and 5 mg/kg doses which then switch to a dose dependent decrease in SAPS at 7.5 mg/kg, 15 mg/kg and 30 mg/kg was observed (FIG. 66). Compared to SAPs, the time spent in the open arms is the primary measure of anxiety indicating that the mixed effects on SAPs did not decrease the overall effect on anxiety at 7.5 mg/kg and 15 mg/kg. The data show that the lowest doses of methylone induce a purely anxiogenic effect with middle doses inducing a mixed anxiogenic-anxiolytic effect and higher doses exerting a purely anxiolytic effect. The 30 mg/kg dose was an effective anxiolytic on all measures and was even more effective than chlordiazepoxide at reducing SAPs.

Figure 64:
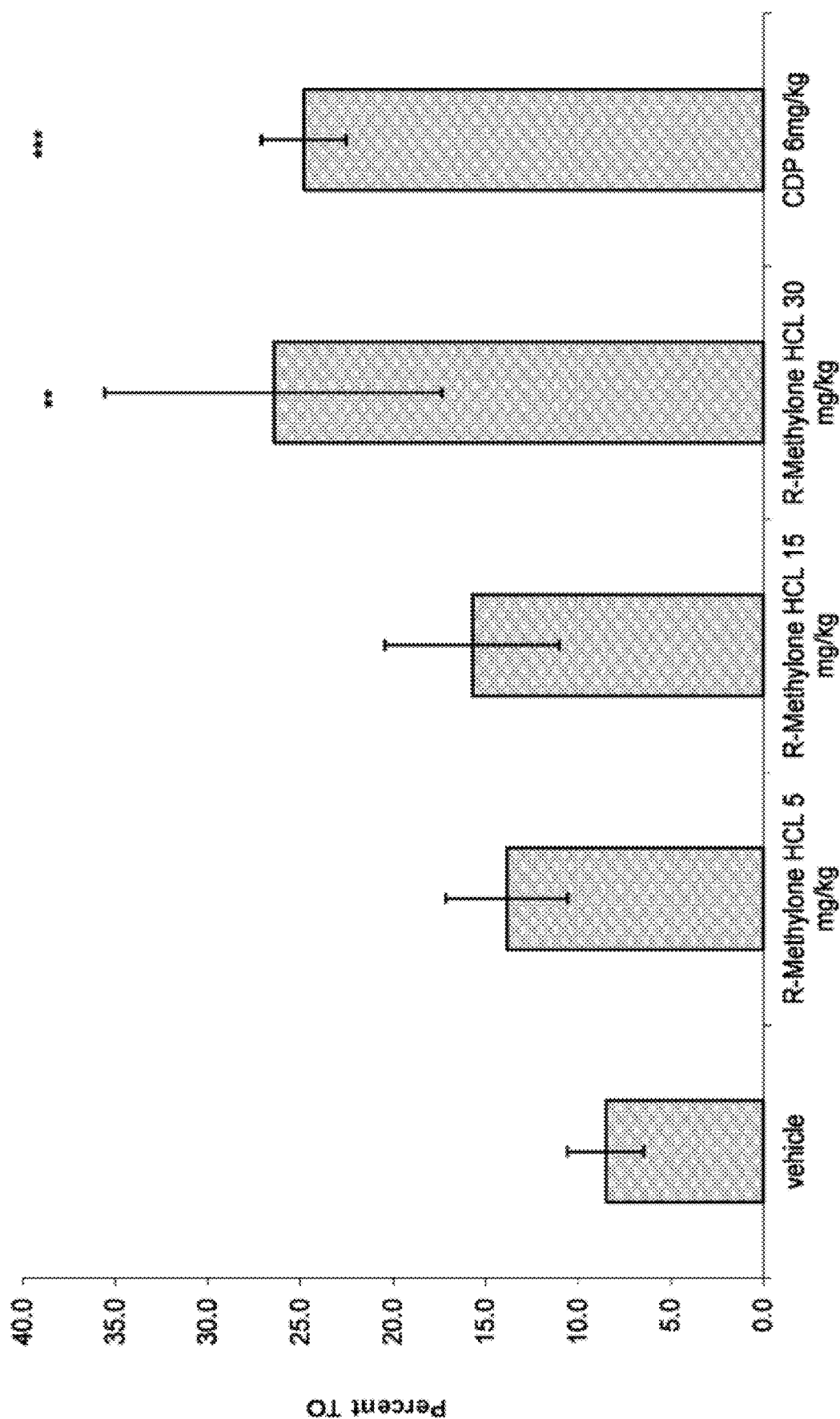
FIG. 64 illustrates the percentage of time spent in the open arms after R-methylone compared to vehicle and chlordiazepoxide control on the elevated zero maze.
Figure 67:
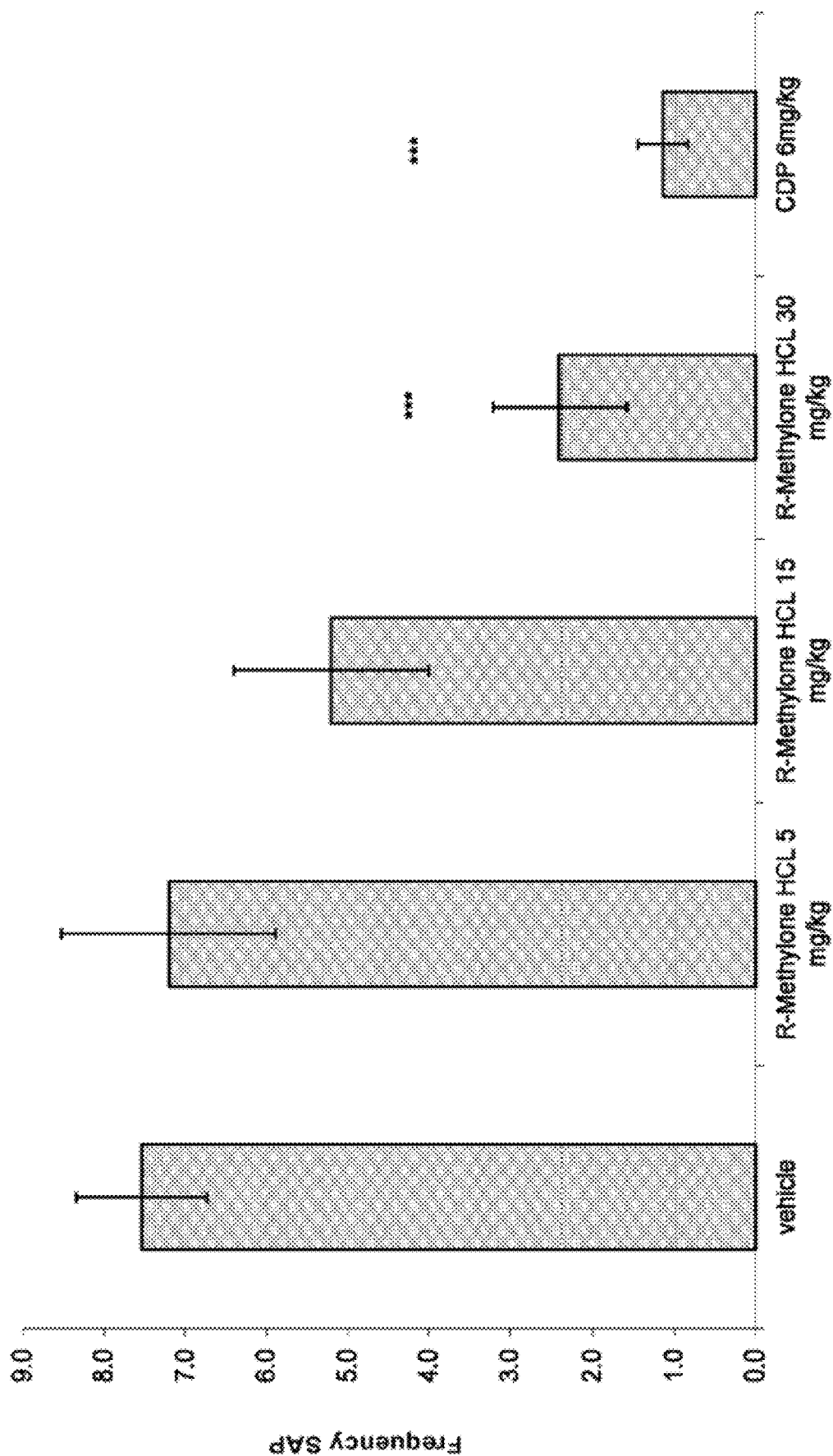
FIG. 67 illustrates the frequency of SAPs after R-methylone compared to vehicle and chlordiazepoxide control on the elevated zero maze.

Surprisingly, in contrast to racemic methylone and S-methylone, R-methylone did not show any anxiogenic effect at any dose. In fact, R-methylone showed a dose dependent increase in time spent in the open arms that was as effective as chlordiazepoxide at 30 mg/kg and also showed a simultaneous dose dependent decrease in SAPs across this range with 30 mg/kg significantly decreasing SAPs to the same level as chlordiazepoxide (FIG. 64 and FIG. 67). This surprising result shows that R-methylone does not have the anxiogenic side effects seen with racemic methylone and S-methylone. Since racemic methylone is comprised of equal amounts of S-methylone and R-methylone, this indicates that the anxiogenic side effects seen with lower doses of racemic methylone are due to the anxiogenic effects of S-methylone.

The data shows that while racemic methylone, S-methylone and R-methylone all have anxiolytic effects as effective as chlordiazepoxide at the high dose level, racemic methylone and S-methylone show anxiogenic effects at lower doses, an effect not seen with R-methylone. There are several critical implications of this finding. The first is that patients treated with racemic methylone or S-methylone must receive a dose high enough to reach the anxiolytic threshold since lower doses may cause anxiety as a side effect and result in worsening of the disorder being treated. This could have especially severe implications for anxiety disorders or depressive disorders including post-traumatic stress disorder, generalized anxiety disorder, panic disorder, major depressive disorder, or treatment resistant depression. All of these indications are associated with an increased level of anxiety. In these cases, a drug-induced increase in anxiety due to improper dosing of racemic methylone or S-methylone could have severe side effects on patients and worsen their underlying disorder. The data presented herein show that patients treated with a racemic methylone or S-methylone must be carefully titrated to avoid the anxiogenic effects and to reach the anxiolytic effect level. The data show that in some embodiments a Risk Evaluation and Mitigation Strategy (REMS) program should be utilized so that patients treated with racemic methylone or S-methylone should undergo an initial dose titration to determine the effective range specific to that patient. This dose titrating protocol would decrease the side effects related to underdosing racemic methylone or S-methylone.

The data also inform Phase 2 and Phase 3 clinical trial design. Clinical trials for neurological and psychiatric disorders often include one or more low dose arms to show a dose dependent effect of the full dose on the disease of interest. However, this data shows that racemic and S-methylone should only be dosed at the full effective dose and a low dose arm should not be included as a comparator as this may lead to harmful side effects on the patients. This data shows that studies of racemic and S-methylone should only use inactive matched placebo or a different standard of care therapeutic as a control. In clinical trials methylone should only be dosed at its effective dose range to avoid harmful side effects to the patients. This would be especially critical in clinical studies of anxiety disorders or depression including post-traumatic stress disorder, generalized anxiety disorder, panic disorder, major depressive disorder, or treatment resistant depression where increased anxiety could worsen the underlying disorder and lead to potentially devastating effects on the patients.

The data show that there is an advantage of R-methylone which is anxiolytic without any anxiogenic effects. In some embodiments, a clinician treating a patient with R-methylone does not need to utilize a specific dose titration protocol to reduce anxiogenic effects. In some embodiments clinical studies of R-methylone have a greater safety margin and are able to use lower doses in different arms of the study to demonstrate a dose dependent effect on the disease of interest. In some embodiments, R-methylone allows greater flexibility in clinical trial design including the safe use of a low dose active comparator to reduce expectancy bias. In some embodiments, R-methylone would be preferred to racemic methylone or S-methylone to treat patients with anxiety or depressive disorders including post-traumatic stress disorder, generalized anxiety disorder, panic disorder, major depressive disorder, or treatment resistant depression. In some embodiments R-methylone is a safer alternative to racemic methylone or S-methylone for the treatment of neurological and psychiatric disorders.

Example 3-30: Methylone Dose Titration Risk Evaluation and Mitigation Strategy (REMS) Protocol General Information on Methylone Treatment Session Initial methylone dosing and subsequent dosing adjustments must be done under the supervision of a qualified healthcare professional in a clinic or inpatient setting. The patient must remain under supervision of the healthcare professional for at least 6 hours and up to approximately 24 hours after the final methylone dose adjustment. The patient will be assessed periodically during the session for anxiety and other effects of methylone. Dose adjustments within a methylone treatment session will be based on changes from baseline levels of anxiety. Postdose anxiety measurement timing and duration of observation after dosing are based on the following information reported by the World Health Organization (WHO 2014):

| Duration of effects of methylone | |
|---|---|
| Effects | Time After Dose |
| Onset | 15 min-60 min |
| Coming Up | 30 min-45 min |
| Plateau | 60 min-90 min |
| Coming Down | 60 min-120 min |
| Duration | 2 hours-3.5 hours |
| Normal After Effects | 6 hours-24 hours |
| Total Duration | 3 hours-5 hours |

Methylone dosing is modified from information reported by the World Health Organization (WHO 2014):

| Methylone dosages | |
|---|---|
| Drug Activity Level | Oral Methylone Dose |
| Threshold | 60 mg-100 mg |
| Light | 100 mg-150 mg |
| Common | 150 mg-200 mg |
| Strong | 200 mg-270 mg |
| Very Strong | ≥270 mg |

In some embodiments, the methylone dosing above is used with racemic methylone. In some embodiments, the methylone dosing above is used with (S)-methylone.

Predose Assessment

The patient's baseline level of anxiety will be measured and recorded.

Initial Methylone Dosing

The patient will receive an initial single oral dose of methylone in the range of approximately 100 mg-200 mg based on oral doses reported as producing moderate effects (Poyatos et al., 2021).

Postdose Assessment

Change from baseline anxiety level will be measured at approximately 1 to 2 hours after dosing based on reported time to achieve peak effects (Poyatos et al., 2021).

Methylone Dose Adjustment

Methylone effects have been maintained by taking a larger initial dose followed by smaller doses (30 mg to 100 mg p.o.) (WHO 2014). Re-dose of one-third to one-half the initial dose usually prolongs duration for approximately one hour (WHO 2014). Accordingly, the dose of methylone will be adjusted based on change from baseline in anxiety as follows:

| Methylone dose adjustment | |
| --- | --- |
| Change from Baseline Anxiety | Methylone Dose Adjustment |
| Increased | Increase dose 30%-50 % and reassess anxiety in approximately 1 hour |
| No Change | |
| Decreased | Increase dose 30%-50 % and reassess anxiety in approximately 1 hour Maintain dose if therapeutic effect achieved or Increase to a maximum of 250 mg total dose to optimize therapeutic effect |

Methylone Discontinuation

The patient will be observed for at least 6 hours after final methylone dose is administered.

The patient may be confined to the inpatient unit for prolonged observation up to approximately 24 hours after last methylone dose if indicated based on persistent effects.

Anxiety that appears after the final methylone titration dose is administered can be managed with an appropriate anxiolytic agent (Prosser and Nelson, 2012). If this is necessary, the patient must remain under observation and undergo periodic reassessment until the supervising healthcare professional determines the patient can be discharged from care.

Poyatos L, et al., A Comparison of Acute Pharmacological Effects of Methylone and MDMA Administration in Humans and Oral Fluid Concentrations as Biomarkers of Exposure. Biology (Basel). 2021 Aug. 17; 10(8):788. Prosser J M, Nelson L S. The toxicology of bath salts: a review of synthetic cathinones. J Med Toxicol. 2012 March; 8(1):33-42. World Health Organization (WHO). Methylone (bk-MDMA). Critical Review Report; WHO: Geneva, Switzerland, 2014.

Example 3-31: A Double-Blind, Randomized, Placebo-Controlled Clinical Trial of Methylone-Assisted Psychotherapy in PTSD A multicenter, randomized, double-blind, placebo-controlled trial is conducted to assess the efficacy and safety of methylone-assisted psychotherapy versus psychotherapy with placebo control in participants diagnosed with at least moderate post-traumatic stress disorder (PTSD).

Rationale

PTSD is a debilitating and often times chronic disorder associated with profound mental, physical, occupational, and functional impairment. PTSD can develop due to exposure to a traumatic event or persistent or recurring threats to an individual. Studies indicate that approximately 10% of individuals exposed to a traumatic event eventually go on to be diagnosed with PTSD (American Psychiatric Association. *Diagnostic and statistical manual of mental disorders*, 5$^{th}$ edition, 2013). PTSD is a complex psychiatric disorder characterized by symptom heterogeneity including avoidance of trauma-related material, emotional blunting and distancing, hyper-vigilance, hyper-arousal, persistent negative alterations in mood, persistent alterations in cognition, disturbing thoughts, disruptions in sleep and/or dreams, and physical or mental distress. Symptoms can be severe and long lasting. Although this symptom heterogeneity may suggest a wide spectrum of separate disturbances, emotional dysregulation is considered to be a core component of this disorder. Particularly germane to the pathogenesis and progression of PTSD, emotional dysregulation in affected individuals is believed to give rise to observable and measurable features such as presence of hypervigilance and attentional biases, enhanced startle response, hyper-arousal, apathetic feeling or emotional numbness, irritability, enhanced memories associated with traumatic events, difficulty in discerning danger versus safety, a generalization of fear, and avoidance of reminders of trauma. Emotional dysregulation may be defined and also measured by elevated emotional reactivity based on abnormal detection or appraisal of emotional triggers involving bottom-up sensory detection and neuronal processing. Biochemical alterations found in individuals diagnosed with PTSD suggest abnormalities in the hypothalamic-pituitary-adrenal (HPA) axis. The HPA axis is known to regulate reactions to stress and controls significant aspects of the neuroendocrine system impacting many homeostatic systems in the body. In a typical flight-or-flight response in a healthy individual, catecholamine and cortisol levels detected in urine rise after exposure to a stressor. In PTSD, many individuals show a low secretion of cortisol and high secretion of catecholamine in response to a stressor indicating a change in catecholamine to cortisol ratio in the urine. More evidence that the HPA axis is impacted in PTSD is found in elevated levels of catecholamines and corticotropin-releasing factor in the brain of many affected individuals.

The initiation and/or maintenance of emotional dysregulation in PTSD may be due to abnormalities in top-down control of emotional responses indicating that cognitive influences and higher order representations may impinge on information and emotional processing. Certainly, some aspects of abnormalities in neuronal processing in PTSD occur either implicitly (e.g., unconsciously) or explicitly (e.g., consciously) indicating involvement of distinct cognitive processes. Exaggerated responses in the amygdala and insular cortex have been demonstrated in meta-analyses in PTSD pathology, as have decreases in activity in other brain regions including the anterior cingulate cortex and aspects the prefrontal cortex including the ventromedial prefrontal cortex. In addition to changes in patterns of neuronal activity in individuals with PTSD, several neuroanatomical changes in PTSD have also been demonstrated. A reduction of total brain volume, intracranial volume, and the volumes in regions such as the hippocampus (particularly localized to the CA3 and dentate gyrus regions), insular cortex, and anterior cingulate cortex have been indicated in occurring in some individuals with PTSD through meta-analyses of structural MRI studies. Animal studies have shown that severe chronic stress leads to atrophy of apical dendrites in the CA3 region of the hippocampus, reduced hippocampus neurogenesis, and elevated granule cell death in the dentate gyrus due to elevated levels of glucocorticoids (Gould E. and Tanapat. (1999). *Stress and hippocampal neurogenesis*. Biol. Psychiatry 46, 1472-1479.) Connections between brain areas such as the amygdala, hippocampus, prefrontal cortex, and hypothalamus can facilitate activation of the HPA axis to illustrate interactions between brain regions with structural changes and affected biochemical regulatory systems in PTSD.

Methylone is a synthetic analog of the psychedelic phenethylamine class of compounds known to act as a mixed reuptake inhibitor/releasing agent of serotonin, norepinephrine, and dopamine and administration of methylone can produce acute modulations of neurotransmission. Methylone administration also has indirect effects on neurohormone release. Methylone can function as a psychoplastogen promoting neuronal growth, modulating neuronal connectivity, and regulating neuronal plasticity through longer term neuronal changes. The combined neurobiological effects of methylone administration on individuals reduce fear of emotional injury or distress, enhance introspection and communication, and increase empathetic feelings and compassion. Additionally, methylone may serve to enhance fear extinction. These combined effects may yield acute and longer-term productive psychological states to enhance behavioral or cognitive-behavioral therapies. Methylone administration may enhance neuronal function at the biochemical and cellular levels to generate or restore favorable neural network pathways and connectivity to increase behavioral or cognitive-behavioral therapy productiveness.

Study Design

This multicenter, randomized, double-blind, placebo-controlled trial is conducted at various sites in the United States with IRB approval from each study site. A flexible dose of methylone hydrochloride salt or placebo, followed by a supplemental half-dose unless contraindicated by patient's previous response or medical history, is also administered during the Treatment Period with psychotherapy in at least 3 blinded monthly Experimental Sessions. The Supplemental Dose extends the duration of drug effects on the participants during an Experimental Session. Methylone test groups are further subdivided into specific groups receiving only racemic methylone hydrochloride salt, S-methylone hydrochloride salt, or R-methylone hydrochloride salt. An optional Risk Evaluation and Mitigation Strategy (REMS) Protocol may be implemented for the racemic methylone, S-methylone, and placebo-groups. The Treatment Period lasts for approximately 12 weeks. During the Treatment Period, each Experimental Session is followed by three Intervening Sessions of non-drug psychotherapy. Each Experimental Session involves an overnight stay. The Primary Outcome measure, the change in Clinician Administered PTSD Scale for DSM-5 (CAPS-5), is determined by a blinded Independent Rater (IR) pool multiple times throughout the study. The study consists of separate periods for each participant. Initially, prospective participants undergo a Screening Period involving an initial eligibility assessment, a medical history intake, informed consent, and enrollment of eligible participants. Next, a Preparation Period is undertaken for enrolled participants involving medication tapering and clinical baseline assessments to confirm each participant meets enrollment criteria. As part of the Preparation Period, a detailed assessment of co-morbidities to PTSD is recorded. Participants may remain on prescribed courses of selective serotonin reuptake inhibitor (SSRI) or serotonin and norepinephrine reuptake inhibitor (SNRI) treatment. Dosages and/or frequency of administration of a prescribed SSRI or SNRI may be adjusted to fit within study parameters. Participants may be required to taper a prescribed course of medication in order to maintain eligibility within the study. The Treatment Period consists of three monthly Experimental Sessions and associated Intervening Sessions of integrative behavioral psychotherapy. The Treatment Period lasts approximately 12 weeks. Following the Treatment Period is a Follow-up Period and Study Conclusion. During the Follow-up Period and Study Conclusion, participants complete 4 weeks with no study visits, followed by a Study Conclusion visit.

| Screening Period-from initial consent to beginning of enrollment (approx. 4 weeks) | | | |
|---|---|---|---|
| Study Visit | | Visit Timing | Description |
| Screening | Screening | Several visits taking place 5-30 days after initial phone call screen | Informed consent obtained and assessment measures of pre-study medications, complete personal and family medical history and all assessed screening measures undertaken. These measures may include any of: PTSD checklist for DSM-5 (PCL-5), Columbia-Suicide Severity Rating Scale (C-SSRS), Montgomery-Asberg Depression Rating Scale (MADRS), Hamilton Depression Rating Scale (HAM-D), Hamilton Anxiety Rating Scale (HAM-A), General Anxiety Disorder-7 (GAD-7), Beck Anxiety Inventory (BAI), Impact of Events Scale (IES), State-Trait Anxiety Inventory (STAI), Edinburgh Postnatal Depression Scale (EPDS), Clinical Global Impressions Scale (CGI-I), Epworth Sleepiness Scale (ESS), and Pittsburgh Sleep Quality Scale. Medical providers are contacted and medical records and laboratory results are obtained. All results and records are reviewed along with interview notes. If eligible, results of Life Events Checklist for DSM-5 (LEC-5) and Structured Clinical Interview for DSM-5 Personality Questionnaire (SCID-5-SPQ) are forwarded to IR. |
| | IR Screening | 2-10 days after initial eligibility determined during Screening Period | Initial eligibility after PCL-5 and initial eligibility are reviewed. Next, IR conducts a since last visit C-SSRS, SCID-5-PD, Dissociative Disorders Interview Schedule (DDIS), and/or International Neuropsychiatric Interview (MINI). Results of IR assessment confirmed over Preparatory Period. |

| Screening Period-from initial consent to beginning of enrollment (approx. 4 weeks) | | | |
|---|---|---|---|
| Study Visit | | Visit Timing | Description |
| Enrollment | Enrollment | 1-14 days after IR Screening | Prior to enrollment, all screening measures are reviewed and any clarification needed with participant is completed by telephone interview. If enrolled, and if it has been determined to taper an ongoing medication, begin a tapering treatment plan of at least 5 half-lives plus at least 5 days for stabilization. Begin collection of Adverse Events (AE). |

| Preparation Period (between 1-12 weeks) | | | |
|---|---|---|---|
| Study Visit | | Visit Timing | Description |
| Preparatory Period | Preparatory Session 1 | Undertaken 0-14 days post-enrollment | Schedule visit timing according to medication tapering needs. Schedule calls in between visits for safety concerns, tapering questions, or other issues related to medical history. Confirm enrollment. |
| | Preparatory Session 2 | Undertaken 2-21 days following Preparation Session 1 | tapering is not needed or is already completed. If still tapering, schedule additional telephone call for continuing assessment of readiness to enter study. |
| | Taper follow-up | 0-7 days following end of medication taper | Schedule baseline CAPS-5. |
| Baseline and Enrollment | Baseline Assessments | Following Preparatory Session 2 | Complete CAPS-5, Sheehan Disability Score (SDS), and Dissociative Subtype of PTSD Scale (DSPS) by IR via in-person or telemedicine appointment. Scores forwarded to therapy monitoring team. Resumption of tapered medicine in symptom management requires. Withdrawal of participants not meeting eligibility criteria at this point. |
| Confirmation | Preparatory Session 3 | 1-7 days following baseline CAPS-5 | Participants complete baseline self-report metrics and schedule Experimental Session 1. |

The Treatment Period schedule follows the Screening Period and the Preparatory Period

| Treatment Period (lasts approximately 12 weeks) | | | |
|---|---|---|---|
| Study Visit | | Visit Timing | Description |
| Treatment 1 | Randomization | 0-10 days following Baseline assessments | Complete following verification participant is still enrolled and Experimental Session 1 is scheduled. Double-blind randomization. |
| | Experimental Session 1 | 8 hours plus overnight observation | Patient's weight is determined for dosage calculation. Baseline STAI assessment. Dose is 100-200 mg p.o. Placebo administered in placebo group at same time interval. |
| | | Optional. Following anxiety assessment 0.75-2 hours after first dose administration | REMS Protocol: Only considered for administration of racemic methylone and S-methylone treatment groups and associated placebo controls. Underdosing of racemic methylone or S-methylone may lead to exacerbation of anxiogenic features necessitating careful assessment of worsening of symptoms. Patients are assessed for anxiety about 0.75 hours after first dose. With no change or increase in anxiety, patients are given a dose of 30%- |

| Study Visit | | Visit Timing | Description |
|---|---|---|---|
| | | | 50% of first dose and anxiety reassessed in about 1 hour. Dose titration up to a maximum cumulative dose of 250 mg. Placebo administered in placebo group at same time interval. If anxiety is decreased, no REMS protocol dose is given at this time. |
| | | 2-2.5 hours after first dose administration | Supplemental Dose: Supplemental half-dose of 50-100 mg administered 2 to 2.5 hours following initial dose administration unless contraindicated. If initial plus REMS protocol doses total a cumulative dose of 250 mg, no Supplemental Dose is given. If initial plus any REMS protocol dose is less than 250 mg, Supplemental Dose is administered 2 to 2.5 hours following initial dose administration. Placebo administered in placebo group at same time intervals. |
| | Intervening Session 1A | Morning following Experimental Session 1 | Behavioral or cognitive-behavioral therapy session lasting 90-120 minutes. Assessment of potential anxiogenic, mixed anxiogenic-anxiolytic, or anxiolytic treatment effects. CAPS-5 assessment. Instructions for participants to complete C-SSRS assessments on every two days following Experimental Session 1. |
| | Intervening Session 1B | 3 to 14 days following Experimental Session 1 | Behavioral or cognitive-behavioral therapy session lasting 60-120 minutes. CAPS-5 assessment. |
| | Intervening Session 1C | 18-34 days following Experimental Session 1 | Behavioral or cognitive-behavioral therapy session lasting 60-120 minutes. Assessments include LEC-5, HAM-A, C-SSRS and CAPS-5. |
| Treatment 2 | Experimental Session 2 | 8 hours plus overnight observation. 19-35 days following Experimental Session 1. | Patient's weight is determined for dosage calculation. Baseline STAI assessment. Dose is 100-200 mg p.o. Placebo administered in placebo group at same time interval. |
| | | Optional. Following anxiety assessment 0.75-2 hours after first dose administration | REMS Protocol: Only considered for administration of racemic methylone and S-methylone treatment groups and associated placebo controls. Underdosing of racemic methylone or S-methylone may lead to exacerbation of anxiogenic features necessitating careful assessment of worsening of symptoms. Patients are assessed for anxiety about 0.75 hours after first dose. With no change or increase in anxiety, patients are given a dose of 30%-50% of first dose and anxiety reassessed in about 1 hour. Dose titration up to a maximum cumulative dose of 250 mg. Placebo administered in placebo group at same time interval. If anxiety is decreased, no REMS protocol dose is given at this time. |
| | | 2-2.5 hours after first dose administration | Supplemental Dose: Supplemental half-dose of 50-100 mg administered 2 to 2.5 hours following initial dose administration unless contraindicated. If initial plus REMS protocol doses total a cumulative dose of 250 mg, no Supplemental Dose is given. If initial plus any REMS protocol dose is less than 250 mg, Supplemental Dose is administered 2 to 2.5 hours following initial dose administration. Placebo administered in placebo group at same time intervals. |
| | Intervening Session 2A | Morning following Experimental Session 2 | Behavioral or cognitive-behavioral therapy session lasting 90-120 minutes. Assessment of potential anxiogenic, mixed anxiogenic-anxiolytic, or anxiolytic treatment effects. CAPS-5 assessment. |

| Treatment Period (lasts approximately 12 weeks) | | | |
|---|---|---|---|
| Study Visit | | Visit Timing | Description |
| | Intervening Session 2B | 3 to 14 days following Experimental Session 2 | Instructions for participants to complete C-SSRS assessments on every two days following Experimental Session 1. Behavioral or cognitive-behavioral therapy session lasting 60-120 minutes. CAPS-5 assessment. |
| | Intervening Session 2C | 18-34 days following Experimental Session 2 | Behavioral or cognitive-behavioral therapy session lasting 60-120 minutes. Assessments include LEC-5, HAM-A, and C-SSRS and CAPS-5.. |
| Treatment 3 | Experimental Session 3 | 8 hours plus overnight observation. 19-35 days following Experimental Session 2. | Patient's weight is determined for dosage calculation. Baseline STAI assessment. Dose is 100-200 mg p.o. Placebo administered in placebo group at same time interval. |
| | | Optional. Following anxiety assessment 0.75-2 hours after first dose administration | REMS Protocol: Only considered for administration of racemic methylone and S-methylone treatment groups and associated placebo controls. Underdosing of racemic methylone or S-methylone may lead to exacerbation of anxiogenic features necessitating careful assessment of worsening of symptoms. Patients are assessed for anxiety about 0.75 hours after first dose. With no change or increase in anxiety, patients are given a dose of 30%-50% of first dose and anxiety reassessed in about 1 hour. Dose titration up to a maximum cumulative dose of 250 mg. Placebo administered in placebo group at same time interval. If anxiety is decreased, no REMS protocol dose is given at this time. |
| | | 2-2.5 hours after first dose administration | Supplemental Dose: Supplemental half-dose of 50-100 mg administered 2 to 2.5 hours following initial dose administration unless contraindicated. If initial plus REMS protocol doses total a cumulative dose of 250 mg, no Supplemental Dose is given. If initial plus any REMS protocol dose is less than 250 mg, Supplemental Dose is administered 2 to 2.5 hours following initial dose administration. Placebo administered in placebo group at same time intervals. |
| | Intervening Session 3A | Morning following Experimental Session 3 | Behavioral or cognitive-behavioral therapy session lasting 90-120 minutes. Assessment of potential anxiogenic, mixed anxiogenic-anxiolytic, or anxiolytic treatment effects. CAPS-5 assessment. Instructions for participants to complete C-SSRS assessments on every two days following Experimental Session 1. |
| | Intervening Session 3B | 3 to 14 days following Experimental Session 3 | Behavioral or cognitive-behavioral therapy session lasting 60-120 minutes. CAPS-5 assessment. |
| | Intervening Session 3C | 18-34 days following Experimental Session 3 | Behavioral or cognitive-behavioral therapy session lasting 60-120 minutes. Assessments include LEC-5, HAM-A, C-SSRS and CAPS-5. |

The Follow-up Period schedule and Study Conclusion follow the Screening Period and the Treatment Period.

| Follow-up Period and Study Conclusion | | |
|---|---|---|
| Study Visit | Visit Timing | Description |
| Follow-up Period | Occurs 2-10 days after Intervening Session 3C. | Occurs about 100-150 days following Baseline assessment. Complete self-reported assessments and patient safety measures. Create exit treatment plan for participant based on results. Final CAPS-5 assessment. Final SDS, HAM-D, and ESS assessments. |
| Study Conclusion | At time of unblinding of group. | Inform participants who finished study protocol of unblinding of groups. If a participant was in a placebo group, offer opportunity to enroll in a open-label safety extension study using either racemic methylone, S-methylone, or R-methylone. |

Dose Selection

This study compares the effects of three blinded Experimental Sessions of psychotherapy in combination with flexible doses of methylone or placebo administered as described below. Non-drug preparatory and intervening psychotherapy sessions are also included. Patient's weight is determined for dosage calculation. Initial dose is 100 mg unless this will result in a dosage of less than 1.5 mg/kg of patient weight. Initial dose thereby adjusted upward in 25 mg increments to deliver the lowest dose possible of at least 1.5 mg/kg of patient weight. Initial dose for Experimental Session 2 and 3 is cumulative dose calculated by adding the initial dose plus REMS protocol dose used the previous Experimental Session for each patient.

| Double-blinded treatment group | Experimental Session | Initial Dose | Optional (REMS) protocol: Dose Titration if underdosing occurs | Supplemental Dose (unless contraindicated) | Cumulative Dose |
|---|---|---|---|---|---|
| Racemic methylone | 1 | 100-200 mg | 30-100 mg | 50-100 mg | 100-300 mg |
| Racemic methylone | 2 | 100-200 mg | 30-100 mg | 50-100 mg | 100-300 mg |
| Racemic methylone | 3 | 100-200 mg | 30-100 mg | 50-100 mg | 100-300 mg |
| S-methylone | 1 | 100-200 mg | 30-100 mg | 50-100 mg | 100-300 mg |
| S-methylone | 2 | 100-200 mg | 30-100 mg | 50-100 mg | 100-300 mg |
| S-methylone | 3 | 100-200 mg | 30-100 mg | 50-100 mg | 100-300 mg |
| R-methylone | 1 | 100-200 mg | N/A | 50-100 mg | 100-300 mg |
| R-methylone | 2 | 100-200 mg | N/A | 50-100 mg | 100-300 mg |
| R-methylone | 3 | 100-200 mg | N/A | 50-100 mg | 100-300 mg |

Randomization and Masking

Randomization occurs prior to the initiation of Experimental Session 1. Each participant is provided the next randomized number in a sequence by a blinded study monitor. Participants are then randomized, according to a computer-generated randomization schedule, 1:1:1:1 to racemic methylone, S-methylone, R-methylone, or placebo. The randomization schedule is prepared and implemented by an independent statistician. Participants, clinicians, and study teams are blinded to treatment allocation. Racemic methylone and S-methylone treatment groups may be subjected to anxiogenic effects due to underdosing of participants. As such, an optional dose titration schedule (REMS protocol) exists for racemic methylone and S-methylone treatment groups if a participant displays no change or a significant worsening of assessed anxiety symptomatology. Participants are assessed for general well-being and anxiety by a medical practitioner about 0.75 hours after the first dose is administered. Assessments performed may include general assessments of physical and mental well-being, a structured clinical interview for DSM-5 (SCID-5) module A1, and/or a STAI assessment and may continue throughout the period of overnight observation.

Subjects then undergo three Intervening Sessions with the first session the morning after the initial dose administration. R-methylone treatment group or placebo group participants qualifying with a significant worsening of assessed anxiety symptomatology would undergo a placebo dose titration administration. Subjects would then undergo three Intervening Sessions with the first session the morning after the placebo dose titration administration. The pharmacist at each site, who prepares the treatments according to the randomization schedule, and an unblinded monitor, who performs drug accountability during the study, are unblinded. No other study personnel are unblinded until after formal locking of the study database. In the event of a medical emergency, the pharmacist is to reveal actual treatment contents to the primary investigator, who is to alert the Sponsor of the emergency. If the participant or study center personnel are unblinded, the subject is to be removed from the study.

Outcomes

The primary objective of this study is to evaluate the efficacy and safety of methylone treatment combined with psychotherapy to treat moderate to severe PTSD compared to identical psychotherapy combined with placebo treatment. Methylone treatment is further subdivided into three separate treatment groups (racemic methylone, S-methylone, and R-methylone) with each treatment subgroup only receiving administration of the single assigned drug. Treatment outcomes are determined based on a change in CAPS-5 Total Severity.

Several secondary objectives are designed for this study. One is an evaluation of clinician-rated functional impairment of methylone treatment combined with psychotherapy to treat moderate to severe PTSD compared to identical psychotherapy combined with placebo treatment. Methylone treatment is further subdivided into three separate treatment groups (racemic methylone, S-methylone, and R-methylone) with each treatment subgroup only receiving administration of the single assigned drug. Treatment outcomes are determined based on a change in SDS. Another secondary objective of this study is to evaluate clinician-rated depression of methylone treatment combined with psychotherapy to treat moderate to severe PTSD compared to identical psychotherapy combined with placebo treatment. Identical study parameters are in place as for the clinician-rated functional impairment assessment except that treatment outcomes are determined based on a change in HAM-D. An additional secondary objective of this study is to evaluate sleep assessments of methylone treatment combined with psychotherapy to treat moderate to severe PTSD compared to identical psychotherapy combined with placebo treatment. Identical study parameters are in place as for the clinician-rated functional impairment assessment except that treatment outcomes are determined based on a change in ESS. Co-morbidities present in participants with a strong positive response to methylone treatment are correlated. Co-morbidities present in participants with weak-to-no positive response to methylone treatment are correlated. Changes to presence or severity of co-morbidities from the Preparation Period to the Study Conclusion are recorded to determine if methylone treatment combined with psychotherapy in moderate to severe PTSD subjects affects co-morbid phenotypes not falling under the constellation of PTSD symptoms.

Participant Populations

Participants are recruited through referrals by other treatment providers or through print or internet advertisements. The Sponsor monitors demographics of individuals assessed for enrollment to encourage diversity and an unbiased representation of the total PTSD population. Participants must be 18 years of age or older, have a confirmed diagnosis of at least moderate PTSD according to PCL-5 at the Screening Period. Medical history intake must indicate a presence of PTSD symptoms for at least 6 months prior to the Screening Period. Participants may be enrolled in the study while remaining on a treatment regimen involving SSRI or SNRI treatment prescribed for PTSD. In some cases, enrolled participants currently taking an SSRI, an SNRI, or another medication are tapered off these medications and stabilized prior to baseline assessments. Participants with a confirmed personality disorder diagnosis are excluded from this study. Participants must be in good general physical health without one or more severe chronic conditions that could affect the safety or tolerability of methylone treatment.

Statistical Analysis

The change from baseline in CAPS-5, SDS, HAM-D, and ESS in participants is analyzed using a mixed effects model for repeated measures (MMRM) to obtain covariance parameter estimates. The model includes treatment center, treatment subtype, baseline assessments, assessment time point, and time point-by-treatment as explanatory variables. Treatment center is treated as a random effect; all other explanatory variables are treated as fixed effects. Model-based point estimates (e.g., least squares means, 95% confidence intervals, and p-values) are reported for each time point. With a sample size of 50 participants per treatment group, this study has 90% power to detect a significant treatment effect, using a two-sided test with an alpha value of 0.05. Additional participants may be enrolled with conditional power analysis conducted at a group-unblinded interim analysis time point for efficacy when 200 participants are enrolled and at least 60% of the blinded participants (N=120) have completed a final CAPS-5 assessment and reached Study Conclusion.

Results

The results indicate that the primary objective is achieved. At the point of Study Conclusion, racemic methylone-treated, S-methylone-treated, and R-methylone-treated participants demonstrate a significant mean reduction in CAPS-5 assessment compared to the placebo group. The S-methylone-treated subgroup achieves a significant mean reduction in CAPS-5 assessment with a lower total dosage of drug compared to the racemic methylone-treated subgroup. The R-methylone-treated subgroup achieves a significant mean reduction in CAPS-5 assessment with a lower total dosage of drug compared to the racemic methylone-treated subgroup. The R-methylone-treated subgroup achieves a significant mean reduction in CAPS-5 assessment with a higher total dosage of drug compared to the racemic methylone-treated subgroup. Significant improvements in CAPS-5 assessments are observed for racemic methylone-treated, S-methylone-treated, and R-methylone-treated participants at time points of Intervening Session 1C, Intervening Session 2C, Intervening Session 3C and Study Conclusion, compared to placebo-treated controls. Significant improvements in CAPS-5 assessments are observed for R-methylone-treated participants at time points of Intervening Session 1C, Intervening Session 2C, Intervening Session 3C, compared to placebo-treated controls without a significant increase in adverse anxiogenic incidents in R-methylone-treated participants.

The results indicate that the secondary objectives of this study are also achieved. At the point of Study Conclusion, racemic methylone-treated, S-methylone-treated, and R-methylone-treated participants demonstrate a significant improvement in clinician-rated functional impairment score as measured by SDS compared to placebo-treated controls. At the point of Study Conclusion, racemic methylone-treated, S-methylone-treated, and R-methylone-treated participants demonstrate a significant improvement depression as measured by HAM-D compared to placebo-treated controls. At the point of Study Conclusion, racemic methylone-treated, S-methylone-treated, and R-methylone-treated participants demonstrate a significant improvement in lessening daytime sleepiness as measured by ESS. At the point of Study Conclusion, R-methylone-treated participants demonstrate a significant improvement in clinician-rated functional impairment score, in depression, and in lessening daytime sleepiness compared to placebo-treated controls without a significant increase in adverse anxiogenic incidents in R-methylone-treated participants.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A crystalline form of racemic 3,4-methylenedioxy-N-methylcathinone (methylone) hydrochloride (Form A), wherein the crystalline methylone hydrochloride (Form A) is characterized as having an X-ray powder diffraction (XRPD) pattern with characteristic peaks at $7.5°\pm0.2$ 2-Theta, $10.3°\pm0.2$ 2-Theta, and $15.1°\pm0.2$ 2-Theta as measured with Cu Kα radiation.

2. The crystalline form of racemic 3,4-methylenedioxy-N-methylcathinone (methylone) hydrochloride (Form A) of claim 1, wherein the crystalline methylone hydrochloride (Form A) is characterized as having an X-ray powder diffraction (XRPD) pattern with further characteristic peaks at $14.7°\pm0.2$ 2-Theta, and $14.9°\pm0.2$ 2-Theta as measured with Cu Kα radiation.

3. A solid dosage form prepared by combining the crystalline Form A of methylone hydrochloride of claim 1 with at least one pharmaceutically acceptable excipient.

4. The solid dosage form of claim 3, wherein the solid dosage form is in the form of a tablet, pill, capsule, or powder.

5. A solid dosage form prepared by combining the crystalline Form A of methylone hydrochloride of claim 2 with at least one pharmaceutically acceptable excipient.

6. The solid dosage form of claim 5, wherein the solid dosage form is in the form of a tablet, pill, capsule, or powder.

7. A method for treating post-traumatic stress disorder in a human subject, comprising administering to the human subject in need thereof a therapeutically effective amount of the crystalline form of racemic methylone hydrochloride of claim 1.

8. The method of claim 7, further comprising administering a serotonin receptor 2A antagonist to the human subject.

9. A method for treating post-traumatic stress disorder in a human subject, comprising administering to the human subject in need thereof a therapeutically effective amount of the crystalline form of racemic methylone hydrochloride of claim 2.

10. The method of claim 9, further comprising administering a serotonin receptor 2A antagonist to the human subject.

11. A method for treating post-traumatic stress disorder in a human subject, comprising administering to the human subject in need thereof a therapeutically effective amount of the solid dosage form of claim 3.

12. The method of claim 11, further comprising administering a serotonin receptor 2A antagonist to the human subject.

13. A method for treating post-traumatic stress disorder in a human subject, comprising administering to the human subject in need thereof a therapeutically effective amount of the solid dosage form of claim 5.

14. The method of claim 13, further comprising administering a serotonin receptor 2A antagonist to the human subject.

* * * * *